US008809369B2

(12) United States Patent
Feng et al.

(10) Patent No.: US 8,809,369 B2
(45) Date of Patent: *Aug. 19, 2014

(54) TETRAHYDROQUINOLINE DERIVATIVES

(75) Inventors: Lichun Feng, Shanghai (CN); Mengwei Huang, Shanghai (CN); Yongfu Liu, Shanghai (CN); Guolong Wu, Shanghai (CN); Shixiang Yan, Shanghai (CN); Hongying Yun, Shanghai (CN); Mingwei Zhou, Shanghai (CN)

(73) Assignee: Hoffmann-La Roche Inc., Nutley, NJ (US)

( * ) Notice: Subject to any disclaimer, the term of this patent is extended or adjusted under 35 U.S.C. 154(b) by 217 days.

This patent is subject to a terminal disclaimer.

(21) Appl. No.: 13/353,351

(22) Filed: Jan. 19, 2012

(65) Prior Publication Data

US 2012/0190677 A1 Jul. 26, 2012

(30) Foreign Application Priority Data

Jan. 26, 2011 (WO) ................ PCT/CN2011/070644

(51) Int. Cl.
| | |
|---|---|
| *C07D 215/48* | (2006.01) |
| *C07D 401/04* | (2006.01) |
| *C07D 401/10* | (2006.01) |
| *C07D 413/10* | (2006.01) |
| *C07D 471/04* | (2006.01) |
| *A61K 31/47* | (2006.01) |
| *A61K 31/4709* | (2006.01) |
| *A61K 31/496* | (2006.01) |
| *A61K 31/5377* | (2006.01) |
| *A61P 3/04* | (2006.01) |
| *A61P 3/10* | (2006.01) |

(52) U.S. Cl.
USPC ....................................................... 514/311

(58) Field of Classification Search
USPC .............. 514/311, 314, 235.2, 235.8, 253.06, 514/232.5, 278; 546/165, 167, 169, 172, 546/173, 180, 18; 544/128, 80
See application file for complete search history.

(56) References Cited

U.S. PATENT DOCUMENTS

| 7,138,412 B2* | 11/2006 | Quan et al. ..................... 514/311 |
| 2013/0023518 A1* | 1/2013 | Chen et al. ................ 514/210.18 |

FOREIGN PATENT DOCUMENTS

WO    2009/100130    8/2009

OTHER PUBLICATIONS

Pang et al., "The Journal of Biological Chemistry" 283:16051-16060 ( 2008).
Hardie et al., "Annual Review of Pharmacology & Toxicology" 47:185-210 ( 2007).
Owen et al., "The Biological Journal" (Part 3), 348:607-614 ( 2000).
El-Mir et al., "The Journal of Biological Chemistry" 275:223-228 ( 2000).
Kadowaki et al., "The Journal of Clinical Investigation" 116:1784-1792 ( 2006).
Hardie et al., "Nature Reviews" 8:774-785 ( 2007).
Cool et al., "Cell Metabolism" 3:403-416 ( 2006).
Zhou et al., "The Journal of Clinical Investigation" 108:1167-1174 ( 2001).
Muoio et al., "Diabetes" 46:1360-1363 ( 1997).
Yamauchi et al., "Nature Medicine" 7:941-946 ( 2001).
Kahn et al., "Cell Metabolism." 1:15-25 ( 2005).
Yamauchi et al., "Nature Medicine" 8:1288-1295 ( 2002).
Minokoshi et al., "Nature" 415:339-343 ( 2002).
Semple et al., "The Journal of Clinical Investigation" 116:581-589 ( 2006).
Fryer et al., "The Journal of Biological Chemistry" 277:25226-25232 ( 2002).
"International Search Report PCT/EP2012/050922—mailed Mar. 2, 2012".
Shaw et al., "Science (NY) New York" 310:1642-1646 ( 2005).
Long et al., "The Journal of Clinical Investigation" 116:1776-1783 ( 2006).
Friedman et al., "Nature" 395:763-770 ( 1998).
Carling, D., "Trends Biochem. Sci." 29:18-24 ( 2004).
Woods et al., "Molecular & Cellular Biology" 20:6704-6711 ( 2000).

* cited by examiner

*Primary Examiner* — Sreeni Padmanabhan
*Assistant Examiner* — Irina Neagu

(57) ABSTRACT

The present invention relates to a compound of formula (I)

(I)

or a pharmaceutically acceptable salt or ester thereof, wherein $R^1$ to $R^8$, $A^1$ to $A^3$ have the are as described herein and compositions including the compounds.

24 Claims, No Drawings

TETRAHYDROQUINOLINE DERIVATIVES

PRIORITY TO RELATED APPLICATION(S)

This application claims the benefit of International Application No. PCT/CN2011/070644, filed Jan. 26, 2011, which is hereby incorporated by reference in its entirety.

FIELD OF THE INVENTION

The invention relates to compounds which are activators of AMP-activated protein kinase (AMPK) and which are useful in the treatment or prophylaxis of diseases that are related to AMPK regulation, such as obesity, dyslipidemia, hyperglycemia, type 1 or type 2 diabetes and cancers.

BACKGROUND OF THE INVENTION

Obesity and type 2 diabetes, hypertension and cardiovascular disease are diseases that feature serious disturbances in glucose or lipid metabolism that severely affect the health and quality of life of affected individuals. In addition, cancer metabolism is known to be different from normal cellular metabolism. The increasing prevalence of these diseases makes finding new drug targets for treating these syndromes an urgent task.

AMP-activated protein kinase acts as a cellular energy sensor and regulator. It is activated by an increase in the cellular AMP:ATP ratio induced by metabolic stress, hormone and nutrient signals and other cellular mechanisms such as phosphorylation and protein-protein interaction. Once activated, AMPK switches on catabolic pathways that generate ATP and switches off ATP-consuming anabolic pathways by acute regulation of the activity of key enzymes in metabolism and chronic regulation of the expression of pivotal transcription factors (Hardie, D G. Nature reviews 8 (2007b), 774-785; Woods, A et al. Molecular and cellular biology 20 (2000), 6704-6711). The growing evidence of AMPK regulatory effects on glucose and lipid metabolism makes it a potential drug target for treatment of diabetes, metabolic syndrome and cancer (Carling, D. Trends Biochem Sci 29 (2004), 18-24; Hardie, D G. Annual review of pharmacology and toxicology 47 (2007a), 185-210; Kahn, B B et al. Cell metabolism 1 (2005), 15-25; Long, Y C et al. The Journal of clinical investigation 116 (2006), 1776-1783).

At the physiological level, this concept has been supported by two adipokines, leptin and adiponectin, both of which exert excellent effects on glucose and lipid metabolism (Friedman, J M and Halaas, J L. Nature 395 (1998), 763-770; Muoio, D M et al. Diabetes 46 (1997), 1360-1363; Yamauchi, T et al. Nature medicine 7 (2001), 941-946). Recent studies suggest that leptin and adiponectin exert their antidiabetic effects by activating AMPK. Leptin stimulates muscle fatty acid oxidation by activating AMPK directly and through a hypothalamic-adrenergic pathway (Minokoshi, Y et al. Nature 415 (2002), 339-343). Adiponectin stimulates glucose uptake and fatty acid oxidation in vitro by activation of AMPK. Furthermore, it exerts its hypoglycemic effect by decreasing PEPCK and G6 Pase expression, whereas the administration of dominant negative al adenovirus reverses the effect in vivo (Yamauchi, T et al. Nature medicine 8 (2002), 1288-1295).

At the pharmacological level, the concept of AMPK as a potential target for treating metabolic syndrome has been further supported by the discovery of two major classes of existing antidiabetic drugs: thiazolidinediones (rosiglitazone, troglitazone and pioglitazone) and biguanides (metformin and phenformin) activate AMPK in cultured cells and in vivo. Rosiglitazone is traditionally considered to be a PPARγ agonist and exerts its antidiabetic effects through differentiation of adipocytes (Semple, R K et al. The Journal of clinical investigation 116 (2006), 581-589). Recent findings indicate that AMPK may be involved in the antidiabetic effects of rosiglitazone (Brunmair, B et al. The Journal of biological chemistry 277 (2002), 25226-25232; Kadowaki, T et al. The Journal of clinical investigation 116 (2006), 1784-1792). In the case of metformin, an existing antidiabetic agent without a defined mechanism of action, recent studies demonstrate that it could activate AMPK in vitro and in vivo by inhibiting complex I (El-Mir, M Y et al. The Journal of biological chemistry 275 (2000), 223-228; Owen, M R et al. The Biochemical journal 348 Pt 3 (2000), 607-614; Zhou, G et al. The Journal of clinical investigation 108 (2001), 1167-1174), and the hypoglycemic effect could be blocked completely by knockout of its upstream kinase LKB1, confirming the key role of AMPK in mediating the antidiabetic effect of metformin (Shaw, R J et al. Science (New York) N.Y. 310 (2005), 1642-1646).

Most recently, Cool and coworkers have identified a small direct AMPK activator, A-769662, which exerts antidiabetic effects in vivo (Cool, B et al. Cell metabolism 3 (2006), 403-416). Li's laboratory has also identified a small AMPK activator, PT1, which activates the inactive forms of AMPK $\alpha 2_{398}$ and $\alpha 1_{394}$ with micromolar activity and exerts some cellular effects (Pang, T et al. The Journal of biological chemistry 283 (2008), 16051-16060).

It has been found that the compounds of the present invention are potent AMPK activators. The compounds of the invention are therefore useful in the treatment or prophylaxis of diseases that are related to AMPK regulation, such as obesity, dyslipidemia, hyperglycemia, type 1 or type 2 diabetes and cancers.

SUMMARY OF THE INVENTION

The invention relates in to a compound of formula (I)

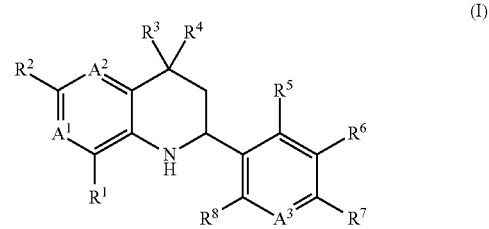

wherein
$A^1$ is nitrogen or —$CR^{10}$—;
$A^2$ is nitrogen or —CH—;
$A^3$ is nitrogen or —$CR^9$—;
one of $R^1$, $R^2$ and $R^{10}$ is -$A^4$-$SO_2$—$R^{11}$ and the other ones are independently selected from hydrogen, alkyl and halogen;
$A^4$ is absent or —$NR^{12}$—C(O)—;
$R^3$ and $R^4$ are independently selected from alkyl and phenyl; or $R^3$ and $R^4$ together with the carbon atom to which they are attached form cycloalkyl;
$R^5$, $R^6$, $R^7$, $R^8$ and $R^9$ are independently selected from the group consisting of hydrogen, alkyl, haloalkyl, alkoxy, halogen, alkylamino, dialkylamino, hydroxyphenyl, morpholinyl, piperazinyl, alkylpiperazinyl, phenylpiperazinyl, phenylaminocarbonyl, oxo-oxazolidinyl, aminocarbonyl, cyano, alkylsulfonyl, alkylphenyl, alkoxyphenyl, alkylphenylpiperazinyl, dialkylphenylpiperazinyl, halophenylpiperazinyl, alkyl-1H-tetrazolyl, cycloalkyl-1H-tetrazolyl, pyrrolidinyl, carboxyalkylamino and carboxycycloalkylamino;

$R^{11}$ is selected from the group consisting of alkyl, cycloalkyl, alkylamino, cycloalkylamino and morpholinyl; and $R^{12}$ is hydrogen or alkyl;

or a pharmaceutically acceptable salt or ester thereof.

The invention also relates to a process for the manufacture of these novel compounds and medicaments containing them. The compounds of the invention have activation effect on AMP (adenosine monophosphate)-activated protein kinase, which results in lowered blood glucose and lipid levels. The invention thus also concerns the use of such compounds for the treatment or prophylaxis of diseases that are related to AMPK regulation, such as obesity, dyslipidemia, hyperglycemia, type 1 or type 2 diabetes, and cancers.

DETAILED DESCRIPTION OF THE INVENTION

The invention relates in to a compound of formula (I)

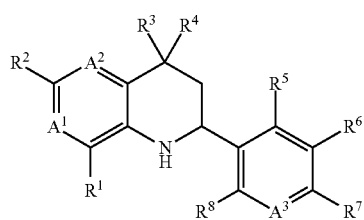

(I)

wherein $A^1$ is nitrogen or —$CR^{10}$—;

$A^2$ is nitrogen or —CH—;

$A^3$ is nitrogen or —$CR^9$—;

one of $R^1$, $R^2$ and $R^{10}$ is -$A^4$-$SO_2$—$R^{11}$ and the other ones are independently selected from hydrogen, alkyl and halogen;

$A^4$ is absent or —$NR^{12}$—C(O)—;

$R^3$ and $R^4$ are independently selected from alkyl and phenyl; or $R^3$ and $R^4$ together with the carbon atom to which they are attached form cycloalkyl;

$R^5$, $R^6$, $R^7$, $R^8$ and $R^9$ are independently selected from the group consisting of hydrogen, alkyl, haloalkyl, alkoxy, halogen, alkylamino, dialkylamino, hydroxyphenyl, morpholinyl, piperazinyl, alkylpiperazinyl, phenylpiperazinyl, phenylaminocarbonyl, oxo-oxazolidinyl, aminocarbonyl, cyano, alkylsulfonyl, alkylphenyl, alkoxyphenyl, alkylphenylpiperazinyl, dialkylphenylpiperazinyl, halophenylpiperazinyl, alkyl-1H-tetrazolyl, cycloalkyl-1H-tetrazolyl, pyrrolidinyl, carboxyalkylamino and carboxycycloalkylamino;

$R^{11}$ is selected from the group consisting of alkyl, cycloalkyl, alkylamino, cycloalkylamino or and morpholinyl; and $R^{12}$ is hydrogen or alkyl;

or a pharmaceutically acceptable salt or ester thereof.

As used herein, the term "alkyl", alone or in combination, signifies a saturated, linear- or branched chain alkyl group containing 1 to 8, preferably 1 to 6, more preferably 1 to 4 carbon atoms, for example methyl, ethyl, propyl, isopropyl, 1-butyl, 2-butyl and tert-butyl. Preferred "alkyl" groups are methyl, ethyl, propyl and butyl, more preferably methyl, ethyl, isopropyl and tert-butyl.

The term "alkoxy", alone or in combination, signifies a group alkyl-O—, wherein the "alkyl" is as defined above; for example methoxy, ethoxy, propoxy, isopropoxy, n-butoxy, i-butoxy, 2-butoxy and t-butoxy. Preferred "alkoxy" groups are methoxy and ethoxy and more preferably methoxy.

The term "cycloalkyl", alone or in combination, refers to a saturated carbon ring containing from 3 to 7 carbon atoms, preferably from 3 to 6 carbon atoms, for example, cyclopropyl, cyclobutyl, cyclopentyl, cyclohexyl and cycloheptyl. Preferred "cycloalkyl" groups are cyclopropyl, cyclopentyl and cyclohexyl.

The term "halogen" means fluorine, chlorine, bromine or iodine. "Halogen" is preferably fluorine, chlorine or bromine.

The term "haloalkyl" means alkyl substituted by halogen. Preferred "haloalkyl" are for example fluoroalkyl, preferably trifluoromethyl.

The term "halophenyl" means phenyl substituted by halogen. Preferred "halophenyl" are for example fluorophenyl.

The term "carboxy", alone or in combination, refers to the group —COOH.

The term "carbonyl", alone or in combination, refers to the group —C(O)—.

The term "amino", alone or in combination, refers to primary (—NH2), secondary (—NH—) or tertiary amino (—N—).

The term "hydroxy", alone or in combination, refers to the group —OH.

The term "sulfonyl", alone or in combination, refers to the group —$S(O)_2$—.

In a particular embodiment of the invention, $A^1$ is nitrogen. In another embodiment, $A^1$ is —$CR^{10}$—.

In another particular embodiment of the invention, $A^2$ is nitrogen. In a further embodiment of the invention, $A^2$ is —CH—.

Still in a particular embodiment of the invention, $A^3$ is nitrogen. $A^3$ can also be —$CR^9$— in a particular embodiment of the compound of formula (I).

The invention further relates to a compound of formula (I), wherein one of $R^1$, $R^2$ and $R^{19}$ is -$A^4$-$SO_2$—$R^{11}$ and the other ones are independently selected from the group consisting of hydrogen, fluoro and chloro.

In a particular embodiment of the invention, one of $R^1$, $R^2$ and $R^{19}$ is -$A^4$-$SO_2$—$R^{11}$, the other ones are independently selected from the group consisting of hydrogen, alkyl and halogen, and $A^4$ is absent.

$A^4$ can also be —$NR^{12}$—C(O)— in a particular embodiment of the compound of formula (I).

In particular, $A^4$ is bound to the rest of the molecule through the carbonyl par, and to $R^{11}$ through the amino part of the amide linkage.

In another particular embodiment of the invention, one of $R^1$, $R^2$ and $R^{10}$ is -$A^4$-$SO_2$—$R^{11}$, the other ones are independently selected from the group consisting of hydrogen, methyl, fluoro and chloro, and $A^4$ is absent.

$A^4$ can also be —$NR^{12}$—C(O)— in a particular embodiment of the compound of formula (I). In the definition of $R^1$, $R^2$ and $R^{10}$, alkyl is in particular methyl. In the definition of $R^1$, $R^2$ and $R^{10}$, halogen is in particular fluoro or chloro.

In particular, $R^1$ is hydrogen, alkyl, alkylsulfonylaminocarbonyl or cycloalkylsulfonylaminocarbonyl. More particularly, $R^1$ is the group consisting of hydrogen, alkylsulfonylaminocarbonyl and cycloalkylsulfonylaminocarbonyl. Furthermore, $R^1$ is in particular the group consisting of hydrogen, methyl, methylsulfonylaminocarbonyl and cyclopropylsulfonylaminocarbonyl, more particularly the group consisting of hydrogen, methylsulfonylaminocarbonyl and cyclopropylsulfonylaminocarbonyl.

In particular, $R^2$ is the group consisting of hydrogen, halogen, alkylsulfonylaminocarbonyl, cycloalkylsulfonylaminocarbonyl and morpholinylsulfonyl. More particularly, $R^2$ is the group consisting of hydrogen, chloro, fluoro, propylsulfonylaminocarbonyl, methylsulfonylaminocarbonyl, cyclopropylsulfonylaminocarbonyl, cyclopropylsulfonylaminocarbonyl and morpholinylsulfonyl. In the definition of $R^3$ and $R^4$, alkyl is in particular methyl. In the definition of $R^3$ and $R^4$, cycloalkyl is in particular cyclopropyl or cyclopentyl.

The compound of formula (I) wherein $R^3$ and $R^4$ are independently selected from alkyl and phenyl is a particular embodiment of the invention.

This invention relates also to a compound of formula (I) wherein $R^3$ and $R^4$ together with the carbon atom to which they are attached form cycloalkyl.

In particular, the invention relates to a compound of formula (I) wherein $R^3$ and $R^4$ are independently selected from methyl and phenyl, or $R^3$ and $R^4$ together with the carbon atom to which they are attached form cyclopropyl or cyclopentyl.

The compound of formula (I) wherein $R^3$ and $R^4$ are independently selected from methyl and phenyl is an embodiment of the invention.

The compound of formula (I) wherein $R^3$ and $R^4$ together with the carbon atom to which they are attached form cyclopropyl or cyclopentyl is another embodiment of the invention.

The compound of formula (I) wherein $R^3$ and $R^4$ are both alkyl at the same time is an embodiment of the invention.

The compound of formula (I) wherein $R^3$ and $R^4$ are both methyl at the same time is another embodiment of the invention.

The compound of formula (I) wherein $R^5$, $R^6$, $R^7$, $R^8$ and $R^9$ are independently selected from the group consisting of hydrogen, alkyl, halogen, cyano, alkoxy, haloalkyl, dialkylamino, carboxyalkylamino, carboxycycloalkylamino, alkylsulfonyl, aminocarbonyl, morpholinyl, pyrrolidinyl, alkylphenyl, hydroxyphenyl, piperazinyl, alkylpiperazinyl, phenylpiperazinyl, alkylphenylpiperazinyl, dialkylphenylpiperazinyl, halophenylpiperazinyl, phenylaminocarbonyl, alkoxyphenyl, oxo-oxazolidinyl, alkyl-1H-tetrazolyl and cycloalkyl-1H-tetrazolyl, is a further object of the invention.

The compound of formula (I) wherein $R^5$ and $R^8$ are independently selected from the group consisting of hydrogen, alkyl and halogen is also an object of the invention.

In the definition of $R^5$ and $R^8$, halogen is in particular fluoro or chloro.

The compound of formula (I) wherein $R^5$ and $R^8$ are independently selected from hydrogen and methyl is a further embodiment of the invention.

The compound of formula (I) wherein $R^5$ and $R^8$ are in particular hydrogen is another embodiment of the invention.

A compound of formula (I) wherein $R^6$ and $R^9$ are independently selected from the group consisting of hydrogen, halogen, cyano, alkoxy, haloalkyl, dialkylamino, carboxyalkylamino, carboxycycloalkylamino, alkylsulfonyl, aminocarbonyl, morpholinyl, pyrrolidinyl, alkylphenyl, hydroxyphenyl, piperazinyl, alkylpiperazinyl, phenylpiperazinyl, alkylphenylpiperazinyl, dialkylphenylpiperazinyl, halophenylpiperazinyl, phenylaminocarbonyl, alkoxyphenyl, oxo-oxazolidinyl, alkyl-1-H-tetrazolyl and cycloalkyl-1-H-tetrazolyl is also a particular embodiment of the invention.

Furthermore, the invention relates to a compound of formula (I) wherein $R^6$ and $R^9$ are independently selected from the group consisting of hydrogen, trifluoromethyl, morpholinyl, pyrrolidinyl, t-butylphenyl, hydroxyphenyl, piperazinyl, phenylpiperazinyl, methylphenylpiperazinyl, fluorophenylpiperazinyl and cyclopropyl-1-H-tetrazolyl.

The invention relates also to a compound of formula (I) wherein one of $R^5$ and $R^8$ is hydrogen and the other one is as defined above.

The invention further relates to a compound of formula (I) wherein one of $R^6$ and $R^9$ is hydrogen and the other one is as defined above.

A compound of formula (I) wherein $R^7$ is hydrogen or halogen is a further particular object of the invention. A compound of formula (I) wherein $R^7$ is hydrogen is a further particular object of the invention.

Moreover, the invention is directed in particular to formula (I) wherein $R^7$ is hydrogen or fluoro. $R^{19}$ is particularly hydrogen or alkylsulfonylaminocarbonyl, more particularly hydrogen or, methylsulfonylaminocarbonyl, more particularly hydrogen.

A compound of formula (I) wherein $R^{11}$ is the group consisting of methyl, propyl, isopropyl, cyclopropyl, isopropylamino, cyclobutylamino and morpholinyl is a particular object of the invention.

A compound of formula (I) wherein $R^{12}$ is hydrogen or methyl is also an object of the invention.

Particular compounds of formula (I) according to the invention can be selected from Cyclopropanesulfonic acid [4,4-dimethyl-2-(3-morpholin-4-yl-phenyl)-1,2,3,4-tetrahydroquinoline-6-carbonyl]-amide;

2'-(5-Fluoro-2-methylphenyl)-N-(methylsulfonyl)-2',3'-dihydro-1'H-spiro[cyclopropane-1,4'-quinoline]-6'-carboxamide;

2'-(2,4-Difluorophenyl)-N-(methylsulfonyl)-2',3'-dihydro-1'H-spiro[cyclopropane-1,4'-quinoline]-6'-carboxamide;

N-[2-(3-Fluoro-5-morpholin-4-yl-phenyl)-4,4-dimethyl-1,2,3,4-tetrahydro-quinoline-6-carbonyl]-methanesulfonamide;

N-(methylsulfonyl)-2'-(3-morpholinophenyl)-2',3'-dihydro-1'H-spiro[cyclopentane-1,4'-quinoline]-6'-carboxamide;

Cyclopropanesulfonic acid [2-(3-fluoro-5-morpholin-4-yl-phenyl)-4,4-dimethyl-1,2,3,4-tetrahydro-quinoline-6-carbonyl]-amide;

N-[2-(3-chloro-4-fluoro-phenyl)-4-methyl-4-phenyl-1,2,3,4-tetrahydro-quinoline-6-carbonyl]-methanesulfonamide;

Propane-1-sulfonic acid [2-(3-chloro-4-fluoro-phenyl)-4,4-dimethyl-1,2,3,4-tetrahydro-quinoline-6-carbonyl]-amide;

Propane-2-sulfonic acid [4,4-dimethyl-2-(3-morpholin-4-yl-phenyl)-1,2,3,4-tetrahydroquinoline-6-carbonyl]-amide;

N-[4,4-dimethyl-2-(3-morpholin-4-yl-phenyl)-1,2,3,4-tetrahydro-quinoline-8-carbonyl]-methanesulfonamide;

Cyclopropanesulfonic acid [4,4-dimethyl-2-(3-morpholin-4-yl-phenyl)-1,2,3,4-tetrahydro-quinoline-8-carbonyl]-amide;

4,4-Dimethyl-6-(morpholine-4-sulfonyl)-2-(3-morpholin-4-yl-phenyl)-1,2,3,4-tetrahydro-quinoline;

4,4-Dimethyl-2-(3-morpholin-4-yl-phenyl)-1,2,3,4-tetrahydro-quinoline-6-sulfonic acid isopropylamide;

4,4-Dimethyl-6-(morpholine-4-sulfonyl)-2-(3-piperazin-1-yl-phenyl)-1,2,3,4-tetrahydro-quinoline;

4,4-Dimethyl-2-(3-morpholin-4-yl-phenyl)-1,2,3,4-tetrahydro-quinoline-6-sulfonic acid cyclobutylamide;

2-(3-Fluoro-5-morpholin-4-yl-phenyl)-4,4-dimethyl-1,2,3,4-tetrahydro-quinoline-6-sulfonic acid cyclobutylamide;

2-(2'-Hydroxy-biphenyl-3-yl)-4,4-dimethyl-1,2,3,4-tetrahydro-quinoline-6-sulfonic acid cyclobutylamide;

N-(4,4-dimethyl-2-pyridin-3-yl-1,2,3,4-tetrahydro-quinoline-6-carbonyl)-methanesulfonamide;

Cyclopropanesulfonic acid (4,4-dimethyl-2-pyridin-3-yl-1,2,3,4-tetrahydro-quinoline-6-carbonyl)-amide;

3-(6-Methanesulfonylaminocarbonyl-4,4-dimethyl-1,2,3,4-tetrahydro-quinolin-2-yl)-N-phenyl-benzamide;

3-(6-Cyclopropanesulfonylaminocarbonyl-4,4-dimethyl-1,
2,3,4-tetrahydro-quinolin-2-yl)-N-phenyl-benzamide;
N-[4,4-dimethyl-2-(2-methyl-5-morpholin-4-yl-phenyl)-1,
2,3,4-tetrahydro-quinoline-6-carbonyl]-methanesulfonamide;
N-[2-(2-chloro-5-morpholin-4-yl-phenyl)-4,4-dimethyl-1,2,
3,4-tetrahydro-quinoline-6-carbonyl]-methanesulfonamide; Cyclopropanesulfonic acid [4,4-dimethyl-2-(2-methyl-5-morpholin-4-yl-phenyl)-1,2,3,4-tetrahydro-quinoline-6-carbonyl]-amide;
Cyclopropanesulfonic acid [2-(2-chloro-5-morpholin-4-yl-phenyl)-4,4-dimethyl-1,2,3,4-tetrahydro-quinoline-6-carbonyl]-amide;
N-{2-[2-chloro-5-(2-oxo-oxazolidin-3-yl)-phenyl]-4,4-dimethyl-1,2,3,4-tetrahydro-quinoline-6-carbonyl}-methanesulfonamide;
N-{4,4-dimethyl-2-[2-methyl-5-(2-oxo-oxazolidin-3-yl)-phenyl]-1,2,3,4-tetrahydro-quinoline-6-carbonyl}-methanesulfonamide;
Cyclopropanesulfonic acid {4,4-dimethyl-2-[2-methyl-5-(2-oxo-oxazolidin-3-yl)-phenyl]-1,2,3,4-tetrahydro-quinoline-6-carbonyl}-amide;
Cyclopropanesulfonic acid {2-[2-chloro-5-(2-oxo-oxazolidin-3-yl)-phenyl]-4,4-dimethyl-1,2,3,4-tetrahydro-quinoline-6-carbonyl}-amide;
N-[4,4-Dimethyl-2-(3-trifluoromethyl-phenyl)-1,2,3,4-tetrahydro-quinoline-6-carbonyl]-methanesulfonamide;
Cyclopropanesulfonic acid [4,4-dimethyl-2-(3-trifluoromethyl-phenyl)-1,2,3,4-tetrahydro-quinoline-6-carbonyl]-amide;
3-(6-Methanesulfonylaminocarbonyl-4,4-dimethyl-1,2,3,4-tetrahydro-quinolin-2-yl)-benzamide;
N-[2-(3-cyano-phenyl)-4,4-dimethyl-1,2,3,4-tetrahydroquinoline-6-carbonyl]-methanesulfonamide;
3-(6-Cyclopropanesulfonylaminocarbonyl-4,4-dimethyl-1,
2,3,4-tetrahydro-quinolin-2-yl)-benzamide; Cyclopropanesulfonic acid [2-(3-cyano-phenyl)-4,4-dimethyl-1,2,
3,4-tetrahydro-quinoline-6-carbonyl]-amide;
N-[2-(3-methoxy-phenyl)-4,4-dimethyl-1,2,3,4-tetrahydro-quinoline-6-carbonyl]-methanesulfonamide;
N-[2-(3-methanesulfonyl-phenyl)-4,4-dimethyl-1,2,3,4-tetrahydro-quinoline-6-carbonyl]-methanesulfonamide;
Cyclopropanesulfonic acid [2-(3-methanesulfonyl-phenyl)-4,4-dimethyl-1,2,3,4-tetrahydro-quinoline-6-carbonyl]-amide;
N-[2-(4'-tert-butyl-biphenyl-3-yl)-4,4-dimethyl-1,2,3,4-tetrahydro-quinoline-6-carbonyl]-methanesulfonamide;
Cyclopropanesulfonic acid [2-(4'-tert-butyl-biphenyl-3-yl)-4,4-dimethyl-1,2,3,4-tetrahydroquinoline-6-carbonyl]-amide;
Cyclopropanesulfonic acid {2-[3-(1-cyclopropyl-1H-tetrazol-5-yl)-phenyl]-4,4-dimethyl-1,2,3,4-tetrahydro-quinoline-6-carbonyl}-amide;
Cyclopropanesulfonic acid {4,4-dimethyl-2-[3-(1-methyl-1H-tetrazol-5-yl)-phenyl]-1,2,3,4-tetrahydro-quinoline-6-carbonyl}-amide;
N-{2-[3-(1-cyclopropyl-1H-tetrazol-5-yl)-phenyl]-4,4-dimethyl-1,2,3,4-tetrahydro-quinoline-6-carbonyl}-methanesulfonamide;
N-{4,4-dimethyl-2-[3-(1-methyl-1H-tetrazol-5-yl)-phenyl]-1,2,3,4-tetrahydro-quinoline-6-carbonyl}-methanesulfonamide;
N-[2-(4'-isopropoxy-biphenyl-3-yl)-4,4-dimethyl-1,2,3,4-tetrahydro-quinoline-6-carbonyl]-methanesulfonamide;
Cyclopropanesulfonic acid [2-(4'-isopropoxy-biphenyl-3-yl)-4,4-dimethyl-1,2,3,4-tetrahydro-quinoline-6-carbonyl]-amide;
Cyclopropanesulfonic acid [2-(2-ethyl-5-morpholin-4-yl-phenyl)-4,4-dimethyl-1,2,3,4-tetrahydro-quinoline-6-carbonyl]-amide;
Cyclopropanesulfonic acid [2-(2-ethyl-phenyl)-4,4-dimethyl-1,2,3,4-tetrahydro-quinoline-6-carbonyl]-amide;
N-(2-{5-[4-(2,4-dimethyl-phenyl)-piperazin-1-yl]-pyridin-3-yl}-4,4-dimethyl-1,2,3,4-tetrahydro-quinoline-6-carbonyl)-methanesulfonamide;
Cyclopropanesulfonic acid (2-{5-[4-(2,4-dimethyl-phenyl)-piperazin-1-yl]-pyridin-3-yl}-4,4-dimethyl-1,2,3,4-tetrahydro-quinoline-6-carbonyl)-amide;
Cyclopropanesulfonic acid {4,4-dimethyl-2-[3-(4-methyl-piperazin-1-yl)-phenyl]-1,2,3,4-tetrahydro-quinoline-6-carbonyl}-amide;
Cyclopropanesulfonic acid [4,4-dimethyl-2-(3-pyrrolidin-1-yl-phenyl)-1,2,3,4-tetrahydroquinoline-6-carbonyl]-amide;
N-(2-{3-[4-(2,4-dimethyl-phenyl)-piperazin-1-yl]-phenyl}-4,4-dimethyl-1,2,3,4-tetrahydroquinoline-6-carbonyl)-methanesulfonamide;
N-[4,4-dimethyl-2-(5-morpholin-4-yl-pyridin-3-yl)-1,2,3,4-tetrahydro-quinoline-6-carbonyl]-methanesulfonamide;
N-[4,4-dimethyl-2-(3-morpholin-4-yl-phenyl)-1,2,3,4-tetrahydro-quinoline-7-carbonyl]-methanesulfonamide;
N-[6-fluoro-4,4-dimethyl-2-(3-morpholin-4-yl-phenyl)-1,2,3,4-tetrahydro-quinoline-8-carbonyl]-methanesulfonamide;
N-{6-fluoro-4,4-dimethyl-2-[3-(4-o-tolyl-piperazin-1-yl)-phenyl]-1,2,3,4-tetrahydro-quinoline-8-carbonyl}-methanesulfonamide;
Cyclopropanesulfonic acid {6-fluoro-4,4-dimethyl-2-[3-(4-o-tolyl-piperazin-1-yl)-phenyl]-1,2,3,4-tetrahydro-quinoline-8-carbonyl}-amide;
N-(6-fluoro-2-{3-[4-(2-fluoro-phenyl)-piperazin-1-yl]-phenyl}-4,4-dimethyl-1,2,3,4-tetrahydro-quinoline-8-carbonyl)-methanesulfonamide;
Cyclopropanesulfonic acid (6-fluoro-2-{3-[4-(2-fluoro-phenyl)-piperazin-1-yl]-phenyl}-4,4-dimethyl-1,2,3,4-tetrahydro-quinoline-8-carbonyl)-amide;
Cyclopropanesulfonic acid [2-(3-dimethylamino-phenyl)-6-fluoro-4,4-dimethyl-1,2,3,4-tetrahydro-quinoline-8-carbonyl]-amide;
N-[6-chloro-4,4-dimethyl-2-(3-morpholin-4-yl-phenyl)-1,2,3,4-tetrahydro-quinoline-8-carbonyl]-methanesulfonamide;
Cyclopropanesulfonic acid [6-chloro-4,4-dimethyl-2-(3-morpholin-4-yl-phenyl)-1,2,3,4-tetrahydro-quinoline-8-carbonyl]-amide;
N-{6-chloro-4,4-dimethyl-2-[3-(2-oxo-oxazolidin-3-yl)-phenyl]-1,2,3,4-tetrahydro-quinoline-8-carbonyl}-methanesulfonamide;
Cyclopropanesulfonic acid {6-chloro-4,4-dimethyl-2-[3-(2-oxo-oxazolidin-3-yl)-phenyl]-1,2,3,4-tetrahydro-quinoline-8-carbonyl}-amide;
Cyclopropanesulfonic acid [4,4,8-trimethyl-2-(3-morpholin-4-yl-phenyl)-1,2,3,4-tetrahydro-quinoline-6-carbonyl]-amide;
N-{4,4-dimethyl-2-[3-(4-methyl-piperazin-1-yl)-phenyl]-1,
2,3,4-tetrahydro-quinoline-8-carbonyl}-methanesulfonamide;
N-{6-fluoro-4,4-dimethyl-2-[3-(4-p-tolyl-piperazin-1-yl)-phenyl]-1,2,3,4-tetrahydro-quinoline-8-carbonyl}-methanesulfonamide;
N-[6-fluoro-4,4-dimethyl-2-(4-methyl-3-pyrrolidin-1-yl-phenyl)-1,2,3,4-tetrahydro-quinoline-8-carbonyl]-methanesulfonamide;

Cyclopropanesulfonic acid [6-fluoro-4,4-dimethyl-2-(4-methyl-3-pyrrolidin-1-yl-phenyl)-1,2,3,4-tetrahydro-quinoline-8-carbonyl]-amide;
N-[6-chloro-4,4-dimethyl-2-(4-methyl-3-pyrrolidin-1-yl-phenyl)-1,2,3,4-tetrahydro-quinoline-8-carbonyl]-methanesulfonamide;
Cyclopropanesulfonic acid [6-chloro-4,4-dimethyl-2-(4-methyl-3-pyrrolidin-1-yl-phenyl)-1,2,3,4-tetrahydro-quinoline-8-carbonyl]-amide;
N-{2-[5-(4-tert-Butyl-phenyl)-pyridin-3-yl]-4,4-dimethyl-1,2,3,4-tetrahydro-quinoline-6-carbonyl}-methanesulfonamide;
Cyclopropanesulfonic acid {2-[5-(4-tert-butyl-phenyl)-pyridin-3-yl]-4,4-dimethyl-1,2,3,4-tetrahydro-quinoline-6-carbonyl}-amide;
Cyclopropanesulfonic acid [4,4-dimethyl-2-(3-morpholin-4-yl-phenyl)-1,2,3,4-tetrahydro-quinoline-6-carbonyl]-methyl-amide;
Cyclopropanesulfonic acid {4,4-dimethyl-2-[3-(4-phenyl-piperazin-1-yl)-phenyl]-1,2,3,4-tetrahydro-quinoline-8-carbonyl}-amide;
Cyclopropanesulfonic acid [2-(3-chloro-4-fluoro-phenyl)-4,4-dimethyl-1,2,3,4-tetrahydro-[1,7]naphthyridine-6-carbonyl]-amide;
Cyclopropanesulfonic acid [6-(3-chloro-4-fluoro-phenyl)-8,8-dimethyl-5,6,7,8-tetrahydro-[1,5]naphthyridine-2-carbonyl]-amide;
Cyclopropanesulfonic acid [8,8-dimethyl-6-(3-morpholin-4-yl-phenyl)-5,6,7,8-tetrahydro-[1,5]naphthyridine-2-carbonyl]-amide;
N-[8,8-dimethyl-6-(3-morpholin-4-yl-phenyl)-5,6,7,8-tetrahydro-[1,5]naphthyridine-2-carbonyl]-methanesulfonamide;
N-[6-(3-chloro-4-fluoro-phenyl)-8,8-dimethyl-5,6,7,8-tetrahydro-[1,5]naphthyridine-2-carbonyl]-methanesulfonamide;
2-{3-[4,4-Dimethyl-6-(morpholine-4-sulfonyl)-1,2,3,4-tetrahydro-quinolin-2-yl]-phenylamino}-2-methyl-propionic acid;
1-{3-[4,4-Dimethyl-6-(morpholine-4-sulfonyl)-1,2,3,4-tetrahydro-quinolin-2-yl]-phenylamino}-cyclopropanecarboxylic acid;
1-[3-(6-Cyclobutylsulfamoyl-4,4-dimethyl-1,2,3,4-tetrahydro-quinolin-2-yl)-phenylamino]-cyclopropanecarboxylic acid;
2-[3-(6-Cyclobutylsulfamoyl-4,4-dimethyl-1,2,3,4-tetrahydro-quinolin-2-yl)-phenylamino]-2-methyl-propionic acid;
2-[3-(6-Cyclobutylsulfamoyl-4,4-dimethyl-1,2,3,4-tetrahydro-quinolin-2-yl)-5-fluoro-phenylamino]-2-methyl-propionic acid; and
1-[3-(6-Cyclobutylsulfamoyl-4,4-dimethyl-1,2,3,4-tetrahydro-quinolin-2-yl)-5-fluoro-phenylamino]-cyclopropanecarboxylic acid.

Further particular compounds of formula (I) can be selected from
Cyclopropanesulfonic acid [4,4-dimethyl-2-(3-morpholin-4-yl-phenyl)-1,2,3,4-tetrahydroquinoline-6-carbonyl]-amide;
Cyclopropanesulfonic acid [2-(3-fluoro-5-morpholin-4-yl-phenyl)-4,4-dimethyl-1,2,3,4-tetrahydro-quinoline-6-carbonyl]-amide;
Propane-2-sulfonic acid [4,4-dimethyl-2-(3-morpholin-4-yl-phenyl)-1,2,3,4-tetrahydroquinoline-6-carbonyl]-amide;
N-[4,4-dimethyl-2-(3-morpholin-4-yl-phenyl)-1,2,3,4-tetrahydro-quinoline-8-carbonyl]-methanesulfonamide;
Cyclopropanesulfonic acid [4,4-dimethyl-2-(3-morpholin-4-yl-phenyl)-1,2,3,4-tetrahydro-quinoline-8-carbonyl]-amide;
4,4-Dimethyl-2-(3-morpholin-4-yl-phenyl)-1,2,3,4-tetrahydro-quinoline-6-sulfonic acid isopropylamide;
4,4-Dimethyl-6-(morpholine-4-sulfonyl)-2-(3-piperazin-1-yl-phenyl)-1,2,3,4-tetrahydro-quinoline;
4,4-Dimethyl-2-(3-morpholin-4-yl-phenyl)-1,2,3,4-tetrahydro-quinoline-6-sulfonic acid cyclobutylamide;
2-(2'-Hydroxy-biphenyl-3-yl)-4,4-dimethyl-1,2,3,4-tetrahydro-quinoline-6-sulfonic acid cyclobutylamide;
N-[4,4-dimethyl-2-(2-methyl-5-morpholin-4-yl-phenyl)-1,2,3,4-tetrahydro-quinoline-6-carbonyl]-methanesulfonamide;
N-[4,4-dimethyl-2-(3-trifluoromethyl-phenyl)-1,2,3,4-tetrahydro-quinoline-6-carbonyl]-methanesulfonamide;
Cyclopropanesulfonic acid [4,4-dimethyl-2-(3-trifluoromethyl-phenyl)-1,2,3,4-tetrahydro-quinoline-6-carbonyl]-amide;
N-[2-(4'-tert-butyl-biphenyl-3-yl)-4,4-dimethyl-1,2,3,4-tetrahydro-quinoline-6-carbonyl]-methanesulfonamide;
Cyclopropanesulfonic acid {2-[3-(1-cyclopropyl-1H-tetrazol-5-yl)-phenyl]-4,4-dimethyl-1,2,3,4-tetrahydro-quinoline-6-carbonyl}-amide;
N-[4,4-dimethyl-2-(3-morpholin-4-yl-phenyl)-1,2,3,4-tetrahydro-quinoline-7-carbonyl]-methanesulfonamide;
N-{6-fluoro-4,4-dimethyl-2-[3-(4-o-tolyl-piperazin-1-yl)-phenyl]-1,2,3,4-tetrahydro-quinoline-8-carbonyl}-methanesulfonamide;
Cyclopropanesulfonic acid {6-fluoro-4,4-dimethyl-2-[3-(4-o-tolyl-piperazin-1-yl)-phenyl]-1,2,3,4-tetrahydro-quinoline-8-carbonyl}-amide;
N-(6-fluoro-2-{3-[4-(2-fluoro-phenyl)-piperazin-1-yl]-phenyl}-4,4-dimethyl-1,2,3,4-tetrahydro-quinoline-8-carbonyl)-methanesulfonamide;
N-[6-fluoro-4,4-dimethyl-2-(4-methyl-3-pyrrolidin-1-yl-phenyl)-1,2,3,4-tetrahydro-quinoline-8-carbonyl]-methanesulfonamide;
Cyclopropanesulfonic acid [6-fluoro-4,4-dimethyl-2-(4-methyl-3-pyrrolidin-1-yl-phenyl)-1,2,3,4-tetrahydro-quinoline-8-carbonyl]-amide;
N-{2-[5-(4-tert-butyl-phenyl)-pyridin-3-yl]-4,4-dimethyl-1,2,3,4-tetrahydro-quinoline-6-carbonyl}-methanesulfonamide;
Cyclopropanesulfonic acid {2-[5-(4-tert-butyl-phenyl)-pyridin-3-yl]-4,4-dimethyl-1,2,3,4-tetrahydro-quinoline-6-carbonyl}-amide;
Cyclopropanesulfonic acid [4,4-dimethyl-2-(3-morpholin-4-yl-phenyl)-1,2,3,4-tetrahydro-quinoline-6-carbonyl]-methyl-amide; and
Cyclopropanesulfonic acid {4,4-dimethyl-2-[3-(4-phenyl-piperazin-1-yl)-phenyl]-1,2,3,4-tetrahydro-quinoline-8-carbonyl}-amide.

The compounds of the present invention can be prepared by any conventional means. Suitable processes for synthesizing these compounds are provided in the schemes below and in the examples. In the following schemes, $R^1, R^2, R^3, R^4, R^5, R^6, R^7, R^8, R^9, R^{10}, R^{11}, R^{12}, A^1, A^2, A^3$ and $A^4$ are as defined above unless otherwise indicated.

The following abbreviations are used in the present specification.

ABBREVIATIONS d: day or days
DMSO: dimethylsulfoxide
g: gram h or hr: hour or hours
HATU: o-(7-azabenzotriazol-1-yl)-N,N,N',N'-tetramethyluronium hexafluorophosphate
HPLC: high performance liquid chromatography
Hz: hertz
mg: milligram
min: minute or minutes
mL: milliliter
mmol: millimole
mM: millimole per liter
MS (ESI): mass spectroscopy (electron spray ionization)
MW: molecular weight
r.t. or R.T.: room temperature
quant. quantitative
μg or μg: microgram
μL or μL: microliter
μM or μM: micro mole per liter aldehyde IV and methylene-alkene VI. Hydrolysis of the tetrahydroquinoline VII followed by acetylsulfonamide formation affords the resulting compound Ia.

In the method outlined in Scheme 1, the imine V can be prepared by a condensation reaction of the substituted aniline III and the substituted aldehyde IV in an organic solvent such as toluene, methanol or ethanol and a mixture thereof, at a temperature between 80 and 140° C. for 2 to 16 hours.

The compound VII can be prepared either by the Aza Diels-Alder reaction between the imine V and the methylene-alkene VI or by the three component Aza Diels-Alder reaction of the aniline III the aldehyde IV and the methylene-alkene VI. This Diels-Alder reaction can be carried out in the presence of a Lewis acid such as ytterbium(III) trifluoromethanesulfonate $(Yb(OTf)_3)$, scandium(III) trifluoromethanesulfonate $(Sc(OTf)_3)$, lanthanum(III) trifluoromethanesulfonate $(La(OTf)_3)$, indium(III) trifluo-

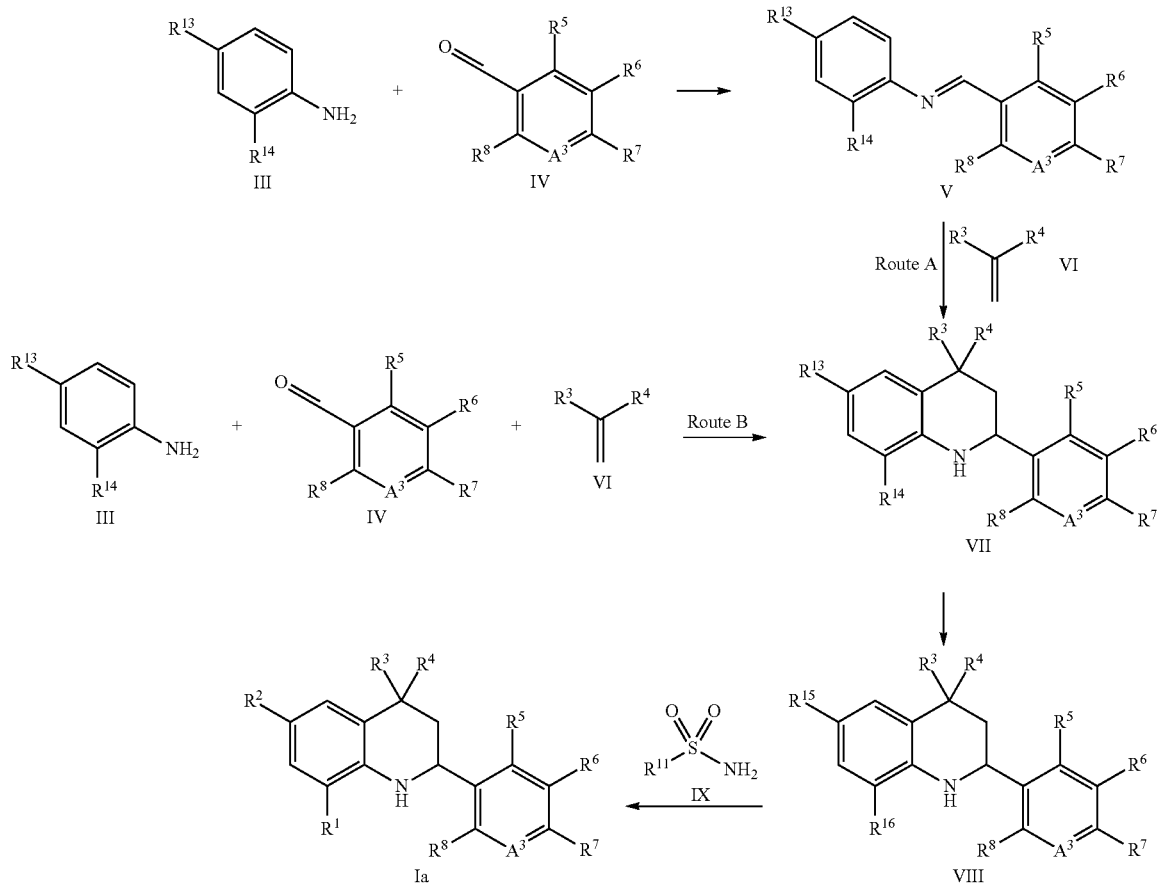

Scheme 1

$A^3$ is nitrogen or —$CR^9$—;
one of $R^1$, $R^2$ is —C(O)—NH—$SO_2$—$R^{11}$ and the other one is selected from hydrogen, alkyl and halogen;
$R^5$, $R^6$, $R^7$, $R^8$ and $R^9$ are independently selected from hydrogen, alkyl, haloalkyl, alkoxy and halogen;
$R^{11}$ is alkyl or cycloalkyl;
one of $R^{13}$, $R^{14}$ is alkyl ester and the other one is selected from hydrogen, alkyl and halogen;
one of $R^{15}$, $R^{16}$ is carboxy and the other one is selected from hydrogen, alkyl and halogen.

The compound of formula Ia can be prepared according to Scheme 1. The aniline III reacts with the aldehyde IV to generate the imine V. The imine V reacts with the methylene-alkene VI to afford the tetrahydroquinoline VII. Alternatively, the tetrahydroquinoline VII can be synthesized via the three component Aza Diels-Alder reaction of the aniline III, the romethanesulfonate $(In(OTf)_3)$, indium trichloride $(InCl_3)$, or boron trifluoride diethyl etherate $(BF_3.Et_2O)$, or a protic acid such as trifluoroacetic acid (TFA) or p-toluenesulfonic acid, in a solvent such as acetonitrile, dichloromethane, tetrahydrofuran, nitromethane, N,N-dimethylformamide, 2,2,2-trifluoroethanol or a mixture thereof, at a temperature between 25 and 100° C. for several hours (reference: Kiselyov, A. S. et al., *Tetrahedron* 54 (1998) 5089).

Hydrolysis of the methyl ester VII to the resulting product VIII can be carried out in the presence of an aqueous inorganic base such as lithium hydroxide, sodium hydroxide, or potassium hydroxide in a solvent such as methanol, 1,4-dioxane or tetrahydrofuran at room temperature or the reflux temperature for several hours.

lamino)carbodiimide hydrochloride salt (EDCI) with or without hydroxybenzotriazole (HOBt), in the presence of a base such as potassium tert-butoxide, sodium tert-butoxide, 1,8-diazabicyclo[5.4.0]undec-7-ene (DBU), triethylamine, N,N-diisopropyl ethylamine or N,N-dimethylaminopyridine (DMAP), in a suitable solvent such as dichloromethane or N,N-dimethylformamide at room temperature for several hours.

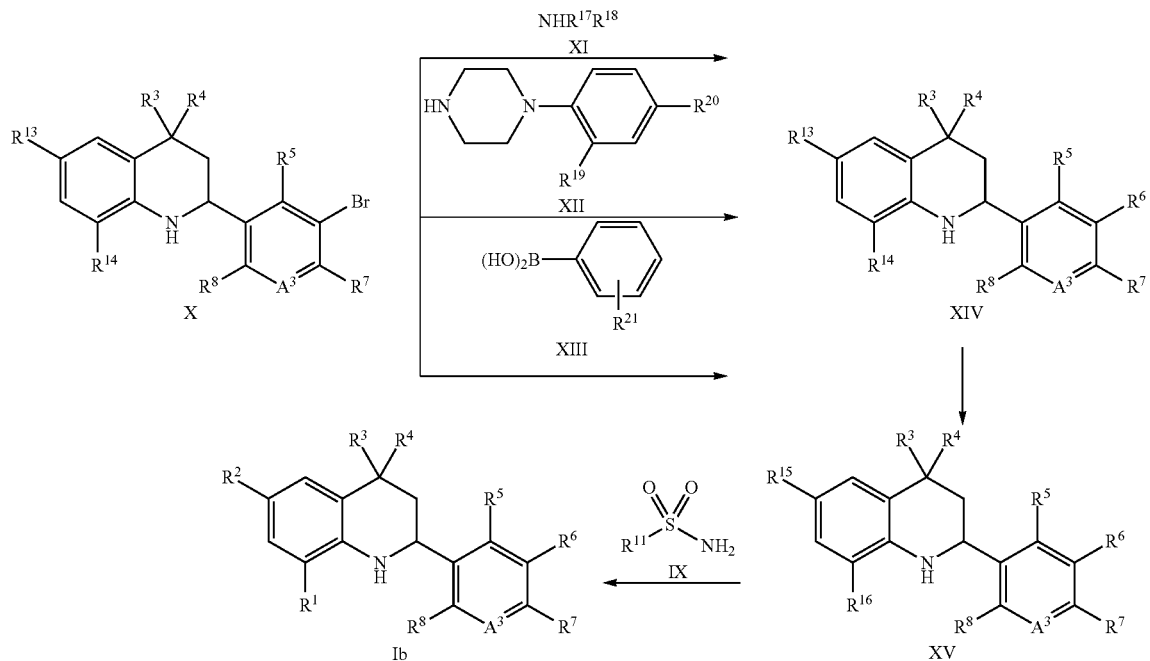

Scheme 2

$A^3$ is nitrogen or —$CR^9$—;

one of $R^1$, $R^2$ is —C(O)—NH—SO$_2$—$R^{11}$ and the other one is selected from hydrogen, alkyl and halogen;

$R^5$, $R^7$, $R^8$ and $R^9$ are independently selected from hydrogen, alkyl, haloalkyl, alkoxyl and halogen;

$R^6$ is alkylamino, dialkylamino, hydroxyphenyl, morpholinyl, piperazinyl, alkylpiperazinyl, phenylpiperazinyl, oxo-oxazolidinyl, alkylphenyl, alkoxyphenyl, alkylphenylpiperazinyl, dialkylphenylpiperazinyl, halophenylpiperazinyl or pyrrolidinyl;

$R^{11}$ is alkyl or cycloalkyl;

one of $R^{13}$, $R^{14}$ is alkyl ester and the other one is selected from hydrogen, alkyl and halogen;

one of $R^{15}$, $R^{16}$ is carboxy and the other one is selected from hydrogen, alkyl and halogen;

$R^{17}$ and $R^{18}$ are alkyl;

or $R^{17}$ and $R^{18}$ together with the nitrogen atom to which they are attached form cycloalkylamine;

$R^{19}$ and $R^{20}$ are independently selected from alkyl and halogen;

$R^{21}$ is hydroxyl, alkoxy or alkyl.

Conversion of carboxylic acid VIII to acetylsulfonamide Ia can be achieved by coupling of carboxylic acid VIII with sulfonamide IX. The reaction can be carried out by treating imidazolide generated from carboxylic acid VIII and 1,1'-carbonyldiimidazole (CDI) with sodium salt generated from sulfonamide IX and sodium hydride in N,N-dimethylformamide at room temperature for several hours. Alternatively, the reaction can be carried out in the presence of a coupling reagent such as dicyclohexyl carbodiimide (DCC), benzotriazol-1-yl-oxy-tris-pyrrolidinophosphonium hexafluorophosphate (PyBOP), o-(7-azabenzotriazol-1-yl)-N,N,N',N'-tetramethyluronium hexafluorophosphate (HATU), o-(1H-benzotriazol-1-yl)-N,N,N',N'-tetramethyluronium hexafluorophosphate (HBTU) or 1-ethyl-3-(3'-dimethy- The compound of formula Ib can be prepared according to Scheme 2. In this process, the compound of formula X can be synthesized as illustrated in Scheme 1, which is functionalized by copper-catalyzed Ullmann coupling reaction, palladium-catalyzed amine coupling or palladium-catalyzed Suzuki coupling reaction. Hydrolysis of the ester XIV followed by acetylsulfonamide formation affords the resulting compound Ib.

The Ullmann coupling reaction as outlined in the Scheme 2 can be carried out in the presence of a copper source such as copper (I) iodide (CuI) or copper (II) trifluoromethanesulfonate and a ligand such as 2,2'-bipyridine, proline, N,N'-dimethyl glycine or ethylene glycol, in the presence of a suitable base such as triethylamine, sodium carbonate, potassium carbonate, cesium carbonate, sodium methoxide, sodium tert-butoxide, and potassium tert-butoxide. The reaction can be carried out in a suitable solvent such as 1,4-dioxane, N,N-dimethylformamide, dimethyl sulfoxide or N-methylpyrrolidinone at a temperature between 100 and 180° C. for 15 to 60 minutes under microwave irradiation. Alternatively, the reactions can be carried out without the use of a microwave at a heated temperature such as 130° C. for a longer reaction time (reference: Ley, S. V. et al., *Angew. Chem. Int. Ed.* 42 (2003) 5400).

The coupling reaction between phenyl substituted piperazine XII and bromide X can be easily carried out in the presence of a palladium catalyst such as palladium acetate (Pd(OAc)$_2$), [1,1'-bis(diphenylphosphino)ferrocene]dichloropalladium(II) (PdCl$_2$(dppf)), or tetrakis(triphenylphosphine)palladium(0), a biphosphine ligand like 2-(di-t-butylphosphino)biphenyl, 2-di-t-butylphosphino-2'-(N,N-dimethylamino)biphenyl, 2-dicyclohexylphosphino-2',6'-dimethoxy-1,1'-biphenyl, 2-dicyclohexylphosphino-2',6'-di-1-propoxy-1,1'-biphenyl or 4,5-bis(diphenylphosphino)-9,9-dimethylxanthene (Xantphos) and a base such as potassium tert-butoxide, sodium carbonate, or cesium carbonate, in an inert solvent such as 1,4-dioxane, N,N-dimethylformamide or toluene, at 120° C. for several hours.

Suzuki coupling reactions can be easily done in the presence of a palladium catalyst such as [1,1'-bis(diphenylphosphino)ferrocene]dichloropalladium(II) (PdCl$_2$(dppf)), tetrakis(triphenylphosphine)palladium(0) or palladium acetate (Pd(OAc)$_2$), and a base such as potassium tert-butoxide, sodium carbonate, cesium carbonate, or sodium hydroxide, in an inert solvent such as N,N-dimethylformamide or dimethyl sulfoxide, at a temperature between 100 and 180° C. for 15 to 30 minutes under microwave irradiation (Lee S. et al., *Bioorg. Med. Chem. Lett.* 15 (2005) 2998). Alternatively, the reactions can be carried out without the use of a microwave at a heated temperature such as 130° C. for a longer reaction time.

Hydrolysis of the methyl ester XIV to the carboxylic acid XV can be carried out in the presence of an aqueous inorganic base such as lithium hydroxide, sodium hydroxide, or potassium hydroxide in a solvent such as methanol, 1,4-dioxane or tetrahydrofuran at room temperature or the reflux temperature for several hours.

Conversion of carboxylic acid XV to acetylsulfonamide Ib can be achieved by treating imidazolides generated from carboxylic acid XV and 1,1'-carbonyldiimidazole (CDI) with sodium salts generated from sulfonamide IX and sodium hydride in N,N-dimethylformamide at room temperature for several hours. Alternatively, the reaction can be carried out in the presence of a coupling reagent such as dicyclohexyl carbodiimide (DCC), benzotriazol-1-yl-oxy-tris-pyrrolidino-phosphonium hexafluorophosphate (PyBOP), o-(7-azabenzotriazol-1-yl)-N,N,N',N'-tetramethyluronium hexafluorophosphate (HATU), o-(1H-benzotriazol-1-yl)-N,N,N',N'-tetramethyluronium hexafluorophosphate (HBTU) or 1-ethyl-3-(3'-dimethylamino)carbodiimide hydrochloride salt (EDCI) with or without hydroxybenzotriazole (HOBt), in the presence of a base such as potassium tert-butoxide, sodium tert-butoxide, 1,8-diazabicyclo[5.4.0]undec-7-ene (DBU), triethylamine, N,N-diisopropyl ethylamine or N,N-dimethylaminopyridine (DMAP), in a suitable solvent such as dichloromethane or N,N-dimethylformamide at room temperature for several hours.

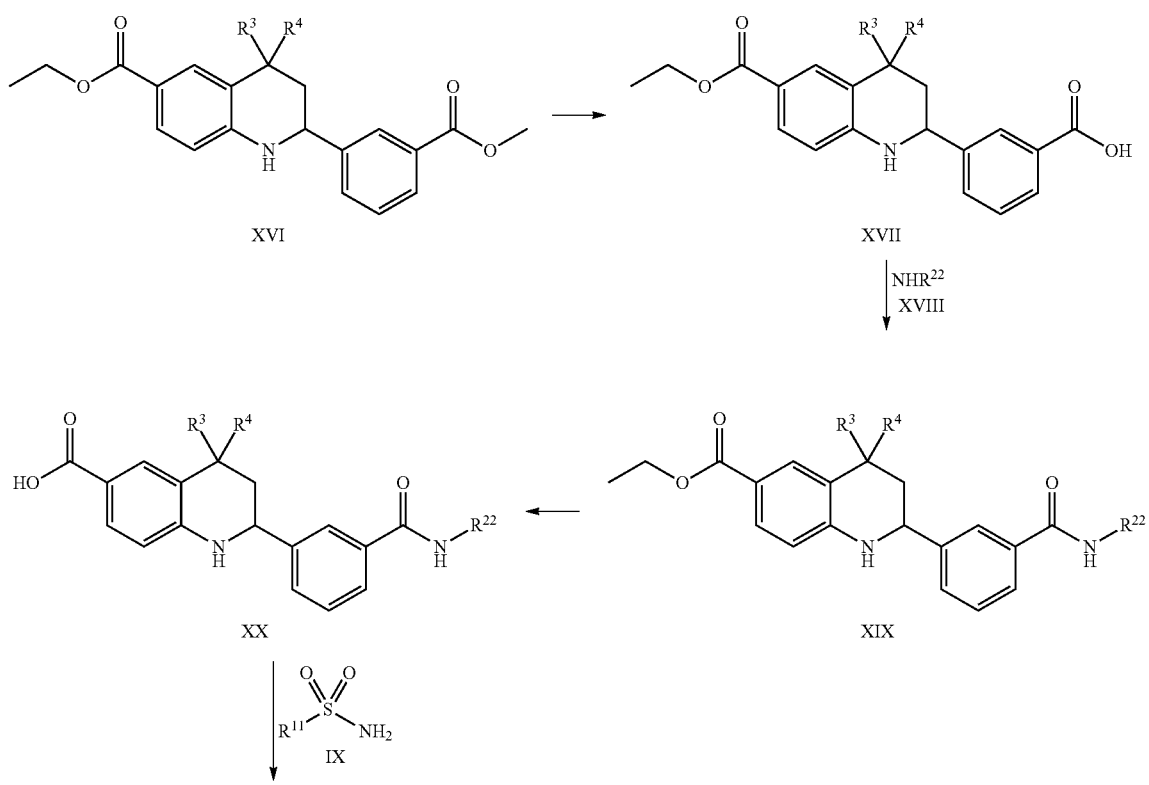

Scheme 3

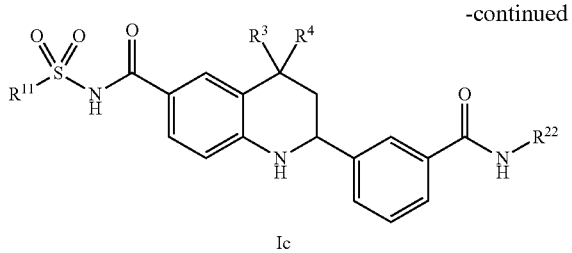

Ic

R[11] is alkyl or cycloalkyl;
R[22] is alkyl, phenyl or phenyl substituted by halogen.

The compound of formula Ic can be prepared according to Scheme 3. In this process, the compound of formula XVI can be synthesized as illustrated in Scheme 1. Selective hydrolysis of methyl ester XVI followed by coupling with amine XVIII affords amide XIX. Hydrolysis of the ethyl ester XIX followed by acetylsulfonamide formation affords the resulting compound Ic. Selective hydrolysis of the methyl ester XVI can be carried out in the presence of an aqueous inorganic base such as lithium hydroxide, sodium hydroxide, or potassium hydroxide in a solvent such as methanol, 1,4-dioxane or tetrahydrofuran at room temperature or the reflux temperature for several hours.

Conversion of the acid XVII to the corresponding amide XIX with suitable amine XVIII can be easily accomplished using methods well known to someone skilled in the art. The reaction is typically carried out in the presence of a coupling reagent such as dicyclohexyl carbodiimide (DCC), benzotriazol-1-yl-oxy-tris-pyrrolidinophosphonium hexafluorophosphate (PyBOP), o-(7-azabenzotriazol-1-yl)-N,N,N',N'-tetramethyluronium hexafluorophosphate (HATU), o-(1H-benzotriazol-1-yl)-N,N,N',N'-tetramethyluronium hexafluorophosphate (HBTU) or 1-ethyl-3-(3'-dimethylamino)carbodiimide hydrochloride salt (EDCI) with or without hydroxybenzotriazole (HOBt), in the presence of a base such as triethylamine or N,N-diisopropyl ethylamine or N,N-dimethylaminopyridine (DMAP). The reaction can be carried out in a solvent such as dichloromethane or N,N-dimethylformamide at room temperature for several hours (reference: Montalbetti, C. A. G. N. et al., *Tetrahedron* 61 (2005) 10827).

Hydrolysis of the methyl ester XIX to the carboxylic acid XX can be carried out in the presence of an aqueous inorganic base such as lithium hydroxide, sodium hydroxide, or potassium hydroxide in a solvent such as methanol, 1,4-dioxane or tetrahydrofuran at room temperature or the reflux temperature for several hours.

Conversion of carboxylic acid XX to acetylsulfonamide Ic can be achieved by coupling of carboxylic acid XX with sulfonamide IX. The reaction can be carried out by treating imidazolide generated from carboxylic acid XX and 1,1'-carbonyldiimidazole (CDI) with sodium salt generated from sulfonamide IX and sodium hydride in N,N-dimethylformamide at room temperature for several hours. Alternatively, the reaction can be carried out in the presence of a coupling reagent such as dicyclohexyl carbodiimide (DCC), benzotriazol-1-yl-oxy-tris-pyrrolidinophosphonium hexafluorophosphate (PyBOP), o-(7-azabenzotriazol-1-yl)-N,N,N',N'-tetramethyluronium hexafluorophosphate (HATU), o-(1H-benzotriazol-1-yl)-N,N,N',N'-tetramethyluronium hexafluorophosphate (HBTU) or 1-ethyl-3-(3'-dimethylamino)carbodiimide hydrochloride salt (EDCI) with or without hydroxybenzotriazole (HOBt), in the presence of a base such as potassium tert-butoxide, sodium tert-butoxide, 1,8-diazabicyclo[5.4.0]undec-7-ene (DBU), triethylamine, N,N-diisopropyl ethylamine or N,N-dimethylaminopyridine (DMAP), in a suitable solvent such as dichloromethane or N,N-dimethylformamide at room temperature for several hours.

Scheme 4

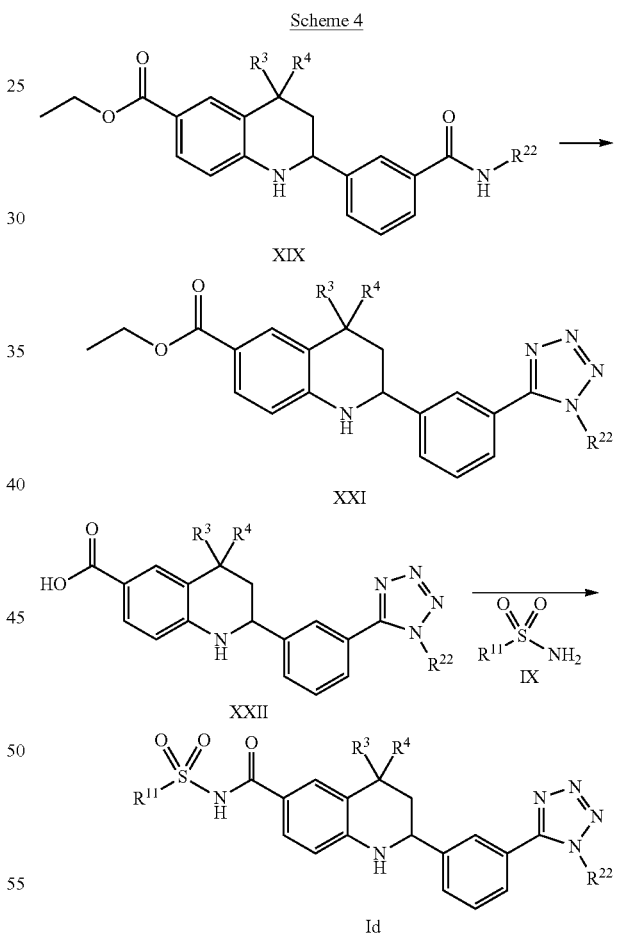

Id

R[11] is alkyl or cycloalkyl;
R[22] is alkyl, phenyl or phenyl substituted by halogen.

The compound of formula Id can be prepared according to Scheme 4. This approach is based on the transformation of the amide XIX to the tetrazole XXI in the presence of sodium azide and tetrachlorosilane. Hydrolysis of the ethyl ester XXI followed by acetylsulfonamide formation affords the resulting compound Id.

Conversion of the amide XIX to the tetrazole XXI can be achieved by treating reverse amide with sodium azide and tetrachlorosilane in acetonitrile at room temperature for several hours.

Hydrolysis of the ethyl ester XXI to the carboxylic acid XXII can be carried out in the presence of an aqueous inorganic base such as lithium hydroxide, sodium hydroxide, or potassium hydroxide in a solvent such as methanol, 1,4-dioxane, tetrahydrofuran or a mixture thereof at room temperature or the reflux temperature for several hours. Conversion of carboxylic acid XXII to acetylsulfonamide Id can be achieved by coupling of carboxylic acid XXII with sulfonamide IX. The reaction can be carried out by treating imidazolide generated from carboxylic acid XXII and 1,1'-carbonyldiimidazole (CDI) with sodium salt generated from sulfonamide IX and sodium hydride in N,N-dimethylformamide at room temperature for several hours. Alternatively, the reaction can be carried out in the presence of a coupling reagent such as dicyclohexyl carbodiimide (DCC), benzotriazol-1-yl-oxy-tris-pyrrolidinophosphonium hexafluorophosphate (PyBOP), o-(7-azabenzotriazol-1-yl)-N,N,N',N'-tetramethyluronium hexafluorophosphate (HATU), o-(1H-benzotriazol-1-yl)-N,N,N',N'-tetramethyluronium hexafluorophosphate (HBTU) or 1-ethyl-3-(3'-dimethylamino)carbodiimide hydrochloride salt (EDCI) with or without hydroxybenzotriazole (HOBt), in the presence of a base such as potassium tert-butoxide, sodium tert-butoxide, 1,8-diazabicyclo[5.4.0]undec-7-ene (DBU), triethylamine, N,N-diisopropyl ethylamine or N,N-dimethylaminopyridine (DMAP), in a suitable solvent such as dichloromethane or N,N-dimethylformamide at room temperature for several hours.

Scheme 5

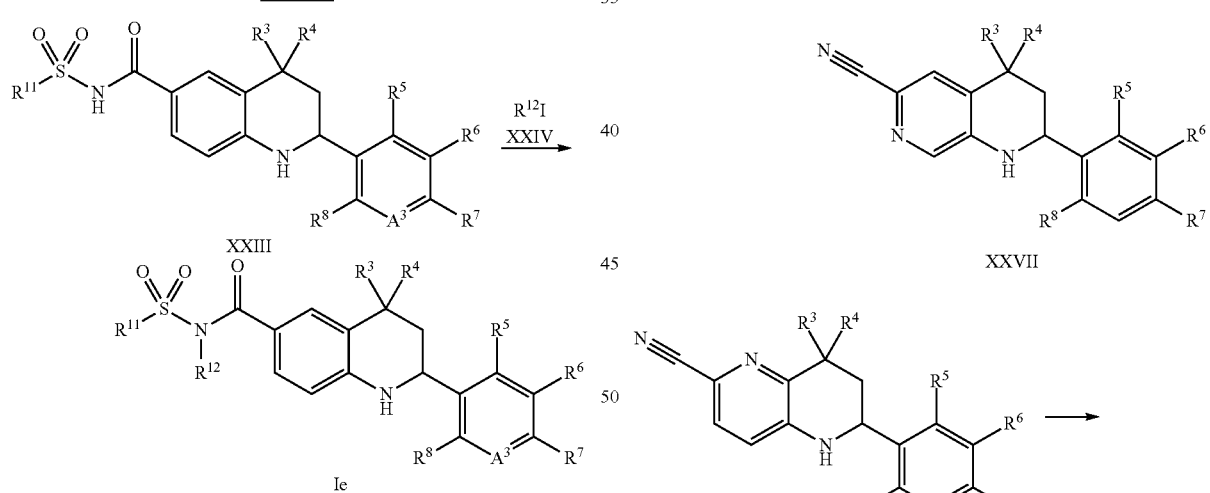

$R^5$, $R^7$, $R^8$ and $R^9$ are independently selected from hydrogen, alkyl, haloalkyl, alkoxy and halogen;
$R^6$ is alkylamino, dialkylamino, morpholinyl, alkylpiperazinyl, phenylpiperazinyl, oxo-oxazolidinyl, alkylphenyl, alkoxyphenyl, alkylphenylpiperazinyl, dialkylphenylpiperazinyl, halophenylpiperazinyl or pyrrolidinyl;
$R^{11}$ is alkyl or cycloalkyl;
$R^{12}$ is alkyl.

The compound of formula Ie can be prepared according to Scheme 5. In this process, the compound Ie can be prepared by direct alkylation of acetylsulfonamide XXIII. The acetylsulfonamide XXIII can be prepared according to Scheme 2. Alkylation of acetylsulfonamide XXIII can be easily accomplished in the presence of a base such as sodium carbonate, potassium carbonate, cesium carbonate, sodium methoxide, sodium tert-butoxide, potassium tert-butoxide or sodium hydride, in a suitable solvent such as N,N-dimethylformamide or tetrahydrofuran at room temperature for several hours.

Scheme 6

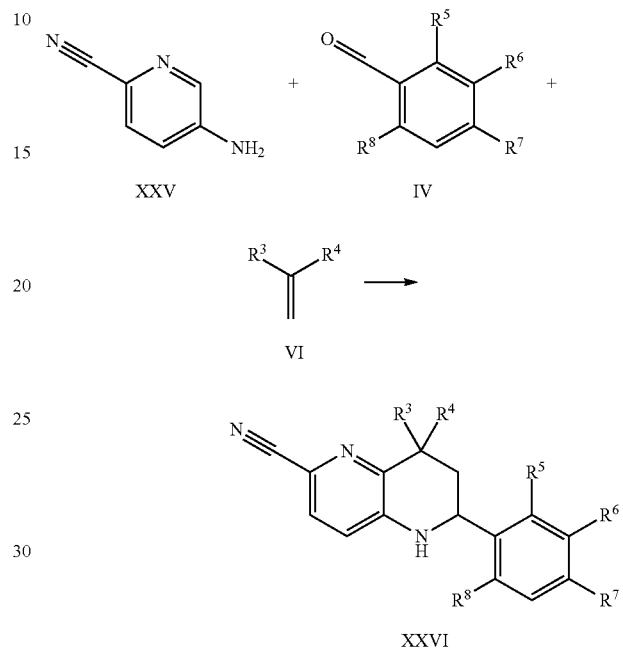

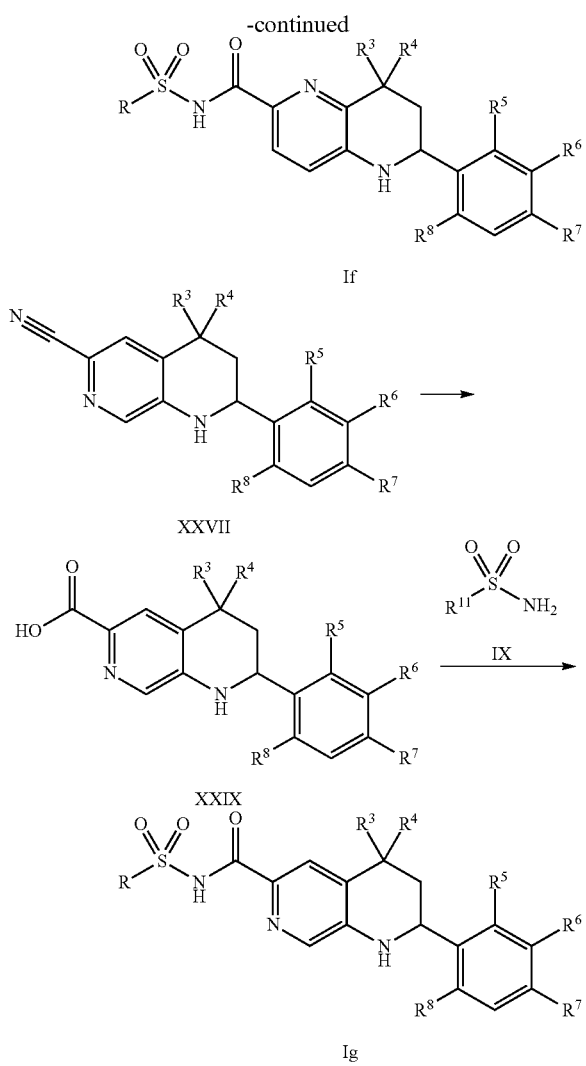

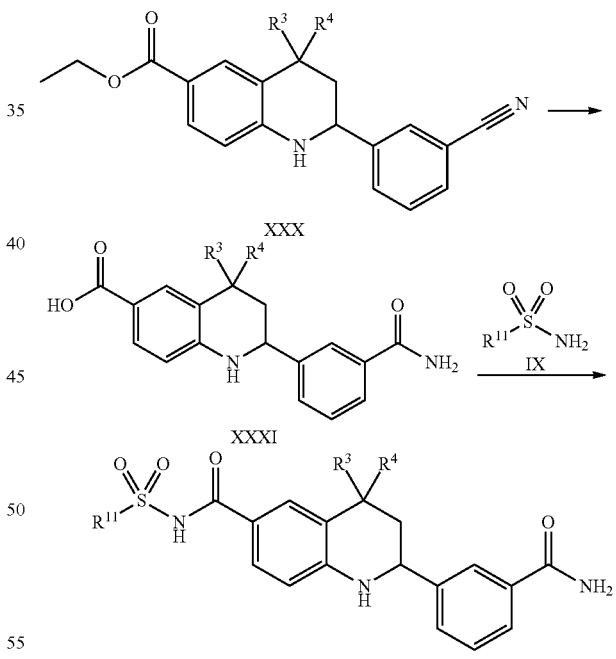

$R^5$, $R^6$, $R^7$, $R^8$ are independently selected from hydrogen, alkyl, haloalkyl, alkoxy and halogen; $R^{11}$ is alkyl or cycloalkyl.

The compound of formula If or Ig can be prepared according to Scheme 6. This approach is based on three-component Aza Diels-Alder reactions using a Lewis acid as the catalyst. Hydrolysis of nitrile XXVI and XXVII to the carboxylic acid XXVIII and XXIX followed by acetylsulfonamide formation affords the resulting compound If or Ig.

This Diels-Alder reaction can be carried out successfully in the presence of a Lewis acid such as ytterbium(III) trifluoromethanesulfonate (Yb(OTf)$_3$), scandium(III) trifluoromethanesulfonate (Sc(OTf)$_3$), lanthanum(III) trifluoromethanesulfonate (La(OTf)$_3$), indium(III) trifluoromethanesulfonate (In(OTf)$_3$), indium trichloride (InCl$_3$), or boron trifluoride diethyl etherate (BF$_3$.Et$_2$O), or a protic acid such as trifluoroacetic acid (TFA) or p-toluenesulfonic acid, in a solvent such as acetonitrile, dichloromethane, tetrahydrofuran, nitromethane, N,N-dimethylformamide, 2,2,2-trifluoroethanol, water or a mixture thereof, at a temperature between 25 and 100° C. for several hours (reference: Kiselyov, A. S. et al., Tetrahedron 54 (1998) 5089).

Hydrolysis of the nitrile XXVI and XXVII to the resulting carboxylic acid XXVIII and XXIX can be accomplished in the presence of 50% sodium hydroxide, lithium hydroxide, or potassium hydroxide in a solvent such as methanol, 1,4-dioxane, ethanol, tetrahydrofuran or a mixture thereof at room temperature or refluxed for several hours.

Conversion of carboxylic acid XXVIII and XXIX to acetylsulfonamide If or Ig can be achieved by coupling of carboxylic acid XXVIII and XXIX with sulfonamide IX separately. The reaction can be carried out by treating imidazolide generated from carboxylic acid XXVIII or XXIX and 1,1'-carbonyldiimidazole (CDI) with sodium salt generated from sulfonamide IX and sodium hydride in N,N-dimethylformamide at room temperature for several hours. Alternatively, the reaction can be carried out in the presence of a coupling reagent such as dicyclohexyl carbodiimide (DCC), benzotriazol-1-yl-oxy-tris-pyrrolidinophosphonium hexafluorophosphate (PyBOP), o-(7-azabenzotriazol-1-yl)-N,N,N',N'-tetramethyluronium hexafluorophosphate (HATU), o-(1H-benzotriazol-1-yl)-N,N,N',N'-tetramethyluronium hexafluorophosphate (HBTU) or 1-ethyl-3-(3'-dimethylamino)carbodiimide hydrochloride salt (EDCI) with or without hydroxybenzotriazole (HOBt), in the presence of a base such as potassium tert-butoxide, sodium tert-butoxide, 1,8-diazabicyclo[5.4.0]undec-7-ene (DBU), triethylamine, N,N-diisopropyl ethylamine or N,N-dimethylaminopyridine (DMAP), in a suitable solvent such as dichloromethane or N,N-dimethylformamide at room temperature for several hours.

Scheme 7

$R^{11}$ is alkyl or cycloalkyl.

The compound of formula Ih can be prepared according to Scheme 7. The starting nitrile XXX can be prepared according to Scheme 1. Hydrolysis of nitrile XXX followed by acetylsulfonamide formation affords the resulting compound Ih.

Hydrolysis of the nitrile XXX to the resulting carboxylic acid XXXI can be accomplished by mixing with 12 N aqueous solution of sodium hydroxide, lithium hydroxide or potassium hydroxide in acetonitrile, at a temperature between 60° C. and 100° C. for several hours.

Conversion of carboxylic acid XXXI to acetylsulfonamide Ih can be achieved by coupling of carboxylic acid XXXI with sulfonamide IX. The reaction can be carried out by treating imidazolide generated from carboxylic acid XXXI and 1,1'-carbonyldiimidazole (CDI) with sodium salt generated from sulfonamide IX and sodium hydride in N,N-dimethylformamide at room temperature for several hours. Alternatively, the reaction can be carried out in the presence of a coupling reagent such as dicyclohexyl carbodiimide (DCC), benzotriazol-1-yl-oxy-tris-pyrrolidinophosphonium hexafluorophosphate (PyBOP), o-(7-azabenzotriazol-1-yl)-N,N,N',N'-tetramethyluronium hexafluorophosphate (HATU), o-(1H-benzotriazol-1-yl)-N,N,N',N'-tetramethyluronium hexafluorophosphate (HBTU) or 1-ethyl-3-(3'-dimethylamino)carbodiimide hydrochloride salt (EDCI) with or without hydroxybenzotriazole (HOBt), in the presence of a base such as potassium tert-butoxide, sodium tert-butoxide, 1,8-diazabicyclo[5.4.0]undec-7-ene (DBU), triethylamine, N,N-diisopropyl ethylamine or N,N-dimethylaminopyridine (DMAP), in a suitable solvent such as dichloromethane or N,N-dimethylformamide at room temperature for several hours.

The compound of formula II can be prepared according to Scheme 8. In this process, the compound of formula XXXIV can be synthesized via the three component Aza Diels-Alder reaction. The desired Ii can be obtained by functionalization of XXXIV through copper-catalyzed Ullmann coupling reaction, palladium-catalyzed amine coupling or palladium-catalyzed Suzuki coupling reaction.

The three component Aza Diels-Alder reaction of the aniline XXXII the aldehyde XXXIII and the methylene-alkene VI can be carried out in the presence of a Lewis acid such as ytterbium(III) trifluoromethanesulfonate (Yb(OTf)$_3$), scandium(III) trifluoromethanesulfonate (Sc(OTf)$_3$), lanthanum(III) trifluoromethanesulfonate (La(OTf)$_3$), indium(III) trifluoromethanesulfonate (In(OTf)$_3$), indium trichloride (InCl$_3$), or boron trifluoride diethyl etherate (BF$_3$.Et$_2$O), or a protic acid such as trifluoroacetic acid (TFA) or p-toluenesulfonic acid, in a solvent such as acetonitrile, dichloromethane, tetrahydrofuran, nitromethane, N,N-dimethylformamide, 2,2,2-trifluoroethanol or a mixture thereof, at a temperature between 25 and 100° C. for several hours (reference: Kiselyov, A. S. et al., *Tetrahedron* 54 (1998) 5089).

The Ullmann coupling reaction as outlined in the Scheme 8 can be carried out in the presence of a copper source such as copper(I) iodide (CuI) or copper(II) trifluoromethane-

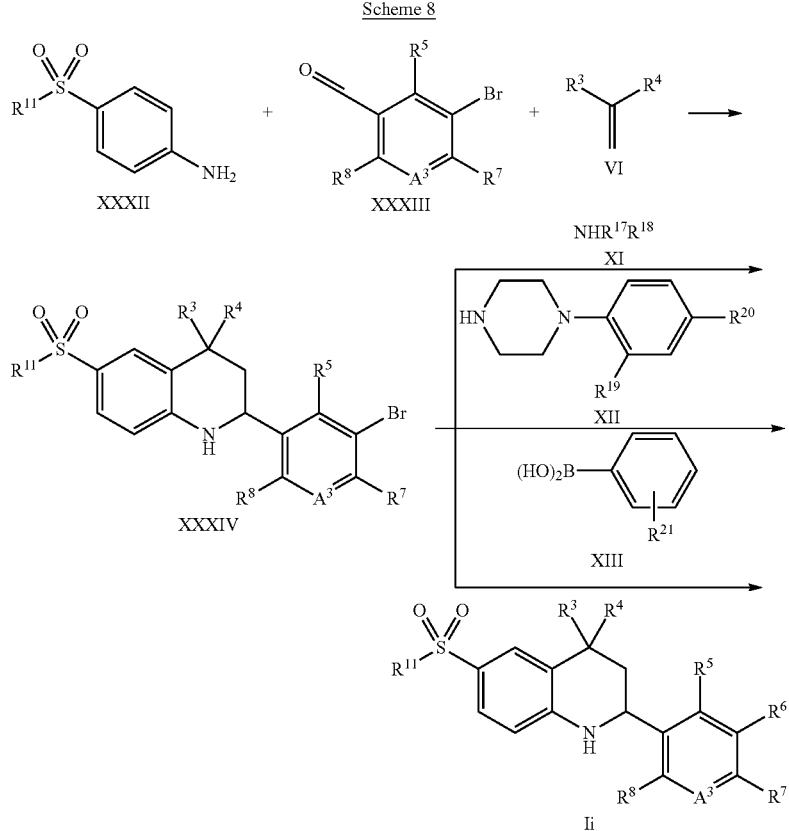

Scheme 8

$A^3$ is nitrogen or —CR$^9$—;

$R^5$, $R^7$, $R^8$ and $R^9$ are independently selected from hydrogen, alkyl, haloalkyl, alkoxyl and halogen;

$R^6$ is alkylamino, dialkylamino, hydroxyphenyl, morpholinyl, piperazinyl, alkylpiperazinyl, phenylpiperazinyl, oxo-oxazolidinyl, alkylphenyl, alkoxyphenyl, alkylphenylpiperazinyl, dialkylphenylpiperazinyl, halophenylpiperazinyl or pyrrolidinyl;

$R^{11}$ is alkylamino, cycloalkylamino or morpholinyl;

$R^{17}$ and $R^{18}$ are alkyl;

or $R^{17}$ and $R^{18}$ together with the nitrogen atom to which they are attached form cycloalkylamine;

$R^{19}$ and $R^{20}$ are independently selected from alkyl and halogen;

$R^{21}$ is hydroxy, alkoxy or alkyl.

sulfonate and a ligand such as 2,2'-bipyridine, proline, N,N'-dimethyl glycine or ethylene glycol, in the presence of a suitable base such as triethylamine, sodium carbonate, potassium carbonate, cesium carbonate, sodium methoxide, sodium tert-butoxide, potassium tert-butoxide. The reaction can be carried out in a suitable solvent such as 1,4-dioxane, N,N-dimethylformamide, dimethyl sulfoxide or N-methylpyrrolidinone at a temperature between 100 and 180° C. for 15 to 60 minutes under microwave irradiation. Alternatively, the reactions can be carried out without the use of a microwave at a heated temperature such as 130° C. for a longer reaction time (reference: Ley, S. V. et al., *Angew. Chem. Int. Ed.* 42 (2003) 5400).

The coupling reaction between phenyl substituted piperazine XII and bromide XXXIV can be easily done in the presence of a palladium catalyst such as palladium acetate $(Pd(OAc)_2)$, [1,1'-bis(diphenylphosphino)ferrocene]dichloropalladium(II) $(PdCl_2(dppf))$, or tetrakis(triphenylphosphine)palladium(0), a biphosphine ligand like 2-(di-t-butylphosphino)biphenyl, 2-di-t-butylphosphino-2'-(N,N-dimethylamino)biphenyl, 2-dicyclohexylphosphino-2',6'-dimethoxy-1,1'-biphenyl, 2-dicyclohexylphosphino-2',6'-di-i-propoxy-1,1'-biphenyl or 4,5-bis(diphenylphosphino)-9,9-dimethylxanthene (Xantphos) and a base such as potassium tert-butoxide, sodium carbonate, or cesium carbonate, in an inert solvent such as 1,4-dioxane, N,N-dimethylformamide or toluene, at 120° C. for several hours.

Suzuki coupling reaction can be easily done in the presence of a palladium catalyst such as palladium acetate $(Pd(OAc)_2)$, tetrakis(triphenylphosphine)palladium(0) or [1,1'-bis(diphenylphosphino)ferrocene]dichloropalladium(II) $(PdCl_2(dppf))$, and a base such as potassium tert-butoxide, sodium carbonate, cesium carbonate, or sodium hydroxide, in an inert solvent such as N,N-dimethylformamide or dimethyl sulfoxide, at a temperature between 100 and 180° C. for 15 to 30 minutes under microwave irradiation (Lee S. et al., *Bioorg. Med. Chem. Lett.* 15 (2005) 2998). Alternatively, the reaction can be carried out without the use of a microwave at a heated temperature such as 130° C. for a longer reaction time.

Scheme 9

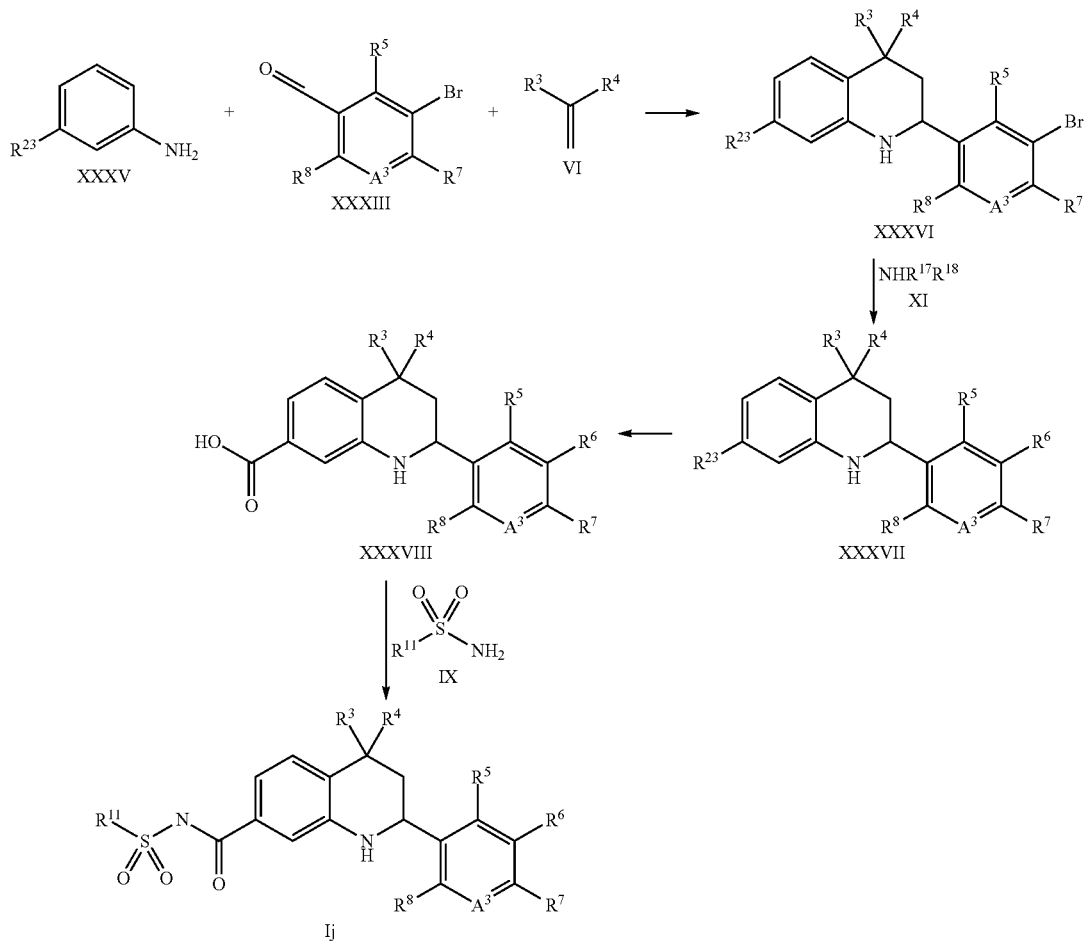

$A^3$ is nitrogen or —$CR^9$—;
$R^5$, $R^7$, $R^8$ and $R^9$ are independently selected from hydrogen, alkyl, haloalkyl, alkoxy and halogen;
$R^6$ is alkylamino, dialkylamino, morpholinyl, piperazinyl, alkylpiperazinyl, oxo-oxazolidinyl or pyrrolidinyl;
$R^{11}$ is alkyl or cycloalkyl;
$R^{17}$ and $R^{18}$ are alkyl;
or $R^{17}$ and $R^{18}$ together with the nitrogen atom to which they are attached form cycloalkylamine;
$R^{23}$ is alkyl ester.

The compound of formula Ij can be prepared according to Scheme 9. In this process, the compound of formula XXXVI can be synthesized via the three component Aza Diels-Alder reaction. The desired Ij can be obtained by functionalization on XXXVI through copper-catalyzed Ullmann coupling reaction.

The three component Aza Diels-Alder reaction of the aniline XXXV the aldehyde XXXIII and the methylene-alkene VI can be carried out in the presence of a Lewis acid such as ytterbium(III) trifluoromethanesulfonate ($Yb(OTf)_3$), scandium(III) trifluoromethanesulfonate ($Sc(OTf)_3$), lanthanum(III) trifluoromethanesulfonate ($La(OTf)_3$), indium(III) trifluoromethanesulfonate ($In(OTf)_3$), indium trichloride ($InCl_3$), or boron trifluoride diethyl etherate ($BF_3.Et_2O$), or a protic acid such as trifluoroacetic acid (TFA) or p-toluenesulfonic acid, in a solvent such as acetonitrile, dichloromethane, tetrahydrofuran, nitromethane, N,N-dimethylformamide, 2,2,2-trifluoroethanol or a mixture thereof, at a temperature between 25 and 100° C. for several hours (reference: Kiselyov, A. S. et al., *Tetrahedron* 54 (1998) 5089).

The Ullmann coupling reaction as outlined in the Scheme 9 can be carried out in the presence of a copper source such as copper(I) iodide (CuI) or copper(II) trifluoromethanesulfonate and a ligand such as 2,2'-bipyridine, proline, N,N'-dimethyl glycine or ethylene glycol, in the presence of a suitable base such as triethylamine, sodium carbonate, potassium carbonate, cesium carbonate, sodium methoxide, sodium tert-butoxide, potassium tert-butoxide. The reaction can be carried out in a suitable solvent such as 1,4-dioxane, N,N-dimethylformamide, dimethyl sulfoxide or N-methylpyrrolidinone at a temperature between 100 and 180° C. for 15 to 60 minutes under microwave irradiation. Alternatively, the reactions can be carried out without the use of a microwave at a heated temperature such as 130° C. for a longer reaction time (reference: Ley, S. V. et al., *Angew. Chem. Int. Ed.* 42 (2003) 5400).

Hydrolysis of the methyl ester XXXVII to the carboxylic acid XXXVIII can be carried out in the presence of an aqueous inorganic base such as lithium hydroxide, sodium hydroxide, or potassium hydroxide in a solvent such as methanol, 1,4-dioxane or tetrahydrofuran at room temperature or refluxed for several hours.

Conversion of carboxylic acid XXXVIII to acetylsulfonamide Ij can be achieved by coupling of carboxylic acid XXXVIII with sulfonamide IX. The reaction can be carried out by treating imidazolide generated from carboxylic acid XXXVIII and 1,1'-carbonyldiimidazole (CDI) with sodium salt generated from sulfonamide IX and sodium hydride in N,N-dimethylformamide at room temperature for several hours. Alternatively, the reaction can be carried out in the presence of a coupling reagent such as dicyclohexyl carbodiimide (DCC), benzotriazol-1-yl-oxy-tris-pyrrolidinophosphonium hexafluorophosphate (PyBOP), o-(7-azabenzotriazol-1-yl)-N,N,N',N'-tetramethyluronium hexafluorophosphate (HATU), o-(1H-benzotriazol-1-yl)-N,N,N',N'-tetramethyluronium hexafluorophosphate (HBTU) or 1-ethyl-3-(3'-dimethylamino)carbodiimide hydrochloride salt (EDCI) with or without hydroxybenzotriazole (HOBt), in the presence of a base such as potassium tert-butoxide, sodium tert-butoxide, 1,8-diazabicyclo[5.4.0]undec-7-ene (DBU), triethylamine, N,N-diisopropyl ethylamine or N,N-dimethylaminopyridine (DMAP), in a suitable solvent such as dichloromethane or N,N-dimethylformamide at room temperature for several hours.

The invention also relates to a process for the preparation of a compound of formula (I) comprising one of the following steps:

(a) the reaction of a compound of formula (A)

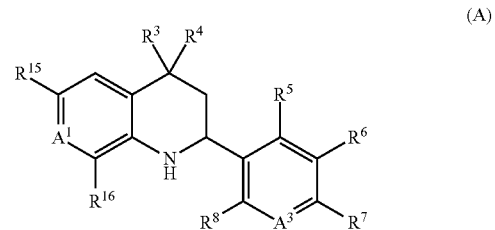

(A)

in the presence of $R^{11}$—$SO_2$—$NH_2$, a coupling reagent and a base;

(b) the reaction of a compound of formula (B)

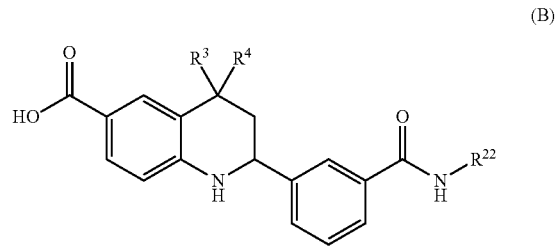

(B)

in the presence of $R^{11}SO_2$—$NH_2$, a coupling reagent and a base;

(c) the reaction of a compound of formula (C)

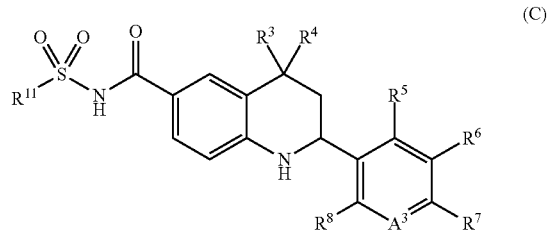

(C)

in the presence of $R^{12}$—I and a base;

(d) the reaction of a compound of formula (D)

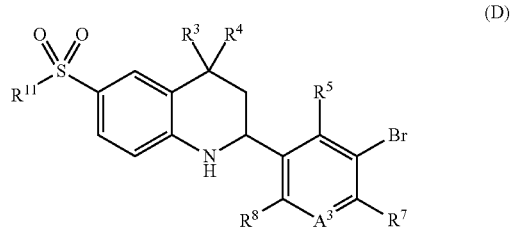

(D)

in the presence of $NHR^{17}R^{18}$, a copper source, a ligand and a base;

(e) the reaction of a compound of formula (E)

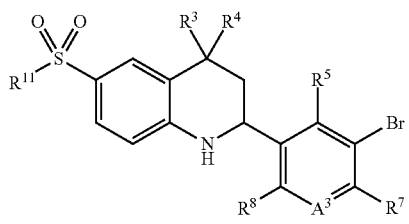

(E)

in the presence of a compound of formula (E-1)

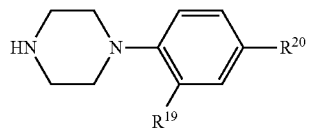

(E-1)

and a palladium catalyst and a base;
(f) the reaction of a compound of formula (F)

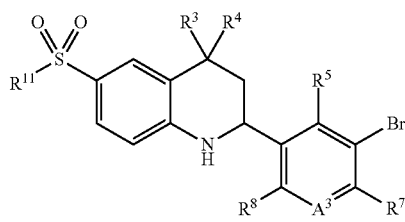

(F)

in the presence of a compound of formula (F-1)

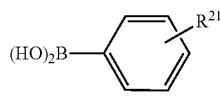

(F-1)

and a palladium catalyst and a base;
(g) the reaction of a compound of formula (G)

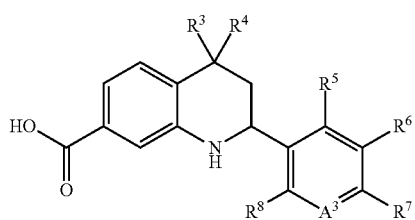

(G)

in the presence of a coupling reagent and a base.
wherein $A^1$, $A^3$, $R^3$, $R^4$, $R^6$ are as defined above; $R^5$, $R^7$, $R^8$ are independently selected from hydrogen, alkyl, haloalkyl, alkoxy and halogen; $R^{11}$ is alkyl or cycloalkyl; $R^{12}$ is alkyl; one of $R^{15}$ and $R^{16}$ is carboxy and the other one is independently selected from hydrogen, alkyl and halogen; $R^{17}$ and $R^{18}$ are alkyl, or $R^{17}$ and $R^{18}$ together with the nitrogen to which they are attached form heterocyclic amine; $R^{19}$ and $R^{20}$ are independently selected from alkyl and halogen; $R^{21}$ is hydroxy, alkoxy or alkyl; and $R^{22}$ is alkyl, phenyl or halophenyl.

In step (a), (b) and (g), the coupling reagent can be for example 1,1'-carbonyldiimidazole (CDI), 1-(3-dimethylaminopropyl)-3-ethylcarbodiimide hydrochloride (EDCI) or o-(7-azabenzotriazol-1-yl)-N,N,N',N'-te-tramethyluronium hexafluorophosphate (HATU). The base can be for example sodium hydride, potassium tert-butoxide, sodium tert-butoxide, 1,8-diazabicyclo[5.4.0]undec-7-ene (DBU), ethyl-diisopropyl-amine or 4-dimethylaminopyridine (DMAP).

In step (c), the base can be for example sodium hydride, sodium tert-butoxide, potassium tert-butoxide, sodium carbonate, potassium carbonate or cesium carbonate.

In step (d)-(f), the base can be for example sodium carbonate, potassium carbonate, cesium carbonate, sodium tert-butoxide, potassium tert-butoxide.

In step (d), the copper source can for example be copper(I) iodide (CuI) or copper(II) trifluoromethanesulfonate. The ligand can be for example 2, 2'-bipyridine, proline, N,N'-dimethyl glycine or ethylene glycol. The reaction can be carried out in a suitable solvent such as 1,4-dioxane, N,N-dimethylformamide, dimethyl sulfoxide or N-methylpyrrolidinone at a temperature between 100 and 180° C. for 15 to 60 minutes under microwave irradiation. Alternatively, the reactions can be carried out without the use of a microwave at a heated temperature such as 130° C. for a longer reaction time.

In step (e), the palladium catalyst can be for example palladium acetate (Pd(OAc)$_2$). The ligand can be for example a biphosphine ligand like 4,5-bis(diphenylphosphino)-9,9-dimethylxanthene (Xantphos). The base can be for example potassium tert-butoxide, sodium carbonate, or cesium carbonate. The reaction can be carried out in an inert solvent such as toluene, at 120° C. for several hours.

In step (f), the palladium catalyst can be for example [1,1'-bis(diphenylphosphino)ferrocene]dichloropalladium(II) (PdCl$_2$(dppf)), or tetrakis(triphenylphosphine)palladium(0). The reaction can be carried out in an inert solvent such as N,N-dimethylformamide or dimethyl sulfoxide, at a temperature between 100 and 180° C. for 15 to 30 minutes under microwave irradiation. Alternatively, the reactions can be carried out without the use of a microwave at a heated temperature such as 130° C. for a longer reaction time.

The invention also relates to a compound of formula (I) for use as therapeutically active substance.

The invention relates in particular to a compound of formula (I) for use as a therapeutically active substance in the treatment or prophylaxis of obesity, dyslipidemia, hyperglycemia, type 1 or type 2 diabetes, in particular type 2 diabetes, or cancer.

The invention also relates to a pharmaceutical composition comprising a compound of formula (I) and a therapeutically inert carrier.

The use of a compound of formula (I) for the preparation of medicaments useful in the treatment or prophylaxis diseases that are related to AMPK regulation is an object of the invention.

The invention relates to the use of a compound of formula (I) for the treatment or prophylaxis of obesity, dyslipidemia, hyperglycemia, type 1 or type 2 diabetes, in particular type 2 diabetes.

The invention relates in particular to the use of a compound of formula (I) for the preparation of a medicament for the treatment or prophylaxis of obesity, dyslipidemia, hyperglycemia, type 1 or type 2 diabetes, in particular type 2 diabetes.

Said medicaments, e.g. in the form of pharmaceutical preparations, can be administered orally, e.g. in the form of tablets, coated tablets, dragées, hard and soft gelatine capsules, solutions, emulsions or suspensions. The administration can, however, also be effected rectally, e.g. in the form of suppositories, or parenterally, e.g. in the form of injection solutions with an effective amount of a compound as defined above.

The above-mentioned pharmaceutical composition can be obtained by processing the compounds according to this invention with pharmaceutically inert inorganic or organic carriers. Lactose, corn starch or derivatives thereof, talc, stearic acids or its salts and the like can be used, for example, as such carriers (or excipients) for tablets, coated tablets, dragées and hard gelatine capsules. Suitable carriers for soft gelatine capsules are, for example, vegetable oils, waxes, fats, semi-solid and liquid polyols and the like. Depending on the nature of the active substance no carriers are, however, usually required in the case of soft gelatine capsules. Suitable carriers for the production of solutions and syrups are, for example, water, polyols, glycerol, vegetable oil and the like. Suitable carriers for suppositories are, for example, natural or hardened oils, waxes, fats, semi-liquid or liquid polyols and the like.

The pharmaceutical composition can, moreover, contain preservatives, solubilizers, stabilizers, wetting agents, emulsifiers, sweeteners, colorants, flavorants, salts for varying the osmotic pressure, buffers, masking agents or antioxidants. They can also contain still other therapeutically active substances.

The dosage depends on various factors such as manner of administration, species, age and/or individual state of health. The doses to be administered daily are about 5-400 mg/kg, preferably about 10-100 mg/kg, and can be taken singly or distributed over several administrations.

A compound of formula (I) when manufactured according to the above process is also an object of the invention.

Furthermore, the invention also relates to a method for the treatment or prophylaxis of diseases that are related to AMPK regulation, which method comprises administering an effective amount of a compound of formula (I).

The invention further relates to a method for the treatment or prophylaxis of obesity, dyslipidemia, hyperglycemia, type 1 or type 2 diabetes, in particular type 2 diabetes, which method comprises administering an effective amount of a compound of formula (I).

Furthermore, the invention also relates to a compound of formula (I) for the preparation of medicaments useful in the treatment of cancers that are related to AMPK regulation. The invention provides a method for the treatment of cancers that are related to AMPK regulation, which method comprises administering an effective amount of a compound of formula (I).

The invention will be illustrated by the following examples which have no limiting character. Unless explicitly otherwise stated, all reactions, reaction conditions, abbreviations and symbols have the meanings well known to a person of ordinary skill in organic chemistry.

EXAMPLES

Materials and Instrumentation

Intermediates and final compounds were purified by flash chromatography using one of the following instruments: i) Biotage SP1 system and the Quad 12/25 Cartridge module. ii) ISCO combi-flash chromatography instrument. Silica gel Brand and pore size: i) KP-SIL 60 Å, particle size: 40-60 μM; ii) CAS registry NO: Silica Gel: 63231-67-4, particle size: 47-60 micron silica gel; iii) ZCX from Qingdao Haiyang Chemical Co., Ltd, pore: 200-300 or 300-400.

Intermediates and final compounds were purified by preparative HPLC on reversed phase column using X Bridge™ Perp C18 (5 μm, OBDTM 30×100 mm) column or SunFire™ Perp C18 (5 μm, OBDTM 30×100 mm) column.

LC/MS spectra were obtained using a MicroMass Plateform LC (Waters™ alliance 2795-ZQ2000). Standard LC/MS conditions were as follows (running time 6 min):
Acidic condition: A: 0.1% formic acid in $H_2O$; B: 0.1% formic acid in acetonitrile;
Basic condition: A: 0.01% $NH_3.H_2O$ in $H_2O$; B: acetonitrile;
Neutral condition: A: $H_2O$; B: acetonitrile.

Mass spectra (MS): generally only ions which indicate the parent mass are reported, and unless otherwise stated the mass ion quoted is the positive mass ion $(M+H)^+$.

The microwave assisted reactions were carried out in a Biotage Initiator Sixty.

NMR Spectra were obtained using Bruke Avance 400 MHz.

All reactions involving air-sensitive reagents were performed under an argon atmosphere. Reagents were used as received from commercial suppliers without further purification unless otherwise noted.

Percentages are intended as mass percentages unless otherwise specified, according to the usual convention.

Example 1

Cyclopropanesulfonic acid [4,4-dimethyl-2-(3-morpholin-4-yl-phenyl)-1,2,3,4-tetrahydro-quinoline-6-carbonyl]-amide

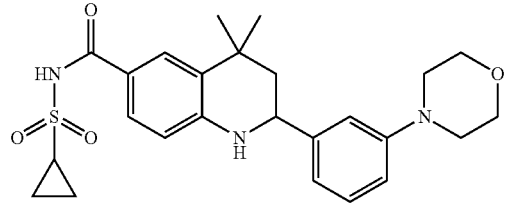 [SMILES: CC1(C)CC(c2cccc(N3CCOCC3)c2)Nc2ccc(C(=O)NS(=O)(=O)C3CC3)cc21]

To a stirred solution of 4-amino-benzoic acid methyl ester (11.3 g, 78.4 mmol) and 3-bromobenzaldehyde (9.2 mL, 78.4 mmol) in acetonitrile (150 mL) were added isobutene (21.0 mL, 313.5 mmol) and ytterbium(III) trifluoromethanesulfonate $(Yb(OTf)_3)$ (5.8 g, 9.5 mmol). The resulting mixture was stirred at 85° C. for 18 h in sealed tube. The mixture was diluted with ethyl acetate (300 mL) and washed with water (100 mL×2) and brine (100 mL×2) and then dried over anhydrous sodium sulfate. The solvent was removed in vacuo and the residue was purified by ISCO combi-flash chromatography (gradient elution, 10-50% ethyl acetate in petroleum ether) to afford 2-(3-bromo-phenyl)-4,4-dimethyl-1,2,3,4-tetrahydro-quinoline-6-carboxylic acid methyl ester (11.7 g, 40.0%) as a light yellow solid: MS (ESI) M+1=374.0.

A mixture solution of 2-(3-bromo-phenyl)-4,4-dimethyl-1,2,3,4-tetrahydro-quinoline-6-carboxylic acid methyl ester (11.2 g, 30.0 mmol), morpholine (26.0 mL, 294.0 mmol), copper(I) iodide (3.4 g, 18.0 mmol), N,N-dimethylglycine hydrochloride (3.4 g, 24.0 mmol), and potassium carbonate (12.4 g, 90.0 mmol) in dimethyl sulfoxide (65 mL) was stirred at 120° C. for 16 h. Then the reaction mixture was cooled to room temperature. The reaction mixture was extracted with ethyl acetate (200 mL×2), washed with saturated aqueous ammonium chloride solution (50 mL×3) and brine (50 mL×2), dried over anhydrous sodium sulfate and then concentrated in vacuo and the residue was purified by ISCO combi-flash chromatography (gradient elution, 30-50% ethyl acetate in petroleum ether) to afford 4,4-dimethyl-2-(3-morpholin-4-yl-phenyl)-1,2,3,4-tetrahydro-quinoline-6-carboxylic acid methyl ester (9.1 g, 80%) as a white solid: MS (ESI) M+1=381.0.

To a stirred mixture solution of 4,4-dimethyl-2-(3-morpholin-4-yl-phenyl)-1,2,3,4-tetrahydro-quinoline-6-carboxylic acid methyl ester (380.0 mg, 1.0 mmol) in methanol (10.0 mL) and tetrahydrofuran (10.0 mL) was added 50% sodium hydroxide in water (1.5 mL). The reaction mixture was stirred at 70° C. for 6 h. The mixture was neutralized with a 3 N aqueous hydrochloric acid solution and extracted with ethyl acetate (2×100 mL), washed with water, dried over anhydrous sodium sulfate and then concentrated in vacuo to afford 4,4-dimethyl-2-(3-morpholin-4-yl-phenyl)-1,2,3,4-tetrahydro-quinoline-6-carboxylic acid (330.0 mg, 90%) as a light white solid which was used for next step without further purification: MS (ESI) M+1=367.1.

To a suspension of 60% sodium hydride (535 mg, 13.7 mmol) in N,N-dimethylformamide (2.5 mL) was added cyclopropanesulfonamide (1.65 g, 13.8 mmol) at room temperature. The resulting mixture was stirred at 25° C. for 1 h to afford Solution A1. A solution of 4,4-dimethyl-2-(3-morpholin-4-yl-phenyl)-1,2,3,4-tetrahydro-quinoline-6-carboxylic acid (300 mg, 0.82 mmol) and 1,1'-carbonyldiimidazole (442 mg, 2.76 mmol) in IV, N-dimethylformamide (2.0 mL) was stirred at 70° C. for 1 h and cooled to room temperature to afford Solution B1. Solution B1 was added to Solution A1 and the resulting mixture was stirred at 25° C. for 1 h. To the reaction mixture was added water (0.5 mL). The mixture was filtered to remove the insoluble solid, and the filtrate was purified by Waters automated flash system (column: Xterra 30 mm×100 mm, sample manager 2767, pump 2525, detector: ZQ mass and UV 2487, solvent system: acetonitrile and 0.1% ammonium hydroxide in water) afforded cyclopropanesulfonic acid [4,4-dimethyl-2-(3-morpholin-4-yl-phenyl)-1,2,3,4-tetrahydro-quinoline-6-carbonyl]-amide (115.4 mg, 30%) as a white solid: MS (ESI) M+1=470.1.

Example 2

2'-(5-Fluoro-2-methylphenyl)-N-(methylsulfonyl)-2',3'-dihydro-1'H-spiro [cyclopropane-1,4'-quinoline]-6'-carboxamide

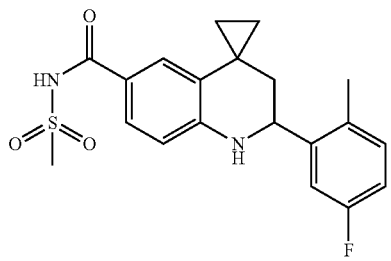 [SMILES: Cc1ccc(F)cc1C1CC2(CC2)c2cc(C(=O)NS(C)(=O)=O)ccc2N1]

The mixture solution of 4-aminobenzoic acid methyl ester (10.8 g, 71.4 mmol), 5-fluoro-2-methylbenzaldehyde (10.0 g, 72.4 mmol) and p-toluenesulfonic acid (271.8 mg, 1.4 mmol) in toluene (150 mL) was heated to reflux for 12 h. Then the reaction mixture was cooled to room temperature. The solvent was removed in vacuo and the residue was washed with ether to afford 4-[(5-fluoro-2-methyl-benzylidene)-amino]-benzoic acid methyl (16.0 g, 82.6%) as a light yellow solid: MS (ESI) M+1=272.0.

To a stirred solution 4-[(5-fluoro-2-methyl-benzylidene)-amino]-benzoic acid methyl (2.7 g, 10.0 mmol) in acetonitrile (16.0 mL) were added methylene-cyclopropane (2.8 mL, 40.0 mol) and scandium(III) trifluoromethanesulfonate (Sc(OTf)$_3$) (980.0 mg, 2.0 mmol). The resulting mixture solution was stirred at 80° C. for 16 h in sealed tube. The mixture solution was diluted with ethyl acetate (300 mL) and washed with water (100 mL×2) and brine (100 mL×2) and then dried over anhydrous sodium sulfate. The solvent was removed in vacuo and the residue was purified by ISCO combi-flash chromatography (gradient elution, 10-50% ethyl acetate in petroleum ether) to afford 2-(5-fluoro-2-methyl-phenyl)-spiro(cyclopropane-1,4'-1',2',3',4'-tetrahydroquinoline)-6-carboxylic acid methyl ester (1.2 g, 37%) as a light yellow solid: MS (ESI) M+1=326.2.

To a stirred solution of 2-(5-fluoro-2-methyl-phenyl)-spiro(cyclopropane-1,4'-1',2',3',4'-tetrahydroquinoline)-6-carboxylic acid methyl ester (800.0 mg, 2.5 mmol) in tetrahydrofuran (10.0 mL) and methanol (10.0 mL) was added 3 N sodium hydroxide (2.0 mL). The reaction mixture was stirred at 80° C. for 6 h, and then diluted with water (10.0 mL), extracted with diethyl ether (20.0 mL). The organic layer was discarded. The aqueous layer was acidified with concentrated hydrochloric acid to pH 4 and extracted with ethyl acetate (40 mL×3). The combined organic layers were dried over anhydrous sodium sulfate. The solvent was removed in vacuo and afforded 2-(5-fluoro-2-methyl-phenyl)-spiro(cyclopropane-1,4'-1',2',3',4'-tetrahydroquinoline)-6-carboxylic acid (650 mg, 85%) as a light yellow powder: MS (ESI) M+1=312.3.

To a suspension of 60% sodium hydride (128 mg, 3.2 mmol) in N,N-dimethylformamide (1.5 mL) was added methanesulfonamide (314 mg, 3.3 mmol) at room temperature. The resulting mixture was stirred at 25° C. for 1 h to afford Solution A2. A solution of 2-(5-fluoro-2-methyl-phenyl)-spiro(cyclopropane-1,4'-1',2',3',4'-tetrahydroquinoline)-6-carboxylic acid (102.0 mg, 0.33 mmol) and 1,1'-carbonyldiimidazole (136 mg, 0.84 mmol) in IV, N-dimethylformamide (2.0 mL) was stirred at 70° C. for 1 h and cooled to room temperature to afford Solution B2. Solution B2 was added to Solution A2 and the resulting mixture was stirred at 25° C. for 1 h. To the reaction mixture was added water (0.5 mL). The mixture was filtered to remove the insoluble solid, and the filtrate was purified by Waters automated flash system (column: Xterra 30 mm×100 mm, sample manager 2767, pump 2525, detector: ZQ mass and UV 2487, solvent system: acetonitrile and 0.1% ammonium hydroxide in water) afforded 2'45-fluoro-2-methylphenyl)-N-(methylsulfonyl)-2',3'-dihydro-1'H-spiro[cyclopropane-1,4'-quinoline]-6'-carboxamide (38.4 mg, 30%) as a white solid: MS (ESI) M+1=389.2.

Example 3

2'-(2,4-Difluorophenyl)-N-(methylsulfonyl)-2',3'-dihydro-1'H-spiro[cyclopropane-1,4'-quinoline]-6'-carboxamide

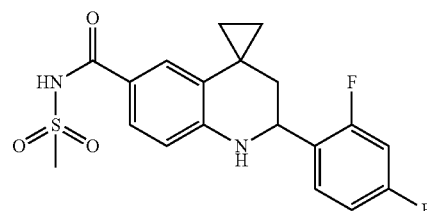

The mixture solution of 4-aminobenzoic acid methyl ester (10.8 g, 71.4 mmol), 2,4-difluoro-benzaldehyde (10.3 g, 72.4 mmol) and p-toluenesulfonic acid (271.8 mg, 1.4 mmol) in toluene (150 mL) was heated to reflux for 12 h. Then the reaction mixture was cooled to room temperature. The solvent was removed in vacuo and the residue was washed with ether to afford 4-{[1-(2,4-difluoro-phenyl)-meth-(E)-ylidene]amino}-benzoic acid methyl ester (19.64 g, quant.) as a light yellow solid: MS (ESI) M+1=276.1.

To a stirred solution 4-{[1-(2,4-difluoro-phenyl)-meth-(E)-ylidene]amino}-benzoic acid methyl ester (2.7 g, 10.0 mmol) in acetonitrile (16.0 mL) were added methylene-cyclopropane (2.8 mL, 40.0 mol) and scandium(III) trifluoromethanesulfonate (Sc(OTf)₃) (980.0 mg, 2.0 mmol). The resulting mixture solution was stirred at 80° C. for 16 h in sealed tube. The mixture solution was diluted with ethyl acetate (300 mL) and washed with water (100 mL×2) and brine (100 mL×2) and then dried over anhydrous sodium sulfate. The solvent was removed in vacuo and the residue was purified by ISCO combi-flash chromatography (gradient elution, 10-50% ethyl acetate in petroleum ether) to afford 2-(2,4-difluoro-phenyl)-spiro(cyclopropane-1,4'-1',2',3',4'-tetrahydroquinoline)-6-carboxylic acid methyl ester (1.3 g, 40%) as a light yellow solid: MS (ESI) M+1=330.2.

To a stirred solution of 2-(2,4-difluoro-phenyl)-spiro(cyclopropane-1,4'-1',2',3',4'-tetrahydroquinoline)-6-carboxylic acid methyl ester (900.0 mg, 2.7 mmol) in tetrahydrofuran (10.0 mL) and methanol (10.0 mL) was added 3 N sodium hydroxide (2.0 mL). The reaction mixture was stirred at 80° C. for 6 h, and then diluted with water (10.0 mL), extracted with diethyl ether (20.0 mL). The organic layer was discarded. The aqueous layer was acidified with concentrated hydrochloric acid to pH 4 and extracted with ethyl acetate (40 mL×3). The combined organic layers were dried over anhydrous sodium sulfate. The solvent was removed in vacuo and afforded 2-(2,4-difluoro-phenyl)-spiro(cyclopropane-1,4'-1',2',3',4'-tetrahydroquinoline)-6-carboxylic acid (765.5 mg, 90%) as a light yellow powder: MS (ESI) M+1=316.1.

To a suspension of 60% sodium hydride (128 mg, 3.2 mmol) in N,N-dimethylformamide (1.5 mL) was added methanesulfonamide (314 mg, 3.3 mmol) at room temperature. The resulting mixture was stirred at 25° C. for 1 h to afford Solution A3. A solution of 2-(2,4-difluoro-phenyl)-spiro(cyclopropane-1,4'-1',2',3',4'-tetrahydroquinoline)-6-carboxylic acid (104.0 mg, 0.33 mmol) and 1,1'-carbonyldiimidazole (136 mg, 0.84 mmol) in N,N-dimethylformamide (2.0 mL) was stirred at 70° C. for 1 h and cooled to room temperature to afford Solution B3. Solution B3 was added to Solution A3 and the resulting mixture was stirred at 25° C. for 1 h. To the reaction mixture was added water (0.5 mL). The mixture was filtered to remove the insoluble solid, and the filtrate was purified by Waters automated flash system (column: Xterra 30 mm×100 mm, sample manager 2767, pump 2525, detector: ZQ mass and UV 2487, solvent system: acetonitrile and 0.1% ammonium hydroxide in water) afforded 2'-(2,4-difluorophenyl)-N-(methylsulfonyl)-2',3'-dihydro-1'H-spiro[cyclopropane-1,4'-quinoline]-6'-carboxamide (39.4 mg, 30%) as a white solid: MS (ESI) M+1=393.0.

Example 4

N-[2-(3-fluoro-5-morpholin-4-yl-phenyl)-4,4-dimethyl-1,2,3,4-tetrahydro-quinoline-6-carbonyl]-methanesulfonamide

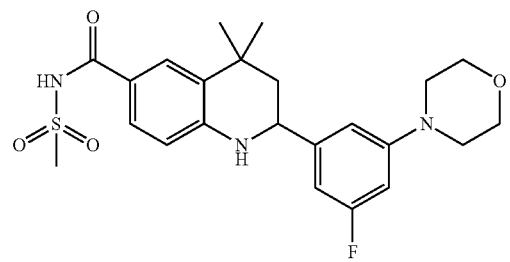 [SMILES: CC1(C)CC(c2cc(F)cc(N3CCOCC3)c2)Nc2ccc(C(=O)NS(C)(=O)=O)cc21]

To a stirred solution of 4-amino-benzoic acid methyl ester (11.3 g, 78.4 mmol) and 3-bromo-5-fluoro-benzaldehyde (15.9 g, 78.4 mmol) in acetonitrile (150 mL) were added isobutene (21.0 mL, 313.5 mmol) and ytterbium(III) trifluoromethanesulfonate (Yb(OTf)₃) (5.8 g, 9.5 mmol). The resulting mixture was stirred at 85° C. for 18 h in sealed tube. The mixture was diluted with ethyl acetate (300 mL) and washed with water (100 mL×2) and brine (100 mL×2) and then dried over anhydrous sodium sulfate. The solvent was removed in vacuo and the residue was purified by ISCO combi-flash chromatography (gradient elution, 10-50% ethyl acetate in petroleum ether) to afford 2-(3-bromo-5-fluoro-phenyl)-4,4-dimethyl-1,2,3,4-tetrahydro-quinoline-6-carboxylic acid methyl ester (12.3 g, 40.0%) as a light yellow solid: MS (ESI) M+1=394.0.

2-(3-bromo-5-fluoro-phenyl)-4,4-dimethyl-1,2,3,4-tetrahydro-quinoline-6-carboxylic acid methyl ester (3.9 g, 10.0 mmol), morpholine (9.0 mL, 95.0 mmol), copper(I) iodide (1.1 g, 6.0 mmol), N,N-dimethylglycine hydrochloride (1.1 g, 8.0 mmol), and potassium carbonate (4.1 g, 30.0 mmol) in dimethyl sulfoxide (20 mL) was stirred at 120° C. for 16 h. Then the reaction mixture was cooled to room temperature. The reaction mixture was extracted with ethyl acetate (200 mL×2), washed with saturated aqueous ammonium chloride solution (50 mL×3) and brine (50 mL×2), dried over anhydrous sodium sulfate and then concentrated in vacuo and the residue was purified by ISCO combi-flash chromatography (gradient elution, 30-50% ethyl acetate in petroleum ether) to afford 2-(3-fluoro-5-morpholin-4-yl-phenyl)-4,4-dimethyl-1,2,3,4-tetrahydro-quinoline-6-carboxylic acid methyl ester (3.2 g, 80%) as a white solid: MS (ESI) M+1=399.0.

To a stirred mixture solution of 2-(3-fluoro-5-morpholin-4-yl-phenyl)-4,4-dimethyl-1,2,3,4-tetrahydro-quinoline-6-carboxylic acid methyl ester (398.0 mg, 1.0 mmol) in methanol (10.0 mL) and tetrahydrofuran (10.0 mL) was added 50% sodium hydroxide in water (1.5 mL). The reaction mixture was stirred at 70° C. for 6 h. The mixture was neutralized with a 3 N aqueous hydrochloric acid solution and extracted with ethyl acetate (2×100 mL), washed with water, dried over anhydrous sodium sulfate and then concentrated in vacuo to afford 2-(3-fluoro-5-morpholin-4-yl-phenyl)-4,4-dimethyl-1,2,3,4-tetrahydro-quinoline-6-carboxylic acid (345.6 mg, 90%) as a light white solid which was used for next step without further purification: MS (ESI) M+1=385.1.

To a suspension of 60% sodium hydride (128 mg, 3.2 mmol) in N,N-dimethylformamide (1.5 mL) was added methanesulfonamide (314 mg, 3.3 mmol) at room temperature. The resulting mixture was stirred at 25° C. for 1 h to afford Solution A4. A solution of 2-(3-fluoro-5-morpholin-4-yl-phenyl)-4,4-dimethyl-1,2,3,4-tetrahydro-quinoline-6-carboxylic acid (126.7 mg, 0.33 mmol) and 1,1'-carbonyldiimidazole (136 mg, 0.84 mmol) in N,N-dimethylformamide (2.0 mL) was stirred at 70° C. for 1 h and cooled to room temperature to afford Solution B4. Solution B4 was added to Solution A4 and the resulting mixture was stirred at 25° C. for 1 h. To the reaction mixture was added water (0.5 mL). The mixture was filtered to remove the insoluble solid, and the filtrate was purified by Waters automated flash system (column: Xterra 30 mm×100 mm, sample manager 2767, pump 2525, detector: ZQ mass and UV 2487, solvent system: acetonitrile and 0.1% ammonium hydroxide in water) afforded N-[2-(3-fluoro-5-morpholin-4-yl-phenyl)-4,4-dimethyl-1,2,3,4-tetrahydro-quinoline-6-carbonyl]-methanesulfonamide (45.6 mg, 30%) as a white solid: MS (ESI) M+1=462.1.

Example 5

N-(methylsulfonyl)-2'-(3-morpholinophenyl)-2',3'-dihydro-1'H-spiro[cyclopentane-1,4'-quinoline]-6'-carboxamide

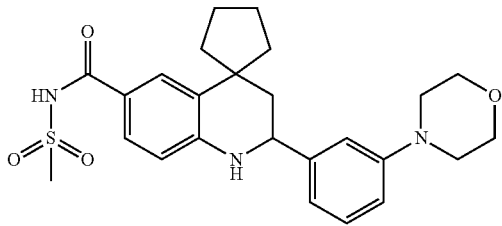 [SMILES: CS(=O)(=O)NC(=O)c1ccc2c(c1)C1(CCCC1)CC(c1cccc(N3CCOCC3)c1)N2]

The mixture solution of 4-aminobenzoic acid methyl ester (10.8 g, 71.4 mmol), 3-bromo-benzaldehyde (13.3 g, 72.4 mmol) and p-toluenesulfonic acid (271.8 mg, 1.4 mmol) in toluene (150 mL) was heated to reflux for 12 h. Then the reaction mixture was cooled to room temperature. The solvent was removed in vacuo and the residue was washed with ether to afford 4-{[1-(3-bromo-phenyl)-meth-(E)-ylidene]amino}-benzoic acid methyl ester (22.6 g, quant.) as a light yellow solid: MS (ESI) M+1=318.0.

To a stirred solution 4-{[1-(3-bromo-phenyl)-meth-(E)-ylidene]amino}-benzoic acid methyl ester (3.2 g, 10.0 mmol) in acetonitrile (16.0 mL) were added methylene-cyclopentane (4.0 mL, 40.0 mol) and scandium(III) trifluoromethanesulfonate (Sc(OTf)$_3$) (980.0 mg, 2.0 mmol). The resulting mixture solution was stirred at 80° C. for 16 h in sealed tube. The mixture solution was diluted with ethyl acetate (300 mL) and washed with water (100 mL×2) and brine (100 mL×2) and then dried over anhydrous sodium sulfate. The solvent was removed in vacuo and the residue was purified by ISCO combi-flash chromatography (gradient elution, 10-50% ethyl acetate in petroleum ether) to afford 2'-(3-bromo-phenyl)-2',3'-dihydro-1'H-spiro[cyclopentane-1,4'-quinoline]-6'-carboxylic acid methyl ester (1.6 g, 40%) as a light yellow solid: MS (ESI) M+1=400.0.

A mixture solution of 2'-(3-bromo-phenyl)-2',3'-dihydro-1'H-spiro[cyclopentane-1,4'-quinoline]-6'-carboxylic acid methyl ester (600 mg, 1.5 mmol), morpholine (2.6 mL, 29.4 mmol), copper(I) iodide (340 mg, 1.8 mmol), N,N-dimethylglycine hydrochloride (340 mg, 2.4 mmol), and potassium carbonate (1.2 g, 9.0 mmol) in dimethyl sulfoxide (6.5 mL) was stirred at 120° C. for 16 h. Then the reaction mixture was cooled to room temperature. The reaction mixture was extracted with ethyl acetate (200 mL×2), washed with saturated aqueous ammonium chloride solution (50 mL×3) and brine (50 mL×2), dried over anhydrous sodium sulfate and then concentrated in vacuo and the residue was purified by ISCO combi-flash chromatography (gradient elution, 30-50% ethyl acetate in petroleum ether) to afford 2'-(3-morpholinophenyl)-2',3'-dihydro-1'H-spiro[cyclopentane-1,4'-quinoline]-6'-carboxylic acid methyl ester (487.2 mg, 80%) as a white solid: MS (ESI) M+1=407.0.

To a stirred solution of 2'-(3-morpholinophenyl)-2',3'-dihydro-1'H-spiro[cyclopentane-1,4'-quinoline]-6'-carboxylic acid methyl ester (406.0 mg, 1.0 mmol) in tetrahydrofuran (10.0 mL) and methanol (10.0 mL) was added 3 N sodium hydroxide (2.0 mL). The reaction mixture was stirred at 80° C. for 6 h, and then diluted with water (10.0 mL), extracted with diethyl ether (20.0 mL). The organic layer was discarded. The aqueous layer was acidified with concentrated hydrochloric acid to pH 4 and extracted with ethyl acetate (40 mL×3). The combined organic layers were dried over anhydrous sodium sulfate. The solvent was removed in vacuo and afforded 2'-(3-morpholinophenyl)-2',3'-dihydro-1'H-spiro[cyclopentane-1,4'-quinoline]-6'-carboxylic acid (352.8 mg, 90%) as a light yellow powder: MS (ESI) M+1=393.1.

To a suspension of 60% sodium hydride (128 mg, 3.2 mmol) in N,N-dimethylformamide (1.5 mL) was added methanesulfonamide (314 mg, 3.3 mmol) at room temperature. The resulting mixture was stirred at 25° C. for 1 h to afford Solution A5. A solution of 2'-(3-morpholinophenyl)-2',3'-dihydro-1'H-spiro[cyclopentane-1,4'-quinoline]-6'-carboxylic acid (129.4 mg, 0.33 mmol) and 1,1'-carbonyldiimidazole (136 mg, 0.84 mmol) in IV, N-dimethylformamide (2.0 mL) was stirred at 70° C. for 1 h and cooled to room temperature to afford Solution B5. Solution B5 was added to Solution A5 and the resulting mixture was stirred at 25° C. for 1 h. To the reaction mixture was added water (0.5 mL). The mixture was filtered to remove the insoluble solid, and the filtrate was purified by Waters automated flash system (column: Xterra 30 mm×100 mm, sample manager 2767, pump 2525, detector: ZQ mass and UV 2487, solvent system: acetonitrile and 0.1% ammonium hydroxide in water) afforded N-(methylsulfonyl)-2'-(3-morpholinophenyl)-2',3'-dihydro-1'H-spiro[cyclopentane-1,4'-quinoline]-6'-carboxamide (46.4 mg, 30%) as a white solid: MS (ESI) M+1=470.2.

Example 6

Cyclopropanesulfonic acid [2-(3-fluoro-5-morpholin-4-yl-phenyl)-4,4-dimethyl-1,2,3,4-tetrahydro-quinoline-6-carbonyl]-amide

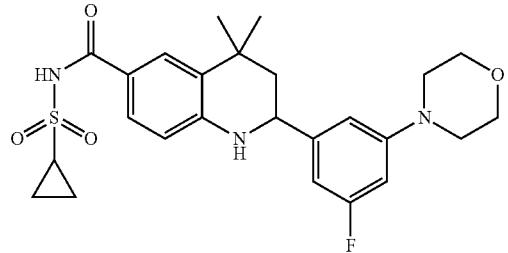 [SMILES: CC1(C)CC(c2cc(F)cc(N3CCOCC3)c2)Nc2ccc(C(=O)NS(=O)(=O)C3CC3)cc21]

To a suspension of 60% sodium hydride (535 mg, 13.7 mmol) in N,N-dimethylformamide (2.5 mL) was added cyclopropanesulfonamide (1.65 g, 13.8 mmol) at room temperature. The resulting mixture was stirred at 25° C. for 1 h to afford Solution A6. A solution of 2-(3-fluoro-5-morpholin-4-yl-phenyl)-4,4-dimethyl-1,2,3,4-tetrahydro-quinoline-6-carboxylic acid (530.0 mg, 1.4 mmol) and 1,1'-carbonyldiimidazole (442 mg, 2.76 mmol) in N,N-dimethylformamide (2.0 mL) was stirred at 70° C. for 1 h and cooled to room temperature to afford Solution B6. Solution B6 was added to Solution A6 and the resulting mixture was stirred at 25° C. for 1 h. To the reaction mixture was added water (0.5 mL). The mixture was filtered to remove the insoluble solid, and the filtrate was purified by Waters automated flash system (column: Xterra 30 mm×100 mm, sample manager 2767, pump 2525, detector: ZQ mass and UV 2487, solvent system: acetonitrile and 0.1% ammonium hydroxide in water) afforded cyclopropanesulfonic acid [2-(3-fluoro-5-morpholin-4-yl-phenyl)-4,4-dimethyl-1,2,3,4-tetrahydro-quinoline-6-carbonyl]-amide (204.5 mg, 30%) as a white solid: MS (ESI) M+1=488.1.

Example 7

N-[2-(3-chloro-4-fluoro-phenyl)-4-methyl-4-phenyl-1,2,3,4-tetrahydro-quinoline-6-carbonyl]-methanesulfonamide

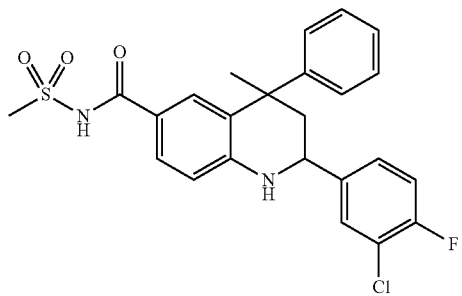 [SMILES: CC1(c2ccccc2)CC(c2ccc(F)c(Cl)c2)Nc2ccc(C(=O)NS(C)(=O)=O)cc21]

To a stirred solution of 4-amino-benzoic acid methyl ester (0.825 g, 5 mmol) and 3-chloro-4-fluoro-benzaldehyde (869 mg, 5.5 mmol) in acetonitrile (50 mL) were added isopropenyl-benzene (2.36 g, 20 mmol) and ytterbium(III) trifluoromethanesulfonate (Yb(OTf)$_3$) (465 mg, 0.75 mmol). The resulting mixture was stirred at 90° C. for 16 h in sealed tube. The mixture was diluted with ethyl acetate (50 mL) and washed with water (30 mL×2) and brine (30 mL×2) and then dried over anhydrous sodium sulfate. The solvent was removed in vacuo and the residue was purified by ISCO combi-flash chromatography (gradient elution, 10-50% ethyl acetate in petroleum ether) to afford 2-(3-chloro-4-fluoro-phenyl)-4-methyl-4-phenyl-1,2,3,4-tetrahydro-quinoline-6-carboxylic acid ethyl ester (850 mg, 40%) as a light yellow solid: MS (ESI) M+1=424.2.

To a stirred mixture solution of 2-(3-chloro-4-fluoro-phenyl)-4-methyl-4-phenyl-1,2,3,4-tetrahydro-quinoline-6-carboxylic acid ethyl ester (423 mg, 1 mmol) in methanol (10 mL) and tetrahydrofuran (20 mL) was added 30% sodium hydroxide in water (10 mL). The reaction mixture was stirred at 60° C. for 6 h. The mixture was neutralized with a 3 N aqueous hydrochloric acid solution and extracted with ethyl acetate (2×100 mL), washed with water, dried over anhydrous sodium sulfate and then concentrated in vacuo to afford 2-(3-chloro-4-fluoro-phenyl)-4-methyl-4-phenyl-1,2,3,4-tetrahydro-quinoline-6-carboxylic acid (380 mg, 95%) as a light white solid which was used for next step without further purification: MS (ESI) M+1=396.1.

To a suspension of 60% sodium hydride (76 mg, 1.88 mmol) in N,N-dimethylformamide (1.5 mL) was added methanesulfonamide (181 mg, 1.9 mmol) at room temperature. The resulting mixture was stirred at 25° C. for 1 h to afford Solution A7. A solution of 2-(3-chloro-4-fluoro-phenyl)-4-methyl-4-phenyl-1,2,3,4-tetrahydro-quinoline-6-carboxylic acid (150 mg, 0.38 mmol) and 1,1'-carbonyldiimidazole (123 mg, 0.76 mmol) in N,N-dimethylformamide (1 mL) was stirred at 70° C. for 1 h and cooled to room temperature to afford Solution B7. Solution B7 was added to Solution A7 and the resulting mixture was stirred at 25° C. for 1 h. To the reaction mixture was added water (0.5 mL). The mixture was filtered to remove the insoluble solid, and the filtrate was purified by Waters automated flash system (column: Xterra 30 mm×100 mm, sample manager 2767, pump 2525, detector: ZQ mass and UV 2487, solvent system: acetonitrile and 0.1% ammonium hydroxide in water) afforded N-[2-(3-chloro-4-fluoro-phenyl)-4-methyl-4-phenyl-1,2,3,4-tetrahydro-quinoline-6-carbonyl]-methanesulfonamide (22 mg, 12%) as a white solid: MS (ESI) M+1=473.3.

Example 8

Propane-1-sulfonic acid [2-(3-chloro-4-fluoro-phenyl)-4,4-dimethyl-1,2,3,4-tetrahydro-quinoline-6-carbonyl]-amide

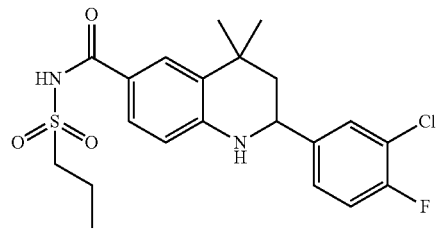 [SMILES: CCCS(=O)(=O)NC(=O)c1ccc2c(c1)C(C)(C)CC(c1ccc(F)c(Cl)c1)N2]

To a stirred solution of 4-amino-benzoic acid methyl ester (11.3 g, 78.4 mmol) and 3-chloro-4-fluoro-benzaldehyde (12.3 g, 78.4 mmol) in acetonitrile (150 mL) were added isobutene (21.0 mL, 313.5 mmol) and ytterbium(III) trifluoromethanesulfonate (Yb(OTf)$_3$) (5.8 g, 9.5 mmol). The resulting mixture was stirred at 85° C. for 18 h in sealed tube. The mixture was diluted with ethyl acetate (300 mL), and washed with water (100 mL×2) and brine (100 mL×2), and then dried over anhydrous sodium sulfate. The solvent was removed in vacuo and the residue was purified by ISCO combi-flash chromatography (gradient elution, 10-50% ethyl acetate in petroleum ether) to afford 2-(3-chloro-4-fluoro-phenyl)-4,4-dimethyl-1,2,3,4-tetrahydro-quinoline-6-carboxylic acid methyl ester (8.4 g, 31.0%) as a light yellow solid: MS (ESI) M+1=348.3.

To a stirred mixture solution of 2-(3-chloro-4-fluoro-phenyl)-4,4-dimethyl-1,2,3,4-tetrahydro-quinoline-6-carboxylic acid methyl ester (348.0 mg, 1.0 mmol) in methanol (10.0 mL) and tetrahydrofuran (10.0 mL) was added 50% sodium hydroxide in water (1.5 mL). The reaction mixture was stirred at 70° C. for 6 h. The mixture was neutralized with a 3 N aqueous hydrochloric acid solution and extracted with ethyl acetate (2×100 mL), washed with water, dried over anhydrous sodium sulfate and then concentrated in vacuo to afford 2-(3- chloro-4-fluoro-phenyl)-4,4-dimethyl-1,2,3,4-tetrahydro-quinoline-6-carboxylic acid (316.4 mg, 95%) as a light white solid which was used for next step without further purification: MS (ESI) M+1=334.1.

To a suspension of 60% sodium hydride (535 mg, 13.7 mmol) in N,N-dimethylformamide (2.5 mL) was added propane-1-sulfonic acid amide (1.01 g, 8.2 mmol) at room temperature. The resulting mixture was stirred at 25° C. for 1 h to afford Solution A8. A solution of 2-(3-chloro-4-fluoro-phenyl)-4,4-dimethyl-1,2,3,4-tetrahydro-quinoline-6-carboxylic acid (273.0 mg, 0.82 mmol) and 1,1'-carbonyldiimidazole (442 mg, 2.76 mmol) in N,N-dimethylformamide (2.0 mL) was stirred at 70° C. for 1 h and cooled to room temperature to afford Solution B8. Solution B8 was added to Solution A8 and the resulting mixture was stirred at 25° C. for 1 h To the reaction mixture was added water (0.5 mL). The mixture was filtered to remove the insoluble solid, and the filtrate was purified by Waters automated flash system (column: Xterra 30 mm×100 mm, sample manager 2767, pump 2525, detector: ZQ mass and UV 2487, solvent system: acetonitrile and 0.1% ammonium hydroxide in water) afforded propane-1-sulfonic acid [2-(3-chloro-4-fluoro-phenyl)-4,4-dimethyl-1,2,3,4-tetrahydro-quinoline-6-carbonyl]-amide (84.7 mg, 23.6%) as a white solid: MS (ESI) M+1=439.1.

Example 9

Propane-2-sulfonic acid [4,4-dimethyl-2-(3-morpholin-4-yl-phenyl)-1,2,3,4-tetrahydro-quinoline-6-carbonyl]-amide

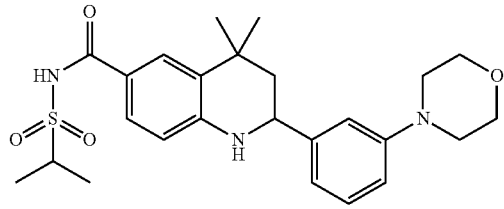 [SMILES: CC(C)S(=O)(=O)NC(=O)c1ccc2c(c1)C(C)(C)CC(c1cccc(N3CCOCC3)c1)N2]

To a suspension of 60% sodium hydride (535 mg, 13.7 mmol) in N,N-dimethylformamide (2.5 mL) was added propane-2-sulfonic acid amide (1.1 g, 13.8 mmol) at room temperature. The resulting mixture was stirred at 25° C. for 1 h to afford Solution A9. A solution of 4,4-dimethyl-2-(3-morpholin-4-yl-phenyl)-1,2,3,4-tetrahydro-quinoline-6-carboxylic acid (300 mg, 0.82 mmol) and 1,1'-carbonyldiimidazole (442 mg, 2.76 mmol) in N,N-dimethylformamide (2.0 mL) was stirred at 70° C. for 1 h and cooled to room temperature to afford Solution B9. Solution B9 was added to Solution A9 and the resulting mixture was stirred at 25° C. for 1 h. To the reaction mixture was added water (0.5 mL). The mixture was filtered to remove the insoluble solid, and the filtrate was purified by Waters automated flash system (column: Xterra 30 mm×100 mm, sample manager 2767, pump 2525, detector: ZQ mass and UV 2487, solvent system: acetonitrile and 0.1% ammonium hydroxide in water) afforded propane-2-sulfonic acid [4,4-dimethyl-2-(3-morpholin-4-yl-phenyl)-1,2,3,4-tetrahydro-quinoline-6-carbonyl]-amide (115.8 mg, 30%) as a white solid: MS (ESI) M+1=472.0.

Example 10

N-[4,4-dimethyl-2-(3-morpholin-4-yl-phenyl)-1,2,3,4-tetrahydro-quinoline-8-carbonyl]-methanesulfonamide

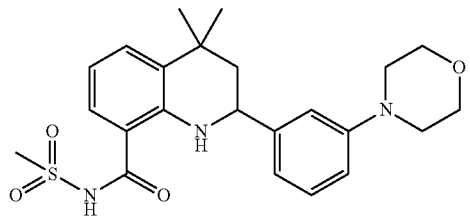 [SMILES: CC1(C)CC(c2cccc(N3CCOCC3)c2)Nc2c(C(=O)NS(C)(=O)=O)cccc21]

To a stirred solution of 2-amino-benzoic acid methyl ester (11.3 g, 78.4 mmol) and 3-bromobenzaldehyde (9.2 mL, 78.4 mmol) in acetonitrile (150 mL) were added isobutene (21.0 mL, 313.5 mmol) and ytterbium(III) trifluoromethanesulfonate (Yb(OTf)$_3$) (5.8 g, 9.5 mmol). The resulting mixture was stirred at 85° C. for 18 h in sealed tube. The mixture was diluted with ethyl acetate (300 mL) and washed with water (100 mL×2) and brine (100 mL×2) and then dried over anhydrous sodium sulfate. The solvent was removed in vacuo and the residue was purified by ISCO combi-flash chromatography (gradient elution, 10-50% ethyl acetate in petroleum ether) to afford 2-(3-bromo-phenyl)-4,4-dimethyl-1,2,3,4-tetrahydro-quinoline-8-carboxylic acid methyl ester (11.7 g, 40.0%) as a light yellow solid: MS (ESI) M+1=374.0.

A mixture solution of 2-(3-bromo-phenyl)-4,4-dimethyl-1,2,3,4-tetrahydro-quinoline-8-carboxylic acid methyl ester (11.2 g, 30.0 mmol), morpholine (26.0 mL, 294.0 mmol), copper(I) iodide (3.4 g, 18.0 mmol), N,N-dimethylglycine hydrochloride (3.4 g, 24.0 mmol), and potassium carbonate (12.4 g, 90.0 mmol) in dimethyl sulfoxide (65 mL) was stirred at 120° C. for 16 h. Then the reaction mixture was cooled to room temperature. The reaction mixture was extracted with ethyl acetate (200 mL×2), washed with saturated aqueous ammonium chloride solution (50 mL×3) and brine (50 mL×2), dried over anhydrous sodium sulfate and then concentrated in vacuo and the residue was purified by ISCO combi-flash chromatography (gradient elution, 30-50% ethyl acetate in petroleum ether) to afford 4,4-dimethyl-2-(3-morpholin-4-yl-phenyl)-1,2,3,4-tetrahydro-quinoline-8-carboxylic acid methyl ester (9.1 g, 80%) as a white solid: MS (ESI) M+1=381.0.

To a stirred mixture solution of 4,4-dimethyl-2-(3-morpholin-4-yl-phenyl)-1,2,3,4-tetrahydro-quinoline-8-carboxylic acid methyl ester (380.0 mg, 1.0 mmol) in methanol (10.0 mL) and tetrahydrofuran (10.0 mL) was added 50% sodium hydroxide in water (1.5 mL). The reaction mixture was stirred at 70° C. for 6 h. The mixture was neutralized with a 3 N aqueous hydrochloric acid solution and extracted with ethyl acetate (2×100 mL), washed with water, dried over anhydrous sodium sulfate and then concentrated in vacuo to afford 4,4-dimethyl-2-(3-morpholin-4-yl-phenyl)-1,2,3,4-tetrahydro-quinoline-8-carboxylic acid (330.0 mg, 90%) as a light white solid which was used for next step without further purification: MS (ESI) M+1=367.1.

To a suspension of 60% sodium hydride (535.0 mg, 13.7 mmol) in N,N-dimethylformamide (2.5 mL) was added methanesulfonamide (1.3 g, 13.8 mmol) at room temperature. The resulting mixture was stirred at 25° C. for 1 h to afford Solution A10. A solution of 4,4-dimethyl-2-(3-morpholin-4-yl-phenyl)-1,2,3,4-tetrahydro-quinoline-8-carboxylic acid (300.0 mg, 0.82 mmol) and 1,1'-carbonyldiimidazole (442.0 mg, 2.76 mmol) in N,N-dimethylformamide (2.0 mL) was stirred at 70° C. for 1 h and cooled to room temperature to afford Solution B10. Solution B10 was added to Solution A10 and the resulting mixture was stirred at 25° C. for 1 h. To the reaction mixture was added water (0.5 mL). The mixture was filtered to remove the insoluble solid, and the filtrate was purified by Waters automated flash system (column: Xterra 30 mm×100 mm, sample manager 2767, pump 2525, detector: ZQ mass and UV 2487, solvent system: acetonitrile and 0.1% ammonium hydroxide in water) afforded N-[4,4-dimethyl-2-(3-morpholin-4-yl-phenyl)-1,2,3,4-tetrahydro-quinoline-8-carbonyl]-methanesulfonamide (109.0 mg, 30%) as a white solid: MS (ESI) M+1=444.2.

Example 11

Cyclopropanesulfonic acid [4,4-dimethyl-2-(3-morpholin-4-yl-phenyl)-1,2,3,4-tetrahydro-quinoline-8-carbonyl]-amide

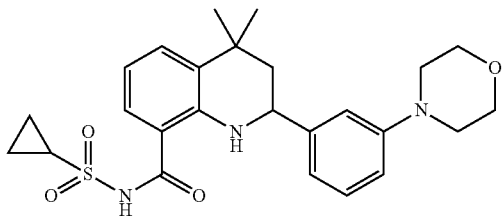 [SMILES: CC1(C)CC(c2cccc(N3CCOCC3)c2)Nc2c(C(=O)NS(=O)(=O)C3CC3)cccc21]

To a suspension of 60% sodium hydride (535.0 mg, 13.7 mmol) in N,N-dimethylformamide (2.5 mL) was added cyclopropanesulfonamide (1.65 g, 13.8 mmol) at room temperature. The resulting mixture was stirred at 25° C. for 1 h to afford Solution 11. A solution of 4,4-dimethyl-2-(3-morpholin-4-yl-phenyl)-1,2,3,4-tetrahydro-quinoline-8-carboxylic acid (300.0 mg, 0.82 mmol) and 1,1'-carbonyldiimidazole (442.0 mg, 2.76 mmol) in N,N-dimethylformamide (2.0 mL) was stirred at 70° C. for 1 h and cooled to room temperature to afford Solution B11. Solution B11 was added to Solution 11 and the resulting mixture was stirred at 25° C. for 1 h. To the reaction mixture was added water (0.5 mL). The mixture was filtered to remove the insoluble solid, and the filtrate was purified by Waters automated flash system (column: Xterra 30 mm×100 mm, sample manager 2767, pump 2525, detector: ZQ mass and UV 2487, solvent system: acetonitrile and 0.1% ammonium hydroxide in water) afforded cyclopropanesulfonic acid [4,4-dimethyl-2-(3-morpholin-4-yl-phenyl)-1,2,3,4-tetrahydro-quinoline-8-carbonyl]-amide (115.4 mg, 30%) as a white solid: MS (ESI) M+1=470.1.

Example 12

4,4-Dimethyl-6-(morpholine-4-sulfonyl)-2-(3-morpholin-4-yl-phenyl)-1,2,3,4-tetrahydro-quinoline

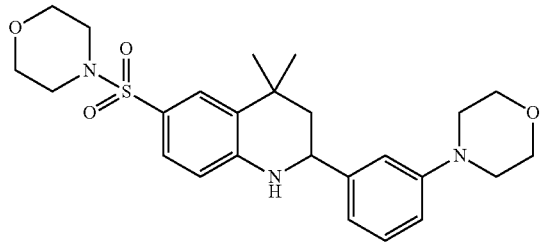 [SMILES: CC1(C)CC(c2cccc(N3CCOCC3)c2)Nc2ccc(S(=O)(=O)N3CCOCC3)cc21]

To a stirred solution of morpholine (5.2 mL, 59.7 mmol) and triethylamine (11.2 mL, 79.6 mmol) in dichloromethane (300 mL) was added the solution of 4-nitro-benzenesulfonyl chloride (8.8 g, 39.8 mmol) in dichloromethane (50 mL) at 0° C. The mixture solution was stirred at room temperature for 4 h and then washed with brine (50 mL×2) and dried over anhydrous sodium sulfate. The solvent was removed in vacuo to afford 4-(4-nitro-benzenesulfonyl)-morpholine (10.0 g, 92.5%) as a white powder: MS (ESI) M+1=273.0.

To a stirred solution of 4-(4-nitro-benzenesulfonyl)-morpholine (5.0 g, 18.4 mmol) ethanol (400 mL) was added iron powder (5.2 g, 92.0 mmol) and the solution of ammonium chloride (10 g, 184.0 mmol) in water (100 mL). After the reaction mixture was refluxed for 3 h, the iron was filtered off and the filtrate was basified to pH 9 by addition of sodium carbonate. The reaction mixture was extracted with ethyl acetate (300 mL×2). The extract was washed with water (130 mL×2) and brine (130 mL×2), dried over anhydrous sodium sulfate. The solvent was removed in vacuo and the residue was purified by ISCO combi-flash chromatography (gradient elution, 20-60% ethyl acetate in petroleum ether) to afford 4-(morpholine-4-sulfonyl)-phenylamine (4.2 g, 95%) as a yellow powder: MS (ESI) M+1=243.1.

To a stirred solution of 4-(morpholine-4-sulfonyl)-phenylamine (3 g, 12.4 mmol) and 3-bromo-benzaldehyde (2.52 g, 13.6 mmol) in acetonitrile (150 mL) were added isobutene (2.7 mL, 37.2 mmoll) and ytterbium(III) trifluoromethanesulfonate (Yb(OTf)$_3$) (1.54 g, 2.5 mmol). The resulting mixture was stirred at 80° C. for 18 h in sealed tube. The mixture solution was diluted with ethyl acetate (300 mL) and washed with water (100 mL×2) and brine (100 mL×2) and then dried over anhydrous sodium sulfate. The solvent was removed in vacuo and the residue was purified by ISCO combi-flash chromatography (gradient elution, 10-40% ethyl acetate in petroleum ether) to afford 2-(3-bromo-phenyl)-4,4-dimethyl-6-(morpholine-4-sulfonyl)-1,2,3,4-tetrahydro-quinoline (2.7 g, 47.4%) as a light yellow solid: MS (ESI) M+1=465.0 & 467.0.

The mixture solution of 2-(3-bromo-phenyl)-4,4-dimethyl-6-(morpholine-4-sulfonyl)-1,2,3,4-tetrahydro-quinoline (150 mg, 0.33 mmol), copper(I) iodide (20 mg, 0.1 mmol), morpholine (1.3 mL, 14.7 mmol), N,N-dimethylglycine hydrochloride (34.0 mg, 0.24 mmol) and potassium carbonate (110 mg, 1.0 mmol) in dimethyl sulfoxide (2.0 mL). was stirred at 120° C. for 16 h. Then the reaction mixture was cooled to room temperature and extracted with ethyl acetate (70 mL×2), washed with water (30 mL×3) and saturated aqueous ammonium chloride solution (30 mL×2), dried over anhydrous sodium sulfate and then concentrated in vacuo. Purification by Waters automated flash system (column: Xterra 30 mm×100 mm, sample manager 2767, pump 2525, detector: ZQ mass and UV 2487, solvent system: acetonitrile and 0.1% ammonium hydroxide in water) afforded 4,4-dimethyl-6-(morpholine-4-sulfonyl)-2-(3-morpholin-4-yl-phenyl)-1,2,3,4-tetrahydro-quinoline (124.3 mg, 80.0%) as a white solid: MS (ESI) M+1=472.2.

Example 13

4,4-Dimethyl-2-(3-morpholin-4-yl-phenyl)-1,2,3,4-tetrahydro-quinoline-6-sulfonic acid isopropylamide

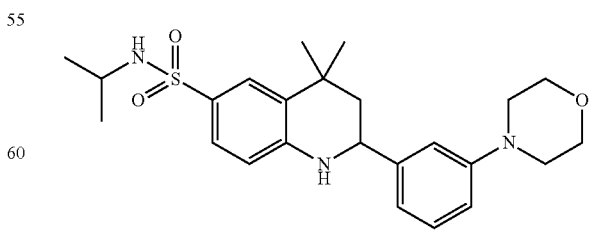

To a stirred solution of isopropylamine (6.8 mL, 79.6 mmol) and triethylamine (16.6 mL, 119.4 mmol) in dichloromethane (300 mL) was added the solution of 4-nitro-benzenesulfonyl chloride (8.8 g, 39.8 mmol) in dichloromethane (50 mL) at 0° C. The mixture solution stirred at room temperature for 4 h. The mixture solution was stirred at room temperature for 4 h and then washed with brine (50 mL×2) and dried over anhydrous sodium sulfate. The solvent was removed in vacuo to afford N-isopropyl-4-nitro-benzenesulfonamide (9.3 g, 96%) as a white powder: MS (ESI) M+1=245.

To a stirred solution of N-isopropyl-4-nitro-benzenesulfonamide (9.0 g, 37.0 mmol) ethanol (500 mL) was added iron powder (11.0 g, 196.0 mmol) and the solution of ammonium chloride (22.0 g, 392.0 mmol) in water (150 mL). After the reaction mixture was refluxed for 3 h, the iron was filtered off and the filtrate was basified to pH 9 by addition of sodium carbonate. The reaction mixture was extracted with ethyl acetate (300 mL×2). The extract was washed with water (130 mL×2) and brine (130 mL×2), dried over anhydrous sodium sulfate. The solvent was removed in vacuo and the residue was purified by ISCO combi-flash chromatography (gradient elution, 20-60% ethyl acetate in petroleum ether) to afford 4-amino-N-isopropyl-benzenesulfonamide (7.0 g, 89%) as a yellow powder: MS (ESI) M+1=215.

To a stirred solution of 4-amino-N-isopropyl-benzenesulfonamide (4.0 g, 18.7 mmol) and 3-bromo-benzaldehyde (3.8 g, 20.5 mmol) in acetonitrile (150 mL) were added isobutene (6.5 mL, 93.5 mmoll) and ytterbium(III) trifluoromethanesulfonate (Yb(OTf)$_3$) (2.4 g, 3.7 mmol). The resulting mixture was stirred at 80° C. for 18 h in sealed tube. The mixture solution was diluted with ethyl acetate (300 mL) and washed with water (100 mL×2) and brine (100 mL×2) and then dried over anhydrous sodium sulfate. The solvent was removed in vacuo and the residue was purified by ISCO combi-flash chromatography (gradient elution, 10-40% ethyl acetate in petroleum ether) to afford 2-(3-bromo-phenyl)-4,4-dimethyl-1,2,3,4-tetrahydro-quinoline-6-sulfonic acid isopropylamide (3.8 g, 47.4%) as a light yellow solid: MS (ESI) M+1=437.1.

The mixture solution of 2-(3-bromo-phenyl)-4,4-dimethyl-1,2,3,4-tetrahydro-quinoline-6-sulfonic acid isopropylamide (392.0 mg, 0.9 mmol), CuI (51.0 mg, 0.27 mmol), N,N-dimethylglycine hydrochloride (75.0 mg, 0.54 mmol), potassium carbonate (373.0 mg, 2.7 mmol) and morpholine (0.78 mL, 9.0 mmol) in DMSO (5.0 mL) was stirred at 120° C. for 16 h under a nitrogen atmosphere. Then the reaction mixture was cooled to room temperature and extracted with ethyl acetate (70 mL×2), washed with water (30 mL×3) and saturated aqueous ammonium chloride solution (30 mL×2), dried over anhydrous sodium sulfate and then concentrated in vacuo. Purification by Waters automated flash system (column: Xterra 30 mm×100 mm, sample manager 2767, pump 2525, detector: ZQ mass and UV 2487, solvent system: acetonitrile and 0.1% ammonium hydroxide in water) afforded 4,4-dimethyl-2-(3-morpholin-4-yl-phenyl)-1,2,3,4-tetrahydro-quinoline-6-sulfonic acid isopropylamide (160.0 mg, 40%) as a light yellow solid: MS (ESI) M+1=444.3.

Example 14

4,4-Dimethyl-6-(morpholine-4-sulfonyl)-2-(3-piperazin-1-yl-phenyl)-1,2,3,4-tetrahydro-quinoline

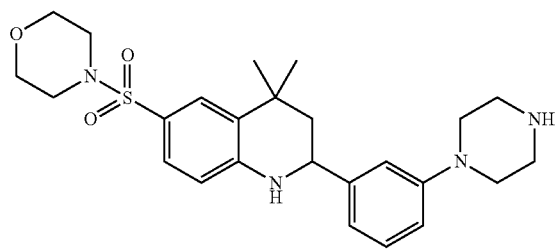 [SMILES: CC1(C)CC(c2cccc(N3CCNCC3)c2)Nc2ccc(S(=O)(=O)N3CCOCC3)cc21]

The mixture solution of 2-(3-bromo-phenyl)-4,4-dimethyl-6-(morpholine-4-sulfonyl)-1,2,3,4-tetrahydro-quinoline (150.0 mg, 0.33 mmol), copper(I) iodide (20.0 mg, 0.1 mmol), piperazine (283.4 mg, 3.3 mmol), N,N-dimethylglycine hydrochloride (34.0 mg, 0.24 mmol) and potassium carbonate (110.0 mg, 1.0 mmol) in dimethyl sulfoxide (2.0 mL). was stirred at 120° C. for 16 h. Then the reaction mixture was cooled to room temperature and extracted with ethyl acetate (70 mL×2), washed with water (30 mL×3) and saturated aqueous ammonium chloride solution (30 mL×2), dried over anhydrous sodium sulfate and then concentrated in vacuo. Purification by Waters automated flash system (column: Xterra 30 mm×100 mm, sample manager 2767, pump 2525, detector: ZQ mass and UV 2487, solvent system: acetonitrile and 0.1% ammonium hydroxide in water) afforded 4,4-dimethyl-6-(morpholine-4-sulfonyl)-2-(3-piperazin-1-yl-phenyl)-1,2,3,4-tetrahydro-quinoline (51.1 mg, 33.0%) as a white solid: MS (ESI) M+1=471.2.

Example 15

4,4-Dimethyl-2-(3-morpholin-4-yl-phenyl)-1,2,3,4-tetrahydro-quinoline-6-sulfonic acid cyclobutylamide

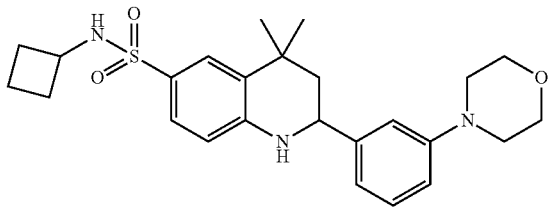 [SMILES: CC1(C)CC(c2cccc(N3CCOCC3)c2)Nc2ccc(S(=O)(=O)NC3CCC3)cc21]

To a stirred solution of cyclobutylamine (4.3 g, 59.7 mmol) and triethylamine (11.2 mL, 79.6 mmol) in dichloromethane (300 mL) was added the solution of 4-nitro-benzenesulfonyl chloride (8.8 g, 39.8 mmol) in dichloromethane (50 mL) at 0° C. The mixture solution was stirred at room temperature for 4 h and then washed with brine (50 mL×2) and dried over anhydrous sodium sulfate. The solvent was removed in vacuo to afford N-cyclobutyl-4-nitro-benzenesulfonamide (9.4 g, 92.5%) as a white powder: MS (ESI) M+1=257.1.

To a stirred solution of N-cyclobutyl-4-nitro-benzenesulfonamide (5.8 g, 18.4 mmol) ethanol (400 mL) was added iron powder (5.2 g, 92.0 mmol) and the solution of ammonium chloride (10 g, 184.0 mmol) in water (100 mL). After the reaction mixture was refluxed for 3 h, the iron was filtered off and the filtrate was basified to pH 9 by addition of sodium carbonate. The reaction mixture was extracted with ethyl acetate (300 mL×2). The extract was washed with water (130 mL×2) and brine (130 mL×2), dried over anhydrous sodium sulfate. The solvent was removed in vacuo and the residue was purified by ISCO combi-flash chromatography (gradient elution, 20-60% ethyl acetate in petroleum ether) to afford 4-amino-N-cyclobutyl-benzenesulfonamide (3.87 g, 93%) as a yellow powder: MS (ESI) M+1=227.0.

To a stirred solution of 4-amino-N-cyclobutyl-benzenesulfonamide (2.8 g, 12.4 mmol) and 3-bromo-benzaldehyde (2.52 g, 13.6 mmol) in acetonitrile (150 mL) were added isobutene (2.7 mL, 37.2 mmoll) and ytterbium(III) trifluoromethanesulfonate (Yb(OTf)$_3$) (1.54 g, 2.5 mmol). The resulting mixture was stirred at 80° C. for 18 h in sealed tube. The mixture solution was diluted with ethyl acetate (300 mL) and washed with water (100 mL×2) and brine (100 mL×2) and then dried over anhydrous sodium sulfate. The solvent was removed in vacuo and the residue was purified by ISCO combi-flash chromatography (gradient elution, 10-40% ethyl acetate in petroleum ether) to afford 2-(3-bromo-phenyl)-4,4-dimethyl-1,2,3,4-tetrahydro-quinoline-6-sulfonic acid cyclobutylamide (2.2 g, 40%) as a light yellow solid: MS (ESI) M+1=449.0 & 451.0.

The mixture solution of 2-(3-bromo-phenyl)-4,4-dimethyl-1,2,3,4-tetrahydro-quinoline-6-sulfonic acid cyclobutylamide (150.0 mg, 0.34 mmol), copper(I) iodide (20.0 mg, 0.1 mmol), N,N-dimethylglycine hydrochloride (37.5 mg, 0.27 mmol), morpholine (0.78 mL, 9.0 mmol) and potassium carbonate (140.0 mg, 1.0 mmol) in dimethyl sulfoxide (2.0 mL). was stirred at 120° C. for 16 h. Then the reaction mixture was cooled to room temperature and extracted with ethyl acetate (70 mL×2), washed with water (30 mL×3) and saturated aqueous ammonium chloride solution (30 mL×2), dried over anhydrous sodium sulfate and then concentrated in vacuo. Purification by Waters automated flash system (column: Xterra 30 mm×100 mm, sample manager 2767, pump 2525, detector: ZQ mass and UV 2487, solvent system: acetonitrile and 0.1% ammonium hydroxide in water) afforded 4,4-dimethyl-2-(3-morpholin-4-yl-phenyl)-1,2,3,4-tetrahydro-quinoline-6-sulfonic acid cyclobutylamide (123.7 mg, 80.0%) as a white solid: MS (ESI) M+1=456.2.

Example 16

2-(3-Fluoro-5-morpholin-4-yl-phenyl)-4,4-dimethyl-1,2,3,4-tetrahydro-quinoline-6-sulfonic acid cyclobutylamide

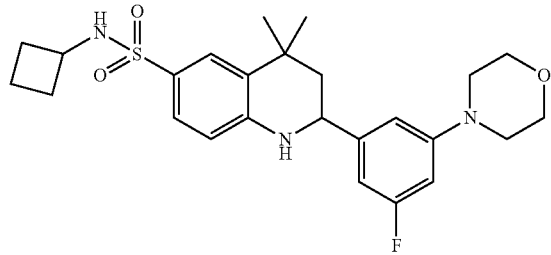 [SMILES: CC1(C)CC(c2cc(F)cc(N3CCOCC3)c2)Nc2ccc(S(=O)(=O)NC3CCC3)cc21]

To a stirred solution of 4-amino-N-cyclobutyl-benzenesulfonamide (2.8 g, 12.4 mmol) and 3-bromo-5-fluoro-benzaldehyde (2.7 g, 13.6 mmol) in acetonitrile (150 mL) were added isobutene (2.7 mL, 37.2 mmol) and ytterbium(III) trifluoromethanesulfonate (Yb(OTf)$_3$) (1.54 g, 2.5 mmol). The resulting mixture was stirred at 80° C. for 18 h in sealed tube. The mixture solution was diluted with ethyl acetate (300 mL) and washed with water (100 mL×2) and brine (100 mL×2) and then dried over anhydrous sodium sulfate. The solvent was removed in vacuo and the residue was purified by ISCO combi-flash chromatography (gradient elution, 10-40% ethyl acetate in petroleum ether) to afford 2-(3-bromo-5-fluoro-phenyl)-4,4-dimethyl-1,2,3,4-tetrahydro-quinoline-6-sulfonic acid cyclobutylamide (2.3 g, 40%) as a light yellow solid: MS (ESI) M+1=467.0.

The mixture solution of 2-(3-bromo-5-fluoro-phenyl)-4,4-dimethyl-1,2,3,4-tetrahydro-quinoline-6-sulfonic acid cyclobutylamide (158.4 mg, 0.34 mmol), copper(I) iodide (20.0 mg, 0.1 mmol), N,N-dimethylglycine hydrochloride (37.5 mg, 0.27 mmol), morpholine (0.78 mL, 9.0 mmol) and potassium carbonate (140.0 mg, 1.0 mmol) in dimethyl sulfoxide (2.0 mL) was stirred at 120° C. for 16 h. Then the reaction mixture was cooled to room temperature and extracted with ethyl acetate (70 mL×2), washed with water (30 mL×3) and saturated aqueous ammonium chloride solution (30 mL×2), dried over anhydrous sodium sulfate and then concentrated in vacuo. Purification by Waters automated flash system (column: Xterra 30 mm×100 mm, sample manager 2767, pump 2525, detector: ZQ mass and UV 2487, solvent system: acetonitrile and 0.1% ammonium hydroxide in water) afforded 2-(3-fluoro-5-morpholin-4-yl-phenyl)-4,4-dimethyl-1,2,3,4-tetrahydro-quinoline-6-sulfonic acid cyclobutylamide (64.3 mg, 40.0%) as a white solid: MS (ESI) M+1=474.2.

Example 17

2-(2'-Hydroxy-biphenyl-3-yl)-4,4-dimethyl-1,2,3,4-tetrahydro-quinoline-6-sulfonic acid cyclobutylamide

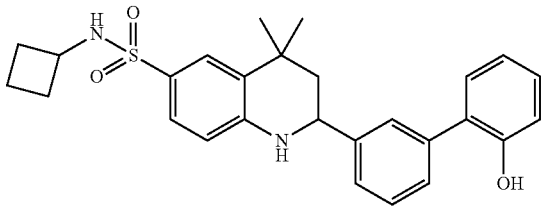 [SMILES: CC1(C)CC(c2cccc(-c3ccccc3O)c2)Nc2ccc(S(=O)(=O)NC3CCC3)cc21]

To a mixture of 2-(3-bromo-phenyl)-4,4-dimethyl-1,2,3,4-tetrahydro-quinoline-6-sulfonic acid cyclobutylamide (748.1 mg, 1.67 mmol), 2-hydroxy-phenylboronic acid (276.0 mg, 2.0 mmol) and tetrakis(triphenylphosphine)palladium(0) (193.0 mg, 0.17 mmol) in dioxane (5.0 mL) was added 2 M sodium carbonate solution in water (1.7 mL). The resulting mixture was subjected to microwave irradiation for 2 h at 110° C. The mixture was diluted with ethyl acetate (200 mL), washed with saturated aqueous sodium bicarbonate solution (50 mL×2), brine, dried over anhydrous sodium sulfate and then concentrated in vacuo. Purification by flash silica gel chromatography (silica gel from QingDao, 200-300 mesh, glass column from Shanghai SD company) (10% ethyl acetate/hexanes) afforded 2-(2'-hydroxy-biphenyl-3-yl)-4,4-dimethyl-1,2,3,4-tetrahydro-quinoline-6-sulfonic acid cyclobutylamide (412.1 mg, 53.4%) as a white solid: MS (ESI) M+1=463.1.

Example 18

N-(4,4-dimethyl-2-pyridin-3-yl-1,2,3,4-tetrahydro-quinoline-6-carbonyl)-methanesulfonamide

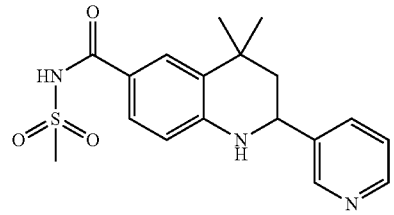 [SMILES: CC1(C)CC(c2cccnc2)Nc2ccc(C(=O)NS(C)(=O)=O)cc21]

To a stirred solution of 4-amino-benzoic acid methyl ester (11.3 g, 78.4 mmol) and pyridine-3-carbaldehyde (8.4 g, 78.4 mmol) in acetonitrile (150 mL) were added isobutene (21.0 mL, 313.5 mmol) and ytterbium(III) trifluoromethane-sulfonate (Yb(OTf)₃) (5.8 g, 9.5 mmol). The resulting mixture was stirred at 85° C. for 18 h in sealed tube. The mixture was diluted with ethyl acetate (300 mL) and washed with water (100 mL×2) and brine (100 mL×2) and then dried over anhydrous sodium sulfate. The solvent was removed in vacuo and the residue was purified by ISCO combi-flash chromatography (gradient elution, 10-50% ethyl acetate in petroleum ether) to afford 4,4-dimethyl-2-pyridin-3-yl-1,2,3,4-tetrahydro-quinoline-6-carboxylic acid methyl ester (9.2 g, 40.0%) as a light yellow solid: MS (ESI) M+1=297.3.

To a stirred mixture solution of 4,4-dimethyl-2-pyridin-3-yl-1,2,3,4-tetrahydro-quinoline-6-carboxylic acid methyl ester (296.0 mg, 1.0 mmol) in methanol (10.0 mL) and tetrahydrofuran (10.0 mL) was added 50% sodium hydroxide in water (1.5 mL). The reaction mixture was stirred at 70° C. for 6 h. The mixture was neutralized with a 3 N aqueous hydrochloric acid solution and extracted with ethyl acetate (2×100 mL), washed with water, dried over anhydrous sodium sulfate and then concentrated in vacuo to afford 4,4-dimethyl-2-pyridin-3-yl-1,2,3,4-tetrahydro-quinoline-6-carboxylic acid (266.4 mg, 90%) as a light white solid which was used for next step without further purification: MS (ESI) M+1=283.1.

To a suspension of 60% sodium hydride (535.0 mg, 13.7 mmol) in N,N-dimethylformamide (2.5 mL) was added methanesulfonamide (1.3 g, 13.8 mmol) at room temperature. The resulting mixture was stirred at 25° C. for 1 h to afford Solution A18. A solution of 4,4-dimethyl-2-pyridin-3-yl-1,2,3,4-tetrahydro-quinoline-6-carboxylic acid (231.2 mg, 0.82 mmol) and 1,1'-carbonyldiimidazole (442.0 mg, 2.76 mmol) in N,N-dimethylformamide (2.0 mL) was stirred at 70° C. for 1 h and cooled to room temperature to afford Solution B18. Solution B18 was added to Solution A18 and the resulting mixture was stirred at 25° C. for 1 h. To the reaction mixture was added water (0.5 mL). The mixture was filtered to remove the insoluble solid, and the filtrate was purified by Waters automated flash system (column: Xterra 30 mm×100 mm, sample manager 2767, pump 2525, detector: ZQ mass and UV 2487, solvent system: acetonitrile and 0.1% ammonium hydroxide in water) afforded N-(4,4-dimethyl-2-pyridin-3-yl-1,2,3,4-tetrahydro-quinoline-6-carbonyl)-methanesulfonamide (88.3 mg, 30%) as a white solid: MS (ESI) M+1=360.2.

Example 19

Cyclopropanesulfonic acid (4,4-dimethyl-2-pyridin-3-yl-1,2,3,4-tetrahydro-quinoline-6-carbonyl)-amide

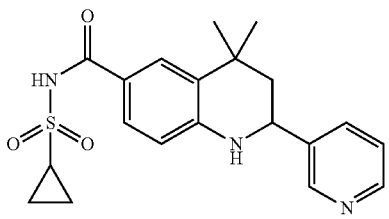 [SMILES: CC1(C)CC(c2cccnc2)Nc2ccc(C(=O)NS(=O)(=O)C3CC3)cc21]

To a suspension of 60% sodium hydride (535.0 mg, 13.7 mmol) in N,N-dimethylformamide (2.5 mL) was added cyclopropanesulfonic acid amide (1.7 g, 13.8 mmol) at room temperature. The resulting mixture was stirred at 25° C. for 1 h to afford Solution A19. A solution of 4,4-dimethyl-2-pyridin-3-yl-1,2,3,4-tetrahydro-quinoline-6-carboxylic acid (231.2 mg, 0.82 mmol) and 1,1'-carbonyldiimidazole (442.0 mg, 2.76 mmol) in N,N-dimethylformamide (2.0 mL) was stirred at 70° C. for 1 h and cooled to room temperature to afford Solution B19. Solution B19 was added to Solution A19 and the resulting mixture was stirred at 25° C. for 1 h. To the reaction mixture was added water (0.5 mL). The mixture was filtered to remove the insoluble solid, and the filtrate was purified by Waters automated flash system (column: Xterra 30 mm×100 mm, sample manager 2767, pump 2525, detector: ZQ mass and UV 2487, solvent system: acetonitrile and 0.1% ammonium hydroxide in water) afforded cyclopropanesulfonic acid (4,4-dimethyl-2-pyridin-3-yl-1,2,3,4-tetrahydro-quinoline-6-carbonyl)-amide (94.7 mg, 30%) as a white solid: MS (ESI) M+1=386.2.

Example 20

3-(6-Methanesulfonylaminocarbonyl-4,4-dimethyl-1,2,3,4-tetrahydro-quinolin-2-yl)-N-phenyl-benzamide

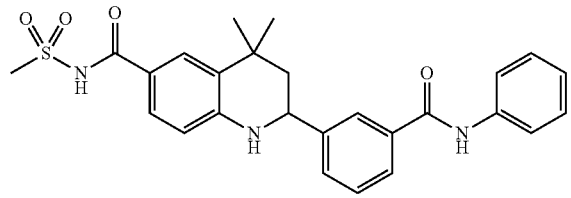 [SMILES: CC1(C)CC(c2cccc(C(=O)Nc3ccccc3)c2)Nc2ccc(C(=O)NS(C)(=O)=O)cc21]

To a stirred solution of 4-amino-benzoic acid methyl ester (8.25 g, 50 mmol) and 3-formyl-benzoic acid methyl ester (9.03 g, 55 mmol) in acetonitrile (200 mL) were added isobutene (14 mL, 200 mmol) and ytterbium(III) trifluoromethanesulfonate (Yb(OTf)₃) (4.65 g, 7.5 mmol). The resulting mixture was stirred at 90° C. for 16 h in sealed tube. The mixture was diluted with ethyl acetate (300 mL) and washed with water (100 mL×2) and brine (100 mL×2) and then dried over anhydrous sodium sulfate. The solvent was removed in vacuo and the residue was purified by ISCO combi-flash chromatography (gradient elution, 10-50% ethyl acetate in petroleum ether) to afford 2-(3-methoxycarbonyl-phenyl)-4,4-dimethyl-1,2,3,4-tetrahydro-quinoline-6-carboxylic acid ethyl ester (8 g, 43%) as a light yellow solid: MS (ESI) M+1=368.2.

A mixture of 2-(3-methoxycarbonyl-phenyl)-4,4-dimethyl-1,2,3,4-tetrahydro-quinoline-6-carboxylic acid ethyl ester (2.5 g, 6.8 mmol) in tetrahydrofuran (20 mL), 2M lithium hydroxide in water (10 mL) was stirred for 4 h at 25° C. The mixture was neutralized with a 2 N aqueous hydrochloric acid solution, diluted with ethyl acetate (100 mL), washed with water, dried over anhydrous sodium sulfate and then concentrated in vacuo to afford 2-(3-carboxy-phenyl)-4,4-dimethyl-1,2,3,4-tetrahydro-quinoline-6-carboxylic acid ethyl ester (1.2 g, 50%) as a light white solid which was used for next step without further purification: MS (ESI) M+1=354.2.

A mixture of 2-(3-carboxy-phenyl)-4,4-dimethyl-1,2,3,4-tetrahydro-quinoline-6-carboxylic acid ethyl ester (706 mg, 2 mmol), aniline (0.22 mL, 2.4 mmol) and o-(7-azabenzotriazol-1-yl)-N,N,N',N'-tetramethyluronium hexafluorophosphate (1.14 g, 3 mmol) in dichloromethane (6 mL) and triethyl-amine (0.7 mL, 5 mmol). The reaction mixture was stirred at 25° C. for 3 h. Then the reaction mixture was extracted with dichloromethane (2×100 mL), washed with water, dried over anhydrous sodium sulfate and concentrated in vacuo to afford 4,4-dimethyl-2-(3-phenylcarbamoyl-phenyl)-1,2,3,4-tetrahydro-quinoline-6-carboxylic acid ethyl ester (800 mg, 93%) as a brown oil which was used for next step without further purification: MS (ESI) M+1=429.2.

To a stirred mixture solution of 4,4-dimethyl-2-(3-phenylcarbamoyl-phenyl)-1,2,3,4-tetrahydro-quinoline-6-carboxylic acid ethyl ester (0.8 g, 1.87 mmol) in methanol (10 mL) and tetrahydrofuran (20 mL) was added 30% sodium hydroxide in water (10 mL). The reaction mixture was stirred at 60° C. for 16 h. The mixture was neutralized with a 3 N aqueous hydrochloric acid solution and extracted with ethyl acetate (2×100 mL), washed with water, dried over anhydrous sodium sulfate and then concentrated in vacuo to afford 4,4-dimethyl-2-(3-phenylcarbamoyl-phenyl)-1,2,3,4-tetrahydro-quinoline-6-carboxylic acid (7 g, 93%) as a light white solid which was used for next step without further purification: MS (ESI) M+1=401.2.

To a suspension of 60% sodium hydride (198 mg, 4.95 mmol) in N,N-dimethylformamide (2 mL) was added methanesulfonamide (475 mg, 5 mmol) at room temperature. The resulting mixture was stirred at 25° C. for 1 h to afford Solution A20. A solution of 4,4-dimethyl-2-(3-phenylcarbamoyl-phenyl)-1,2,3,4-tetrahydro-quinoline-6-carboxylic acid (400 mg, 1 mmol) and 1,1'-carbonyldiimidazole (324 mg, 2 mmol) in N,N-dimethylformamide (2 mL) was stirred at 70° C. for 1 h and cooled to room temperature to afford Solution B20. Solution B20 was added to Solution A20 and the resulting mixture was stirred at 25° C. for 1 h. To the reaction mixture was added water (0.5 mL). The mixture was filtered to remove the insoluble solid, and the filtrate was purified by Waters automated flash system (column: Xterra 30 mm×100 mm, sample manager 2767, pump 2525, detector: ZQ mass and UV 2487, solvent system: acetonitrile and 0.1% ammonium hydroxide in water) afforded 3-(6-methanesulfonylaminocarbonyl-4,4-dimethyl-1,2,3,4-tetrahydro-quinolin-2-yl)-N-phenyl-benzamide (35 mg, 7%) as a white solid: MS (ESI) M+1=478.2.

Example 21

3-(6-Cyclopropanesulfonylaminocarbonyl-4,4-dimethyl-1,2,3,4-tetrahydro-quinolin-2-yl)-N-phenyl-benzamide

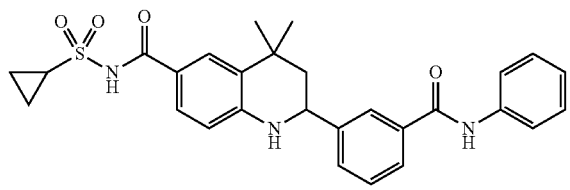 [SMILES: CC1(C)CC(c2cccc(C(=O)Nc3ccccc3)c2)Nc2ccc(C(=O)NS(=O)(=O)C3CC3)cc21]

To a suspension of 60% sodium hydride (198 mg, 4.95 mmol) in N,N-dimethylformamide (2 mL) was added cyclopropanesulfonic acid amide (605 mg, 5 mmol) at room temperature. The resulting mixture was stirred at 25° C. for 1 h to afford Solution A21. A solution of 4,4-dimethyl-2-(3-phenylcarbamoyl-phenyl)-1,2,3,4-tetrahydro-quinoline-6-carboxylic acid (400 mg, 1 mmol) and 1,1'-carbonyldiimidazole (324 mg, 2 mmol) in N,N-dimethylformamide (2 mL) was stirred at 70° C. for 1 h and cooled to room temperature to afford Solution B21. Solution B21 was added to Solution A21 and the resulting mixture was stirred at 25° C. for 1 h. To the reaction mixture was added water (0.5 mL). The mixture was filtered to remove the insoluble solid, and the filtrate was purified by Waters automated flash system (column: Xterra 30 mm×100 mm, sample manager 2767, pump 2525, detector: ZQ mass and UV 2487, solvent system: acetonitrile and 0.1% ammonium hydroxide in water) afforded 3-(6-cyclopropanesulfonylaminocarbonyl-4,4-dimethyl-1,2,3,4-tetrahydro-quinolin-2-yl)-N-phenyl-benzamide (30 mg, 6%) as a white solid: MS (ESI) M+1=504.2.

Example 22

N-[4,4-dimethyl-2-(2-methyl-5-morpholin-4-yl-phenyl)-1,2,3,4-tetrahydro-quinoline-6-carbonyl]-methanesulfonamide

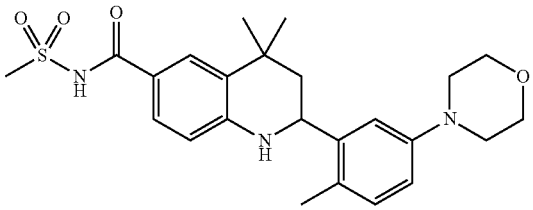 [SMILES: Cc1ccc(N2CCOCC2)cc1C1CC(C)(C)c2cc(C(=O)NS(C)(=O)=O)ccc2N1]

To a stirred solution of 4-amino-benzoic acid methyl ester (8.25 g, 50 mmol) and 5-bromo-2-methyl-benzaldehyde (12 g, 60 mmol) in acetonitrile (200 mL) were added isobutene (14 mL, 0.2 mmol) and ytterbium(III) trifluoromethanesulfonate (Yb(OTf)$_3$) (4.65 g, 7.5 mmol). The resulting mixture was stirred at 85° C. for 16 h in sealed tube. The mixture was diluted with ethyl acetate (300 mL) and washed with water (100 mL×2) and brine (100 mL×2) and then dried over anhydrous sodium sulfate. The solvent was removed in vacuo and the residue was purified by ISCO combi-flash chromatography (gradient elution, 10-50% ethyl acetate in petroleum ether) to afford 2-(5-bromo-2-methyl-phenyl)-4,4-dimethyl-1,2,3,4-tetrahydro-quinoline-6-carboxylic acid methyl ester (7.1 g, 35%) as a light yellow solid: MS (ESI) M+1=402.0.

A mixture solution of 2-(5-bromo-2-methyl-phenyl)-4,4-dimethyl-1,2,3,4-tetrahydro-quinoline-6-carboxylic acid methyl ester (3.5 g, 8.7 mmol), morpholine (7.6 mL, 87 mmol), copper(I) iodide (1 g, 5.22 mmol), N,N-dimethylglycine hydrochloride (0.97 g, 6.96 mmol), and potassium carbonate (3.6 g, 26.1 mmol) in dimethyl sulfoxide (25 mL) was stirred at 120° C. for 16 h. Then the reaction mixture was cooled to room temperature. The reaction mixture was extracted with ethyl acetate (200 mL×2), washed with saturated aqueous ammonium chloride solution (50 mL×3) and brine (50 mL×2), dried over anhydrous sodium sulfate and then concentrated in vacuo and the residue was purified by ISCO combi-flash chromatography (gradient elution, 30-50% ethyl acetate in petroleum ether) to afford 4,4-dimethyl-2-(2-methyl-5-morpholin-4-yl-phenyl)-1,2,3,4-tetrahydro-quinoline-6-carboxylic acid ethyl ester (3.2 g, 90%) as a white solid: MS (ESI) M+1=409.0.

To a stirred mixture solution of 4,4-dimethyl-2-(2-methyl-5-morpholin-4-yl-phenyl)-1,2,3,4-tetrahydro-quinoline-6-carboxylic acid ethyl ester (3.2 g, 7.8 mmol) in methanol (50 mL) and tetrahydrofuran (50 mL) was added 30% sodium hydroxide in water (10 mL). The reaction mixture was stirred at 60° C. for 3 h. The mixture was neutralized with a 3 N aqueous hydrochloric acid solution and extracted with ethyl acetate (2×100 mL), washed with water, dried over anhydrous sodium sulfate and then concentrated in vacuo to afford 4,4-dimethyl-2-(2-methyl-5-morpholin-4-yl-phenyl)-1,2,3,4-tetrahydro-quinoline-6-carboxylic acid (2.4 g, 80%) as a light white solid which was used for next step without further purification: MS (ESI) M+1=381.1.

To a suspension of 60% sodium hydride (560 mg, 14 mmol) in N,N-dimethylformamide (5 mL) was added methanesulfonamide (1.33 g, 14 mmol) at room temperature. The resulting mixture was stirred at 25° C. for 1 h to afford Solution A22. A solution of 4,4-dimethyl-2-(2-methyl-5-morpholin-4-yl-phenyl)-1,2,3,4-tetrahydro-quinoline-6-carboxylic acid (800 mg, 2 mmol) and 1,1'-carbonyldiimidazole (690 mg, 4 mmol) in N,N-dimethylformamide (3 mL) was stirred at 70° C. for 1 h and cooled to room temperature to afford Solution B22. Solution B22 was added to Solution A22 and the resulting mixture was stirred at 25° C. for 1 h. To the reaction mixture was added water (0.5 mL). The mixture was filtered to remove the insoluble solid, and the filtrate was purified by Waters automated flash system (column: Xterra 30 mm×100 mm, sample manager 2767, pump 2525, detector: ZQ mass and UV 2487, solvent system: acetonitrile and 0.1% ammonium hydroxide in water) afforded N-[4,4-dimethyl-2-(2-methyl-5-morpholin-4-yl-phenyl)-1,2,3,4-tetrahydro-quinoline-6-carbonyl]-methanesulfonamide (239 mg, 26%) as a white solid: MS (ESI) M+1=458.1.

Example 23

N-[2-(2-chloro-5-morpholin-4-yl-phenyl)-4,4-dimethyl-1,2,3,4-tetrahydro-quinoline-6-carbonyl]-methanesulfonamide

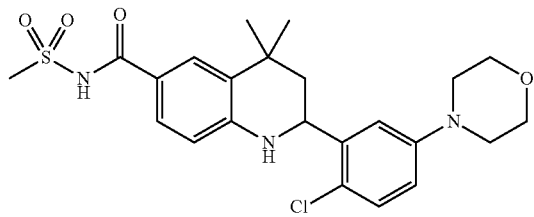 [SMILES: CC1(C)CC(c2cc(N3CCOCC3)ccc2Cl)Nc2ccc(C(=O)NS(C)(=O)=O)cc21]

To a stirred solution of 4-amino-benzoic acid methyl ester (8.25 g, 50 mmol) and 5-bromo-2-chloro-benzaldehyde (13.2 g, 60 mmol) in acetonitrile (200 mL) were added isobutene (14 mL, 0.2 mmol) and ytterbium(III) trifluoromethanesulfonate (Yb(OTf)$_3$) (4.65 g, 7.5 mmol). The resulting mixture was stirred at 85° C. for 16 h in sealed tube. The mixture was diluted with ethyl acetate (300 mL) and washed with water (100 mL×2) and brine (100 mL×2) and then dried over anhydrous sodium sulfate. The solvent was removed in vacuo and the residue was purified by ISCO combi-flash chromatography (gradient elution, 10-50% ethyl acetate in petroleum ether) to afford 2-(5-bromo-2-chloro-phenyl)-4,4-dimethyl-1,2,3,4-tetrahydro-quinoline-6-carboxylic acid methyl ester (6.99 g, 33%) as a light yellow solid: MS (ESI) M+1=422.0.

A mixture solution of 2-(5-bromo-2-chloro-phenyl)-4,4-dimethyl-1,2,3,4-tetrahydro-quinoline-6-carboxylic acid methyl ester (3 g, 7 mmol), morpholine (6.2 mL, 71 mmol), copper(I) iodide (0.8 g, 4.2 mmol), N,N-dimethylglycine hydrochloride (0.78 g, 5.6 mmol), and potassium carbonate (2.9 g, 21 mmol) in dimethyl sulfoxide (25 mL) was stirred at 120° C. for 16 h. Then the reaction mixture was cooled to room temperature. The reaction mixture was extracted with ethyl acetate (200 mL×2), washed with saturated aqueous ammonium chloride solution (50 mL×3) and brine (50 mL×2), dried over anhydrous sodium sulfate and then concentrated in vacuo and the residue was purified by ISCO combi-flash chromatography (gradient elution, 30-50% ethyl acetate in petroleum ether) to afford 2-(2-chloro-5-morpholin-4-yl-phenyl)-4,4-dimethyl-1,2,3,4-tetrahydro-quinoline-6-carboxylic acid ethyl ester (2.8 g, 93%) as a white solid: MS (ESI) M+1=429.1.

To a stirred mixture solution of 2-(2-chloro-5-morpholin-4-yl-phenyl)-4,4-dimethyl-1,2,3,4-tetrahydro-quinoline-6-carboxylic acid ethyl ester (2.8 g, 6.5 mmol) in methanol (50 mL) and tetrahydrofuran (50 mL) was added 30% sodium hydroxide in water (10 mL). The reaction mixture was stirred at 60° C. for 16 h. The mixture was neutralized with a 3 N aqueous hydrochloric acid solution and extracted with ethyl acetate (100 mL×2), washed with water, dried over anhydrous sodium sulfate and then concentrated in vacuo to afford 2-(2-chloro-5-morpholin-4-yl-phenyl)-4,4-dimethyl-1,2,3,4-tetrahydro-quinoline-6-carboxylic acid (2.4 g, 92%) as a light white solid which was used for next step without further purification: MS (ESI) M+1=401.1.

To a suspension of 60% sodium hydride (650 mg, 16 mmol) in N,N-dimethylformamide (5 mL) was added methanesulfonamide (1.53 g, 16 mmol) at room temperature. The resulting mixture was stirred at 25° C. for 1 h to afford Solution A23. A solution of 2-(2-chloro-5-morpholin-4-yl-phenyl)-4,4-dimethyl-1,2,3,4-tetrahydro-quinoline-6-carboxylic acid (900 mg, 2.3 mmol) and 1,1'-carbonyldiimidazole (730 mg, 4.5 mmol) in N,N-dimethylformamide (3 mL) was stirred at 70° C. for 1 h and cooled to room temperature to afford Solution B23. Solution B23 was added to Solution A23 and the resulting mixture was stirred at 25° C. for 1 h. To the reaction mixture was added water (0.5 mL). The mixture was filtered to remove the insoluble solid, and the filtrate was purified by Waters automated flash system (column: Xterra 30 mm×100 mm, sample manager 2767, pump 2525, detector: ZQ mass and UV 2487, solvent system: acetonitrile and 0.1% ammonium hydroxide in water) afforded N-[2-(2-chloro-5-morpholin-4-yl-phenyl)-4,4-dimethyl-1,2,3,4-tetrahydro-quinoline-6-carbonyl]-methanesulfonamide (190 mg, 17%) as a white solid: MS (ESI) M+1=478.0.

Example 24

Cyclopropanesulfonic acid [4,4-dimethyl-2-(2-methyl-5-morpholin-4-yl-phenyl)-1,2,3,4-tetrahydro-quinoline-6-carbonyl]-amide

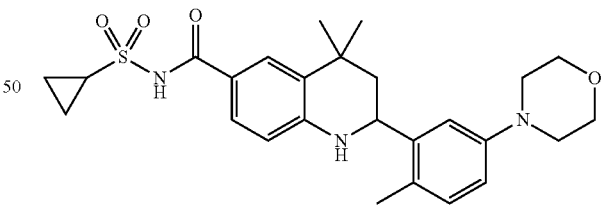

To a suspension of 60% sodium hydride (560 mg, 14 mmol) in N,N-dimethylformamide (5 mL) was added cyclopropanesulfonic acid amide (1.33 g, 14 mmol) at room temperature. The resulting mixture was stirred at 25° C. for 1 h to afford Solution A24. A solution of 4,4-dimethyl-2-(2-methyl-5-morpholin-4-yl-phenyl)-1,2,3,4-tetrahydro-quinoline-6-carboxylic acid (800 mg, 2 mmol) and 1,1'-carbonyldiimidazole (690 mg, 4 mmol) in N,N-dimethylformamide (3 mL) was stirred at 70° C. for 1 h and cooled to room temperature to afford Solution B24. Solution B24 was added to Solution A24 and the resulting mixture was stirred at 25° C. for 1 h. To the reaction mixture was added water (0.5 mL). The mixture was filtered to remove the insoluble solid, and the filtrate was purified by Waters automated flash system (column: Xterra 30 mm×100 mm, sample manager 2767, pump 2525, detector: ZQ mass and UV 2487, solvent system: acetonitrile and 0.1% ammonium hydroxide in water) afforded cyclopropanesulfonic acid [4,4-dimethyl-2-(2-methyl-5-morpholin-4-yl-phenyl)-1,2,3,4-tetrahydro-quinoline-6-carbonyl]-amide (90 mg, 9%) as a white solid: MS (ESI) M+1=484.1.

Example 25

Cyclopropanesulfonic acid [2-(2-chloro-5-morpholin-4-yl-phenyl)-4,4-dimethyl-1,2,3,4-tetrahydro-quinoline-6-carbonyl]-amide

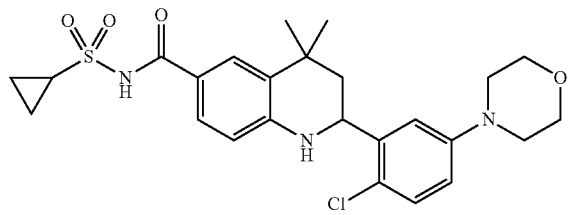 [SMILES: CC1(C)CC(c2cc(N3CCOCC3)ccc2Cl)Nc2ccc(C(=O)NS(=O)(=O)C3CC3)cc21]

To a suspension of 60% sodium hydride (650 mg, 16 mmol) in N,N-dimethylformamide (5 mL) was added cyclopropanesulfonic acid amide (1.53 g, 16 mmol) at room temperature. The resulting mixture was stirred at 25° C. for 1 h to afford Solution A25. A solution of 2-(2-chloro-5-morpholin-4-yl-phenyl)-4,4-dimethyl-1,2,3,4-tetrahydro-quinoline-6-carboxylic acid (900 mg, 2.3 mmol) and 1,1'-carbonyldiimidazole (730 mg, 4.5 mmol) in N,N-dimethylformamide (3 mL) was stirred at 70° C. for 1 h and cooled to room temperature to afford Solution B25. Solution B25 was added to Solution A25 and the resulting mixture was stirred at 25° C. for 1 h. To the reaction mixture was added water (0.5 mL). The mixture was filtered to remove the insoluble solid, and the filtrate was purified by Waters automated flash system (column: Xterra 30 mm×100 mm, sample manager 2767, pump 2525, detector: ZQ mass and UV 2487, solvent system: acetonitrile and 0.1% ammonium hydroxide in water) afforded cyclopropanesulfonic acid [2-(2-chloro-5-morpholin-4-yl-phenyl)-4,4-dimethyl-1,2,3,4-tetrahydro-quinoline-6-carbonyl]-amide (260 mg, 22%) as a white solid: MS (ESI) M+1=504.1.

Example 26

N-{2-[2-chloro-5-(2-oxo-oxazolidin-3-yl)-phenyl]-4,4-dimethyl-1,2,3,4-tetrahydro-quinoline-6-carbonyl}-methanesulfonamide

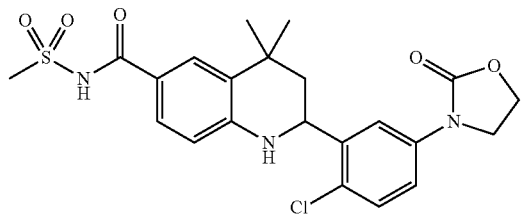 [SMILES: CC1(C)CC(c2cc(N3CCOC3=O)ccc2Cl)Nc2ccc(C(=O)NS(C)(=O)=O)cc21]

To a stirred mixture solution of 2-(5-bromo-2-chloro-phenyl)-4,4-dimethyl-1,2,3,4-tetrahydro-quinoline-6-carboxylic acid methyl ester (1.5 g, 3.56 mmol) in methanol (20 mL) and tetrahydrofuran (20 mL) was added 30% sodium hydroxide in water (10 mL). The reaction mixture was stirred at 60° C. for 6 h. The mixture was neutralized with a 3 N aqueous hydrochloric acid solution and extracted with ethyl acetate (2×100 mL), washed with water, dried over anhydrous sodium sulfate and then concentrated in vacuo to afford 2-(5-bromo-2-chloro-phenyl)-4,4-dimethyl-1,2,3,4-tetrahydro-quinoline-6-carboxylic acid (1.39 g, 99%) as a light white solid which was used for next step without further purification: MS (ESI) M+1=394.0.

A mixture solution of 2-(5-bromo-2-chloro-phenyl)-4,4-dimethyl-1,2,3,4-tetrahydro-quinoline-6-carboxylic acid methyl ester (1.39 g, 3.53 mmol), oxazolidin-2-one (323 mg, 3.7 mmol), copper(I) iodide (135 mg, 0.71 mmol), N,N'-dimethyl-ethane-1,2-diamine (0.152 mL, 1.41 mmol), and potassium carbonate (1.46 g, 10.6 mmol) in acetonitrile (30 mL) was stirred at 90° C. for 72 h. Then the reaction mixture was cooled to room temperature. The reaction mixture was extracted with ethyl acetate (200 mL×2), washed with saturated aqueous ammonium chloride solution (50 mL×3) and brine (50 mL×2), dried over anhydrous sodium sulfate and then concentrated in vacuo and the residue was purified by ISCO combi-flash chromatography (gradient elution, 30-50% ethyl acetate in petroleum ether) to afford 2-[2-chloro-5-(2-oxo-oxazolidin-3-yl)-phenyl]-4,4-dimethyl-1,2,3,4-tetrahydro-quinoline-6-carboxylic acid (0.7 g, 49%) as a white solid: MS (ESI) M+1=401.0.

To a suspension of 60% sodium hydride (70 mg, 1.75 mmol) in N,N-dimethylformamide (3 mL) was added methanesulfonamide (166 mg, 1.75 mmol) at room temperature. The resulting mixture was stirred at 25° C. for 1 h to afford Solution A26. A solution of 2-[2-chloro-5-(2-oxo-oxazolidin-3-yl)-phenyl]-4,4-dimethyl-1,2,3,4-tetrahydro-quinoline-6-carboxylic acid (100 mg, 0.25 mmol) and 1,1'-carbonyldiimidazole (81 mg, 0.5 mmol) in N,N-dimethylformamide (2 mL) was stirred at 70° C. for 1 h and cooled to room temperature to afford Solution B26. Solution B26 was added to Solution A26 and the resulting mixture was stirred at 25° C. for 1 h. To the reaction mixture was added water (0.5 mL). The mixture was filtered to remove the insoluble solid, and the filtrate was purified by Waters automated flash system (column: Xterra 30 mm×100 mm, sample manager 2767, pump 2525, detector: ZQ mass and UV 2487, solvent system: acetonitrile and 0.1% ammonium hydroxide in water) afforded N-{2-[2-chloro-5-(2-oxo-oxazolidin-3-yl)-phenyl]-4,4-dimethyl-1,2,3,4-tetrahydro-quinoline-6-carbonyl}-methanesulfonamide (13 mg, 11%) as a white solid: MS (ESI) M+1=478.0.

Example 27

N-{4,4-dimethyl-2-[2-methyl-5-(2-oxo-oxazolidin-3-yl)-phenyl]-1,2,3,4-tetrahydro-quinoline-6-carbonyl}-methanesulfonamide

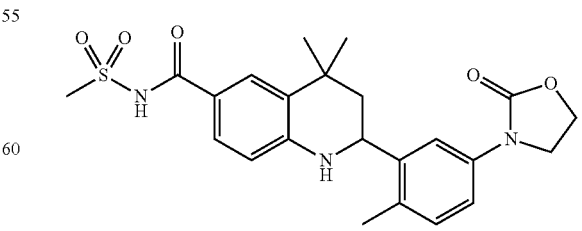

To a stirred mixture solution of 2-(5-bromo-2-methyl-phenyl)-4,4-dimethyl-1,2,3,4-tetrahydro-quinoline-6-carboxylic acid methyl ester (1.5 g, 3.56 mmol) in methanol (20 mL)

and tetrahydrofuran (20 mL) was added 30% sodium hydroxide in water (10 mL). The reaction mixture was stirred at 60° C. for 6 h. The mixture was neutralized with a 3 N aqueous hydrochloric acid solution and extracted with ethyl acetate (2×100 mL), washed with water, dried over anhydrous sodium sulfate and then concentrated in vacuo to afford 2-(5-bromo-2-methyl-phenyl)-4,4-dimethyl-1,2,3,4-tetrahydro-quinoline-6-carboxylic acid (1.36 g, 97%) as a light white solid which was used for next step without further purification: MS (ESI) M+1=374.0 & 376.0.

A mixture solution of 2-(5-bromo-2-methyl-phenyl)-4,4-dimethyl-1,2,3,4-tetrahydro-quinoline-6-carboxylic acid (1.36 g, 3.64 mmol), oxazolidin-2-one (330 mg, 3.82 mmol), copper(I) iodide (139 mg, 0.73 mmol), N,N'-dimethyl-ethane-1,2-diamine (0.157 mL, 1.46 mmol), and potassium carbonate (1.51 g, 10.9 mmol) in acetonitrile (25 mL) was stirred at 90° C. for 72 h. Then the reaction mixture was cooled to room temperature. The reaction mixture was extracted with ethyl acetate (200 mL×2), washed with saturated aqueous ammonium chloride solution (50 mL×3) and brine (50 mL×2), dried over anhydrous sodium sulfate and then concentrated in vacuo and the residue was purified by ISCO combi-flash chromatography (gradient elution, 30-50% ethyl acetate in petroleum ether) to afford 4,4-dimethyl-2-[2-methyl-5-(2-oxo-oxazolidin-3-yl)-phenyl]-1,2,3,4-tetrahydro-quinoline-6-carboxylic acid (0.4 g, 29%) as a white solid: MS (ESI) M+1=381.1.

To a suspension of 60% sodium hydride (185 mg, 4.62 mmol) in N,N-dimethylformamide (3 mL) was added methanesulfonamide (439 mg, 4.62 mmol) at room temperature. The resulting mixture was stirred at 25° C. for 1 h to afford Solution A27. A solution of 4,4-dimethyl-2-[2-methyl-5-(2-oxo-oxazolidin-3-yl)-phenyl]-1,2,3,4-tetrahydro-quinoline-6-carboxylic acid (250 mg, 0.66 mmol) and 1,1'-carbonyldiimidazole (214 mg, 1.32 mmol) in N,N-dimethylformamide (2 mL) was stirred at 70° C. for 1 h and cooled to room temperature to afford Solution B27. Solution B27 was added to Solution A27 and the resulting mixture was stirred at 25° C. for 1 h. To the reaction mixture was added water (0.5 mL). The mixture was filtered to remove the insoluble solid, and the filtrate was purified by Waters automated flash system (column: Xterra 30 mm×100 mm, sample manager 2767, pump 2525, detector: ZQ mass and UV 2487, solvent system: acetonitrile and 0.1% ammonium hydroxide in water) afforded N-{4,4-dimethyl-2-[2-methyl-5-(2-oxo-oxazolidin-3-yl)-phenyl]-1,2,3,4-tetrahydro-quinoline-6-carbonyl}-methanesulfonamide (8 mg, 2%) as a white solid: MS (ESI) M+1=458.0.

Example 28

Cyclopropanesulfonic acid {4,4-dimethyl-2-[2-methyl-5-(2-oxo-oxazolidin-3-yl)-phenyl]-1,2,3,4-tetrahydro-quinoline-6-carbonyl}-amide

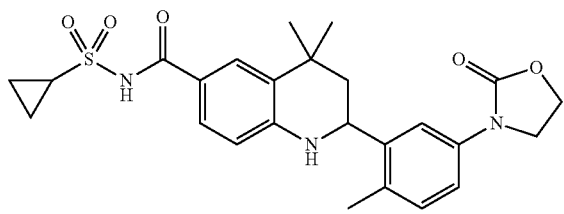 [SMILES: Cc1ccc(N2CCOC2=O)cc1C1CC(C)(C)c2cc(C(=O)NS(=O)(=O)C3CC3)ccc2N1]

To a suspension of 60% sodium hydride (63 mg, 1.58 mmol) in N,N-dimethylformamide (3 mL) was added cyclopropanesulfonic acid amide (192 mg, 1.58 mmol) at room temperature. The resulting mixture was stirred at 25° C. for 1 h to afford Solution A28. A solution of 4,4-dimethyl-2-[2-methyl-5-(2-oxo-oxazolidin-3-yl)-phenyl]-1,2,3,4-tetrahydro-quinoline-6-carboxylic acid (60 mg, 0.16 mmol) and 1,1'-carbonyldiimidazole (51 mg, 0.32 mmol) in N,N-dimethylformamide (1.5 mL) was stirred at 70° C. for 1 h and cooled to room temperature to afford Solution B28. Solution B28 was added to Solution A28 and the resulting mixture was stirred at 25° C. for 1 h. To the reaction mixture was added water (0.5 mL). The mixture was filtered to remove the insoluble solid, and the filtrate was purified by Waters automated flash system (column: Xterra 30 mm×100 mm, sample manager 2767, pump 2525, detector: ZQ mass and UV 2487, solvent system: acetonitrile and 0.1% ammonium hydroxide in water) afforded cyclopropanesulfonic acid {4,4-dimethyl-2-[2-methyl-5-(2-oxo-oxazolidin-3-yl)-phenyl]-1,2,3,4-tetrahydro-quinoline-6-carbonyl}-amide (15 mg, 19%) as a white solid: MS (ESI) M+1=484.1.

Example 29

Cyclopropanesulfonic acid {2-[2-chloro-5-(2-oxo-oxazolidin-3-yl)-phenyl]-4,4-dimethyl-1,2,3,4-tetrahydro-quinoline-6-carbonyl}-amide

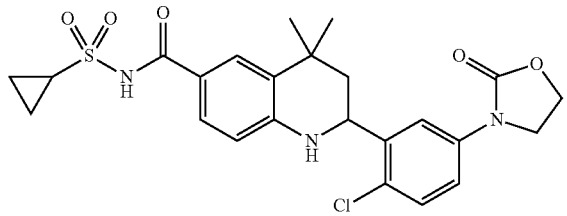 [SMILES: CC1(C)CC(c2cc(N3CCOC3=O)ccc2Cl)Nc2ccc(C(=O)NS(=O)(=O)C3CC3)cc21]

To a suspension of 60% sodium hydride (176 mg, 4.4 mmol) in N,N-dimethylformamide (3 mL) was added cyclopropanesulfonic acid amide (530 mg, 4.4 mmol) at room temperature. The resulting mixture was stirred at 25° C. for 1 h to afford Solution A29. A solution of 2-[2-chloro-5-(2-oxo-oxazolidin-3-yl)-phenyl]-4,4-dimethyl-1,2,3,4-tetrahydro-quinoline-6-carboxylic acid (250 mg, 0.62 mmol) and 1,1'-carbonyldiimidazole (203 mg, 1.25 mmol) in N,N-dimethylformamide (2 mL) was stirred at 70° C. for 1 h and cooled to room temperature to afford Solution B29. Solution B29 was added to Solution A29 and the resulting mixture was stirred at 25° C. for 1 h. To the reaction mixture was added water (0.5 mL). The mixture was filtered to remove the insoluble solid, and the filtrate was purified by Waters automated flash system (column: Xterra 30 mm×100 mm, sample manager 2767, pump 2525, detector: ZQ mass and UV 2487, solvent system: acetonitrile and 0.1% ammonium hydroxide in water) afforded cyclopropanesulfonic acid {2-[2-chloro-5-(2-oxo-oxazolidin-3-yl)-phenyl]-4,4-dimethyl-1,2,3,4-tetrahydro-quinoline-6-carbonyl}-amide (85 mg, 27%) as a white solid: MS (ESI) M+1=504.0.

Example 30

N-[4,4-dimethyl-2-(3-trifluoromethyl-phenyl)-1,2,3,4-tetrahydro-quinoline-6-carbonyl]-methanesulfonamide

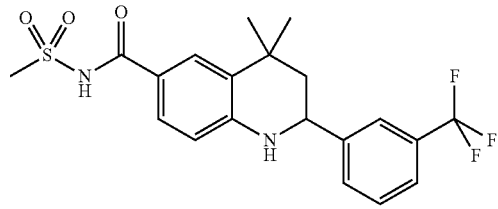 [SMILES: CC1(C)CC(c2cccc(C(F)(F)F)c2)Nc2ccc(C(=O)NS(C)(=O)=O)cc21]

A mixture of 4-aminobenzoic acid ethyl ester (3.3 g, 20 mmol), 3-trifluoromethyl benzaldehyde (3.48 g, 20 mmol) and ytterbium(III) triflate hydrate (1.86 g, 3 mmol) in acetonitrile (150 mL) was cooled to 0° C. in a sealed reaction bottle. Then a cooled solution of isobutene (5.6 g, 100 mmol) was added into. The reaction mixture was heated to 90° C. and stirred for 12 h. The solvent was removed in vacuo and the residue was purified on flash silica gel chromatography (silica gel from QingDao, 200-300 mesh, glass column from Shanghai SD company) (10% ethyl acetate/hexanes) to afford 4,4-dimethyl-2-(3-trifluoromethyl-phenyl)-1,2,3,4-tetrahydroquinoline-6-carboxylic acid ethyl ester (3.0 g, 40%) as a white solid: MS (ESI) M+1=378.3.

A mixture of 4,4-dimethyl-2-(3-trifluoromethyl-phenyl)-1,2,3,4-tetrahydro-quinoline-6-carboxylic acid ethyl ester (3.0 g, 7.96 mmol), lithium hydroxide hydrate (3.34 g, 79.6 mmol), water (10 mL) in methanol (10 mL) and tetrahydrofuran (20 mL) was stirred at 60° C. for 12 h. The mixture was neutralized with a 3 mol/L aqueous hydrochloric acid solution and extracted with ethyl acetate (2×50 mL), washed with water, dried over anhydrous sodium sulfate and then concentrated in vacuo to afford 4,4-dimethyl-2-(3-trifluoromethyl-phenyl)-1,2,3,4-tetrahydro-quinoline-6-carboxylic acid (2.64 g, 95%) as a white solid which was used for next step without further purification: MS (ESI) M+1=350.4.

To a suspension of methanesulfonamide (480 mg, 5.0 mmol) in N,N-dimethylformamide (5 mL) was added sodium hydride (200 mg, 5.0 mmol). The resulting mixture was stirred at 25° C. for 1 h to afford Solution A30. A solution of 4,4-dimethyl-2-(3-trifluoromethyl-phenyl)-1,2,3,4-tetrahydro-quinoline-6-carboxylic acid (350 mg, 1.0 mmol) and 1,1'-carbonyldiimidazole (320 mg, 2.0 mmol) in N,N-dimethylformamide (5 mL) was stirred at 70° C. for 1 h and cooled to room temperature to afford Solution B30. Solution B30 was added to Solution A30 and the resulting mixture was stirred at 25° C. for 1 h. To the reaction mixture was added water (0.5 mL). The mixture was filtered to remove the insoluble solid, and the filtrate was purified by Waters automated flash system (column: Xterra 30 mm×100 mm, sample manager 2767, pump 2525, detector: ZQ mass and UV 2487, solvent system: acetonitrile and 0.1% ammonium hydroxide in water) afforded N-[4,4-dimethyl-2-(3-trifluoromethyl-phenyl)-1,2,3,4-tetrahydro-quinoline-6-carbonyl]-methanesulfonamide (170 mg, 40%) as a white solid: MS (ESI) M+1=427.3.

Example 31

Cyclopropanesulfonic acid [4,4-dimethyl-2-(3-trifluoromethyl-phenyl)-1,2,3,4-tetrahydro-quinoline-6-carbonyl]-amide

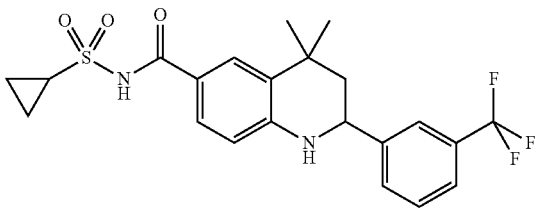 [SMILES: CC1(C)CC(c2cccc(C(F)(F)F)c2)Nc2ccc(C(=O)NS(=O)(=O)C3CC3)cc21]

To a suspension of cyclopropanesulfonamide (610 mg, 5.0 mmol) in N,N-dimethylformamide (5 mL) was added sodium hydride (200 mg, 5.0 mmol). The resulting mixture was stirred at 25° C. for 1 h to afford Solution A31. A solution of 4,4-dimethyl-2-(3-trifluoromethyl-phenyl)-1,2,3,4-tetrahydro-quinoline-6-carboxylic acid (350 mg, 1.0 mmol) and 1,1'-carbonyldiimidazole (320 mg, 2.0 mmol) in N,N-dimethylformamide (5 mL) was stirred at 70° C. for 1 h and cooled to room temperature to afford Solution B31. Solution B31 was added to Solution A31 and the resulting mixture was stirred at 25° C. for 1 h. To the reaction mixture was added water (0.5 mL). The mixture was filtered to remove the insoluble solid, and the filtrate was purified by Waters automated flash system (column: Xterra 30 mm×100 mm, sample manager 2767, pump 2525, detector: ZQ mass and UV 2487, solvent system: acetonitrile and 0.1% ammonium hydroxide in water) afforded cyclopropanesulfonic acid [4,4-dimethyl-2-(3-trifluoromethyl-phenyl)-1,2,3,4-tetrahydro-quinoline-6-carbonyl]-amide (140 mg, 30%) as a white solid: MS (ESI) M+1=453.3.

Example 32

3-(6-Methanesulfonylaminocarbonyl-4,4-dimethyl-1,2,3,4-tetrahydroquinolin-2-yl)-benzamide

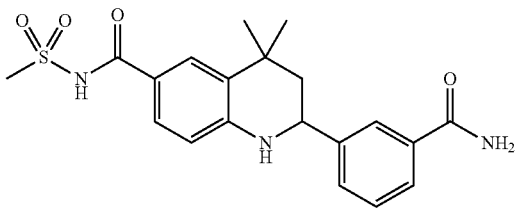 [SMILES: CC1(C)CC(c2cccc(C(N)=O)c2)Nc2ccc(C(=O)NS(C)(=O)=O)cc21]

A mixture of 4-aminobenzoic acid ethyl ester (3.3 g, 20 mmol), 3-formyl-benzonitrile (2.62 g, 20 mmol) and ytterbium(III) triflate hydrate (1.86 g, 3 mmol) in acetonitrile (150 mL) was cooled to 0° C. in a sealed reaction bottle. Then a cooled solution of isobutene (5.6 g, 100 mmol) was added into. The reaction mixture was heated to 90° C. and stirred for 12 h. The solvent was removed in vacuo and the residue was purified on flash silica gel chromatography (silica gel from QingDao, 200-300 mesh, glass column from Shanghai SD company) (10% ethyl acetate/hexanes) to afford 2-(3-cyano-phenyl)-4,4-dimethyl-1,2,3,4-tetrahydro-quinoline-6-carboxylic acid ethyl ester (3.0 g, 45%) as a white solid: MS (ESI) M+1=335.3.

A mixture of 2-(3-cyano-phenyl)-4,4-dimethyl-1,2,3,4-tetrahydro-quinoline-6-carboxylic acid ethyl ester (3.0 g, 7.96 mmol), sodium hydroxide (1.8 g, 44.9 mmol), water (15 mL) in acetonitrile (30 mL) was stirred at 60° C. for 4 h. The mixture was neutralized with a 3 N aqueous hydrochloric acid solution and extracted with ethyl acetate (2×50 mL), washed with water, dried over anhydrous sodium sulfate and then concentrated in vacuo to afford 2-(3-carbamoyl-phenyl)-4,4-dimethyl-1,2,3,4-tetrahydro-quinoline-6-carboxylic acid (0.58 g, 20%) as a white solid which was used for next step without further purification: MS (ESI) M+1=325.2.

To a suspension of methanesulfonamide (160 mg, 1.65 mmol) in N,N-dimethylformamide (3 mL) was added sodium hydride (66 mg, 1.65 mmol). The resulting mixture was stirred at 25° C. for 1 h to afford Solution A32. A solution of 2-(3-carbamoyl-phenyl)-4,4-dimethyl-1,2,3,4-tetrahydro-quinoline-6-carboxylic acid (100 mg, 0.33 mmol) and 1,1'-carbonyldiimidazole (110 mg, 0.66 mmol) in N,N-dimethylformamide (3 mL) was stirred at 70° C. for 1 h and cooled to room temperature to afford Solution B32. Solution B32 was added to Solution A32 and the resulting mixture was stirred at 25° C. for 1 h. To the reaction mixture was added water (0.5 mL). The mixture was filtered to remove the insoluble solid, and the filtrate was purified by Waters automated flash system (column: Xterra 30 mm×100 mm, sample manager 2767, pump 2525, detector: ZQ mass and UV 2487, solvent system: acetonitrile and 0.1% ammonium hydroxide in water) afforded 3-(6-methanesulfonylaminocarbonyl-4,4-dimethyl-1,2,3,4-tetrahydro-quinolin-2-yl)-benzamide (13 mg, 10%) as a white solid: MS (ESI) M+1=402.3.

Example 33

N-[2-(3-cyano-phenyl)-4,4-dimethyl-1,2,3,4-tetrahydro-quinoline-6-carbonyl]-methanesulfonamide

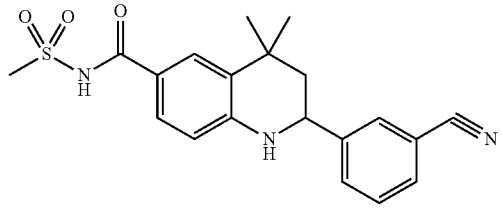 [SMILES: CC1(C)CC(c2cccc(C#N)c2)Nc2ccc(C(=O)NS(C)(=O)=O)cc21]

A mixture of 4-aminobenzoic acid ethyl ester (3.3 g, 20 mmol), 3-formyl-benzonitrile (2.62 g, 20 mmol) and ytterbium(III) triflate hydrate (1.86 g, 3 mmol) in acetonitrile (150 mL) was cooled to 0° C. in a sealed reaction bottle. Then a cooled solution of isobutene (5.6 g, 100 mmol) was added into. The reaction mixture was heated to 90° C. and stirred for 12 h. The solvent was removed in vacuo and the residue was purified on flash silica gel chromatography (silica gel from QingDao, 200-300 mesh, glass column from Shanghai SD company)(10% ethyl acetate/hexanes) to afford 2-(3-cyano-phenyl)-4,4-dimethyl-1,2,3,4-tetrahydro-quinoline-6-carboxylic acid ethyl ester (3.0 g, 45%) as a white solid: MS (ESI) M+1=335.3.

A mixture of 2-(3-cyano-phenyl)-4,4-dimethyl-1,2,3,4-tetrahydro-quinoline-6-carboxylic acid ethyl ester (3.0 g, 7.96 mmol), sodium hydroxide (1.8 g, 44.9 mmol), water (15 mL) in acetonitrile (30 mL) was stirred at 60° C. for 4 h. The mixture was neutralized with a 3 mol/L aqueous hydrochloric acid solution and extracted with ethyl acetate (2×50 mL), washed with water, dried over anhydrous sodium sulfate and then concentrated in vacuo to afford 2-(3-cyano-phenyl)-4,4-dimethyl-1,2,3,4-tetrahydro-quinoline-6-carboxylic acid (1.65 g, 60%) as a white solid which was used for next step without further purification: MS (ESI) M+1=307.2.

To a suspension of methanesulfonamide (160 mg, 1.65 mmol) in N,N-dimethylformamide (3 mL) was added sodium hydride (66 mg, 1.65 mmol). The resulting mixture was stirred at 25° C. for 1 h to afford Solution A33. A solution of 2-(3-cyano-phenyl)-4,4-dimethyl-1,2,3,4-tetrahydro-quinoline-6-carboxylic acid (100 mg, 0.33 mmol) and 1,1'-carbonyldiimidazole (110 mg, 0.66 mmol) in N,N-dimethylformamide (3 mL) was stirred at 70° C. for 1 h and cooled to room temperature to afford Solution B33. Solution B33 was added to Solution A33 and the resulting mixture was stirred at 25° C. for 1 h. To the reaction mixture was added water (0.5 mL). The mixture was filtered to remove the insoluble solid, and the filtrate was purified by Waters automated flash system (column: Xterra 30 mm×100 mm, sample manager 2767, pump 2525, detector: ZQ mass and UV 2487, solvent system: acetonitrile and 0.1% ammonium hydroxide in water) afforded N-[2-(3-cyano-phenyl)-4,4-dimethyl-1,2,3,4-tetrahydro-quinoline-6-carbonyl]-methanesulfonamide (25 mg, 20%) as a white solid: MS (ESI) M+1=384.3.

Example 34

3-(6-Cyclopropanesulfonylaminocarbonyl-4,4-dimethyl-1,2,3,4-tetrahydro-quinolin-2-yl)-benzamide

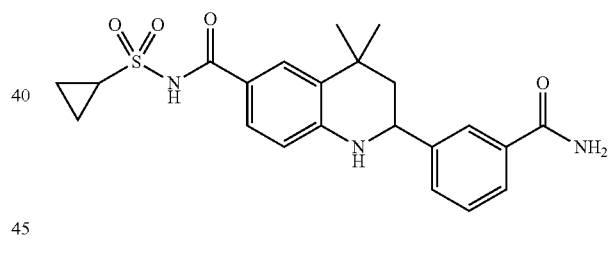

To a suspension of cyclopropanesulfonic acid amide (200 mg, 1.65 mmol) in N,N-dimethylformamide (3 mL) was added sodium hydride (66 mg, 1.65 mmol). The resulting mixture was stirred at 25° C. for 1 h to afford Solution A34. A solution of 2-(3-carbamoyl-phenyl)-4,4-dimethyl-1,2,3,4-tetrahydro-quinoline-6-carboxylic acid (100 mg, 0.33 mmol) and 1,1'-carbonyldiimidazole (110 mg, 0.66 mmol) in N,N-dimethylformamide (3 mL) was stirred at 70° C. for 1 h and cooled to room temperature to afford Solution B34. Solution B34 was added to Solution A34 and the resulting mixture was stirred at 25° C. for 1 h. To the reaction mixture was added water (0.5 mL). The mixture was filtered to remove the insoluble solid, and the filtrate was purified by Waters automated flash system (column: Xterra 30 mm×100 mm, sample manager 2767, pump 2525, detector: ZQ mass and UV 2487, solvent system: acetonitrile and 0.1% ammonium hydroxide in water) afforded 3-(6-cyclopropanesulfonylaminocarbonyl-4,4-dimethyl-1,2,3,4-tetrahydro-quinolin-2-yl)-benzamide (10 mg, 24%) as a white solid: MS (ESI) M+1=428.3.

Example 35

Cyclopropanesulfonic acid [2-(3-cyano-phenyl)-4,4-dimethyl-1,2,3,4-tetrahydro-quinoline-6-carbonyl]-amide

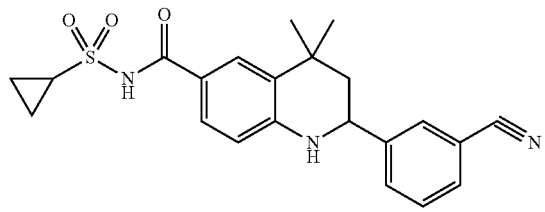 [SMILES: CC1(C)CC(c2cccc(C#N)c2)Nc2ccc(C(=O)NS(=O)(=O)C3CC3)cc21]

To a suspension of cyclopropanesulfonic acid amide (200 mg, 1.65 mmol) in N,N-dimethylformamide (3 mL) was added sodium hydride (66 mg, 1.65 mmol). The resulting mixture was stirred at 25° C. for 1 h to afford Solution A35. A solution of 2-(3-cyno-phenyl)-4,4-dimethyl-1,2,3,4-tetrahydro-quinoline-6-carboxylic acid (100 mg, 0.33 mmol) and 1,1'-carbonyldiimidazole (110 mg, 0.66 mmol) in N,N-dimethylformamide (3 mL) was stirred at 70° C. for 1 h and cooled to room temperature to afford Solution B35. Solution B35 was added to Solution A35 and the resulting mixture was stirred at 25° C. for 1 h. To the reaction mixture was added water (0.5 mL). The mixture was filtered to remove the insoluble solid, and the filtrate was purified by Waters automated flash system (column: Xterra 30 mm×100 mm, sample manager 2767, pump 2525, detector: ZQ mass and UV 2487, solvent system: acetonitrile and 0.1% ammonium hydroxide in water) afforded cyclopropanesulfonic acid [2-(3-cyano-phenyl)-4,4-dimethyl-1,2,3,4-tetrahydro-quinoline-6-carbonyl]-amide (10 mg, 24%) as a white solid: MS (ESI) M+1=410.3.

Example 36

N-[2-(3-methoxy-phenyl)-4,4-dimethyl-1,2,3,4-tetrahydro-quinoline-6-carbonyl]-methanesulfonamide

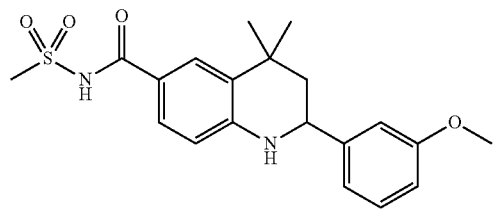

A mixture of 4-aminobenzoic acid ethyl ester (3.3 g, 20 mmol), 3-methoxy benzaldehyde (2.72 g, 20 mmol) and ytterbium(III) triflate hydrate (1.86 g, 3 mmol) in acetonitrile (150 mL) was cooled to 0° C. in a sealed reaction bottle. Then a cooled solution of isobutene (5.6 g, 100 mmol) was added into. The reaction mixture was heated to 90° C. and stirred for 12 h. The solvent was removed in vacuo and the residue was purified on flash silica gel chromatography (silica gel from QingDao, 200-300 mesh, glass column from Shanghai SD company) (10% ethyl acetate/hexanes) to afford N-[2-(3-methoxy-phenyl)-4,4-dimethyl-1,2,3,4-tetrahydro-quinoline-6-carbonyl]-methanesulfonamide (1.0 g, 15%) as a white solid: MS (ESI) M+1=340.3.

A mixture of N-[2-(3-methoxy-phenyl)-4,4-dimethyl-1,2,3,4-tetrahydro-quinoline-6-carbonyl]-methanesulfonamide (1.0 g, 2.95 mmol), sodium hydroxide (0.59 g, 14.75 mmol), water (15 mL) in acetonitrile (30 mL) was stirred at 60° C. for 12 h. The mixture was neutralized with a 3 N aqueous hydrochloric acid solution and extracted with ethyl acetate (2×50 mL), washed with water, dried over anhydrous sodium sulfate and then concentrated in vacuo to afford 2-(3-methoxy-phenyl)-4,4-dimethyl-1,2,3,4-tetrahydro-quinoline-6-carboxylic acid (0.83 g, 90%) as a white solid which was used for next step without further purification: MS (ESI) M+1=312.2.

To a suspension of methanesulfonamide (480 mg, 5.0 mmol) in N,N-dimethylformamide (5 mL) was added sodium hydride (200 mg, 5.0 mmol). The resulting mixture was stirred at 25° C. for 1 h to afford Solution A36. A solution of 2-(3-methoxy-phenyl)-4,4-dimethyl-1,2,3,4-tetrahydro-quinoline-6-carboxylic acid (310 mg, 1.0 mmol) and 1,1'-carbonyldiimidazole (320 mg, 2.0 mmol) in N,N-dimethylformamide (5 mL) was stirred at 70° C. for 1 h and cooled to room temperature to afford Solution B36. Solution B36 was added to Solution A36 and the resulting mixture was stirred at 25° C. for 1 h. To the reaction mixture was added water (0.5 mL). The mixture was filtered to remove the insoluble solid, and the filtrate was purified by Waters automated flash system (column: Xterra 30 mm×100 mm, sample manager 2767, pump 2525, detector: ZQ mass and UV 2487, solvent system: acetonitrile and 0.1% ammonium hydroxide in water) afforded N-[2-(3-methoxy-phenyl)-4,4-dimethyl-1,2,3,4-tetrahydro-quinoline-6-carbonyl]-methanesulfonamide (116 mg, 30%) as a white solid: MS (ESI) M+1=389.3.

Example 37

N-[2-(3-methanesulfonyl-phenyl)-4,4-dimethyl-1,2,3,4-tetrahydro-quinoline-6-carbonyl]-methanesulfonamide

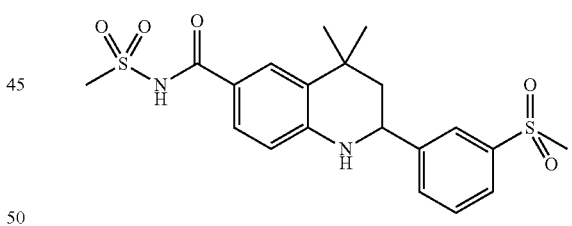

A mixture of 4-aminobenzoic acid ethyl ester (3.3 g, 20 mmol), 3-methanesulfonyl benzaldehyde (3.68 g, 20 mmol) and ytterbium(III) triflate hydrate (1.86 g, 3 mmol) in acetonitrile (150 mL) was cooled to 0° C. in a sealed reaction bottle. Then a cooled solution of isobutene (5.6 g, 100 mmol) was added into. The reaction mixture was heated to 90° C. and stirred for 12 h. The solvent was removed in vacuo and the residue was purified on flash silica gel chromatography (silica gel from QingDao, 200-300 mesh, glass column from Shanghai SD company) (10% ethyl acetate/hexanes) to afford 2-(3-methanesulfonyl-phenyl)-4,4-dimethyl-1,2,3,4-tetrahydro-quinoline-6-carboxylic acid ethyl ester (3.3 g, 43%) as a white solid: MS (ESI) M+1=388.3.

A mixture of 2-(3-methanesulfonyl-phenyl)-4,4-dimethyl-1,2,3,4-tetrahydro-quinoline-6-carboxylic acid ethyl ester (3.3 g, 8.53 mmol), sodium hydroxide (3.41 g, 85.3 mmol), water (10 mL) in acetonitrile (30 mL) was stirred at 60° C. for 12 h. The mixture was neutralized with a 3 mol/L aqueous hydrochloric acid solution and extracted with ethyl acetate (2×50 mL), washed with water, dried over anhydrous sodium sulfate and then concentrated in vacuo to afford 2-(3-methanesulfonyl-phenyl)-4,4-dimethyl-1,2,3,4-tetrahydro-quinoline-6-carboxylic acid (2.76 g, 90%) as a white solid which was used for next step without further purification: MS (ESI) M+1=360.3.

To a suspension of methanesulfonamide (480 mg, 5.0 mmol) in N,N-dimethylformamide (5 mL) was added sodium hydride (200 mg, 5.0 mmol). The resulting mixture was stirred at 25° C. for 1 h to afford Solution A37. A solution of 2-(3-methanesulfonyl-phenyl)-4,4-dimethyl-1,2,3,4-tetrahydro-quinoline-6-carboxylic acid (359 mg, 1.0 mmol) and 1,1'-carbonyldiimidazole (320 mg, 2.0 mmol) in N,N-dimethylformamide (5 mL) was stirred at 70° C. for 1 h and cooled to room temperature to afford Solution B37. Solution B37 was added to Solution A37 and the resulting mixture was stirred at 25° C. for 1 h. To the reaction mixture was added water (0.5 mL). The mixture was filtered to remove the insoluble solid, and the filtrate was purified by Waters automated flash system (column: Xterra 30 mm×100 mm, sample manager 2767, pump 2525, detector: ZQ mass and UV 2487, solvent system: acetonitrile and 0.1% ammonium hydroxide in water) afforded N-[2-(3-methanesulfonyl-phenyl)-4,4-dimethyl-1,2,3,4-tetrahydro-quinoline-6-carbonyl]-methanesulfonamide (100 mg, 23%) as a white solid: MS (ESI) M+1=437.3.

Example 38

Cyclopropanesulfonic acid [2-(3-methanesulfonyl-phenyl)-4,4-dimethyl-1,2,3,4-tetrahydro-quinoline-6-carbonyl]-amide

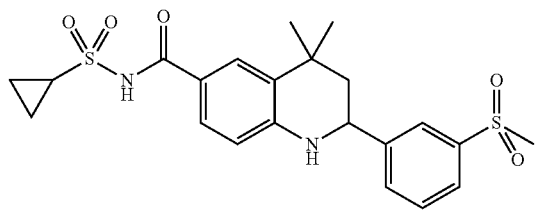 [SMILES: CC1(C)CC(c2cccc(S(C)(=O)=O)c2)Nc2ccc(C(=O)NS(=O)(=O)C3CC3)cc21]

To a suspension of cyclopropanesulfonic acid amide (605 mg, 5.0 mmol) in N,N-dimethylformamide (5 mL) was added sodium hydride (200 mg, 5.0 mmol). The resulting mixture was stirred at 25° C. for 1 h to afford Solution A38. A solution of 2-(3-methanesulfonyl-phenyl)-4,4-dimethyl-1,2,3,4-tetrahydro-quinoline-6-carboxylic acid (359 mg, 1.0 mmol) and 1,1'-carbonyldiimidazole (320 mg, 2.0 mmol) in N,N-dimethylformamide (5 mL) was stirred at 70° C. for 1 h and cooled to room temperature to afford Solution B38. Solution B38 was added to Solution A38 and the resulting mixture was stirred at 25° C. for 1 h. To the reaction mixture was added water (0.5 mL). The mixture was filtered to remove the insoluble solid, and the filtrate was purified by Waters automated flash system (column: Xterra 30 mm×100 mm, sample manager 2767, pump 2525, detector: ZQ mass and UV 2487, solvent system: acetonitrile and 0.1% ammonium hydroxide in water) afforded cyclopropanesulfonic acid [2-(3-methanesulfonyl-phenyl)-4,4-dimethyl-1,2,3,4-tetrahydro-quinoline-6-carbonyl]-amide (60 mg, 13%) as a white solid: MS (ESI) M+1=463.4.

Example 39

N-[2-(4'-tert-butyl-biphenyl-3-yl)-4,4-dimethyl-1,2,3,4-tetrahydro-quinoline-6-carbonyl]-methanesulfonamide

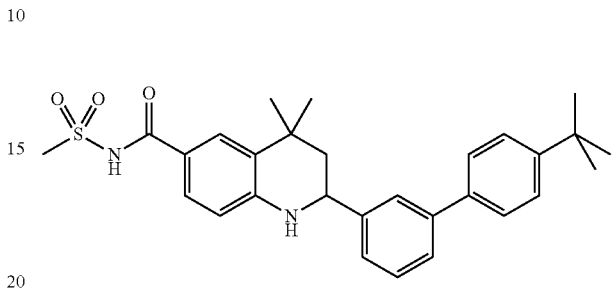

A mixture of 4-aminobenzoic acid ethyl ester (16.5 g, 100 mmol), 3-bromo benzaldehyde (18.5 g, 100 mmol) and ytterbium(III) triflate hydrate (12.4 g, 20 mmol) in acetonitrile (350 mL) was cooled to 0° C. in a sealed reaction bottle. Then a cooled solution of isobutene (28 g, 500 mmol) was added into. The reaction mixture was heated to 90° C. and stirred for 12 h. The solvent was removed in vacuo and the residue was purified on flash silica gel chromatography (silica gel from QingDao, 200-300 mesh, glass column from Shanghai SD company) (10% ethyl acetate/hexanes) to afford 2-(3-bromo-phenyl)-4,4-dimethyl-1,2,3,4-tetrahydro-quinoline-6-carboxylic acid ethyl ester (16.7 g, 43%) as a white solid: MS (ESI) M+1=388.0.

A mixture of 2-(3-bromo-phenyl)-4,4-dimethyl-1,2,3,4-tetrahydro-quinoline-6-carboxylic acid ethyl ester (1.0 g, 2.6 mmol), 4-tert-butylbenzeneboronic acid (0.50 g, 2.6 mmol), bis(triphenylphosphine)palladium (II) chloride (180 mg, 0.26 mmol) and 2 M sodium carbonate (3.9 mL, 7.8 mmol) in dioxane (5 mL) was heated for 3 h at 120° C. After coiling to room temperature, the mixture was treated with ethyl acetate (50 mL) and washed with water (20 mL). The organic layer was dried over anhydrous sodium sulfate and concentrated in vacuo. Purification on flash silica gel chromatography (silica gel from QingDao, 200-300 mesh, glass column from Shanghai SD company) (10% ethyl acetate/hexanes) to afford 2-(4'-tert-butyl-biphenyl-3-yl)-4,4-dimethyl-1,2,3,4-tetrahydro-quinoline-6-carboxylic acid ethyl ester (0.36 g, 31%) as a white solid: MS (ESI) M+1=442.2.

A mixture of 2-(4'-tert-butyl-biphenyl-3-yl)-4,4-dimethyl-1,2,3,4-tetrahydro-quinoline-6-carboxylic acid ethyl ester (0.17 g, 0.37 mmol) in ethanol (3 mL) and tetrahydrofuran (5 mL), 30% sodium hydroxide in water (1 mL). The reaction mixture was stirred at 60° C. for 12 h. The mixture was neutralized with a 3 N aqueous hydrochloric acid solution and extracted with ethyl acetate (2×50 mL), washed with water, dried over anhydrous sodium sulfate and then concentrated in vacuo to afford 2-(4'-tert-butyl-biphenyl-3-yl)-4,4-dimethyl-1,2,3,4-tetrahydro-quinoline-6-carboxylic acid (0.29 g, 90%) as a white solid which was used for next step without further purification: MS (ESI) M+1=414.2.

A mixture of 2-(4'-tert-butyl-biphenyl-3-yl)-4,4-dimethyl-1,2,3,4-tetrahydro-quinoline-6-carboxylic acid (100 mg, 0.24 mmol), 1-3-dimethylaminopropyl-3-ethylcarbodiimide hydrochloride (70 mg, 0.36 mmol), 4-dimethylaminopyridine (44 mg, 0.36 mmol), methane sulfonamide (68.4 mg, 0.72 mmol) in dichloromethane (10 mL) was refluxed for 12 h. Removal of the solvent to afford the oil residue. Purification by Waters automated flash system (column: Xterra 30 mm×100 mm, sample manager 2767, pump 2525, detector: ZQ mass and UV 2487, solvent system: acetonitrile and 0.1% formic acid in water) afforded N-[2-(4'-tert-butyl-biphenyl-3-yl)-4,4-dimethyl-1,2,3,4-tetrahydro-quinoline-6-carbonyl]-methanesulfonamide (23.5 mg, 20%) as a light yellow solid: MS (ESI) M+1=491.

Example 40

Cyclopropanesulfonic acid [2-(4'-tert-butyl-biphenyl-3-yl)-4,4-dimethyl-1,2,3,4-tetrahydro-quinoline-6-carbonyl]-amide

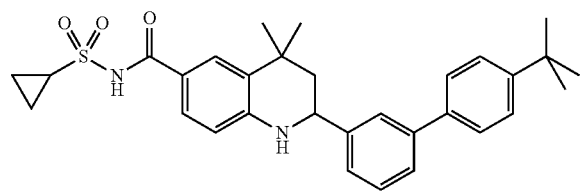 [SMILES: CC(C)(C)c1ccc(-c2cccc(C3CC(C)(C)c4cc(C(=O)NS(=O)(=O)C5CC5)ccc4N3)c2)cc1]

A mixture of 2-(4'-tert-butyl-biphenyl-3-yl)-4,4-dimethyl-1,2,3,4-tetrahydro-quinoline-6-carboxylic acid (100 mg, 0.24 mmol), 1-(3-dimethylaminopropyl)-3-ethylcarbodiimide hydrochloride (70 mg, 0.36 mmol), 4-dimethylaminopyridine (44 mg, 0.36 mmol), cyclopropane sulfonic acid amide (85 mg, 0.72 mmol) in dichloromethane (10 mL) was refluxed for 12 h. Removal of the solvent to afford the oil residue. Purification by Waters automated flash system (column: Xterra 30 mm×100 mm, sample manager 2767, pump 2525, detector: ZQ mass and UV 2487, solvent system: acetonitrile and 0.1% formic acid in water) afforded cyclopropanesulfonic acid [2-(4'-tert-butyl-biphenyl-3-yl)-4,4-dimethyl-1,2,3,4-tetrahydro-quinoline-6-carbonyl]-amide (12 mg, 10%) as a light yellow solid: MS (ESI) M+1=517.2.

Example 41

Cyclopropanesulfonic acid {2-[3-(1-cyclopropyl-1H-tetrazol-5-yl)-phenyl]-4,4-dimethyl-1,2,3,4-tetrahydro-quinoline-6-carbonyl}-amide

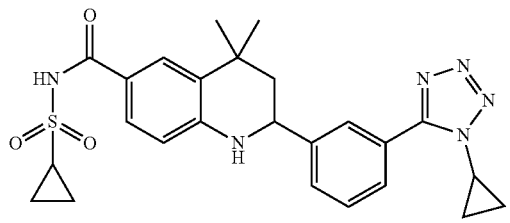 [SMILES: CC1(C)CC(c2cccc(-c3nnnn3C3CC3)c2)Nc2ccc(C(=O)NS(=O)(=O)C3CC3)cc21]

To a stirred solution of 4-amino-benzoic acid ethyl ester (12.9 g, 78.4 mmol) and 3-formyl-benzoic acid methyl ester (12.9 g, 78.4 mmol) in acetonitrile (150 mL) were added isobutene (21.0 mL, 313.5 mmol) and ytterbium(III) trifluoromethanesulfonate (Yb(OTf)$_3$) (5.8 g, 9.5 mmol). The resulting mixture was stirred at 85° C. for 18 h in sealed tube. The mixture was diluted with ethyl acetate (300 mL) and washed with water (100 mL×2) and brine (100 mL×2) and then dried over anhydrous sodium sulfate. The solvent was removed in vacuo and the residue was purified by ISCO combi-flash chromatography (gradient elution, 10-50% ethyl acetate in petroleum ether) to afford 2-(3-methoxycarbonyl-phenyl)-4,4-dimethyl-1,2,3,4-tetrahydro-quinoline-6-carboxylic acid ethyl ester (10.1 g, 35.0%) as a light yellow solid: MS (ESI) M+1=368.1.

To a stirred mixture solution of 2-(3-methoxycarbonyl-phenyl)-4,4-dimethyl-1,2,3,4-tetrahydro-quinoline-6-carboxylic acid ethyl ester (3.7 g, 10.0 mmol) in tetrahydrofuran (20.0 mL) was added 4.0 N lithium hydroxide in water (12.0 mL). The reaction mixture was stirred at room temperature for 6 h. The mixture was neutralized with a 3 N aqueous hydrochloric acid solution and extracted with ethyl acetate (2×100 mL), washed with water, dried over anhydrous sodium sulfate and then concentrated in vacuo to afford 2-(3-carboxy-phenyl)-4,4-dimethyl-1,2,3,4-tetrahydro-quinoline-6-carboxylic acid ethyl ester (3.6 g, quant.) as a light white solid which was used for next step without further purification: MS (ESI) M+1=354.1.

The mixture solution of 2-(3-carboxy-phenyl)-4,4-dimethyl-1,2,3,4-tetrahydro-quinoline-6-carboxylic acid ethyl ester (1.2 g, 3.3 mmol), o-(7-azabenzotriazol-1-yl)-N,N,N',N'-tetramethyluronium hexafluorophosphate (HATU) (1.52 g, 4.0 mmol), triethylamine (2.0 mL), cyclopropylamine (330.6 mg, 5.8 mmol) in dry dichloromethane (20.0 mL) was stirred at room temperature for 1 hour, LC/MS showed that reaction finished completely. The reaction mixture was extracted with ethyl acetate, washed with brine, dried over anhydrous sodium sulfate and concentrated in vacuo to afford 2-(3-cyclopropylcarbamoyl-phenyl)-4,4-dimethyl-1,2,3,4-tetrahydro-quinoline-6-carboxylic acid ethyl ester (1.3 g, quant.) as a light yellow solid which was used for next step without further purification: MS (ESI) M+1=393.1.

To a stirred solution of tetrachlorosilane (5.3 mL, 46.3 mmol), sodium azide (5.6 g, 87 mmol) in dry acetonitrile (20 mL) was added 2-(3-cyclopropylcarbamoyl-phenyl)-4,4-dimethyl-1,2,3,4-tetrahydro-quinoline-6-carboxylic acid ethyl ester (1.3 g, 3.3 mmol) at room temperature. Then the mixture solution was stirred at room temperature for over night. LC/MS showed that reaction finished completely. The reaction mixture was poured into ice-cold saturated aqueous sodium bicarbonate solution and extracted with ethyl acetate (150 mL×2), washed with brine, dried over anhydrous sodium sulfate and concentrated in vacuo. Purification by flash silica gel chromatography (silica gel from QingDao, 200-300 mesh, glass column from Shanghai SD company) (30% ethyl acetate/hexanes) afforded 2-[3-(1-cyclopropyl-1H-tetrazol-5-yl)-phenyl]-4,4-dimethyl-1,2,3,4-tetrahydro-quinoline-6-carboxylic acid ethyl ester (908.2 mg, 66%) as a white solid: MS (ESI) M+1=418.1.

To a stirred mixture solution of 2-[3-(1-cyclopropyl-1H-tetrazol-5-yl)-phenyl]-4,4-dimethyl-1,2,3,4-tetrahydro-quinoline-6-carboxylic acid ethyl ester (908.0 mg, 2.2 mmol) in methanol (10.0 mL) and tetrahydrofuran (10.0 mL) was added 50% sodium hydroxide in water (2.0 mL). The reaction mixture was stirred at 70° C. for 6 h. The mixture was neutralized with a 3 N aqueous hydrochloric acid solution and extracted with ethyl acetate (100 mL×2), washed with water, dried over anhydrous sodium sulfate and then concentrated in vacuo. Purification by Waters automated flash system (column: Xterra 30 mm×100 mm, sample manager 2767, pump 2525, detector: ZQ mass and UV 2487, solvent system: acetonitrile and 0.1% ammonium hydroxide in water) afforded 2-[3-(1-cyclopropyl-1H-tetrazol-5-yl)-phenyl]-4,4-dimethyl-1,2,3,4-tetrahydro-quinoline-6-carboxylic acid (770.2 mg, 90%) as a off-yellow solid: MS (ESI) M+1=390.1.

To a suspension of 60% sodium hydride (535 mg, 13.7 mmol) in N,N-dimethylformamide (2.5 mL) was added cyclopropanesulfonamide (1.65 g, 13.8 mmol) at room temperature. The resulting mixture was stirred at 25° C. for 1 h to afford Solution A41. A solution of 2-[3-(1-cyclopropyl-1H-tetrazol-5-yl)-phenyl]-4,4-dimethyl-1,2,3,4-tetrahydro-quinoline-6-carboxylic acid (544.6 mg, 1.4 mmol) and 1,1'-carbonyldiimidazole (442 mg, 2.76 mmol) in N,N-dimethylformamide (2.0 mL) was stirred at 70° C. for 1 h and cooled to room temperature to afford Solution B41. Solution B41 was added to Solution A41 and the resulting mixture was stirred at 25° C. for 1 h. To the reaction mixture was added water (0.5 mL). The mixture was filtered to remove the insoluble solid, and the filtrate was purified by Waters automated flash system (column: Xterra 30 mm×100 mm, sample manager 2767, pump 2525, detector: ZQ mass and UV 2487, solvent system: acetonitrile and 0.1% ammonium hydroxide in water) afforded cyclopropanesulfonic acid {2-[3-(1-cyclopropyl-1H-tetrazol-5-yl)-phenyl]-4,4-dimethyl-1,2,3,4-tetrahydro-quinoline-6-carbonyl}-amide (206.6 mg, 30%) as a white solid: MS (ESI) M+1=493.2.

Example 42

Cyclopropanesulfonic acid {4,4-dimethyl-2-[3-(1-methyl-1H-tetrazol-5-yl)-phenyl]-1,2,3,4-tetrahydro-quinoline-6-carbonyl}-amide

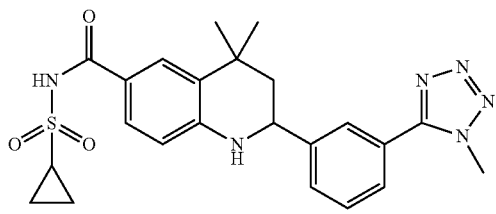 [SMILES: Cn1nnnc1-c1cccc(C2CC(C)(C)c3cc(C(=O)NS(=O)(=O)C4CC4)ccc3N2)c1]

The mixture solution of 2-(3-carboxy-phenyl)-4,4-dimethyl-1,2,3,4-tetrahydro-quinoline-6-carboxylic acid ethyl ester (1.2 g, 3.3 mmol), o-(7-azabenzotriazol-1-yl)-N,N,N',N'-tetramethyluronium hexafluorophosphate (HATU) (1.52 g, 4.0 mmol), triethylamine (2.0 mL), methylamine (228.1 mg, 5.8 mmol) in dry dichloromethane (20.0 mL) was stirred at room temperature for 1 hour, LC/MS showed that reaction finished completely. The reaction mixture was extracted with ethyl acetate, washed with brine, dried over anhydrous sodium sulfate and concentrated in vacuo to afford 4,4-dimethyl-2-(3-methylcarbamoyl-phenyl)-1,2,3,4-tetrahydro-quinoline-6-carboxylic acid ethyl ester (1.23 g, quant.) as a light yellow solid which was used for next step without further purification: MS (ESI) M+1=367.1.

To a stirred solution of tetrachlorosilane (5.3 mL, 46.3 mmol), sodium azide (5.6 g, 87 mmol) in dry acetonitrile (20 mL) was added 4,4-dimethyl-2-(3-methylcarbamoyl-phenyl)-1,2,3,4-tetrahydro-quinoline-6-carboxylic acid ethyl ester (1.23 g, 3.3 mmol) at room temperature. Then the mixture solution was stirred at room temperature for over night. LC/MS showed that reaction finished completely. The reaction mixture was poured into ice-cold saturated aqueous sodium bicarbonate solution and extracted with ethyl acetate (150 mL×2), washed with brine, dried over anhydrous sodium sulfate and concentrated in vacuo. Purification by flash silica gel chromatography (silica gel from QingDao, 200-300 mesh, glass column from Shanghai SD company) (30% ethyl acetate/hexanes) afforded 4,4-dimethyl-2-[3-(1-methyl-1H-tetrazol-5-yl)-phenyl]-1,2,3,4-tetrahydro-quinoline-6-carboxylic acid ethyl ester (851.6 mg, 66%) as a white solid: MS (ESI) M+1=392.1.

To a stirred mixture solution of 24,4-dimethyl-2-[3-(1-methyl-1H-tetrazol-5-yl)-phenyl]-1,2,3,4-tetrahydro-quinoline-6-carboxylic acid ethyl ester (851.0 mg, 2.2 mmol) in methanol (10.0 mL) and tetrahydrofuran (10.0 mL) was added 50% sodium hydroxide in water (2.0 mL). The reaction mixture was stirred at 70° C. for 6 h. The mixture was neutralized with a 3 N aqueous hydrochloric acid solution and extracted with ethyl acetate (100 mL×2), washed with water, dried over anhydrous sodium sulfate and then concentrated in vacuo. Purification by Waters automated flash system (column: Xterra 30 mm×100 mm, sample manager 2767, pump 2525, detector: ZQ mass and UV 2487, solvent system: acetonitrile and 0.1% ammonium hydroxide in water) afforded 4,4-dimethyl-2-[3-(1-methyl-1H-tetrazol-5-yl)-phenyl]-1,2,3,4-tetrahydro-quinoline-6-carboxylic acid (718.7 mg, 90%) as a off-yellow solid: MS (ESI) M+1=364.1.

To a suspension of 60% sodium hydride (267.5 mg, 6.9 mmol) in N,N-dimethylformamide (2.5 mL) was added cyclopropanesulfonamide (0.83 g, 6.9 mmol) at room temperature. The resulting mixture was stirred at 25° C. for 1 h to afford Solution A42. A solution of 4,4-dimethyl-2-[3-(1-methyl-1H-tetrazol-5-yl)-phenyl]-1,2,3,4-tetrahydro-quinoline-6-carboxylic acid (254.1 mg, 0.7 mmol) and 1,1'-carbonyldiimidazole (221.0 mg, 1.4 mmol) in N,N-dimethylformamide (2.0 mL) was stirred at 70° C. for 1 h and cooled to room temperature to afford Solution B42. Solution B42 was added to Solution A42 and the resulting mixture was stirred at 25° C. for 1 h. To the reaction mixture was added water (0.5 mL). The mixture was filtered to remove the insoluble solid, and the filtrate was purified by Waters automated flash system (column: Xterra 30 mm×100 mm, sample manager 2767, pump 2525, detector: ZQ mass and UV 2487, solvent system: acetonitrile and 0.1% ammonium hydroxide in water) afforded cyclopropanesulfonic acid {4,4-dimethyl-2-[3-(1-methyl-1H-tetrazol-5-yl)-phenyl]-1,2,3,4-tetrahydro-quinoline-6-carbonyl}-amide (97.8 mg, 30%) as a white solid: MS (ESI) M+1=467.1.

Example 43

N-{2-[3-(1-cyclopropyl-1H-tetrazol-5-yl)-phenyl]-4,4-dimethyl-1,2,3,4-tetrahydro-quinoline-6-carbonyl}-methanesulfonamide

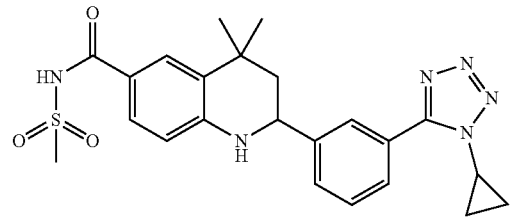 [SMILES: CC1(C)CC(c2cccc(-c3nnnn3C3CC3)c2)Nc2ccc(C(=O)NS(C)(=O)=O)cc21]

To a suspension of 60% sodium hydride (535.0 mg, 13.7 mmol) in N,N-dimethylformamide (2.5 mL) was added methanesulfonamide (1.3 g, 13.8 mmol) at room temperature. The resulting mixture was stirred at 25° C. for 1 h to afford Solution A43. A solution of 2-[3-(1-cyclopropyl-1H-tetrazol-5-yl)-phenyl]-4,4-dimethyl-1,2,3,4-tetrahydro-quinoline-6-carboxylic acid (544.6 mg, 1.4 mmol) and 1,1'-carbonyldiimidazole (442.0 mg, 2.76 mmol) in N,N-dimethylformamide (2.0 mL) was stirred at 70° C. for 1 h and cooled to room temperature to afford Solution B43. Solution B43 was added to Solution A43 and the resulting mixture was stirred at 25° C. for 1 h. To the reaction mixture was added water (0.5 mL). The mixture was filtered to remove the insoluble solid, and the filtrate was purified by Waters automated flash system (column: Xterra 30 mm×100 mm, sample manager 2767, pump 2525, detector: ZQ mass and UV 2487, solvent system: acetonitrile and 0.1% ammonium hydroxide in water) afforded N-{2-[3-(1-cyclopropyl-1H-tetrazol-5-yl)-phenyl]-4,4-dimethyl-1,2,3,4-tetrahydro-quinoline-6-carbonyl}-methanesulfonamide (195.7 mg, 30%) as a white solid: MS (ESI) M+1=467.2.

Example 44

N-{4,4-dimethyl-2-[3-(1-methyl-1H-tetrazol-5-yl)-phenyl]-1,2,3,4-tetrahydro-quinoline-6-carbonyl}-methanesulfonamide

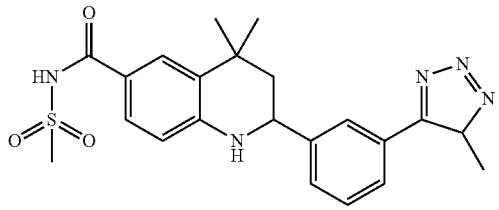 [SMILES: CC1N=NN=C1c1cccc(C2CC(C)(C)c3cc(C(=O)NS(C)(=O)=O)ccc3N2)c1]

To a suspension of 60% sodium hydride (267.5 mg, 6.9 mmol) in N,N-dimethylformamide (2.5 mL) was added methanesulfonamide (655.5 mg, 6.9 mmol) at room temperature. The resulting mixture was stirred at 25° C. for 1 h to afford Solution A44. A solution of 4,4-dimethyl-2-[3-(1-methyl-1H-tetrazol-5-yl)-phenyl]-1,2,3,4-tetrahydro-quinoline-6-carboxylic acid (254.1 mg, 0.7 mmol) and 1,1'-carbonyldiimidazole (221.0 mg, 1.4 mmol) in N,N-dimethylformamide (2.0 mL) was stirred at 70° C. for 1 h and cooled to room temperature to afford Solution B44. Solution B44 was added to Solution A44 and the resulting mixture was stirred at 25° C. for 1 h. To the reaction mixture was added water (0.5 mL). The mixture was filtered to remove the insoluble solid, and the filtrate was purified by Waters automated flash system (column: Xterra 30 mm×100 mm, sample manager 2767, pump 2525, detector: ZQ mass and UV 2487, solvent system: acetonitrile and 0.1% ammonium hydroxide in water) afforded N-{4,4-dimethyl-2-[3-(1-methyl-1H-tetrazol-5-yl)-phenyl]-1,2,3,4-tetrahydro-quinoline-6-carbonyl}-methanesulfonamide (97.8 mg, 30%) as a white solid: MS (ESI) M+1=441.1.

Example 45

N-[2-(4'-isopropoxy-biphenyl-3-yl)-4,4-dimethyl-1,2,3,4-tetrahydro-quinoline-6-carbonyl]-methanesulfonamide

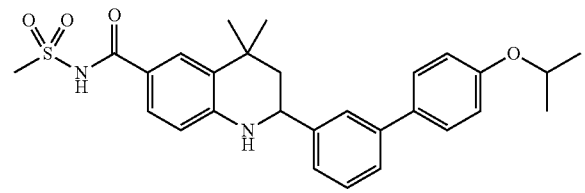 [SMILES: CC(C)Oc1ccc(-c2cccc(C3CC(C)(C)c4cc(C(=O)NS(C)(=O)=O)ccc4N3)c2)cc1]

A mixture of 2-(3-bromo-phenyl)-4,4-dimethyl-1,2,3,4-tetrahydro-quinoline-6-carboxylic acid ethyl ester (0.43 g, 1.1 mmol), 4-isopropoxy benzeneboronic acid (0.40 g, 2.2 mmol), bis(triphenylphosphine)palladium (II) chloride (77.2 mg, 0.11 mmol) and 2 M sodium carbonate (1.6 mL, 3.2 mmol) in dioxane (5 mL) was heated for 3 h at 120° C. After coiling to room temperature, the mixture was treated with ethyl acetate (50 mL) and washed with water (20 mL). The organic layer was dried over anhydrous sodium sulfate and concentrated in vacuo. Purification on flash silica gel chromatography (silica gel from QingDao, 200-300 mesh, glass column from Shanghai SD company) (10% ethyl acetate/hexanes) to afford 2-(4'-isopropoxy-biphenyl-3-yl)-4,4-dimethyl-1,2,3,4-tetrahydro-quinoline-6-carboxylic acid ethyl ester (0.44 g, 90%) as a white solid: MS (ESI) M+1=444.1.

A mixture of 2-(4'-isopropoxy-biphenyl-3-yl)-4,4-dimethyl-1,2,3,4-tetrahydro-quinoline-6-carboxylic acid ethyl ester (0.44 g, 1.0 mmol) in ethanol (5 mL) and tetrahydrofuran (20 mL), 30% sodium hydroxide in water (2 mL). The reaction mixture was stirred at 60° C. for 12 h. The mixture was neutralized with a 3 N aqueous hydrochloric acid solution and extracted with ethyl acetate (2×50 mL), washed with water, dried over anhydrous sodium sulfate and then concentrated in vacuo to afford 2-(4'-isopropoxy-biphenyl-3-yl)-4,4-dimethyl-1,2,3,4-tetrahydro-quinoline-6-carboxylic acid (0.40 g, 91%) as a white solid which was used for next step without further purification: MS (ESI) M+1=416.1.

A mixture of 2-(4'-isopropoxy-biphenyl-3-yl)-4,4-dimethyl-1,2,3,4-tetrahydro-quinoline-6-carboxylic acid (120 mg, 0.29 mmol), 1-(3-dimethylaminopropyl)-3-ethylcarbodiimide hydrochloride (83 mg, 0.43 mmol), 4-dimethylaminopyridine (52.5 mg, 0.43 mmol), methane sulfonamide (83 mg, 0.87 mmol) in dichloromethane (10 mL) was refluxed for 12 h. Removal of the solvent to afford the oil residue. Purification by Waters automated flash system (column: Xterra 30 mm×100 mm, sample manager 2767, pump 2525, detector: ZQ mass and UV 2487, solvent system: acetonitrile and 0.1% formic acid in water) afforded N-[2-(4'-isopropoxy-biphenyl-3-yl)-4,4-dimethyl-1,2,3,4-tetrahydro-quinoline-6-carbonyl]-methanesulfonamide (28.5 mg, 20%) as a light yellow solid: MS (ESI) M+1=493.1.

Example 46

Cyclopropanesulfonic acid [2-(4'-isopropoxy-biphenyl-3-yl)-4,4-dimethyl-1,2,3,4-tetrahydro-quinoline-6-carbonyl]-amide

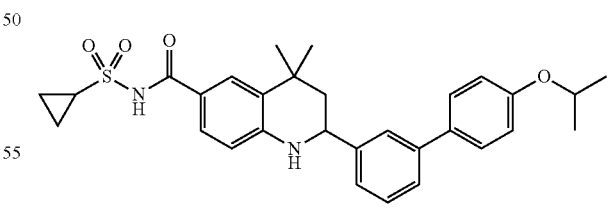

A mixture of 2-(4'-isopropoxy-biphenyl-3-yl)-4,4-dimethyl-1,2,3,4-tetrahydro-quinoline-6-carboxylic acid (120 mg, 0.29 mmol), 1-3-dimethylaminopropyl-3-ethylcarbodiimide hydrochloride (83 mg, 0.43 mmol), 4-dimethylaminopyridine (52.5 mg, 0.43 mmol), cyclopropane sulfonic acid amide (110 mg, 0.87 mmol) in dichloromethane (10 mL) was refluxed for 12 h. Removal of the solvent afforded an oil residue. Purification by Waters automated flash system (column: Xterra 30 mm×100 mm, sample manager 2767, pump 2525, detector: ZQ mass and UV 2487, solvent system: acetonitrile and 0.1% formic acid in water) afforded cyclopropanesulfonic acid [2-(4'-isopropoxy-biphenyl-3-yl)-4,4-dimethyl-1,2,3,4-tetrahydro-quinoline-6-carbonyl]-amide (45 mg, 30%) as a light yellow solid: MS (ESI) M+1=519.1.

Example 47

Cyclopropanesulfonic acid [2-(2-ethyl-5-morpholin-4-yl-phenyl)-4,4-dimethyl-1,2,3,4-tetrahydro-quinoline-6-carbonyl]-amide

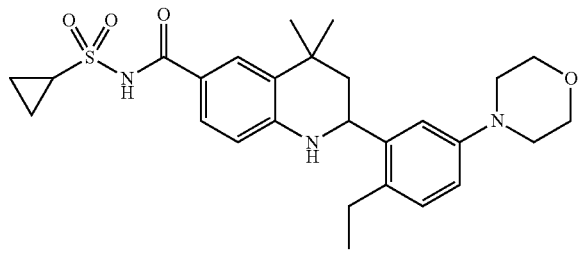 [SMILES: CCc1ccc(N2CCOCC2)cc1C1CC(C)(C)c2cc(C(=O)NS(=O)(=O)C3CC3)ccc2N1]

To a stirred solution of 4-amino-benzoic acid methyl ester (1 g, 6 mmol) and 5-bromo-2-ethyl-benzaldehyde (1.2 g, 5.6 mmol) in acetonitrile (40 mL) were added isobutene (1.7 mL, 24 mmol) and ytterbium(III) trifluoromethanesulfonate (Yb(OTf)$_3$) (0.55 g, 0.9 mmol). The resulting mixture was stirred at 85° C. for 16 h in sealed tube. The mixture was diluted with ethyl acetate (100 mL) and washed with water (50 mL×2) and brine (50 mL×2) and then dried over anhydrous sodium sulfate. The solvent was removed in vacuo and the residue was purified by ISCO combi-flash chromatography (gradient elution, 10-50% ethyl acetate in petroleum ether) to afford 2-(5-bromo-2-ethyl-phenyl)-4,4-dimethyl-1,2,3,4-tetrahydro-quinoline-6-carboxylic acid methyl ester (1.5 g, 64%) as a light yellow solid: MS (ESI) M+1=416.0.

A mixture solution of 2-(5-bromo-2-ethyl-phenyl)-4,4-dimethyl-1,2,3,4-tetrahydro-quinoline-6-carboxylic acid methyl ester (1.5 g, 9.1 mmol), morpholine (3.17 mL, 36.4 mmol), copper(I) iodide (1.04 g, 5.5 mmol), N,N-dimethylglycine hydrochloride (1.02 g, 7.3 mmol), and potassium carbonate (3.77 g, 27.3 mmol) in dimethyl sulfoxide (20 mL) was stirred at 120° C. for 12 h. Then the reaction mixture was cooled to room temperature. The reaction mixture was extracted with ethyl acetate (200 mL×2), washed with saturated aqueous ammonium chloride solution (50 mL×3) and brine (50 mL×2), dried over anhydrous sodium sulfate and then concentrated in vacuo and the residue was purified by ISCO combi-flash chromatography (gradient elution, 30-50% ethyl acetate in petroleum ether) to afford 2-(2-ethyl-5-morpholin-4-yl-phenyl)-4,4-dimethyl-1,2,3,4-tetrahydro-quinoline-6-carboxylic acid ethyl ester (0.6 g, 15%) as a white solid: MS (ESI) M+1=423.1.

To a stirred mixture solution of 2-(2-ethyl-5-morpholin-4-yl-phenyl)-4,4-dimethyl-1,2,3,4-tetrahydro-quinoline-6-carboxylic acid ethyl ester (0.6 g, 1.4 mmol) in methanol (10 mL) and tetrahydrofuran (20 mL) was added 30% sodium hydroxide in water (10 mL). The reaction mixture was stirred at 60° C. for 12 h. The mixture was neutralized with a 3 N aqueous hydrochloric acid solution and extracted with ethyl acetate (2×100 mL), washed with water, dried over anhydrous sodium sulfate and then concentrated in vacuo to afford 2-(2-ethyl-5-morpholin-4-yl-phenyl)-4,4-dimethyl-1,2,3,4-tetrahydro-quinoline-6-carboxylic acid (0.5 g, 89%) as a light white solid which was used for next step without further purification: MS (ESI) M+1=395.2.

To a suspension of 60% sodium hydride (356 mg, 8.9 mmol) in N,N-dimethylformamide (4 mL) was added cyclopropanesulfonic acid amide (1 g, 8.9 mmol) at room temperature. The resulting mixture was stirred at 25° C. for 1 h to afford Solution A47. A solution of 2-(2-ethyl-5-morpholin-4-yl-phenyl)-4,4-dimethyl-1,2,3,4-tetrahydro-quinoline-6-carboxylic acid (500 mg, 1.27 mmol) and 1,1'-carbonyldiimidazole (412 mg, 2.54 mmol) in N,N-dimethylformamide (2 mL) was stirred at 70° C. for 1 h and cooled to room temperature to afford Solution B47. Solution B47 was added to Solution A47 and the resulting mixture was stirred at 25° C. for 1 h. To the reaction mixture was added water (0.5 mL). The mixture was filtered to remove the insoluble solid, and the filtrate was purified by Waters automated flash system (column: Xterra 30 mm×100 mm, sample manager 2767, pump 2525, detector: ZQ mass and UV 2487, solvent system: acetonitrile and 0.1% ammonium hydroxide in water) afforded cyclopropanesulfonic acid [2-(2-ethyl-5-morpholin-4-yl-phenyl)-4,4-dimethyl-1,2,3,4-tetrahydro-quinoline-6-carbonyl]-amide (100 mg, 15%) as a white solid: MS (ESI) M+1=498.1.

Example 48

Cyclopropanesulfonic acid [2-(2-ethyl-phenyl)-4,4-dimethyl-1,2,3,4-tetrahydro-quinoline-6-carbonyl]-amide

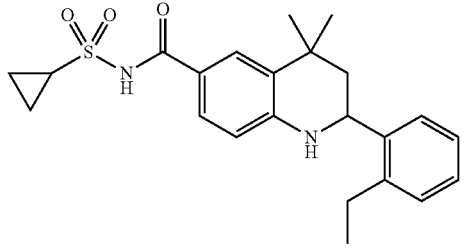 [SMILES: CCc1ccccc1C1CC(C)(C)c2cc(C(=O)NS(=O)(=O)C3CC3)ccc2N1]

To a stirred solution of 4-amino-benzoic acid methyl ester (1 g, 6 mmol) and 2-ethyl-benzaldehyde (1.2 g, 8.9 mmol) in acetonitrile (40 mL) were added isobutene (1.7 mL, 24 mmol) and ytterbium(III) trifluoromethanesulfonate (Yb(OTf)$_3$) (0.55 g, 0.9 mmol). The resulting mixture was stirred at 85° C. for 16 h in sealed tube. The mixture was diluted with ethyl acetate (100 mL) and washed with water (50 mL×2) and brine (50 mL×2) and then dried over anhydrous sodium sulfate. The solvent was removed in vacuo and the residue was purified by ISCO combi-flash chromatography (gradient elution, 10-50% ethyl acetate in petroleum ether) to afford 2-(2-ethyl-phenyl)-4,4-dimethyl-1,2,3,4-tetrahydro-quinoline-6-carboxylic acid methyl ester (1 g, 49%) as a light yellow solid: MS (ESI) M+1=337.0.

To a stirred mixture solution of 2-(2-ethyl-phenyl)-4,4-dimethyl-1,2,3,4-tetrahydro-quinoline-6-carboxylic acid methyl ester (0.6 g, 1.78 mmol) in methanol (10 mL) and tetrahydrofuran (20 mL) was added 30% sodium hydroxide in water (10 mL). The reaction mixture was stirred at 60° C. for 12 h. The mixture was neutralized with a 3 N aqueous hydrochloric acid solution and extracted with ethyl acetate (2×100 mL), washed with water, dried over anhydrous sodium sulfate and then concentrated in vacuo to afford 2-(2-ethyl-phenyl)-4,4-dimethyl-1,2,3,4-tetrahydro-quinoline-6- carboxylic acid (0.5 g, 90%) as a light white solid which was used for next step without further purification: MS (ESI) M+1=310.1.

To a suspension of 60% sodium hydride (381 mg, 9.52 mmol) in N,N-dimethylformamide (4 mL) was added cyclopropanesulfonic acid amide (1.15 g, 9.52 mmol) at room temperature. The resulting mixture was stirred at 25° C. for 1 h to afford Solution A48. A solution of 2-(2-ethyl-5-morpholin-4-yl-phenyl)-4,4-dimethyl-1,2,3,4-tetrahydro-quinoline-6-carboxylic acid (420 mg, 1.36 mmol) and 1,1'-carbonyldiimidazole (441 mg, 2.72 mmol) in N,N-dimethylformamide (2 mL) was stirred at 70° C. for 1 h and cooled to room temperature to afford Solution B48. Solution B48 was added to Solution A48 and the resulting mixture was stirred at 25° C. for 1 h. To the reaction mixture was added water (0.5 mL). The mixture was filtered to remove the insoluble solid, and the filtrate was purified by Waters automated flash system (column: Xterra 30 mm×100 mm, sample manager 2767, pump 2525, detector: ZQ mass and UV 2487, solvent system: acetonitrile and 0.1% ammonium hydroxide in water) afforded cyclopropanesulfonic acid [2-(2-ethyl-phenyl)-4,4-dimethyl-1,2,3,4-tetrahydro-quinoline-6-carbonyl]-amide (100 mg, 17%) as a white solid: MS (ESI) M+1=413.1.

Example 49

N-(2-{5-[4-(2,4-dimethyl-phenyl)-piperazin-1-yl]-pyridin-3-yl}-4,4-dimethyl-1,2,3,4-tetrahydro-quinoline-6-carbonyl)-methanesulfonamide

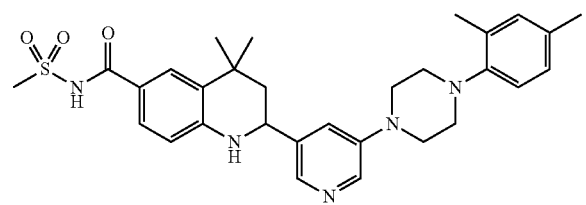

A mixture of 4-aminobenzoic acid ethyl ester (16.5 g, 100 mmol), 5-bromo-pyridine-3-carbaldehyde (18.6 g, 100 mmol) and ytterbium(III) triflate hydrate (12.4 g, 20 mmol) in acetonitrile (350 mL) was cooled to 0° C. in a sealed reaction bottle. Then a cooled solution of isobutene (28 g, 500 mmol) was added into. The reaction mixture was heated to 90° C. and stirred for 12 h. The solvent was removed in vacuo and the residue was purified on flash silica gel chromatography (silica gel from QingDao, 200-300 mesh, glass column from Shanghai SD company) (20% ethyl acetate/hexanes) to afford 2-(5-bromo-pyridin-3-yl)-4,4-dimethyl-1,2,3,4-tetrahydro-quinoline-6-carboxylic acid ethyl ester (16 g, 41%) as a white solid: MS (ESI) M+1=389.0.

A mixture of 2-(5-bromo-pyridin-3-yl)-4,4-dimethyl-1,2,3,4-tetrahydro-quinoline-6-carboxylic acid ethyl ester (0.39 g, 1.0 mmol), 1-(2,4-dimethyl-phenyl)-piperazine (0.29 g, 1.5 mmol), palladium (II) acetate (6.73 mg, 0.03 mmol), xantphos (23 mg, 0.04 mmol) and cesium carbonate (0.65, 2.0 mmol) in toluene (10 mL) was heated for 3 h at 120° C. After colling to room temperature, the mixture was treated with ethyl acetate (50 mL) and washed with water (20 mL). The organic layer was dried over anhydrous sodium sulfate and concentrated in vacuo. Purification on flash silica gel chromatography (silica gel from QingDao, 200-300 mesh, glass column from Shanghai SD company) (50% ethyl acetate/hexanes) to afford 2-{5-[4-(2,4-dimethyl-phenyl)-piperazin-1-yl]-pyridin-3-yl}-4,4-dimethyl-1,2,3,4-tetrahydro-quinoline-6-carboxylic acid ethyl ester (0.30 g, 60%) as a white solid: MS (ESI) M+1=499.3.

A mixture of 2-{5-[4-(2,4-dimethyl-phenyl)-piperazin-1-yl]-pyridin-3-yl}-4,4-dimethyl-1,2,3,4-tetrahydro-quinoline-6-carboxylic acid ethyl ester (0.30 g, 0.60 mmol) in methanol (3 mL) and tetrahydrofuran (10 mL), 30% sodium hydroxide in water (1 mL). The reaction mixture was stirred at 60° C. for 12 h. The mixture was neutralized with a 3 N aqueous hydrochloric acid solution and extracted with ethyl acetate (2×50 mL), washed with water, dried over anhydrous sodium sulfate and then concentrated in vacuo to afford 2-{5-[4-(2,4-dimethyl-phenyl)-piperazin-1-yl]-pyridin-3-yl}-4,4-dimethyl-1,2,3,4-tetrahydro-quinoline-6-carboxylic acid (0.25 g, 90%) as a white solid which was used for next step without further purification: MS (ESI) M+1=471.3.

A mixture of 2-{5-[4-(2,4-dimethyl-phenyl)-piperazin-1-yl]-pyridin-3-yl}-4,4-dimethyl-1,2,3,4-tetrahydro-quinoline-6-carboxylic acid (100 mg, 0.21 mmol), 1-(3-dimethylaminopropyl)-3-ethylcarbodiimide hydrochloride (60 mg, 0.31 mmol), 4-dimethylaminopyridine (38 mg, 0.31 mmol), methane sulfonamide (60 mg, 0.63 mmol) in dichloromethane (10 mL) was refluxed for 12 h. Removal of the solvent to afford the oil residue. Purification by Waters automated flash system (column: Xterra 30 mm×100 mm, sample manager 2767, pump 2525, detector: ZQ mass and UV 2487, solvent system: acetonitrile and 0.1% formic acid in water) afforded N-(2-{5-[4-(2,4-dimethyl-phenyl)-piperazin-1-yl]-pyridin-3-yl}-4,4-dimethyl-1,2,3,4-tetrahydro-quinoline-6-carbonyl)-methanesulfonamide (34.5 mg, 30%) as a light yellow solid: MS (ESI) M+1=548.3.

Example 50

Cyclopropanesulfonic acid (2-{5-[4-(2,4-dimethyl-phenyl)-piperazin-1-yl]-pyridin-3-yl}-4,4-dimethyl-1,2,3,4-tetrahydro-quinoline-6-carbonyl)-amide

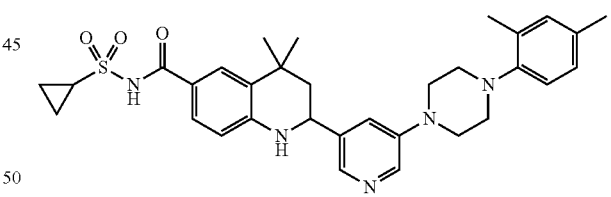

A mixture of 2-{5-[4-(2,4-dimethyl-phenyl)-piperazin-1-yl]-pyridin-3-yl}-4,4-dimethyl-1,2,3,4-tetrahydro-quinoline-6-carboxylic acid (100 mg, 0.21 mmol), 1-(3-dimethylaminopropyl)-3-ethylcarbodiimide hydrochloride (60 mg, 0.31 mmol), 4-dimethylaminopyridine (38 mg, 0.31 mmol), cyclopropane sulfonic acid amide (76 mg, 0.63 mmol) in dichloromethane (10 mL) was refluxed for 12 h. Removal of the solvent to afford the oil residue. Purification by Waters automated flash system (column: Xterra 30 mm×100 mm, sample manager 2767, pump 2525, detector: ZQ mass and UV 2487, solvent system: acetonitrile and 0.1% formic acid in water) afforded cyclopropanesulfonic acid (2-{5-[4-(2,4-dimethyl-phenyl)-piperazin-1-yl]-pyridin-3-yl}-4,4-dimethyl-1,2,3,4-tetrahydro-quinoline-6-carbonyl)-amide (12 mg, 10%) as a light yellow solid: MS (ESI) M+1=574.3.

Example 51

Cyclopropanesulfonic acid {4,4-dimethyl-2-[3-(4-methyl-piperazin-1-yl)-phenyl]-1,2,3,4-tetrahydro-quinoline-6-carbonyl}-amide

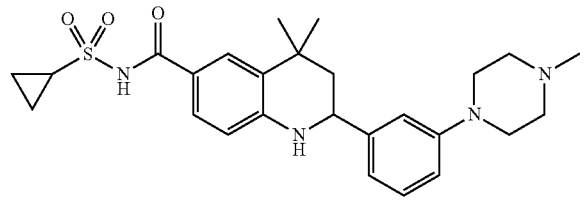 [SMILES: CN1CCN(c2cccc(C3CC(C)(C)c4cc(C(=O)NS(=O)(=O)C5CC5)ccc4N3)c2)CC1]

A mixture solution of 2-(3-bromo-phenyl)-4,4-dimethyl-1,2,3,4-tetrahydro-quinoline-6-carboxylic acid methyl ester (1.94 g, 5 mmol), 1-methyl-piperazine (2.2 mL, 20 mmol), copper(I) iodide (0.38 g, 2 mmol), N,N-dimethylglycine hydrochloride (0.42 g, 3 mmol), and potassium carbonate (2.07 g, 15 mmol) in dimethyl sulfoxide (10 mL) was stirred at 120° C. for 16 h. Then the reaction mixture was cooled to room temperature. The reaction mixture was extracted with ethyl acetate (50 mL×2), washed with saturated aqueous ammonium chloride solution (20 mL×3) and brine (20 mL×2), dried over anhydrous sodium sulfate and then concentrated in vacuo and the residue was purified by ISCO combi-flash chromatography (gradient elution, 30-50% ethyl acetate in petroleum ether) to afford 4,4-dimethyl-2-[3-(4-methyl-piperazin-1-yl)-phenyl]-1,2,3,4-tetrahydro-quinoline-6-carboxylic acid methyl ester (0.61 g, 30%) as a yellow solid: MS (ESI) M+1=407.1.

To a stirred mixture solution of 4,4-dimethyl-2-[3-(4-methyl-piperazin-1-yl)-phenyl]-1,2,3,4-tetrahydro-quinoline-6-carboxylic acid methyl ester (610 mg, 1.49 mmol) in methanol (7.5 mL) and tetrahydrofuran (15 mL) was added 30% sodium hydroxide in water (7.5 mL). The reaction mixture was stirred at 60° C. for 16 h. The mixture was neutralized with a 3 N aqueous hydrochloric acid solution and extracted with ethyl acetate (2×50 mL), washed with water, dried over anhydrous sodium sulfate and then concentrated in vacuo to afford 4,4-dimethyl-2-[3-(4-methyl-piperazin-1-yl)-phenyl]-1,2,3,4-tetrahydro-quinoline-6-carboxylic acid (564 mg, 99%) as a light white solid which was used for next step without further purification: MS (ESI) M+1=380.2.

To a suspension of 60% sodium hydride (448 mg, 11.2 mmol) in N,N-dimethylformamide (3 mL) was added cyclopropanesulfonic acid amide (1.35 g, 11.2 mmol) at room temperature. The resulting mixture was stirred at 25° C. for 1 h to afford Solution A51. A solution of 4,4-dimethyl-2-[3-(4-methyl-piperazin-1-yl)-phenyl]-1,2,3,4-tetrahydro-quinoline-8-carboxylic acid (564 mg, 1.5 mmol) and 1,1'-carbonyldiimidazole (519 mg, 3.2 mmol) in N,N-dimethylformamide (1.5 mL) was stirred at 70° C. for 1 h and cooled to room temperature to afford Solution B51. Solution B51 was added to Solution A51 and the resulting mixture was stirred at 25° C. for 1 h. To the reaction mixture was added water (0.5 mL). The mixture was filtered to remove the insoluble solid, and the filtrate was purified by Waters automated flash system (column: Xterra 30 mm×100 mm, sample manager 2767, pump 2525, detector: ZQ mass and UV 2487, solvent system: acetonitrile and 0.1% ammonium hydroxide in water) afforded cyclopropanesulfonic acid {4,4-dimethyl-2-[3-(4-methyl-piperazin-1-yl)-phenyl]-1,2,3,4-tetrahydro-quinoline-6-carbonyl}-amide (140 mg, 10%) as a white solid: MS (ESI) M+1=483.3.

Example 52

Cyclopropanesulfonic acid [4,4-dimethyl-2-(3-pyrrolidin-1-yl-phenyl)-1,2,3,4-tetrahydro-quinoline-6-carbonyl]-amide

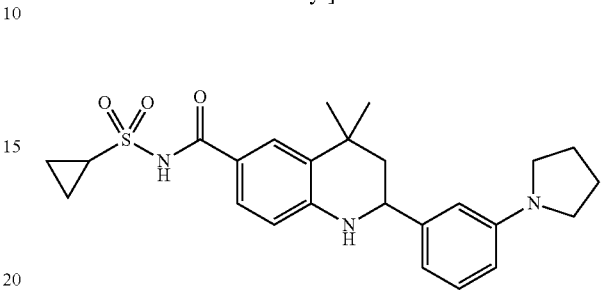

A mixture solution of 2-(3-bromo-phenyl)-4,4-dimethyl-1,2,3,4-tetrahydro-quinoline-6-carboxylic acid methyl ester (1.94 g, 5 mmol), pyrrolidine (2.1 mL, 25 mmol), copper(I) iodide (0.38 g, 2 mmol), N,N-dimethylglycine hydrochloride (0.42 g, 3 mmol), and potassium carbonate (2.07 g, 15 mmol) in dimethyl sulfoxide (10 mL) was stirred at 120° C. for 16 h. Then the reaction mixture was cooled to room temperature. The reaction mixture was extracted with ethyl acetate (50 mL×2), washed with saturated aqueous ammonium chloride solution (20 mL×3) and brine (20 mL×2), dried over anhydrous sodium sulfate and then concentrated in vacuo and the residue was purified by ISCO combi-flash chromatography (gradient elution, 30-50% ethyl acetate in petroleum ether) to afford 4,4-dimethyl-2-(3-pyrrolidin-1-yl-phenyl)-1,2,3,4-tetrahydro-quinoline-6-carboxylic acid methyl ester (1.7 g, 90%) as a yellow solid: MS (ESI) M+1=379.1.

To a stirred mixture solution of 4,4-dimethyl-2-(3-pyrrolidin-1-yl-phenyl)-1,2,3,4-tetrahydro-quinoline-6-carboxylic acid methyl ester (1.7 g, 4.5 mmol) in methanol (20 mL) and tetrahydrofuran (40 mL) was added 30% sodium hydroxide in water (20 mL). The reaction mixture was stirred at 60° C. for 16 h. The mixture was neutralized with a 3 N aqueous hydrochloric acid solution and extracted with ethyl acetate (2×50 mL), washed with water, dried over anhydrous sodium sulfate and then concentrated in vacuo to afford 4,4-dimethyl-2-(3-pyrrolidin-1-yl-phenyl)-1,2,3,4-tetrahydro-quinoline-6-carboxylic acid (1.4 g, 99%) as a light white solid which was used for next step without further purification: MS (ESI) M+1=351.0.

To a suspension of 60% sodium hydride (800 mg, 20 mmol) in N,N-dimethylformamide (4 mL) was added cyclopropanesulfonic acid amide (2.4 g, 20 mmol) at room temperature. The resulting mixture was stirred at 25° C. for 1 h to afford Solution A52. A solution of 4,4-dimethyl-2-(3-pyrrolidin-1-yl-phenyl)-1,2,3,4-tetrahydro-quinoline-6-carboxylic acid (1 g, 2.86 mmol) and 1,1'-carbonyldiimidazole (930 mg, 5.71 mmol) in N,N-dimethylformamide (3 mL) was stirred at 70° C. for 1 h and cooled to room temperature to afford Solution B52. Solution B52 was added to Solution A52 and the resulting mixture was stirred at 25° C. for 1 h. To the reaction mixture was added water (0.5 mL). The mixture was filtered to remove the insoluble solid, and the filtrate was purified by Waters automated flash system (column: Xterra 30 mm×100 mm, sample manager 2767, pump 2525, detector: ZQ mass and UV 2487, solvent system: acetonitrile and 0.1% ammonium hydroxide in water) afforded cyclopropanesulfonic acid [4,4-dimethyl-2-(3-pyrrolidin-1-yl-phenyl)-1,2,3,4-tetrahydro-quinoline-6-carbonyl]-amide (107 mg, 8%) as a brown solid: MS (ESI) M+1=454.2.

Example 53

N-(2-{3-[4-(2,4-dimethyl-phenyl)-piperazin-1-yl]-phenyl}-4,4-dimethyl-1,2,3,4-tetrahydro-quinoline-6-carbonyl)-methanesulfonamide

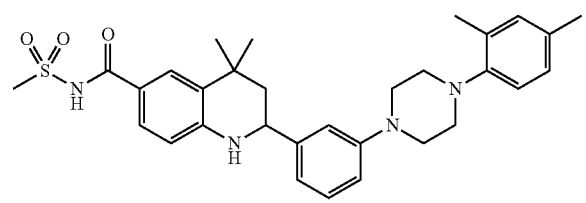

A mixture of 2-(3-bromo-phenyl)-4,4-dimethyl-1,2,3,4-tetrahydro-quinoline-6-carboxylic acid ethyl ester (0.39 g, 1.0 mmol), 1-(2,4-dimethyl-phenyl)-piperazine (0.29 g, 1.5 mmol), palladium (II) acetate (6.73 mg, 0.03 mmol), xantphos (23 mg, 0.04 mmol) and cesium carbonate (0.65, 2.0 mmol) in toluene (10 mL) was heated for 3 h at 120° C. After colling to room temperature, the mixture was treated with ethyl acetate (50 mL) and washed with water (20 mL). The organic layer was dried over anhydrous sodium sulfate and concentrated in vacuo. Purification on flash silica gel chromatography (silica gel from QingDao, 200-300 mesh, glass column from Shanghai SD company) (50% ethyl acetate/hexanes) to afford 2-{3-[4-(2,4-dimethyl-phenyl)-piperazin-1-yl]-phenyl}-4,4-dimethyl-1,2,3,4-tetrahydro-quinoline-6-carboxylic acid ethyl ester (0.28 g, 56%) as a white solid: MS (ESI) M+1=498.3.

A mixture of 2-{3-[4-(2,4-dimethyl-phenyl)-piperazin-1-yl]-phenyl}-4,4-dimethyl-1,2,3,4-tetrahydro-quinoline-6-carboxylic acid ethyl ester (0.28 g, 0.56 mmol) in methanol (3 mL) and tetrahydrofuran (10 mL), 30% sodium hydroxide in water (1 mL). The reaction mixture was stirred at 60° C. for 12 h. The mixture was neutralized with a 3 N aqueous hydrochloric acid solution and extracted with ethyl acetate (2×50 mL), washed with water, dried over anhydrous sodium sulfate and then concentrated in vacuo to afford 2-{3-[4-(2,4-dimethyl-phenyl)-piperazin-1-yl]-phenyl}-4,4-dimethyl-1,2,3,4-tetrahydro-quinoline-6-carboxylic acid (0.25 g, 90%) as a white solid which was used for next step without further purification: MS (ESI) M+1=470.3.

A mixture of 2-{3-[4-(2,4-dimethyl-phenyl)-piperazin-1-yl]-phenyl}-4,4-dimethyl-1,2,3,4-tetrahydro-quinoline-6-carboxylic acid (100 mg, 0.21 mmol), 1-3-dimethylaminopropyl-3-ethylcarbodiimide hydrochloride (60 mg, 0.31 mmol), 4-dimethylaminopyridine (38 mg, 0.31 mmol), methane sulfonamide (60 mg, 0.63 mmol) in dichloromethane (10 mL) was refluxed for 12 h. Removal of the solvent to afford the oil residue. Purification by Waters automated flash system (column: Xterra 30 mm×100 mm, sample manager 2767, pump 2525, detector: ZQ mass and UV 2487, solvent system: acetonitrile and 0.1% formic acid in water) afforded N-(2-{3-[4-(2,4-dimethyl-phenyl)-piperazin-1-yl]-phenyl}-4,4-dimethyl-1,2,3,4-tetrahydro-quinoline-6-carbonyl)-methanesulfonamide (23 mg, 20%) as a light yellow solid: MS (ESI) M+1=547.3.

Example 54

Cyclopropanesulfonic acid [4,4-dimethyl-2-(5-morpholin-4-yl-pyridin-3-yl)-1,2,3,4-tetrahydro-quinoline-6-carbonyl]-amide

A mixture of 2-(5-bromo-pyridin-3-yl)-4,4-dimethyl-1,2,3,4-tetrahydro-quinoline-6-carboxylic acid ethyl ester (0.39 g, 1.0 mmol), morpholine (0.35 g, 4 mmol), copper (I) iodide (114 mg, 0.6 mmol), N,N-dimethyl glycine hydrochloride (112 mg, 0.8 mmol) and potassium carbonate (0.42 g, 3 mmol) in dimethylsulfoxide (10 mL) was heated for 12 h at 120° C. After colling to room temperature, the mixture was treated with ethyl acetate (50 mL) and washed with water (20 mL). The organic layer was dried over anhydrous sodium sulfate and concentrated in vacuo. Purification on flash silica gel chromatography (silica gel from QingDao, 200-300 mesh, glass column from Shanghai SD company) (30% ethyl acetate/hexanes) to afford 4,4-dimethyl-2-(5-morpholin-4-yl-pyridin-3-yl)-1,2,3,4-tetrahydro-quinoline-6-carboxylic acid ethyl ester (0.20 g, 51%) as a white solid: MS (ESI) M+1=396.3.

A mixture of 4,4-dimethyl-2-(5-morpholin-4-yl-pyridin-3-yl)-1,2,3,4-tetrahydro-quinoline-6-carboxylic acid ethyl ester (0.40 g, 1.0 mmol) in methanol (3 mL) and tetrahydrofuran (10 mL), 30% sodium hydroxide in water (1 mL). The reaction mixture was stirred at 60° C. for 12 h. The mixture was neutralized with a 3 N aqueous hydrochloric acid solution and extracted with ethyl acetate (2×50 mL), washed with water, dried over anhydrous sodium sulfate and then concentrated in vacuo to afford 4,4-dimethyl-2-(5-morpholin-4-yl-pyridin-3-yl)-1,2,3,4-tetrahydro-quinoline-6-carboxylic acid (0.30 g, 81%) as a white solid which was used for next step without further purification: MS (ESI) M+1=368.2;

A mixture of 4,4-dimethyl-2-(5-morpholin-4-yl-pyridin-3-yl)-1,2,3,4-tetrahydro-quinoline-6-carboxylic acid (200 mg, 0.54 mmol), 1-3-dimethylaminopropyl-3-ethylcarbodiimide hydrochloride (160 mg, 0.82 mmol), 4-dimethylaminopyridine (100 mg, 0.82 mmol), cyclopropane sulfonic acid amide (196 mg, 1.62 mmol) in dichloromethane (10 mL) was refluxed for 12 h. Removal of the solvent to afford the oil residue. Purification by Waters automated flash system (column: Xterra 30 mm×100 mm, sample manager 2767, pump 2525, detector: ZQ mass and UV 2487, solvent system: acetonitrile and 0.1% formic acid in water) afforded cyclopropanesulfonic acid [4,4-dimethyl-2-(5-morpholin-4-yl-pyridin-3-yl)-1,2,3,4-tetrahydro-quinoline-6-carbonyl]-amide (38 mg, 15%) as a light yellow solid: MS (ESI) M+1=471.2.

Example 55

N-[4,4-dimethyl-2-(3-morpholin-4-yl-phenyl)-1,2,3,4-tetrahydro-quinoline-7-carbonyl]-methanesulfonamide

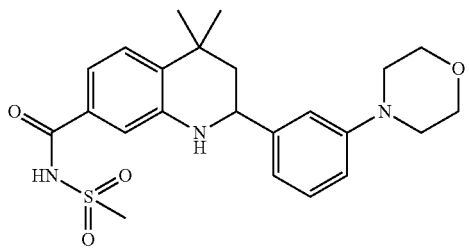 [SMILES: CC1(C)CC(c2cccc(N3CCOCC3)c2)Nc2cc(C(=O)NS(C)(=O)=O)ccc21]

To a stirred solution of 3-amino-benzoic acid methyl ester (11.3 g, 78.4 mmol) and 3-bromobenzaldehyde (9.2 mL, 78.4 mmol) in acetonitrile (150 mL) were added isobutene (21.0 mL, 313.5 mmol) and ytterbium(III) trifluoromethanesulfonate (Yb(OTf)$_3$) (5.8 g, 9.5 mmol). The resulting mixture was stirred at 85° C. for 18 h in sealed tube. The mixture was diluted with ethyl acetate (300 mL) and washed with water (100 mL×2) and brine (100 mL×2) and then dried over anhydrous sodium sulfate. The solvent was removed in vacuo and the residue was purified by ISCO combi-flash chromatography (gradient elution, 10-50% ethyl acetate in petroleum ether) to afford 2-(3-bromo-phenyl)-4,4-dimethyl-1,2,3,4-tetrahydro-quinoline-7-carboxylic acid methyl ester (11.7 g, 40.0%) as a light yellow solid: MS (ESI) M+1=374.

A mixture solution of 2-(3-bromo-phenyl)-4,4-dimethyl-1,2,3,4-tetrahydro-quinoline-7-carboxylic acid methyl ester (11.2 g, 30.0 mmol), morpholine (26.0 mL, 294.0 mmol), copper(I) iodide (3.4 g, 18.0 mmol), N,N-dimethylglycine hydrochloride (3.4 g, 24.0 mmol), and potassium carbonate (12.4 g, 90.0 mmol) in dimethyl sulfoxide (65 mL) was stirred at 120° C. for 16 h. Then the reaction mixture was cooled to room temperature. The reaction mixture was extracted with ethyl acetate (200 mL×2), washed with saturated aqueous ammonium chloride solution (50 mL×3) and brine (50 mL×2), dried over anhydrous sodium sulfate and then concentrated in vacuo and the residue was purified by ISCO combi-flash chromatography (gradient elution, 30-50% ethyl acetate in petroleum ether) to afford 4,4-dimethyl-2-(3-morpholin-4-yl-phenyl)-1,2,3,4-tetrahydro-quinoline-7-carboxylic acid methyl ester (9.1 g, 80%) as a white solid: MS (ESI) M+1=381.0.

To a stirred mixture solution of 4,4-dimethyl-2-(3-morpholin-4-yl-phenyl)-1,2,3,4-tetrahydro-quinoline-7-carboxylic acid methyl ester (380.0 mg, 1.0 mmol) in methanol (10.0 mL) and tetrahydrofuran (10.0 mL) was added 50% sodium hydroxide in water (1.5 mL). The reaction mixture was stirred at 70° C. for 6 h. The mixture was neutralized with a 3 N aqueous hydrochloric acid solution and extracted with ethyl acetate (2×100 mL), washed with water, dried over anhydrous sodium sulfate and then concentrated in vacuo to afford 4,4-dimethyl-2-(3-morpholin-4-yl-phenyl)-1,2,3,4-tetrahydro-quinoline-7-carboxylic acid (330.0 mg, 90%) as a light white solid which was used for next step without further purification: MS (ESI) M+1=367.1.

To a suspension of 60% sodium hydride (535.0 mg, 13.7 mmol) in N,N-dimethylformamide (2.5 mL) was added methanesulfonamide (1.3 g, 13.8 mmol) at room temperature. The resulting mixture was stirred at 25° C. for 1 h to afford Solution A55. A solution of 4,4-dimethyl-2-(3-morpholin-4-yl-phenyl)-1,2,3,4-tetrahydro-quinoline-7-carboxylic acid (300.0 mg, 0.82 mmol) and 1,1'-carbonyldiimidazole (442.0 mg, 2.76 mmol) in N,N-dimethylformamide (2.0 mL) was stirred at 70° C. for 1 h and cooled to room temperature to afford Solution B55. Solution B55 was added to Solution A55 and the resulting mixture was stirred at 25° C. for 1 h. To the reaction mixture was added water (0.5 mL). The mixture was filtered to remove the insoluble solid, and the filtrate was purified by Waters automated flash system (column: Xterra 30 mm×100 mm, sample manager 2767, pump 2525, detector: ZQ mass and UV 2487, solvent system: acetonitrile and 0.1% ammonium hydroxide in water) afforded N-[4,4-dimethyl-2-(3-morpholin-4-yl-phenyl)-1,2,3,4-tetrahydro-quinoline-7-carbonyl]-methanesulfonamide (109.0 mg, 30%) as a white solid: MS (ESI) M+1=444.2.

Example 56

N-[6-fluoro-4,4-dimethyl-2-(3-morpholin-4-yl-phenyl)-1,2,3,4-tetrahydro-quinoline-8-carbonyl]-methanesulfonamide

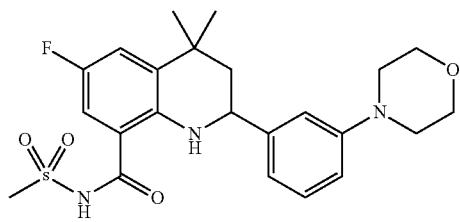

To a stirred solution of 2-amino-5-fluoro-benzoic acid methyl ester (8.46 g, 50 mmol) and 3-bromobenzaldehyde (6.4 mL, 55 mmol) in acetonitrile (200 mL) were added isobutene (14 mL, 200 mmol) and ytterbium(III) trifluoromethanesulfonate (Yb(OTf)$_3$) (4.65 g, 7.5 mmol). The resulting mixture was stirred at 85° C. for 16 h in sealed tube. The mixture was diluted with ethyl acetate (300 mL) and washed with water (100 mL×2) and brine (100 mL×2) and then dried over anhydrous sodium sulfate. The solvent was removed in vacuo and the residue was purified by ISCO combi-flash chromatography (gradient elution, 10-50% ethyl acetate in petroleum ether) to afford 2-(3-bromo-phenyl)-6-fluoro-4,4-dimethyl-1,2,3,4-tetrahydro-quinoline-8-carboxylic acid methyl ester (10 g, 51%) as a light yellow solid: MS (ESI) M+1=392.0 & 394.0.

A mixture solution of 2-(3-bromo-phenyl)-6-fluoro-4,4-dimethyl-1,2,3,4-tetrahydro-quinoline-8-carboxylic acid methyl ester (5 g, 12.7 mmol), morpholine (11.1 mL, 125 mmol), copper(I) iodide (1.43 g, 7.5 mmol), N,N-dimethylglycine hydrochloride (1.4 g, 10 mmol), and potassium carbonate (5.2 g, 75 mmol) in dimethyl sulfoxide (20 mL) was stirred at 120° C. for 16 h. Then the reaction mixture was cooled to room temperature. The reaction mixture was extracted with ethyl acetate (150 mL×2), washed with saturated aqueous ammonium chloride solution (50 mL×3) and brine (50 mL×2), dried over anhydrous sodium sulfate and then concentrated in vacuo and the residue was purified by ISCO combi-flash chromatography (gradient elution, 30-50% ethyl acetate in petroleum ether) to afford 6-fluoro-4,4-dimethyl-2-(3-morpholin-4-yl-phenyl)-1,2,3,4-tetrahydro-quinoline-8-carboxylic acid (3 g, 61%) as a white solid: MS (ESI) M+1=385.1.

To a suspension of 60% sodium hydride (360 mg, 9 mmol) in N,N-dimethylformamide (5 mL) was added methanesulfonamide (865 mg, 9.1 mmol) at room temperature. The resulting mixture was stirred at 25° C. for 1 h to afford Solution A56. A solution of 6-fluoro-4,4-dimethyl-2-(3-morpholin-4-yl-phenyl)-1,2,3,4-tetrahydro-quinoline-8-carboxylic acid (500 mg, 1.3 mmol) and 1,1'-carbonyldiimidazole (422 mg, 2.6 mmol) in N,N-dimethylformamide (3 mL) was stirred at 70° C. for 1 h and cooled to room temperature to afford Solution B56. Solution B56 was added to Solution A56 and the resulting mixture was stirred at 25° C. for 1 h. To the reaction mixture was added water (0.5 mL). The mixture was filtered to remove the insoluble solid, and the filtrate was purified by Waters automated flash system (column: Xterra 30 mm×100 mm, sample manager 2767, pump 2525, detector: ZQ mass and UV 2487, solvent system: acetonitrile and 0.1% ammonium hydroxide in water) afforded N-[6-fluoro-4,4-dimethyl-2-(3-morpholin-4-yl-phenyl)-1,2,3,4-tetrahydro-quinoline-8-carbonyl]-methanesulfonamide (270 mg, 45%) as a white solid: MS (ESI) M+1=462.1.

Example 57

N-{6-fluoro-4,4-dimethyl-2-[3-(4-o-tolyl-piperazin-1-yl)-phenyl]-1,2,3,4-tetrahydro-quinoline-8-carbonyl}-methanesulfonamide

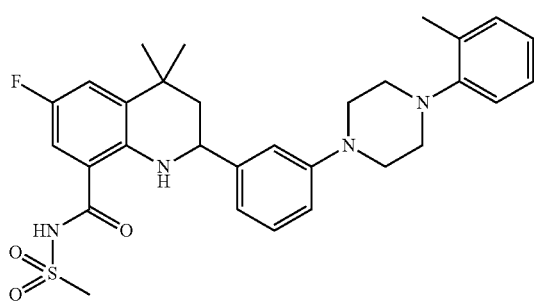 [SMILES: Cc1ccccc1N1CCN(c2cccc(C3CC(C)(C)c4cc(F)cc(C(=O)NS(C)(=O)=O)c4N3)c2)CC1]

A mixture of 2-amino-5-fluoro-benzoic acid methyl ester (12.1 g, 71.4 mmol), 3-bromo-benzaldehyde (13.2 g, 71.4 mmol) and ytterbium(III) triflate hydrate (4.4 g, 71.4 mmol) in acetonitrile (200 mL) was cooled to 0° C. in a sealed reaction bottle. Then a cooled solution of isobutene (28 g, 500 mmol) was added into. The reaction mixture was heated to 90° C. and stirred for 12 h. The solvent was removed in vacuo and the residue was purified on flash silica gel chromatography (silica gel from QingDao, 200-300 mesh, glass column from Shanghai SD company) (20% ethyl acetate/hexanes) to afford 2-(3-bromo-phenyl)-6-fluoro-4,4-dimethyl-1,2,3,4-tetrahydro-quinoline-8-carboxylic acid methyl ester (16 g, 57%) as a white solid: MS (ESI) M+1=392.1.

A mixture of 2-(3-bromo-phenyl)-6-fluoro-4,4-dimethyl-1,2,3,4-tetrahydro-quinoline-8-carboxylic acid methyl ester (3.0 g, 7.65 mmol), 1-o-tolyl-piperazine hydrochloride (1.95 g, 9.2 mmol), palladium (II) acetate (172 mg, 0.77 mmol), xantphos (266 mg, 0.46 mmol) and cesium carbonate (5.0 g, 15.3 mmol) in toluene (20 mL) was heated for 3 h at 120° C. After colling to room temperature, the mixture was treated with ethyl acetate (50 mL) and washed with water (20 mL). The organic layer was dried over anhydrous sodium sulfate and concentrated in vacuo. Purification on flash silica gel chromatography (silica gel from QingDao, 200-300 mesh, glass column from Shanghai SD company) (50% ethyl acetate/hexanes) to afford 6-fluoro-4,4-dimethyl-2-[3-(4-o-tolyl-piperazin-1-yl)-phenyl]-1,2,3,4-tetrahydro-quinoline-8-carboxylic acid methyl ester (2.2 g, 60%) as a white solid: MS (ESI) M+1=488.4.

A mixture of 6-fluoro-4,4-dimethyl-2-[3-(4-o-tolyl-piperazin-1-yl)-phenyl]-1,2,3,4-tetrahydro-quinoline-8-carboxylic acid methyl ester (0.36 g, 0.74 mmol) in methanol (3 mL) and tetrahydrofuran (10 mL), 30% sodium hydroxide in water (1 mL). The reaction mixture was stirred at 60° C. for 12 h. The mixture was neutralized with a 3 N aqueous hydrochloric acid solution and extracted with ethyl acetate (2×50 mL), washed with water, dried over anhydrous sodium sulfate and then concentrated in vacuo to afford 6-fluoro-4,4-dimethyl-2-[3-(4-o-tolyl-piperazin-1-yl)-phenyl]-1,2,3,4-tetrahydro-quinoline-8-carboxylic acid (0.32 g, 90%) as a white solid which was used for next step without further purification: MS (ESI) M+1=474.3.

A mixture of 6-fluoro-4,4-dimethyl-2-[3-(4-o-tolyl-piperazin-1-yl)-phenyl]-1,2,3,4-tetrahydro-quinoline-8-carboxylic acid (100 mg, 0.21 mmol), 1-3-dimethylaminopropyl-3-ethylcarbodiimide hydrochloride (60 mg, 0.31 mmol), 4-dimethylaminopyridine (38 mg, 0.31 mmol), methane sulfonamide (60 mg, 0.63 mmol) in dichloromethane (10 mL) was refluxed for 12 h. Removal of the solvent to afford the oil residue. Purification by Waters automated flash system (column: Xterra 30 mm×100 mm, sample manager 2767, pump 2525, detector: ZQ mass and UV 2487, solvent system: acetonitrile and 0.1% formic acid in water) afforded N-{6-fluoro-4,4-dimethyl-2-[3-(4-o-tolyl-piperazin-1-yl)-phenyl]-1,2,3,4-tetrahydro-quinoline-8-carbonyl}-methanesulfonamide (34.5 mg, 30%) as a light yellow solid: MS (ESI) M+1=551.4.

Example 58

Cyclopropanesulfonic acid {6-fluoro-4,4-dimethyl-2-[3-(4-o-tolyl-piperazin-1-yl)-phenyl]-1,2,3,4-tetrahydro-quinoline-8-carbonyl}-amide

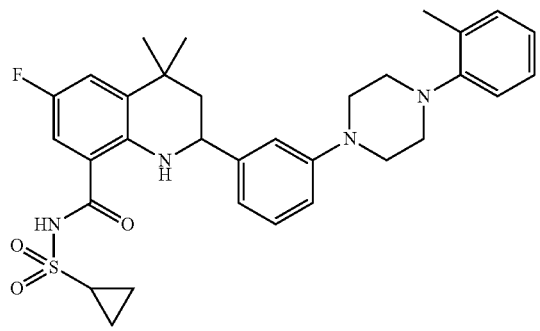 [SMILES: Cc1ccccc1N1CCN(c2cccc(C3CC(C)(C)c4cc(F)cc(C(=O)NS(=O)(=O)C5CC5)c4N3)c2)CC1]

A mixture of 6-fluoro-4,4-dimethyl-2-[3-(4-o-tolyl-piperazin-1-yl)-phenyl]-1,2,3,4-tetrahydro-quinoline-8-carboxylic acid (100 mg, 0.21 mmol), 1-3-dimethylaminopropyl-3-ethylcarbodiimide hydrochloride (60 mg, 0.31 mmol), 4-dimethylaminopyridine (38 mg, 0.31 mmol), cyclopropane sulfonic acid amide (76 mg, 0.63 mmol) in dichloromethane (10 mL) was refluxed for 12 h. Removal of the solvent to afford the oil residue. Purification by Waters automated flash system (column: Xterra 30 mm×100 mm, sample manager 2767, pump 2525, detector: ZQ mass and UV 2487, solvent system: acetonitrile and 0.1% formic acid in water) afforded cyclopropanesulfonic acid {6-fluoro-4,4-dimethyl-2-[3-(4- o-tolyl-piperazin-1-yl)-phenyl]-1,2,3,4-tetrahydro-quinoline-8-carbonyl}-amide (36 mg, 30%) as a light yellow solid: MS (ESI) M+1=577.3.

Example 59

N-(6-fluoro-2-{3-[4-(2-fluoro-phenyl)-piperazin-1-yl]-phenyl}-4,4-dimethyl-1,2,3,4-tetrahydro-quinoline-8-carbonyl)-methanesulfonamide

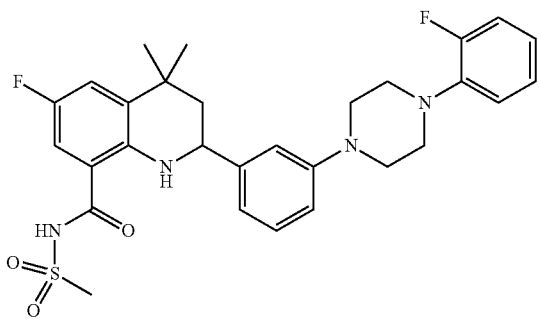 [SMILES: CC1(C)CC(c2cccc(N3CCN(c4ccccc4F)CC3)c2)Nc2c(C(=O)NS(C)(=O)=O)cc(F)cc21]

A mixture of 2-(3-bromo-phenyl)-6-fluoro-4,4-dimethyl-1,2,3,4-tetrahydro-quinoline-8-carboxylic acid methyl ester (392 mg, 1.0 mmol), 1-(2-fluorophenyl)-piperazine (216 mg, 1.2 mmol), palladium (II) acetate (11.2 mg, 0.05 mmol), xantphos (34.7 mg, 0.06 mmol) and cesium carbonate (652 mg, 2 mmol) in toluene (5 mL) was heated for 3 h at 120° C. After colling to room temperature, the mixture was treated with ethyl acetate (50 mL) and washed with water (20 mL). The organic layer was dried over anhydrous sodium sulfate and concentrated in vacuo. Purification on flash silica gel chromatography (silica gel from QingDao, 200-300 mesh, glass column from Shanghai SD company) (50% ethyl acetate/hexanes) to afford 6-fluoro-2-{3-[4-(2-fluoro-phenyl)-piperazin-1-yl]-phenyl}-4,4-dimethyl-1,2,3,4-tetrahydro-quinoline-8-carboxylic acid methyl ester (0.3 g, 60%) as a white solid: MS (ESI) M+1=492.1.

A mixture of afford 6-fluoro-2-{3-[4-(2-fluoro-phenyl)-piperazin-1-yl]-phenyl}-4,4-dimethyl-1,2,3,4-tetrahydro-quinoline-8-carboxylic acid methyl ester (0.30 g, 0.61 mmol) in methanol (3 mL) and tetrahydrofuran (10 mL), 30% sodium hydroxide in water (1 mL). The reaction mixture was stirred at 60° C. for 12 h. The mixture was neutralized with a 3 N aqueous hydrochloric acid solution and extracted with ethyl acetate (2×50 mL), washed with water, dried over anhydrous sodium sulfate and then concentrated in vacuo to afford 6-fluoro-2-{3-[4-(2-fluoro-phenyl)-piperazin-1-yl]-phenyl}-4,4-dimethyl-1,2,3,4-tetrahydro-quinoline-8-carboxylic acid (0.26 g, 90%) as a white solid which was used for next step without further purification: MS (ESI) M+1=478.3.

A mixture of 6-fluoro-2-{3-[4-(2-fluoro-phenyl)-piperazin-1-yl]-phenyl}-4,4-dimethyl-1,2,3,4-tetrahydro-quinoline-8-carboxylic acid (100 mg, 0.21 mmol), 1-3-dimethylaminopropyl-3-ethylcarbodiimide hydrochloride (60 mg, 0.31 mmol), 4-dimethylaminopyridine (38 mg, 0.31 mmol), methane sulfonamide (60 mg, 0.63 mmol) in dichloromethane (10 mL) was refluxed for 12 h. Removal of the solvent to afford the oil residue. Purification by Waters automated flash system (column: Xterra 30 mm×100 mm, sample manager 2767, pump 2525, detector: ZQ mass and UV 2487, solvent system: acetonitrile and 0.1% formic acid in water) afforded N-(6-fluoro-2-{3-[4-(2-fluoro-phenyl)-piperazin-1-yl]-phenyl}-4,4-dimethyl-1,2,3,4-tetrahydro-quinoline-8-carbonyl)-methanesulfonamide (34.7 mg, 30%) as a light yellow solid: MS (ESI) M+1=555.3.

Example 60

Cyclopropanesulfonic acid (6-fluoro-2-{3-[4-(2-fluoro-phenyl)-piperazin-1-yl]-phenyl}-4,4-dimethyl-1,2,3,4-tetrahydro-quinoline-8-carbonyl)-amide

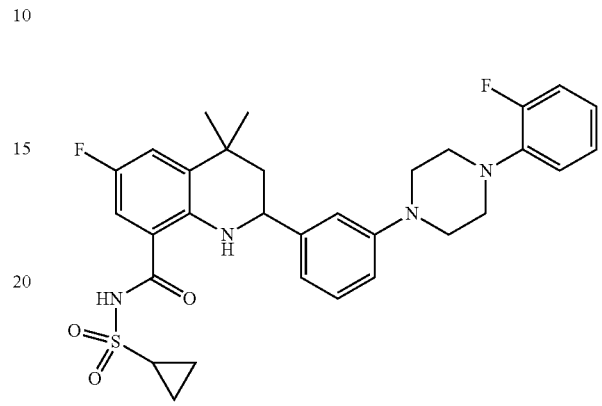

A mixture of 6-fluoro-4,4-dimethyl-2-[3-(4-o-tolyl-piperazin-1-yl)-phenyl]-1,2,3,4-tetrahydro-quinoline-8-carboxylic acid (100 mg, 0.21 mmol), 1-3-dimethylaminopropyl-3-ethylcarbodiimide hydrochloride (60 mg, 0.31 mmol), 4-dimethylaminopyridine (38 mg, 0.31 mmol), cyclopropane sulfonic acid amide (76 mg, 0.63 mmol) in dichloromethane (10 mL) was refluxed for 12 h. Removal of the solvent to afford the oil residue. Purification by Waters automated flash system (column: Xterra 30 mm×100 mm, sample manager 2767, pump 2525, detector: ZQ mass and UV 2487, solvent system: acetonitrile and 0.1% formic acid in water) afforded cyclopropanesulfonic acid (6-fluoro-2-{3-[4-(2-fluoro-phenyl)-piperazin-1-yl]-phenyl}-4,4-dimethyl-1,2,3,4-tetrahydroquinoline-8-carbonyl)-amide (36.5 mg, 30%) as a light yellow solid: MS (ESI) M+1=581.3.

Example 61

Cyclopropanesulfonic acid [6-chloro-2-(3-dimethylamino-phenyl)-4,4-dimethyl-1,2,3,4-tetrahydro-quinoline-8-carbonyl]-amide

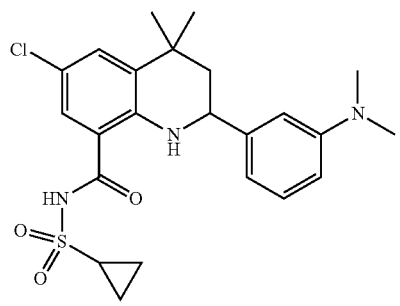 [SMILES: CN(C)c1cccc(C2CC(C)(C)c3cc(Cl)cc(C(=O)NS(=O)(=O)C4CC4)c3N2)c1]

A mixture of 2-amino-chloro-fluoro-benzoic acid methyl ester (11 g, 60 mmol), 3-bromo-benzaldehyde (11 g, 60 mmol) and ytterbium(III) triflate hydrate (3.72 g, 6.0 mmol) in acetonitrile (100 mL) was cooled to 0° C. in a sealed reaction bottle. Then a cooled solution of isobutene (16.8 g, 300 mmol) was added into. The reaction mixture was heated to 90° C. and stirred for 12 h. The solvent was removed in vacuo and the residue was purified on flash silica gel chromatography (silica gel from QingDao, 200-300 mesh, glass column from Shanghai SD company) (20% ethyl acetate/hexanes) to afford 2-(3-bromo-phenyl)-6-chloro-4,4-dimethyl-1,2,3,4-tetrahydro-quinoline-8-carboxylic acid methyl ester (14 g, 57%) as a white solid: MS (ESI) M+1=408.0.

A mixture of 2-(3-bromo-phenyl)-6-chloro-4,4-dimethyl-1,2,3,4-tetrahydro-quinoline-8-carboxylic acid methyl ester (0.82 g, 1.0 mmol), dimethyl amine hydrochloride (0.65 g, 8 mmol), copper (I) iodide (230 mg, 1.2 mmol), N,N-dimethyl glycine hydrochloride (220 mg, 1.6 mmol) and potassium carbonate (0.83 g, 6 mmol) in dimethylsulfoxide (20 mL) was heated for 12 h at 120° C. After colling to room temperature, the mixture was treated with ethyl acetate (50 mL) and washed with water (20 mL). The organic layer was dried over anhydrous sodium sulfate and concentrated in vacuo. Purification on flash silica gel chromatography (silica gel from QingDao, 200-300 mesh, glass column from Shanghai SD company) (30% ethyl acetate/hexanes) to afford 6-chloro-2-(3-dimethylamino-phenyl)-4,4-dimethyl-1,2,3,4-tetrahydro-quinoline-8-carboxylic acid (0.37 g, 51%) as a white solid: MS (ESI) M+1=359.2.

A mixture of 6-chloro-2-(3-dimethylamino-phenyl)-4,4-dimethyl-1,2,3,4-tetrahydro-quinoline-8-carboxylic acid (150 mg, 0.42 mmol), 1-3-dimethylaminopropyl-3-ethylcarbodiimide hydrochloride (120 mg, 0.63 mmol), 4-dimethylaminopyridine (77 mg, 0.63 mmol), cyclopropane sulfonic acid amide (150 mg, 1.26 mmol) in dichloromethane (10 mL) was refluxed for 12 h. Removal of the solvent to afford the oil residue. Purification by Waters automated flash system (column: Xterra 30 mm×100 mm, sample manager 2767, pump 2525, detector: ZQ mass and UV 2487, solvent system: acetonitrile and 0.1% formic acid in water) afforded cyclopropanesulfonic acid [6-chloro-2-(3-dimethylamino-phenyl)-4,4-dimethyl-1,2,3,4-tetrahydro-quinoline-8-carbonyl]-amide (39 mg, 20%) as a light yellow solid: MS (ESI) M+1=462.2.

Example 62

N-[6-chloro-4,4-dimethyl-2-(3-morpholin-4-yl-phenyl)-1,2,3,4-tetrahydro-quinoline-8-carbonyl]-methanesulfonamide

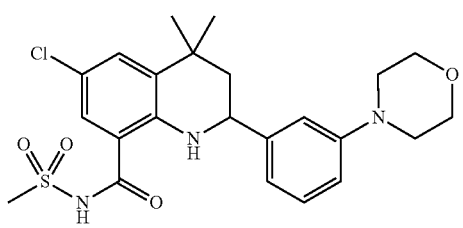 [SMILES: CC1(C)CC(c2cccc(N3CCOCC3)c2)Nc2c(C(=O)NS(C)(=O)=O)cc(Cl)cc21]

To a stirred solution of 2-amino-5-chloro-benzoic acid methyl ester (9.25 g, 50 mmol) and 3-bromobenzaldehyde (6.4 mL, 55 mmol) in acetonitrile (200 mL) were added isobutene (14 mL, 200 mmol) and ytterbium(III) trifluoromethanesulfonate (Yb(OTf)$_3$) (4.65 g, 7.5 mmol). The resulting mixture was stirred at 85° C. for 16 h in sealed tube. The mixture was diluted with ethyl acetate (300 mL) and washed with water (100 mL×2) and brine (100 mL×2) and then dried over anhydrous sodium sulfate. The solvent was removed in vacuo and the residue was purified by ISCO combi-flash chromatography (gradient elution, 10-50% ethyl acetate in petroleum ether) to afford 2-(3-bromo-phenyl)-6-chloro-4,4-dimethyl-1,2,3,4-tetrahydro-quinoline-8-carboxylic acid methyl ester (8.9 g, 45%) as a light yellow solid: MS (ESI) M+1=408.0 & 410.0.

A mixture solution of 2-(3-bromo-phenyl)-6-chloro-4,4-dimethyl-1,2,3,4-tetrahydro-quinoline-8-carboxylic acid methyl ester (8.9 g, 7 mmol), morpholine (6.1 mL, 70 mmol), copper(I) iodide (0.4 g, 2.1 mmol), N,N-dimethylglycine hydrochloride (0.4 g, 2.8 mmol), and potassium carbonate (2.9 g, 21 mmol) in dimethyl sulfoxide (20 mL) was stirred at 120° C. for 16 h. Then the reaction mixture was cooled to room temperature. The reaction mixture was extracted with ethyl acetate (150 mL×2), washed with saturated aqueous ammonium chloride solution (50 mL×3) and brine (50 mL×2), dried over anhydrous sodium sulfate and then concentrated in vacuo and the residue was purified by ISCO combi-flash chromatography (gradient elution, 30-50% ethyl acetate in petroleum ether) to afford 6-chloro-4,4-dimethyl-2-(3-morpholin-4-yl-phenyl)-1,2,3,4-tetrahydro-quinoline-8-carboxylic acid (2.7 g, 96%) as a white solid: MS (ESI) M+1=401.2.

To a suspension of 60% sodium hydride (361 mg, 9 mmol) in N,N-dimethylformamide (5 mL) was added methanesulfonamide (865 mg, 9.1 mmol) at room temperature. The resulting mixture was stirred at 25° C. for 1 h to afford Solution A62. A solution of 6-chloro-4,4-dimethyl-2-(3-morpholin-4-yl-phenyl)-1,2,3,4-tetrahydro-quinoline-8-carboxylic acid (520 mg, 1.3 mmol) and 1,1'-carbonyldiimidazole (422 mg, 2.6 mmol) in N,N-dimethylformamide (3 mL) was stirred at 70° C. for 1 h and cooled to room temperature to afford Solution B62. Solution B62 was added to Solution A62 and the resulting mixture was stirred at 25° C. for 1 h. To the reaction mixture was added water (0.5 mL). The mixture was filtered to remove the insoluble solid, and the filtrate was purified by Waters automated flash system (column: Xterra 30 mm×100 mm, sample manager 2767, pump 2525, detector: ZQ mass and UV 2487, solvent system: acetonitrile and 0.1% ammonium hydroxide in water) afforded N-[6-chloro-4,4-dimethyl-2-(3-morpholin-4-yl-phenyl)-1,2,3,4-tetrahydro-quinoline-8-carbonyl]-methanesulfonamide (50 mg, 8%) as a white solid: MS (ESI) M+1=478.2.

Example 63

Cyclopropanesulfonic acid [6-chloro-4,4-dimethyl-2-(3-morpholin-4-yl-phenyl)-1,2,3,4-tetrahydro-quinoline-8-carbonyl]-amide

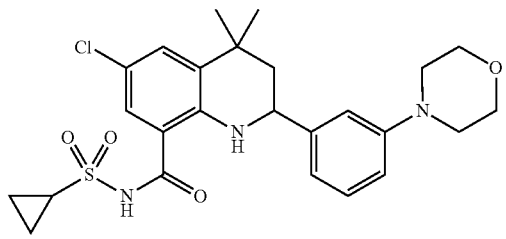 [SMILES: CC1(C)CC(c2cccc(N3CCOCC3)c2)Nc2c(C(=O)NS(=O)(=O)C3CC3)cc(Cl)cc21]

To a suspension of cyclopropanesulfonic acid amide (1.1 g, 9.1 mmol) in N,N-dimethylformamide (3 mL) was added sodium hydride (361 mg, 9 mmol). The resulting mixture was stirred at 25° C. for 1 h to afford Solution A63. A solution of 6-chloro-4,4-dimethyl-2-(3-morpholin-4-yl-phenyl)-1,2,3, 4-tetrahydro-quinoline-8-carboxylic acid (520 mg, 1.3 mmol) and 1,1'-carbonyldiimidazole (422 mg, 2.6 mmol) in N,N-dimethylformamide (3 mL) was stirred at 70° C. for 1 h and cooled to room temperature to afford Solution B63. Solution B63 was added to Solution A63 and the resulting mixture was stirred at 25° C. for 1 h. To the reaction mixture was added water (0.5 mL). The mixture was filtered to remove the insoluble solid, and the filtrate was purified by Waters automated flash system (column: Xterra 30 mm×100 mm, sample manager 2767, pump 2525, detector: ZQ mass and UV 2487, solvent system: acetonitrile and 0.1% ammonium hydroxide in water) afforded cyclopropanesulfonic acid [6-chloro-4,4-dimethyl-2-(3-morpholin-4-yl-phenyl)-1,2,3,4-tetrahydro-quinoline-8-carbonyl]-amide (25 mg, 4%) as a white solid: MS (ESI) M+1=504.2.

Example 64

N-{6-chloro-4,4-dimethyl-2-[3-(2-oxo-oxazolidin-3-yl)-phenyl]-1,2,3,4-tetrahydro-quinoline-8-carbonyl}-methanesulfonamide

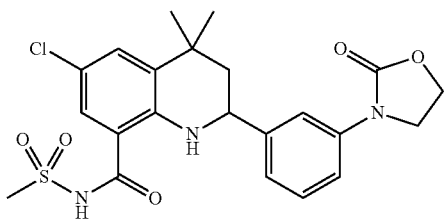 [SMILES: CC1(C)CC(c2cccc(N3CCOC3=O)c2)Nc2c(C(=O)NS(C)(=O)=O)cc(Cl)cc21]

A mixture of 2-(3-bromo-phenyl)-6-chloro-4,4-dimethyl-1,2,3,4-tetrahydro-quinoline-8-carboxylic acid methyl ester (1 g, 2.5 mmol), oxazolidin-2-one (230 mg, 2.63 mmol), copper(I) iodide (95 mg, 0.5 mmol), N,N'-dimethyl-ethane-1,2-diamine (0.11 mL, 1 mmol), and potassium carbonate (1.04 g, 7.5 mmol) in dimethyl sulfoxide (10 mL). The reaction mixture was stirred at 120° C. for 16 h. Then the reaction mixture cooled to room temperature. The reaction mixture was extracted with ethyl acetate (2×50 mL), washed with water (2×20 mL) and saturated aqueous ammonium chloride solution (2×20 mL), dried over anhydrous sodium sulfate and then concentrated in vacuo. Purification by Waters automated flash system (column: Xterra 30 mm×100 mm, sample manager 2767, pump 2525, detector: ZQ mass and UV 2487, solvent system: acetonitrile and 0.1% ammonium hydroxide in water) afforded 6-chloro-4,4-dimethyl-2-[3-(2-oxo-oxazolidin-3-yl)-phenyl]-1,2,3,4-tetrahydro-quinoline-8-carboxylic acid (0.8 g, 80%) as a white solid: MS (ESI) M+1=400.1.

To a suspension of methanesulfonamide (665 mg, 7 mmol) in N,N-dimethylformamide (3 mL) was added sodium hydride (280 mg, 7 mmol). The resulting mixture was stirred at 25° C. for 1 h to afford Solution A64. A solution of 6-chloro-4,4-dimethyl-2-[3-(2-oxo-oxazolidin-3-yl)-phenyl]-1,2,3,4-tetrahydro-quinoline-8-carboxylic acid (400 mg, 1 mmol) and 1,1'-carbonyldiimidazole (325 mg, 2 mmol) in N,N-dimethylformamide (2 mL) was stirred at 70° C. for 1 h and cooled to room temperature to afford Solution B64. Solution B64 was added to Solution A64 and the resulting mixture was stirred at 25° C. for 1 h. To the reaction mixture was added water (0.5 mL). The mixture was filtered to remove the insoluble solid, and the filtrate was purified by Waters automated flash system (column: Xterra 30 mm×100 mm, sample manager 2767, pump 2525, detector: ZQ mass and UV 2487, solvent system: acetonitrile and 0.1% ammonium hydroxide in water) afforded N-{6-chloro-4,4-dimethyl-2-[3-(2-oxo-oxazolidin-3-yl)-phenyl]-1,2,3,4-tetrahydro-quinoline-8-carbonyl}-methanesulfonamide (37 mg, 7%) as a white solid: MS (ESI) M+1=478.0.

Example 65

Cyclopropanesulfonic acid {6-chloro-4,4-dimethyl-2-[3-(2-oxo-oxazolidin-3-yl)-phenyl]-1,2,3,4-tetrahydro-quinoline-8-carbonyl}-amide

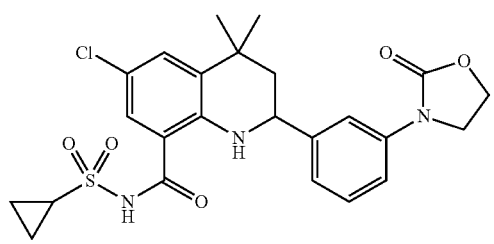 [SMILES: CC1(C)CC(c2cccc(N3CCOC3=O)c2)Nc2c(C(=O)NS(=O)(=O)C3CC3)cc(Cl)cc21]

To a suspension of cyclopropanesulfonic acid amide (847 mg, 7 mmol) in N,N-dimethylformamide (3 mL) was added sodium hydride (280 mg, 7 mmol). The resulting mixture was stirred at 25° C. for 1 h to afford Solution A65. A solution of 6-chloro-4,4-dimethyl-2-[3-(2-oxo-oxazolidin-3-yl)-phenyl]-1,2,3,4-tetrahydro-quinoline-8-carboxylic acid (400 mg, 1 mmol) and 1,1'-carbonyldiimidazole (325 mg, 2 mmol) in N,N-dimethylformamide (2 mL) was stirred at 70° C. for 1 h and cooled to room temperature to afford Solution B65. Solution B65 was added to Solution A65 and the resulting mixture was stirred at 25° C. for 1 h. To the reaction mixture was added water (0.5 mL). The mixture was filtered to remove the insoluble solid, and the filtrate was purified by Waters automated flash system (column: Xterra 30 mm×100 mm, sample manager 2767, pump 2525, detector: ZQ mass and UV 2487, solvent system: acetonitrile and 0.1% ammonium hydroxide in water) afforded cyclopropanesulfonic acid {6-chloro-4,4-dimethyl-2-[3-(2-oxo-oxazolidin-3-yl)-phenyl]-1,2,3,4-tetrahydro-quinoline-8-carbonyl}-amide (120 mg, 24%) as a white solid: MS (ESI) M+1=504.0.

Example 66

Cyclopropanesulfonic acid [4,4,8-trimethyl-2-(3-morpholin-4-yl-phenyl)-1,2,3,4-tetrahydro-quinoline-6-carbonyl]-amide

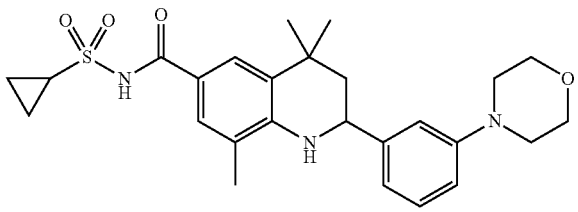 [SMILES: Cc1cc(C(=O)NS(=O)(=O)C2CC2)cc2c1NC(c1cccc(N3CCOCC3)c1)CC2(C)C]

To a stirred solution of 4-amino-3-methyl-benzoic acid methyl ester (11.55 g, 70 mmol) and 3-bromobenzaldehyde (8.2 mL, 70 mmol) in acetonitrile (150 mL) were added isobutene (17 mL, 242 mmol) and ytterbium(III) trifluoromethanesulfonate (Yb(OTf)$_3$) (5.2 g, 8.4 mmol). The resulting mixture was stirred at 90° C. for 20 h in sealed tube. The mixture was diluted with ethyl acetate (300 mL) and washed with water (100 mL×2) and brine (100 mL×2) and then dried over anhydrous sodium sulfate. The solvent was removed in vacuo and the residue was purified by ISCO combi-flash chromatography (gradient elution, 10-50% ethyl acetate in petroleum ether) to afford 2-(3-bromo-phenyl)-4,4,8-trimethyl-1,2,3,4-tetrahydro-quinoline-6-carboxylic acid methyl ester (8.15 g, 30%) as a light yellow solid: MS (ESI) M+1=388.0 & 390.0.

A mixture solution of 2-(3-bromo-phenyl)-4,4,8-trimethyl-1,2,3,4-tetrahydro-quinoline-6-carboxylic acid methyl ester (1.4 g, 3.6 mmol), morpholine (4.3 mL, 50 mmol), copper(I) iodide (274 mg, 1.44 mmol), N,N-dimethylglycine hydrochloride (0.3 g, 2.16 mmol), and potassium carbonate (1.49 g, 10.8 mmol) in dimethyl sulfoxide (10 mL) was stirred at 120° C. for 16 h. Then the reaction mixture was cooled to room temperature. The reaction mixture was extracted with ethyl acetate (150 mL×2), washed with saturated aqueous ammonium chloride solution (50 mL×3) and brine (50 mL×2), dried over anhydrous sodium sulfate and then concentrated in vacuo and the residue was purified by ISCO combi-flash chromatography (gradient elution, 30-50% ethyl acetate in petroleum ether) to afford 4,4,8-trimethyl-2-(3-morpholin-4-yl-phenyl)-1,2,3,4-tetrahydro-quinoline-6-carboxylic acid methyl ester (1.4 g, 98%) as a white solid: MS (ESI) M+1=394.2.

To a stirred mixture solution of 4,4,8-trimethyl-2-(3-morpholin-4-yl-phenyl)-1,2,3,4-tetrahydro-quinoline-6-carboxylic acid methyl ester (1.4 g, 3.55 mmol) in methanol (5 mL) and tetrahydrofuran (10 mL) was added 30% sodium hydroxide in water (5 mL). The reaction mixture was stirred at 60° C. for 16 h. The mixture was neutralized with a 3 N aqueous hydrochloric acid solution and extracted with ethyl acetate (2×50 mL), washed with water, dried over anhydrous sodium sulfate and then concentrated in vacuo to afford 4,4,8-trimethyl-2-(3-morpholin-4-yl-phenyl)-1,2,3,4-tetrahydro-quinoline-6-carboxylic acid (0.9 g, 66%) as a light white solid which was used for next step without further purification: MS (ESI) M+1=381.0.

To a suspension of 60% sodium hydride (664 mg, 16.6 mmol) in N,N-dimethylformamide (5 mL) was added cyclopropanesulfonic acid amide (2.01 g, 16.6 mmol) at room temperature. The resulting mixture was stirred at 25° C. for 1 h to afford Solution A66. A solution of 4,4,8-trimethyl-2-(3-morpholin-4-yl-phenyl)-1,2,3,4-tetrahydro-quinoline-6-carboxylic acid (0.9 g, 2.37 mmol) and 1,1'-carbonyldiimidazole (768 mg, 4.74 mmol) in N,N-dimethylformamide (5 mL) was stirred at 70° C. for 1 h and cooled to room temperature to afford Solution B66. Solution B66 was added to Solution A66 and the resulting mixture was stirred at 25° C. for 1 h. To the reaction mixture was added water (0.5 mL). The mixture was filtered to remove the insoluble solid, and the filtrate was purified by Waters automated flash system (column: Xterra 30 mm×100 mm, sample manager 2767, pump 2525, detector: ZQ mass and UV 2487, solvent system: acetonitrile and 0.1% ammonium hydroxide in water) afforded cyclopropanesulfonic acid [4,4,8-trimethyl-2-(3-morpholin-4-yl-phenyl)-1,2,3,4-tetrahydro-quinoline-6-carbonyl]-amide (107 mg, 9%) as a brown solid: MS (ESI) M+1=484.2.

Example 67

N-{4,4-dimethyl-2-[3-(4-methyl-piperazin-1-yl)-phenyl]-1,2,3,4-tetrahydro-quinoline-8-carbonyl}-methanesulfonamide

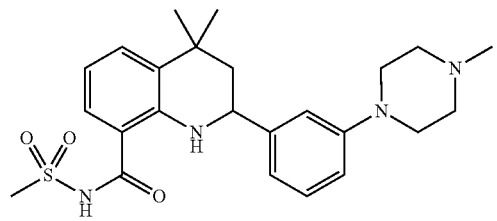

To a stirred solution of 2-amino-benzoic acid methyl ester (10 g, 60.5 mmol) and 3-bromobenzaldehyde (8 mL, 60.5 mmol) in acetonitrile (200 mL) were added isobutene (17 mL, 242 mmol) and ytterbium(III) trifluoromethanesulfonate (Yb(OTf)$_3$) (4.5 g, 7.3 mmol). The resulting mixture was stirred at 90° C. for 16 h in sealed tube. The mixture was diluted with ethyl acetate (300 mL) and washed with water (100 mL×2) and brine (100 mL×2) and then dried over anhydrous sodium sulfate. The solvent was removed in vacuo and the residue was purified by ISCO combi-flash chromatography (gradient elution, 10-50% ethyl acetate in petroleum ether) to afford 2-(3-bromo-phenyl)-4,4-dimethyl-1,2,3,4-tetrahydro-quinoline-8-carboxylic acid methyl ester (9 g, 40%) as a light yellow solid: MS (ESI) M+1=374.0 & 375.9.

A mixture solution of 2-(3-bromo-phenyl)-4,4-dimethyl-1,2,3,4-tetrahydro-quinoline-8-carboxylic acid methyl ester (1.5 g, 4 mmol), 1-methyl-piperazine (1.8 mL, 16 mmol), copper(I) iodide (0.46 g, 2.4 mmol), N,N-dimethylglycine hydrochloride (0.45 g, 3.2 mmol), and potassium carbonate (1.66 g, 12 mmol) in dimethyl sulfoxide (10 mL) was stirred at 120° C. for 16 h. Then the reaction mixture was cooled to room temperature. The reaction mixture was extracted with ethyl acetate (50 mL×2), washed with saturated aqueous ammonium chloride solution (20 mL×3) and brine (20 mL×2), dried over anhydrous sodium sulfate and then concentrated in vacuo and the residue was purified by ISCO combi-flash chromatography (gradient elution, 30-50% ethyl acetate in petroleum ether) to afford 4,4-dimethyl-2-[3-(4-methyl-piperazin-1-yl)-phenyl]-1,2,3,4-tetrahydro-quinoline-8-carboxylic acid methyl ester (0.2 g, 13%) as a white solid: MS (ESI) M+1=394.2.

To a stirred mixture solution of 4,4-dimethyl-2-[3-(4-methyl-piperazin-1-yl)-phenyl]-1,2,3,4-tetrahydro-quinoline-8-carboxylic acid methyl ester (200 mg, 0.5 mmol) in methanol (10 mL) and tetrahydrofuran (10 mL) was added 30% sodium hydroxide in water (1.5 mL). The reaction mixture was stirred at 60° C. for 6 h. The mixture was neutralized with a 3 N aqueous hydrochloric acid solution and extracted with ethyl acetate (2×50 mL), washed with water, dried over anhydrous sodium sulfate and then concentrated in vacuo to afford 4,4-dimethyl-2-[3-(4-methyl-piperazin-1-yl)-phenyl]-1,2,3,4-tetrahydro-quinoline-8-carboxylic acid (180 mg, 95%) as a light white solid which was used for next step without further purification: MS (ESI) M+1=380.2.

To a suspension of 60% sodium hydride (73 mg, 1.82 mmol) in N,N-dimethylformamide (2 mL) was added methanesulfonamide (173 mg, 1.82 mmol) at room temperature. The resulting mixture was stirred at 25° C. for 1 h to afford Solution A67. A solution of 4,4-dimethyl-2-[3-(4-methylpiperazin-1-yl)-phenyl]-1,2,3,4-tetrahydro-quinoline-8-carboxylic acid (100 mg, 0.26 mmol) and 1,1'-carbonyldiimidazole (84 mg, 0.52 mmol) in N,N-dimethylformamide (1.5 mL) was stirred at 70° C. for 1 h and cooled to room temperature to afford Solution B67. Solution B67 was added to Solution A67 and the resulting mixture was stirred at 25° C. for 1 h. To the reaction mixture was added water (0.5 mL). The mixture was filtered to remove the insoluble solid, and the filtrate was purified by Waters automated flash system (column: Xterra 30 mm×100 mm, sample manager 2767, pump 2525, detector: ZQ mass and UV 2487, solvent system: acetonitrile and 0.1% ammonium hydroxide in water) afforded N-{4,4-dimethyl-2-[3-(4-methyl-piperazin-1-yl)-phenyl]-1, 2,3,4-tetrahydro-quinoline-8-carbonyl}-methanesulfonamide (35 mg, 46%) as a white solid: MS (ESI) M+1=457.3.

Example 68

N-{6-fluoro-4,4-dimethyl-2-[3-(4-p-tolyl-piperazin-1-yl)-phenyl]-1,2,3,4-tetrahydro-quinoline-8-carbonyl}-methanesulfonamide

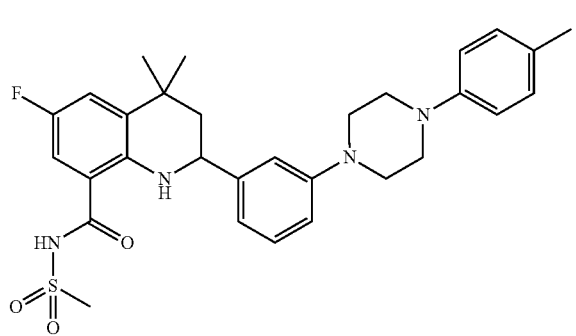 [SMILES: Cc1ccc(N2CCN(c3cccc(C4CC(C)(C)c5cc(F)cc(C(=O)NS(C)(=O)=O)c5N4)c3)CC2)cc1]

A mixture of 2-(3-bromo-phenyl)-6-fluoro-4,4-dimethyl-1,2,3,4-tetrahydro-quinoline-8-carboxylic acid methyl ester (500 mg, 1.28 mmol), 1-p-tolyl-piperazine dihydrochloride (410 mg, 1.92 mmol), palladium (II) acetate (14.4 mg, 0.064 mmol), xantphos (44.4 mg, 0.077 mmol) and cesium carbonate (830 mg, 2.56 mmol) in toluene (10 mL) was heated for 3 h at 120° C. After colling to room temperature, the mixture was treated with ethyl acetate (50 mL) and washed with water (20 mL). The organic layer was dried over anhydrous sodium sulfate and concentrated in vacuo. Purification on flash silica gel chromatography (silica gel from QingDao, 200-300 mesh, glass column from Shanghai SD company) (50% ethyl acetate/hexanes) to afford 6-fluoro-4,4-dimethyl-2-[3-(4-p-tolyl-piperazin-1-yl)-phenyl]-1,2,3,4-tetrahydro-quinoline-8-carboxylic acid methyl ester (0.37 g, 60%) as a white solid: MS (ESI) M+1=488.3.

A mixture of afford 6-fluoro-4,4-dimethyl-2-[3-(4-p-tolyl-piperazin-1-yl)-phenyl]-1,2,3,4-tetrahydro-quinoline-8-carboxylic acid methyl ester (0.20 g, 0.41 mmol) in methanol (3 mL) and tetrahydrofuran (10 mL), 30% sodium hydroxide in water (1 mL). The reaction mixture was stirred at 60° C. for 12 h. The mixture was neutralized with a 3 N aqueous hydrochloric acid solution and extracted with ethyl acetate (2×50 mL), washed with water, dried over anhydrous sodium sulfate and then concentrated in vacuo to afford 6-fluoro-4,4-dimethyl-2-[3-(4-p-tolyl-piperazin-1-yl)-phenyl]-1,2,3,4-tetrahydro-quinoline-8-carboxylic acid (0.17 g, 90%) as a white solid which was used for next step without further purification: MS (ESI) M+1=474.3.

A mixture of 6-fluoro-4,4-dimethyl-2-[3-(4-p-tolyl-piperazin-1-yl)-phenyl]-1,2,3,4-tetrahydro-quinoline-8-carboxylic acid (150 mg, 0.32 mmol), 1-3-dimethylaminopropyl-3-ethylcarbodiimide hydrochloride (91 mg, 0.48 mmol), 4-dimethylaminopyridine (59 mg, 0.48 mmol), methane sulfonamide (91.2 mg, 0.96 mmol) in dichloromethane (10 mL) was refluxed for 12 h. Removal of the solvent to afford the oil residue. Purification by Waters automated flash system (column: Xterra 30 mm×100 mm, sample manager 2767, pump 2525, detector: ZQ mass and UV 2487, solvent system: acetonitrile and 0.1% formic acid in water) afforded N-{6-fluoro-4,4-dimethyl-2-[3-(4-p-tolyl-piperazin-1-yl)-phenyl]-1,2,3, 4-tetrahydro-quinoline-8-carbonyl}-methanesulfonamide (35 mg, 20%) as a light yellow solid: MS (ESI) M+1=551.3.

Example 69

N-[6-fluoro-4,4-dimethyl-2-(3-pyrrolidin-1-yl-phenyl)-1,2,3,4-tetrahydro-quinoline-8-carbonyl]-methanesulfonamide

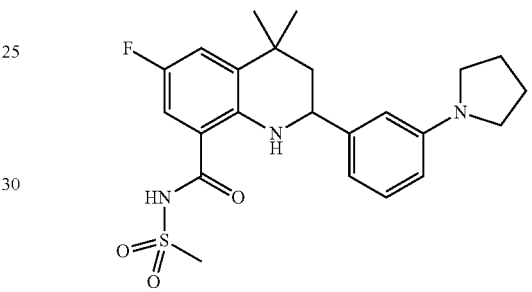

A mixture of 2-(3-bromo-phenyl)-6-fluoro-4,4-dimethyl-1,2,3,4-tetrahydro-quinoline-8-carboxylic acid methyl ester (500 mg, 1.28 mmol), pyrrolidine (140 mg, 1.92 mmol), palladium (II) acetate (14.4 mg, 0.064 mmol), xantphos (44.4 mg, 0.077 mmol) and cesium carbonate (830 mg, 2.56 mmol) in toluene (10 mL) was heated for 3 h at 120° C. After colling to room temperature, the mixture was treated with ethyl acetate (50 mL) and washed with water (20 mL). The organic layer was dried over anhydrous sodium sulfate and concentrated in vacuo. Purification on flash silica gel chromatography (silica gel from QingDao, 200-300 mesh, glass column from Shanghai SD company) (50% ethyl acetate/hexanes) to afford 6-fluoro-4,4-dimethyl-2-(3-pyrrolidin-1-yl-phenyl)-1,2,3,4-tetrahydro-quinoline-8-carboxylic acid methyl ester (0.32 g, 65%) as a white solid: MS (ESI) M+1=383.3.

A mixture of afford 6-fluoro-4,4-dimethyl-2-(3-pyrrolidin-1-yl-phenyl)-1,2,3,4-tetrahydro-quinoline-8-carboxylic acid methyl ester (0.32 g, 0.81 mmol) in methanol (3 mL) and tetrahydrofuran (10 mL), 30% sodium hydroxide in water (1 mL). The reaction mixture was stirred at 60° C. for 12 h. The mixture was neutralized with a 3 N aqueous hydrochloric acid solution and extracted with ethyl acetate (2×50 mL), washed with water, dried over anhydrous sodium sulfate and then concentrated in vacuo to afford 6-fluoro-4,4-dimethyl-2-(3-pyrrolidin-1-yl-phenyl)-1,2,3,4-tetrahydro-quinoline-8-carboxylic acid (0.28 g, 90%) as a white solid which was used for next step without further purification: MS (ESI) M+1=369.3.

A mixture of 6-fluoro-4,4-dimethyl-2-(3-pyrrolidin-1-yl-phenyl)-1,2,3,4-tetrahydro-quinoline-8-carboxylic acid (150 mg, 0.32 mmol), 1-3-dimethylaminopropyl-3-ethylcarbodiimide hydrochloride (91 mg, 0.48 mmol), 4-dimethylaminopyridine (59 mg, 0.48 mmol), methane sulfonamide (91.2 mg, 0.96 mmol) in dichloromethane (10 mL) was refluxed for 12 h. Removal of the solvent to afford the oil residue. Purification by Waters automated flash system (column: Xterra 30 mm×100 mm, sample manager 2767, pump 2525, detector: ZQ mass and UV 2487, solvent system: acetonitrile and 0.1% formic acid in water) afforded N-[6-fluoro-4,4-dimethyl-2-(3-pyrrolidin-1-yl-phenyl)-1,2,3,4-tetrahydro-quinoline-8-carbonyl]-methanesulfonamide (36 mg, 20%) as a light yellow solid: MS (ESI) M+1=446.3.

Example 70

Cyclopropanesulfonic acid [6-fluoro-4,4-dimethyl-2-(3-pyrrolidin-1-yl-phenyl)-1,2,3,4-tetrahydro-quinoline-8-carbonyl]-amide

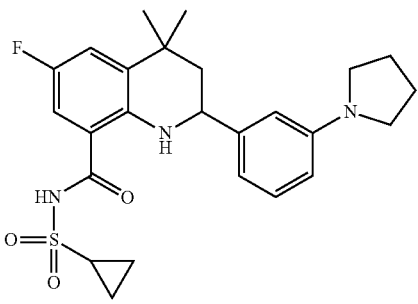 [SMILES: CC1(C)CC(c2cccc(N3CCCC3)c2)Nc2c(C(=O)NS(=O)(=O)C3CC3)cc(F)cc21]

A mixture of 6-fluoro-4,4-dimethyl-2-(3-pyrrolidin-1-yl-phenyl)-1,2,3,4-tetrahydro-quinoline-8-carboxylic acid (150 mg, 0.32 mmol), 1-3-dimethylaminopropyl-3-ethylcarbodiimide hydrochloride (91 mg, 0.48 mmol), 4-dimethylaminopyridine (59 mg, 0.48 mmol), cyclopropane sulfonic acid amide (149 mg, 1.23 mmol) in dichloromethane (10 mL) was refluxed for 12 h. Removal of the solvent to afford the oil residue. Purification by Waters automated flash system (column: Xterra 30 mm×100 mm, sample manager 2767, pump 2525, detector: ZQ mass and UV 2487, solvent system: acetonitrile and 0.1% formic acid in water) afforded cyclopropanesulfonic acid [6-fluoro-4,4-dimethyl-2-(3-pyrrolidin-1-yl-phenyl)-1,2,3,4-tetrahydro-quinoline-8-carbonyl]-amide (38.6 mg, 20%) as a light yellow solid: MS (ESI) M+1=472.3.

Example 71

N-[6-chloro-4,4-dimethyl-2-(3-pyrrolidin-1-yl-phenyl)-1,2,3,4-tetrahydro-quinoline-8-carbonyl]-methanesulfonamide

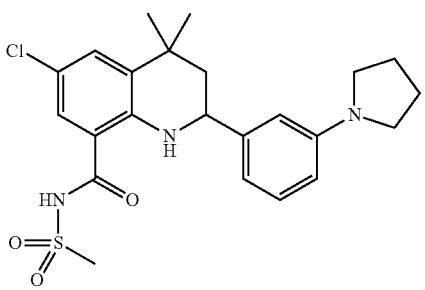 [SMILES: CC1(C)CC(c2cccc(N3CCCC3)c2)Nc2c(C(=O)NS(C)(=O)=O)cc(Cl)cc21]

A mixture of 2-(3-bromo-phenyl)-6-chloro-4,4-dimethyl-1,2,3,4-tetrahydro-quinoline-8-carboxylic acid methyl ester (0.82 g, 2.0 mmol), pyrrolidine (0.28 g, 4 mmol), copper (I) iodide (230 mg, 1.2 mmol), N,N-dimethyl glycine hydrochloride (220 mg, 1.6 mmol) and potassium carbonate (0.83 g, 6 mmol) in dimethylsulfoxide (20 mL) was heated for 12 h at 120° C. After colling to room temperature, the mixture was treated with ethyl acetate (50 mL) and washed with water (20 mL). The organic layer was dried over anhydrous sodium sulfate and concentrated in vacuo. Purification on flash silica gel chromatography (silica gel from QingDao, 200-300 mesh, glass column from Shanghai SD company) (30% ethyl acetate/hexanes) to afford 6-chloro-4,4-dimethyl-2-(3-pyrrolidin-1-yl-phenyl)-1,2,3,4-tetrahydro-quinoline-8-carboxylic acid (0.31 g, 40%) as a white solid: MS (ESI) M+1=385.2.

A mixture of 6-chloro-4,4-dimethyl-2-(3-pyrrolidin-1-yl-phenyl)-1,2,3,4-tetrahydro-quinoline-8-carboxylic acid (200 mg, 0.52 mmol), 1-(3-dimethylaminopropyl)-3-ethylcarbodiimide hydrochloride (140 mg, 0.78 mmol), 4-dimethylaminopyridine (95 mg, 0.78 mmol), methane sulfonamide (150 mg, 1.56 mmol) in dichloromethane (10 mL) was refluxed for 12 h. Removal of the solvent to afford the oil residue. Purification by Waters automated flash system (column: Xterra 30 mm×100 mm, sample manager 2767, pump 2525, detector: ZQ mass and UV 2487, solvent system: acetonitrile and 0.1% formic acid in water) afforded N-[6-chloro-4,4-dimethyl-2-(3-pyrrolidin-1-yl-phenyl)-1,2,3,4-tetrahydro-quinoline-8-carbonyl]-methanesulfonamide (48 mg, 20%) as a light yellow solid: MS (ESI) M+1=462.2.

Example 72

Cyclopropanesulfonic acid [6-chloro-4,4-dimethyl-2-(3-pyrrolidin-1-yl-phenyl)-1,2,3,4-tetrahydro-quinoline-8-carbonyl]-amide

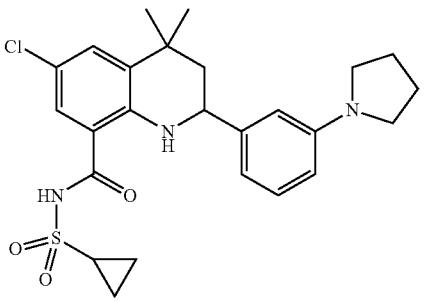 [SMILES: CC1(C)CC(c2cccc(N3CCCC3)c2)Nc2c(C(=O)NS(=O)(=O)C3CC3)cc(Cl)cc21]

A mixture of 6-chloro-4,4-dimethyl-2-(3-pyrrolidin-1-yl-phenyl)-1,2,3,4-tetrahydro-quinoline-8-carboxylic acid (200 mg, 0.52 mmol), 1-3-dimethylaminopropyl-3-ethylcarbodiimide hydrochloride (140 mg, 0.78 mmol), 4-dimethylaminopyridine (95 mg, 0.78 mmol), cyclopropane sulfonic acid amide (190 mg, 1.56 mmol) in dichloromethane (10 mL) was refluxed for 12 h. Removal of the solvent to afford the oil residue. Purification by Waters automated flash system (column: Xterra 30 mm×100 mm, sample manager 2767, pump 2525, detector: ZQ mass and UV 2487, solvent system: acetonitrile and 0.1% formic acid in water) afforded cyclopropanesulfonic acid [6-chloro-4,4-dimethyl-2-(3-pyrrolidin-1-ylphenyl)-1,2,3,4-tetrahydro-quinoline-8-carbonyl]-amide (51 mg, 20%) as a light yellow solid: MS (ESI) M+1=488.2.

Example 73

N-{2-[5-(4-tert-butyl-phenyl)-pyridin-3-yl]-4,4-dimethyl-1,2,3,4-tetrahydro-quinoline-6-carbonyl}-methanesulfonamide

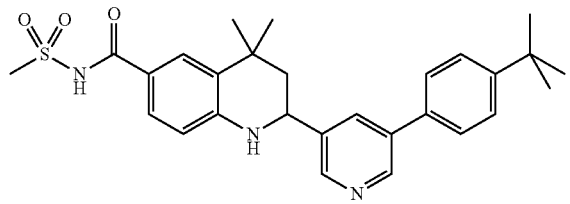 [SMILES: CC(C)(C)c1ccc(-c2cncc(C3CC(C)(C)c4cc(C(=O)NS(C)(=O)=O)ccc4N3)c2)cc1]

A mixture of 2-(5-bromo-pyridin-3-yl)-4,4-dimethyl-1,2,3,4-tetrahydro-quinoline-6-carboxylic acid ethyl ester (1.0 g, 2.57 mmol), 4-tert-butylbenzeneboronic acid (0.7 g, 3.86 mmol), tetra(triphenylphosphine)palladium (150 mg, 0.13 mmol) and cesium carbonate (1.7 g, 5.14 mmol) in dimethyl formamide (10 mL) was heated for 3 h at 120° C. After coiling to room temperature, the mixture was treated with ethyl acetate (50 mL) and washed with water (20 mL). The organic layer was dried over anhydrous sodium sulfate and concentrated in vacuo. Purification on flash silica gel chromatography (silica gel from QingDao, 200-300 mesh, glass column from Shanghai SD company) (10% ethyl acetate/hexanes) to afford 2-[5-(4-tert-butyl-phenyl)-pyridin-3-yl]-4,4-dimethyl-1,2,3,4-tetrahydro-quinoline-6-carboxylic acid ethyl ester (0.8 g, 70%) as a white solid: MS (ESI) M+1=443.3.

A mixture of 2-[5-(4-tert-butyl-phenyl)-pyridin-3-yl]-4,4-dimethyl-1,2,3,4-tetrahydro-quinoline-6-carboxylic acid ethyl ester (1.0 g, 2.3 mmol) in ethanol (10 mL) and tetrahydrofuran (50 mL), 30% sodium hydroxide in water (10 mL). The reaction mixture was stirred at 60° C. for 12 h. The mixture was neutralized with a 3 N aqueous hydrochloric acid solution and extracted with ethyl acetate (2×50 mL), washed with water, dried over anhydrous sodium sulfate and then concentrated in vacuo to afford 2-[5-(4-tert-butyl-phenyl)-pyridin-3-yl]-4,4-dimethyl-1,2,3,4-tetrahydro-quinoline-6-carboxylic acid (0.87 g, 90%) as a white solid which was used for next step without further purification: MS (ESI) M+1=415.3.

A mixture of 2-[5-(4-tert-butyl-phenyl)-pyridin-3-yl]-4,4-dimethyl-1,2,3,4-tetrahydro-quinoline-6-carboxylic acid (200 mg, 0.48 mmol), 1-3-dimethylaminopropyl-3-ethylcarbodiimide hydrochloride (130 mg, 0.72 mmol), 4-dimethylaminopyridine (88 mg, 0.72 mmol), methane sulfonamide (140 mg, 1.44 mmol) in dichloromethane (20 mL) was refluxed for 12 h. Removal of the solvent to afford the oil residue. Purification by Waters automated flash system (column: Xterra 30 mm×100 mm, sample manager 2767, pump 2525, detector: ZQ mass and UV 2487, solvent system: acetonitrile and 0.1% formic acid in water) afforded N-{2-[5-(4-tert-Butyl-phenyl)-pyridin-3-yl]-4,4-dimethyl-1,2,3,4-tetrahydro-quinoline-6-carbonyl}-methanesulfonamide (47 mg, 20%) as a light yellow solid: MS (ESI) M+1=492.3.

Example 74

Cyclopropanesulfonic acid {2-[5-(4-tert-butyl-phenyl)-pyridin-3-yl]-4,4-dimethyl-1,2,3,4-tetrahydro-quinoline-6-carbonyl}-amide

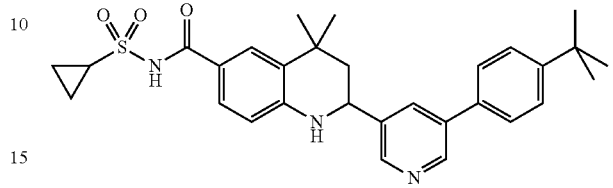

A mixture of 2-[5-(4-tert-butyl-phenyl)-pyridin-3-yl]-4,4-dimethyl-1,2,3,4-tetrahydro-quinoline-6-carboxylic acid (200 mg, 0.48 mmol), 1-3-dimethylaminopropyl-3-ethylcarbodiimide hydrochloride (130 mg, 0.72 mmol), 4-dimethylaminopyridine (88 mg, 0.72 mmol), cyclopropane sulfonic acid amide (170 mg, 1.44 mmol) in dichloromethane (20 mL) was refluxed for 12 h. Removal of the solvent to afford the oil residue. Purification by Waters automated flash system (column: Xterra 30 mm×100 mm, sample manager 2767, pump 2525, detector: ZQ mass and UV 2487, solvent system: acetonitrile and 0.1% formic acid in water) afforded cyclopropanesulfonic acid {2-[5-(4-tert-butyl-phenyl)-pyridin-3-yl]-4,4-dimethyl-1,2,3,4-tetrahydro-quinoline-6-carbonyl}-amide (50 mg, 20%) as a light yellow solid: MS (ESI) M+1=518.3.

Example 75

Cyclopropanesulfonic acid [4,4-dimethyl-2-(3-morpholin-4-yl-phenyl)-1,2,3,4-tetrahydro-quinoline-6-carbonyl]-methyl-amide

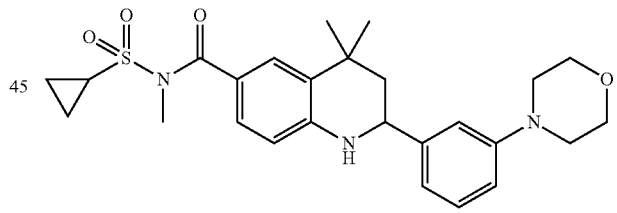

To a mixture of cyclopropanesulfonic acid [4,4-dimethyl-2-(3-morpholin-4-yl-phenyl)-1,2,3,4-tetrahydro-quinoline-6-carbonyl]-amide (100 mg, 0.21 mmol), and potassium carbonate (89.4 mg, 0.64 mmol) in N,N-dimethylformamide (4 mL) was added idomethane (0.02 mL, 0.32 mmol). The reaction mixture was stirred at 25° C. for 3 h. The reaction mixture was extracted with ethyl acetate (2×50 mL), washed with water (2×20 mL), dried over anhydrous sodium sulfate and then concentrated in vacuo. Purification by Waters automated flash system (column: Xterra 30 mm×100 mm, sample manager 2767, pump 2525, detector: ZQ mass and UV 2487, solvent system: acetonitrile and 0.1% ammonium hydroxide in water) afforded cyclopropanesulfonic acid [4,4-dimethyl-2-(3-morpholin-4-yl-phenyl)-1,2,3,4-tetrahydro-quinoline-6-carbonyl]-methyl-amide (20 mg, 19%) as a white solid: MS (ESI) M+1=484.3.

Example 76

Cyclopropanesulfonic acid {4,4-dimethyl-2-[3-(4-phenyl-piperazin-1-yl)-phenyl]-1,2,3,4-tetrahydro-quinoline-8-carbonyl}-amide

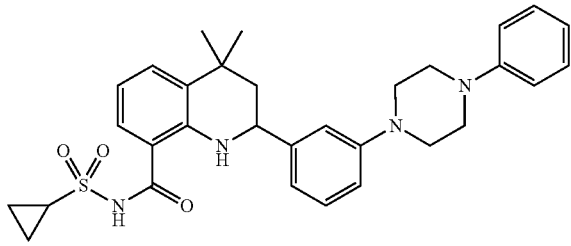 [SMILES: CC1(C)CC(c2cccc(N3CCN(c4ccccc4)CC3)c2)Nc2c(C(=O)NS(=O)(=O)C3CC3)cccc21]

A mixture of 2-(3-bromo-phenyl)-3,3-dimethyl-1,2,3,4-tetrahydro-quinoline-8-carboxylic acid ethyl ester (1.5 g, 4 mmol), 1-Phenyl-piperazine (2.45 mL, 16 mmol), copper(I) iodide (0.46 g, 2.4 mmol), N,N-dimethylglycine hydrochloride (0.45 g, 3.2 mmol), and potassium carbonate (1.66 g, 12 mmol) in dimethyl sulfoxide (10 mL). The reaction mixture was stirred at 120° C. for 16 h. Then the reaction mixture was cooled to room temperature. The reaction mixture was extracted with ethyl acetate (2×50 mL), washed with water (2×20 mL) and saturated aqueous ammonium chloride solution (2×20 mL), dried over anhydrous sodium sulfate and then concentrated in vacuo. Purification by Waters automated flash system (column: Xterra 30 mm×100 mm, sample manager 2767, pump 2525, detector: ZQ mass and UV 2487, solvent system: acetonitrile and 0.1% ammonium hydroxide in water) afforded 4,4-dimethyl-2-[3-(4-phenyl-piperazin-1-yl)-phenyl]-1,2,3,4-tetrahydro-quinoline-8-carboxylic acid (750 mg, 40%) as a white solid: MS (ESI) M+1=442.1.

To a suspension of cyclopropanesulfonic acid amide (96 mg, 0.8 mmol) in N,N-dimethylformamide (1.5 mL) was added sodium hydride (32 mg, 0.8 mmol). The resulting mixture was stirred at 25° C. for 1 h to afford Solution A76. A solution of 4,4-dimethyl-2-[3-(4-phenyl-piperazin-1-yl)-phenyl]-1,2,3,4-tetrahydro-quinoline-8-carboxylic acid (50 mg, 0.11 mmol) and 1,1'-carbonyldiimidazole (37 mg, 0.23 mmol) in N,N-dimethylformamide (2 mL) was stirred at 70° C. for 1 h and cooled to room temperature to afford Solution B76. Solution B76 was added to Solution A76 and the resulting mixture was stirred at 25° C. for 1 h. To the reaction mixture was added water (0.5 mL). The mixture was filtered to remove the insoluble solid, and the filtrate was purified by Waters automated flash system (column: Xterra 30 mm×100 mm, sample manager 2767, pump 2525, detector: ZQ mass and UV 2487, solvent system: acetonitrile and 0.1% ammonium hydroxide in water) afforded cyclopropanesulfonic acid {4,4-dimethyl-2-[3-(4-phenyl-piperazin-1-yl)-phenyl]-1,2,3,4-tetrahydro-quinoline-8-carbonyl}-amide (15 mg, 24%) as a white solid: MS (ESI) M+1=545.2.

Example 77

Cyclopropanesulfonic acid [2-(3-chloro-4-fluoro-phenyl)-4,4-dimethyl-1,2,3,4-tetrahydro-[1,7]naphthyridine-6-carbonyl]-amide

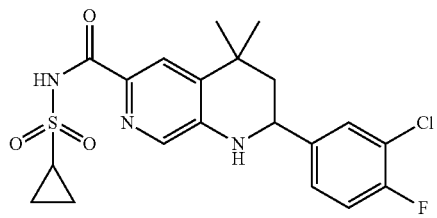 [SMILES: CC1(C)CC(c2ccc(F)c(Cl)c2)Nc2cnc(C(=O)NS(=O)(=O)C3CC3)cc21]

To a stirred solution of 5-amino-pyridine-2-carbonitrile (9.3 g, 78.4 mmol) and 3-chloro-4-fluoro-benzaldehyde (12.3 g, 78.4 mmol) in acetonitrile (150 mL) were added isobutene (21.0 mL, 313.5 mmol) and ytterbium(III) trifluoromethanesulfonate (Yb(OTf)$_3$) (5.8 g, 9.5 mmol). The resulting mixture was stirred at 85° C. for 18 h in sealed tube. The mixture was diluted with ethyl acetate (300 mL) and washed with water (100 mL×2) and brine (100 mL×2) and then dried over anhydrous sodium sulfate. The solvent was removed in vacuo and the residue was purified by ISCO combi-flash chromatography (gradient elution, 10-50% ethyl acetate in petroleum ether) to afford 2-(3-chloro-4-fluoro-phenyl)-4,4-dimethyl-1,2,3,4-tetrahydro-[1,7]naphthyridine-6-carbonitrile (1.2 g, 5.0%) as a light yellow solid: MS (ESI) M+1=316.0.

To a stirred mixture solution of 2-(3-chloro-4-fluoro-phenyl)-4,4-dimethyl-1,2,3,4-tetrahydro-[1,7]naphthyridine-6-carbonitrile (315.0 mg, 1.0 mmol) in ethanol (10.0 mL) was added 50% sodium hydroxide in water (3.5 mL). The reaction mixture was stirred at 90° C. for 6 h. The mixture was neutralized with a 3 N aqueous hydrochloric acid solution and extracted with ethyl acetate (2×100 mL), washed with water, dried over anhydrous sodium sulfate and then concentrated in vacuo to afford 2-(3-chloro-4-fluoro-phenyl)-4,4-dimethyl-1,2,3,4-tetrahydro-[1,7]naphthyridine-6-carboxylic acid (317.9 mg, 95%) as a light white solid which was used for next step without further purification: MS (ESI) M+1=335.1.

To a suspension of 60% sodium hydride (267.5 mg, 6.9 mmol) in N,N-dimethylformamide (2.5 mL) was added cyclopropanesulfonamide (0.83 g, 6.9 mmol) at room temperature. The resulting mixture was stirred at 25° C. for 1 h to afford Solution A77. A solution of 2-(3-chloro-4-fluoro-phenyl)-4,4-dimethyl-1,2,3,4-tetrahydro-[1,7]naphthyridine-6-carboxylic acid (233.8 mg, 0.7 mmol) and 1,1'-carbonyldiimidazole (221.0 mg, 1.4 mmol) in N,N-dimethylformamide (2.0 mL) was stirred at 70° C. for 1 h and cooled to room temperature to afford Solution B77. Solution B77 was added to Solution A77 and the resulting mixture was stirred at 25° C. for 1 h. To the reaction mixture was added water (0.5 mL). The mixture was filtered to remove the insoluble solid, and the filtrate was purified by Waters automated flash system (column: Xterra 30 mm×100 mm, sample manager 2767, pump 2525, detector: ZQ mass and UV 2487, solvent system: acetonitrile and 0.1% ammonium hydroxide in water) afforded cyclopropanesulfonic acid [2-(3-chloro-4-fluoro-phenyl)-4,4-dimethyl-1,2,3,4-tetrahydro-[1,7]naphthyridine-6-carbonyl]-amide (72.2 mg, 23.6%) as a white solid: MS (ESI) M+1=438.2.

Example 78

Cyclopropanesulfonic acid [6-(3-chloro-4-fluorophenyl)-8,8-dimethyl-5,6,7,8-tetrahydro-[1,5]naphthyridine-2-carbonyl]-amide

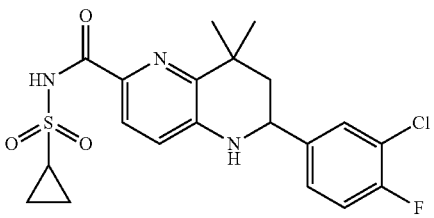 [SMILES: CC1(C)CC(c2ccc(F)c(Cl)c2)Nc2ccc(C(=O)NS(=O)(=O)C3CC3)nc21]

To a stirred solution of 5-amino-pyridine-2-carbonitrile (9.3 g, 78.4 mmol) and 3-chloro-4-fluoro-benzaldehyde (12.3 g, 78.4 mmol) in acetonitrile (150 mL) were added isobutene (21.0 mL, 313.5 mmol) and ytterbium(III) trifluoromethanesulfonate (Yb(OTf)$_3$) (5.8 g, 9.5 mmol). The resulting mixture was stirred at 85° C. for 18 h in sealed tube. The mixture was diluted with ethyl acetate (300 mL) and washed with water (100 mL×2) and brine (100 mL×2) and then dried over anhydrous sodium sulfate. The solvent was removed in vacuo and the residue was purified by ISCO combi-flash chromatography (gradient elution, 10-50% ethyl acetate in petroleum ether) to afford 6-(3-chloro-4-fluoro-phenyl)-8,8-dimethyl-5,6,7,8-tetrahydro-[1,5]naphthyridine-2-carbonitrile (3.2 g, 13.5%) as a light yellow solid: MS (ESI) M+1=316.0.

To a stirred mixture solution of 6-(3-chloro-4-fluoro-phenyl)-8,8-dimethyl-5,6,7,8-tetrahydro-[1,5]naphthyridine-2-carbonitrile (630.0 mg, 2.0 mmol) in ethanol (10.0 mL) was added 50% sodium hydroxide in water (8.5 mL). The reaction mixture was stirred at 90° C. for 6 h. The mixture was neutralized with a 3 N aqueous hydrochloric acid solution and extracted with ethyl acetate (2×100 mL), washed with water, dried over anhydrous sodium sulfate and then concentrated in vacuo to afford 6-(3-chloro-4-fluoro-phenyl)-8,8-dimethyl-5,6,7,8-tetrahydro-[1,5]naphthyridine-2-carboxylic acid (635.9 mg, 95%) as a light white solid which was used for next step without further purification: MS (ESI) M+1=335.1.

To a suspension of 60% sodium hydride (267.5 mg, 6.9 mmol) in N,N-dimethylformamide (2.5 mL) was added cyclopropanesulfonamide (0.83 g, 6.9 mmol) at room temperature. The resulting mixture was stirred at 25° C. for 1 h to afford Solution A78. A solution of 6-(3-chloro-4-fluoro-phenyl)-8,8-dimethyl-5,6,7,8-tetrahydro-[1,5]naphthyridine-2-carboxylic acid (233.8 mg, 0.7 mmol) and 1,1'-carbonyldiimidazole (221.0 mg, 1.4 mmol) in N,N-dimethylformamide (2.0 mL) was stirred at 70° C. for 1 h and cooled to room temperature to afford Solution B78. Solution B78 was added to Solution A78 and the resulting mixture was stirred at 25° C. for 1 h. To the reaction mixture was added water (0.5 mL). The mixture was filtered to remove the insoluble solid, and the filtrate was purified by Waters automated flash system (column: Xterra 30 mm×100 mm, sample manager 2767, pump 2525, detector: ZQ mass and UV 2487, solvent system: acetonitrile and 0.1% ammonium hydroxide in water) afforded cyclopropanesulfonic acid [6-(3-chloro-4-fluoro-phenyl)-8,8-dimethyl-5,6,7,8-tetrahydro-[1,5]naphthyridine-2-carbonyl]-amide (122.4 mg, 40%) as a white solid: MS (ESI) M+1=438.1.

Example 79

Cyclopropanesulfonic acid [8,8-dimethyl-6-(3-morpholin-4-yl-phenyl)-5,6,7,8-tetrahydro-[1,5]naphthyridine-2-carbonyl]-amide

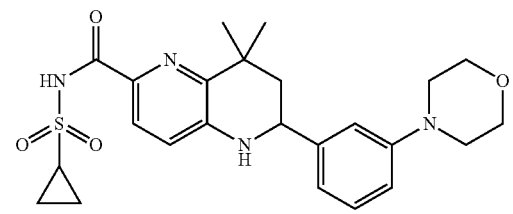 [SMILES: CC1(C)CC(c2cccc(N3CCOCC3)c2)Nc2ccc(C(=O)NS(=O)(=O)C3CC3)nc21]

The mixture solution of 5-amino-pyridine-2-carbonitrile (9.3 g, 78.4 mmol), 3-morpholin-4-yl-benzaldehyde (15.0 g, 78.4 mmol) and p-toluenesulfonic acid (271.8 mg, 1.4 mmol) in toluene (150 mL) was heated to reflux for 12 h. Then the reaction mixture was cooled to room temperature. The solvent was removed in vacuo and the residue was washed with ether to afford 5-{[1-(3-morpholin-4-yl-phenyl)-meth-(E)-ylidene]-amino}-pyridine-2-carbonitrile (22.9 g, quant.) as a light yellow solid: MS (ESI) M+1=293.0.

To a stirred solution of 5-{[1-(3-morpholin-4-yl-phenyl)-meth-(E)-ylidene]amino}-pyridine-2-carbonitrile (22.9 g, 78.4 mmol) in acetonitrile (150 mL) were added isobutene (21.0 mL, 313.5 mmol) and ytterbium(III) trifluoromethanesulfonate (Yb(OTf)$_3$) (5.8 g, 9.5 mmol). The resulting mixture was stirred at 90° C. for 18 h in sealed tube. The mixture was diluted with ethyl acetate (300 mL) and washed with water (100 mL×2) and brine (100 mL×2) and then dried over anhydrous sodium sulfate. The solvent was removed in vacuo and the residue was purified by ISCO combi-flash chromatography (gradient elution, 10-50% ethyl acetate in petroleum ether) to afford 8,8-dimethyl-6-(3-morpholin-4-yl-phenyl)-5,6,7,8-tetrahydro-[1,5]naphthyridine-2-carbonitrile (3.3 g, 12.1%) as a light yellow solid: MS (ESI) M+1=349.1.

To a stirred mixture solution of 8,8-dimethyl-6-(3-morpholin-4-yl-phenyl)-5,6,7,8-tetrahydro-[1,5]naphthyridine-2-carbonitrile (698.0 mg, 2.0 mmol) in ethanol (10.0 mL) was added 50% sodium hydroxide in water (8.5 mL). The reaction mixture was stirred at 90° C. for 6 h. The mixture was neutralized with a 3 N aqueous hydrochloric acid solution and extracted with ethyl acetate (2×100 mL), washed with water, dried over anhydrous sodium sulfate and then concentrated in vacuo to afford 8,8-dimethyl-6-(3-morpholin-4-yl-phenyl)-5,6,7,8-tetrahydro-[1,5]naphthyridine-2-carboxylic acid (660.6 mg, 90%) as a light white solid which was used for next step without further purification: MS (ESI) M+1=368.1.

To a suspension of 60% sodium hydride (267.5 mg, 6.9 mmol) in N,N-dimethylformamide (2.5 mL) was added cyclopropanesulfonamide (0.83 g, 6.9 mmol) at room temperature. The resulting mixture was stirred at 25° C. for 1 h to afford Solution A79. A solution of 8,8-dimethyl-6-(3-morpholin-4-yl-phenyl)-5,6,7,8-tetrahydro-[1,5]naphthyridine-2-carboxylic acid (256.9 mg, 0.7 mmol) and 1,1'-carbonyldiimidazole (221.0 mg, 1.4 mmol) in N,N-dimethylformamide (2.0 mL) was stirred at 70° C. for 1 h and cooled to room temperature to afford Solution B79. Solution B79 was added to Solution A79 and the resulting mixture was stirred at 25° C. for 1 h. To the reaction mixture was added water (0.5 mL). The mixture was filtered to remove the insoluble solid, and the filtrate was purified by Waters automated flash system (column: Xterra 30 mm×100 mm, sample manager 2767, pump 2525, detector: ZQ mass and UV 2487, solvent system: acetonitrile and 0.1% ammonium hydroxide in water) afforded cyclopropanesulfonic acid [8,8-dimethyl-6-(3-morpholin-4-yl-phenyl)-5,6,7,8-tetrahydro-[1,5]naphthyridine-2-carbonyl]-amide (98.7 mg, 30%) as a white solid: MS (ESI) M+1=471.2.

Example 80

N-[8,8-dimethyl-6-(3-morpholin-4-yl-phenyl)-5,6,7,8-tetrahydro-[1,5]naphthyridine-2-carbonyl]-methanesulfonamide

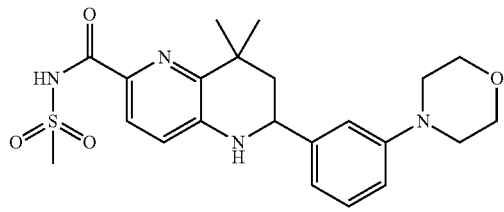 [SMILES: CC1(C)CC(c2cccc(N3CCOCC3)c2)Nc2ccc(C(=O)NS(C)(=O)=O)nc21]

To a suspension of 60% sodium hydride (267.5 mg, 6.9 mmol) in N,N-dimethylformamide (2.5 mL) was added methanesulfonamide (0.66 g, 6.9 mmol) at room temperature. The resulting mixture was stirred at 25° C. for 1 h to afford Solution A80. A solution of 8,8-dimethyl-6-(3-morpholin-4-yl-phenyl)-5,6,7,8-tetrahydro-[1,5]naphthyridine-2-carboxylic acid (256.9 mg, 0.7 mmol) and 1,1'-carbonyldiimidazole (221.0 mg, 1.4 mmol) in N,N-dimethylformamide (2.0 mL) was stirred at 70° C. for 1 h and cooled to room temperature to afford Solution B80. Solution B80 was added to Solution A80 and the resulting mixture was stirred at 25° C. for 1 h. To the reaction mixture was added water (0.5 mL). The mixture was filtered to remove the insoluble solid, and the filtrate was purified by Waters automated flash system (column: Xterra 30 mm×100 mm, sample manager 2767, pump 2525, detector: ZQ mass and UV 2487, solvent system: acetonitrile and 0.1% ammonium hydroxide in water) afforded N-[8,8-dimethyl-6-(3-morpholin-4-yl-phenyl)-5,6,7,8-tetrahydro-[1,5]naphthyridine-2-carbonyl]-methanesulfonamide (93.2 mg, 30%) as a white solid: MS (ESI) M+1=445.1.

Example 81

N-[6-(3-chloro-4-fluoro-phenyl)-8,8-dimethyl-5,6,7,8-tetrahydro-[1,5]naphthyridine-2-carbonyl]-methanesulfonamide

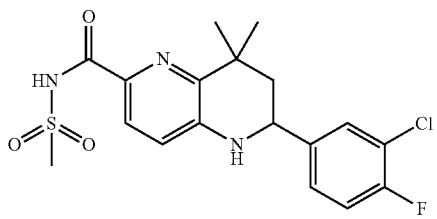 [SMILES: CC1(C)CC(c2ccc(F)c(Cl)c2)Nc2ccc(C(=O)NS(C)(=O)=O)nc21]

To a suspension of 60% sodium hydride (267.5 mg, 6.9 mmol) in N,N-dimethylformamide (2.5 mL) was added methanesulfonamide (0.66 g, 6.9 mmol) at room temperature. The resulting mixture was stirred at 25° C. for 1 h to afford Solution A81. A solution of 6-(3-chloro-4-fluoro-phenyl)-8,8-dimethyl-5,6,7,8-tetrahydro-[1,5]naphthyridine-2-carboxylic acid (233.8 mg, 0.7 mmol) and 1,1'-carbonyldiimidazole (221.0 mg, 1.4 mmol) in N,N-dimethylformamide (2.0 mL) was stirred at 70° C. for 1 h and cooled to room temperature to afford Solution B81. Solution B81 was added to Solution A81 and the resulting mixture was stirred at 25° C. for 1 h. To the reaction mixture was added water (0.5 mL). The mixture was filtered to remove the insoluble solid, and the filtrate was purified by Waters automated flash system (column: Xterra 30 mm×100 mm, sample manager 2767, pump 2525, detector: ZQ mass and UV 2487, solvent system: acetonitrile and 0.1% ammonium hydroxide in water) afforded N-[6-(3-chloro-4-fluoro-phenyl)-8,8-dimethyl-5,6,7,8-tetrahydro-[1,5]naphthyridine-2-carbonyl]-methanesulfonamide (115.1 mg, 40%) as a white solid: MS (ESI) M+1=412.1.

Example 82

2-{3-[4,4-Dimethyl-6-(morpholine-4-sulfonyl)-1,2,3,4-tetrahydro-quinolin-2-yl]-phenylamino}-2-methyl-propionic acid

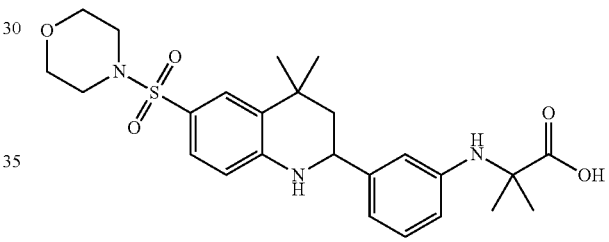

To a stirred solution of morpholine (5.2 mL, 59.7 mmol) and triethylamine (11.2 mL, 79.6 mmol) in dichloromethane (300 mL) was added the solution of 4-nitro-benzenesulfonyl chloride (8.8 g, 39.8 mmol) in dichloromethane (50 mL) at 0° C. The mixture was stirred at room temperature for 4 h and then washed with brine (50 mL×2) and dried over anhydrous sodium sulfate. The solvent was removed in vacuo to afford 4-(4-nitro-benzenesulfonyl)-morpholine (10.0 g, 92.5%) as a white powder: MS (ESI) M+1=273.0.

To a stirred solution of 4-(4-nitro-benzenesulfonyl)-morpholine (5.0 g, 18.4 mmol) ethanol (400 mL) was added iron powder (5.2 g, 92.0 mmol) and the solution of ammonium chloride (10 g, 184.0 mmol) in water (100 mL). After the reaction mixture was refluxed for 3 h, the iron was filtered off and the filtrate was basified to pH 9 by addition of sodium carbonate. The reaction mixture was extracted with ethyl acetate (300 mL×2). The extract was washed with water (130 mL×2) and brine (130 mL×2), dried over anhydrous sodium sulfate. The solvent was removed in vacuo and the residue was purified by ISCO combi-flash chromatography (gradient elution, 20-60% ethyl acetate in petroleum ether) to afford 4-(morpholine-4-sulfonyl)-phenylamine (4.2 g, 95%) as a yellow powder: MS (ESI) M+1=243.1.

To a stirred solution of 4-(morpholine-4-sulfonyl)-phenylamine (3 g, 12.4 mmol) and 3-bromo-benzaldehyde (2.52 g, 13.6 mmol) in acetonitrile (150 mL) were added isobutene (2.7 mL, 37.2 mmoll) and ytterbium(III) trifluoromethanesulfonate (Yb(OTf)₃) (1.54 g, 2.5 mmol). The resulting mixture was stirred at 80° C. for 18 h in sealed tube. The mixture was diluted with ethyl acetate (300 mL) and washed with water (100 mL×2) and brine (100 mL×2) and then dried over anhydrous sodium sulfate. The solvent was removed in vacuo and the residue was purified by ISCO combi-flash chromatography (gradient elution, 10-40% ethyl acetate in petroleum ether) to afford 2-(3-bromo-phenyl)-4,4-dimethyl-6-(morpholine-4-sulfonyl)-1,2,3,4-tetrahydro-quinoline (2.7 g, 47.4%) as a light yellow solid: MS (ESI) M+1=465.0 & 467.0.

A mixture solution of 2-(3-bromo-phenyl)-4,4-dimethyl-6-(morpholine-4-sulfonyl)-1,2,3,4-tetrahydro-quinoline (150 mg, 0.33 mmol), copper(I) iodide (20 mg, 0.1 mmol), 2-amino-2-methyl-propionic acid (135 mg, 1.3 mmol) and potassium carbonate (110 mg, 1.0 mmol) in dimethyl sulfoxide (2.0 mL) was stirred at 120° C. for 16 h. Then the reaction mixture was cooled to room temperature and extracted with ethyl acetate (70 mL×2), washed with water (30 mL×3) and saturated aqueous ammonium chloride solution (30 mL×2), dried over anhydrous sodium sulfate and then concentrated in vacuo. Purification by Waters automated flash system (column: Xterra 30 mm×100 mm, sample manager 2767, pump 2525, detector: ZQ mass and UV 2487, solvent system: acetonitrile and 0.1% ammonium hydroxide in water) afforded 2-{3-[4,4-dimethyl-6-(morpholine-4-sulfonyl)-1,2,3,4-tetrahydro-quinolin-2-yl]-phenylamino}-2-methyl-propionic acid (90 mg, 56.0%) as a white solid: MS (ESI) M+1=488.0.

Example 83

1-{3-[4,4-Dimethyl-6-(morpholine-4-sulfonyl)-1,2,3,4-tetrahydro-quinolin-2-yl]-phenylamino}-cyclopropanecarboxylic acid

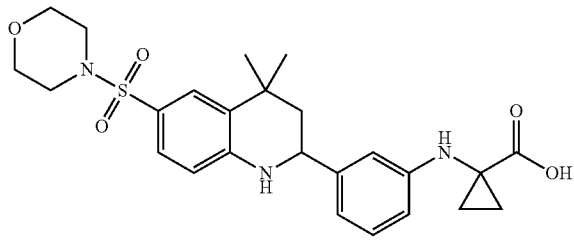 [SMILES: CC1(C)CC(c2cccc(NC3(C(=O)O)CC3)c2)Nc2ccc(S(=O)(=O)N3CCOCC3)cc21]

A mixture solution of 2-(3-bromo-phenyl)-4,4-dimethyl-6-(morpholine-4-sulfonyl)-1,2,3,4-tetrahydro-quinoline (150 mg, 0.33 mmol), copper(I) iodide (20 mg, 0.1 mmol), 1-amino-cyclopropanecarboxylic acid (135 mg, 1.3 mmol) and potassium carbonate (110 mg, 1.0 mmol) in dimethyl sulfoxide (2.0 mL) was stirred at 120° C. for 16 h. Then the reaction mixture was cooled to room temperature and extracted with ethyl acetate (70 mL×2), washed with water (30 mL×3) and saturated aqueous ammonium chloride solution (30 mL×2), dried over anhydrous sodium sulfate and then concentrated in vacuo. Purification by Waters automated flash system (column: Xterra 30 mm×100 mm, sample manager 2767, pump 2525, detector: ZQ mass and UV 2487, solvent system: acetonitrile and 0.1% ammonium hydroxide in water) afforded 1-{3-[4,4-dimethyl-6-(morpholine-4-sulfonyl)-1,2,3,4-tetrahydro-quinolin-2-yl]-phenylamino}-cyclopropanecarboxylic acid (128 mg, 80%) as a white solid: MS (ESI) M+1=486.1.

Example 84

1-[3-(6-Cyclobutylsulfamoyl-4,4-dimethyl-1,2,3,4-tetrahydro-quinolin-2-yl)-phenylamino]-cyclopropanecarboxylic acid

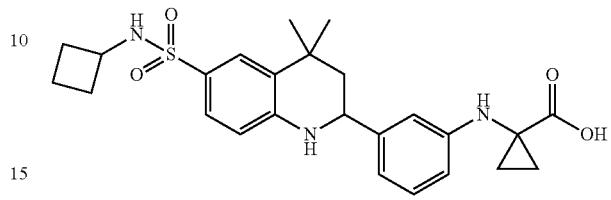

To a stirred solution of cyclobutylamine (4.3 g, 59.7 mmol) and triethylamine (11.2 mL, 79.6 mmol) in dichloromethane (300 mL) was added the solution of 4-nitro-benzenesulfonyl chloride (8.8 g, 39.8 mmol) in dichloromethane (50 mL) at 0° C. The mixture was stirred at room temperature for 4 h and then washed with brine (50 mL×2) and dried over anhydrous sodium sulfate. The solvent was removed in vacuo to afford N-cyclobutyl-4-nitro-benzenesulfonamide (9.4 g, 92.5%) as a white powder: MS (ESI) M+1=257.1.

To a stirred solution of N-cyclobutyl-4-nitro-benzenesulfonamide (5.8 g, 18.4 mmol) ethanol (400 mL) was added iron powder (5.2 g, 92.0 mmol) and the solution of ammonium chloride (10 g, 184.0 mmol) in water (100 mL). After the reaction mixture was refluxed for 3 h, the iron was filtered off and the filtrate was basified to pH 9 by addition of sodium carbonate. The reaction mixture was extracted with ethyl acetate (300 mL×2). The extract was washed with water (130 mL×2) and brine (130 mL×2), dried over anhydrous sodium sulfate. The solvent was removed in vacuo and the residue was purified by ISCO combi-flash chromatography (gradient elution, 20-60% ethyl acetate in petroleum ether) to afford 4-amino-N-cyclobutyl-benzenesulfonamide (3.87 g, 93%) as a yellow powder: MS (ESI) M+1=227.0.

To a stirred solution of 4-amino-N-cyclobutyl-benzenesulfonamide (2.8 g, 12.4 mmol) and 3-bromo-benzaldehyde (2.52 g, 13.6 mmol) in acetonitrile (150 mL) were added isobutene (2.7 mL, 37.2 mmoll) and ytterbium(III) trifluoromethanesulfonate (Yb(OTf)$_3$) (1.54 g, 2.5 mmol). The resulting mixture was stirred at 80° C. for 18 h in sealed tube, then diluted with ethyl acetate (300 mL) and washed with water (100 mL×2) and brine (100 mL×2) and then dried over anhydrous sodium sulfate. The solvent was removed in vacuo and the residue was purified by ISCO combi-flash chromatography (gradient elution, 10-40% ethyl acetate in petroleum ether) to afford 2-(3-bromo-phenyl)-4,4-dimethyl-1,2,3,4-tetrahydro-quinoline-6-sulfonic acid cyclobutylamide (2.2 g, 40%) as a light yellow solid: MS (ESI) M+1=449.0 & 451.0.

A mixture solution of 2-(3-bromo-phenyl)-4,4-dimethyl-1,2,3,4-tetrahydro-quinoline-6-sulfonic acid cyclobutylamide (150 mg, 0.34 mmol), copper(I) iodide (20 mg, 0.1 mmol), 1-amino-cyclopropanecarboxylic acid (138 mg, 1.3 mmol) and potassium carbonate (140 mg, 1.0 mmol) in dimethyl sulfoxide (2.0 mL) was stirred at 120° C. for 16 h. Then the reaction mixture was cooled to room temperature and extracted with ethyl acetate (70 mL×2), washed with water (30 mL×3) and saturated aqueous ammonium chloride solution (30 mL×2), dried over anhydrous sodium sulfate and then concentrated in vacuo. Purification by Waters automated flash system (column: Xterra 30 mm×100 mm, sample manager

Example 85

2-[3-(6-Cyclobutylsulfamoyl-4,4-dimethyl-1,2,3,4-tetrahydro-quinolin-2-yl)-phenylamino]-2-methyl-propionic acid

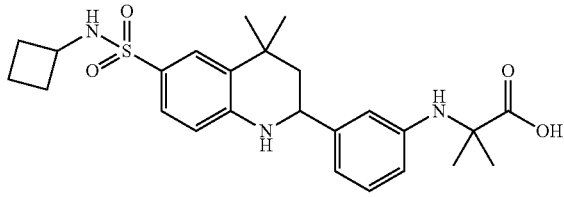 [SMILES: CC(C)(Nc1cccc(C2CC(C)(C)c3cc(S(=O)(=O)NC4CCC4)ccc3N2)c1)C(=O)O]

A mixture solution of 2-(3-bromo-phenyl)-4,4-dimethyl-1,2,3,4-tetrahydro-quinoline-6-sulfonic acid cyclobutylamide (150 mg, 0.34 mmol), copper(I) iodide (20 mg, 0.1 mmol), 2-amino-2-methyl-propionic acid (138 mg, 1.3 mmol) and potassium carbonate (140 mg, 1.0 mmol) in dimethyl sulfoxide (2.0 mL) was stirred at 120° C. for 16 h. Then the reaction mixture was cooled to room temperature and extracted with ethyl acetate (70 mL×2), washed with water (30 mL×3) and saturated aqueous ammonium chloride solution (30 mL×2), dried over anhydrous sodium sulfate and then concentrated in vacuo. Purification by Waters automated flash system (column: Xterra 30 mm×100 mm, sample manager 2767, pump 2525, detector: ZQ mass and UV 2487, solvent system: acetonitrile and 0.1% ammonium hydroxide in water) afforded 2-[3-(6-cyclobutylsulfamoyl-4,4-dimethyl-1,2,3,4-tetrahydro-quinolin-2-yl)-phenylamino]-2-methyl-propionic acid (112.1 mg, 70.0%) as a white solid: MS (ESI) M+1=472.1.

Example 86

2-[3-(6-Cyclobutylsulfamoyl-4,4-dimethyl-1,2,3,4-tetrahydro-quinolin-2-yl)-5-fluoro-phenylamino]-2-methyl-propionic acid

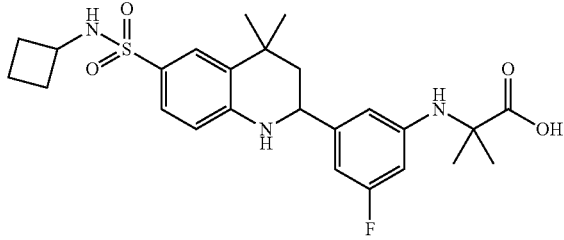 [SMILES: CC(C)(Nc1cc(F)cc(C2CC(C)(C)c3cc(S(=O)(=O)NC4CCC4)ccc3N2)c1)C(=O)O]

To a stirred solution of 4-amino-N-cyclobutyl-benzenesulfonamide (2.8 g, 12.4 mmol) and 3-bromo-5-fluoro-benzaldehyde (2.8 g, 13.6 mmol) in acetonitrile (150 mL) were added isobutene (2.7 mL, 37.2 mmoll) and ytterbium(III) trifluoromethanesulfonate (Yb(OTf)$_3$) (1.54 g, 2.5 mmol). The resulting mixture was stirred at 80° C. for 18 h in sealed tube, then diluted with ethyl acetate (300 mL) and washed with water (100 mL×2) and brine (100 mL×2) and then dried over anhydrous sodium sulfate. The solvent was removed in vacuo and the residue was purified by ISCO combi-flash chromatography (gradient elution, 10-40% ethyl acetate in petroleum ether) to afford 2-(3-bromo-5-fluoro-phenyl)-4,4-dimethyl-1,2,3,4-tetrahydro-quinoline-6-sulfonic acid cyclobutylamide (2.4 g, 42%) as a light yellow solid: MS (ESI) M+1=467.0 & 469.0.

A mixture solution of 2-(3-bromo-5-fluoro-phenyl)-4,4-dimethyl-1,2,3,4-tetrahydro-quinoline-6-sulfonic acid cyclobutylamide (150 mg, 0.32 mmol), copper(I) iodide (20 mg, 0.1 mmol), 2-amino-2-methyl-propionic acid (135 mg, 1.3 mmol) and potassium carbonate (140 mg, 1.0 mmol) in dimethyl sulfoxide (2.0 mL) was stirred at 120° C. for 16 h. Then the reaction mixture was cooled to room temperature and extracted with ethyl acetate (70 mL×2), washed with water (30 mL×3) and saturated aqueous ammonium chloride solution (30 mL×2), dried over anhydrous sodium sulfate and then concentrated in vacuo. Purification by Waters automated flash system (column: Xterra 30 mm×100 mm, sample manager 2767, pump 2525, detector: ZQ mass and UV 2487, solvent system: acetonitrile and 0.1% ammonium hydroxide in water) afforded 2-[3-(6-cyclobutylsulfamoyl-4,4-dimethyl-1,2,3,4-tetrahydro-quinolin-2-yl)-5-fluoro-phenylamino]-2-methyl-propionic acid (79.8 mg, 51.0%) as a white solid: MS (ESI) M+1=490.1.

Example 87

1-[3-(6-Cyclobutylsulfamoyl-4,4-dimethyl-1,2,3,4-tetrahydro-quinolin-2-yl)-5-fluoro-phenylamino]-cyclopropanecarboxylic acid

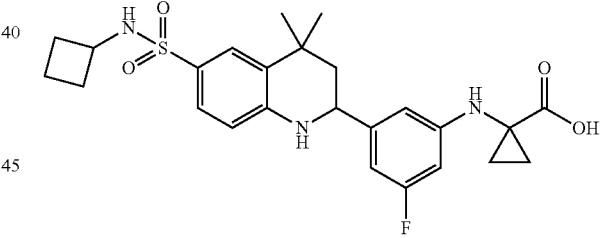

A mixture solution of 2-(3-bromo-5-fluoro-phenyl)-4,4-dimethyl-1,2,3,4-tetrahydro-quinoline-6-sulfonic acid cyclobutylamide (150 mg, 0.32 mmol), copper(I) iodide (20 mg, 0.1 mmol), 1-amino-cyclopropanecarboxylic acid (135 mg, 1.3 mmol) and potassium carbonate (140 mg, 1.0 mmol) in dimethyl sulfoxide (2.0 mL) was stirred at 120° C. for 16 h. Then the reaction mixture was cooled to room temperature and extracted with ethyl acetate (70 mL×2), washed with water (30 mL×3) and saturated aqueous ammonium chloride solution (30 mL×2), dried over anhydrous sodium sulfate and then concentrated in vacuo. Purification by Waters automated flash system (column: Xterra 30 mm×100 mm, sample manager 2767, pump 2525, detector: ZQ mass and UV 2487, solvent system: acetonitrile and 0.1% ammonium hydroxide in water) afforded 1-[3-(6-cyclobutylsulfamoyl-4,4-dimethyl-1,2,3,4-tetrahydro-quinolin-2-yl)-5-fluoro-phenylamino]-cyclopropanecarboxylic acid (73.2 mg, 47.0%) as a white solid: MS (ESI) M+1=488.1.

Example 88

The following procedure was applied.
Evaluation of p-AMPK and p-ACC expression level in L6 cell line by Western-Blot
This method evaluates the changes of AMP-activated protein kinase (AMPK) and ACC (acetyl-CoA carboxylase) activity by small molecular modulators through detecting the level of p-AMPK and p-ACC proteins in L6 cells using Western blot.

L6 Cell Preparation

L6 cells are maintained in DMEM medium supplemented with 10% FBS in 10-cm dishes. Prior to compounds treatment, L6 cells are seeded in 12-well-plates at concentration of $3 \times 10^4$ cells per well. After 24 hours of incubation in 12-well plates, L6 cells are differentiated by replacing the 10% FBS-DMEM medium with 2% FBS-DMEM. Differentiation usually takes 5 days, during which the culture medium is changed every 2 days.

Compound Treatment

The compound concentrations typically range from 32 µM to 0.5 µM with 2-fold dilution in 2 ml DMEM and 7 doses. The final DMSO concentration is 0.4%. Berberine is used as a positive control at concentration of 16 µM. Before compound treatment, starve L6 cells for 2 hours by replacing the medium with DMEM, and then gently aspirate the media from each well. Add the compounds into the plates and incubate at 37 degree 5% $CO_2$ for 2 hours.

Lysate L6 Cells

Prepare lysis buffer (RIPA buffer with protease-inhibitors and phosphorate-inhibitors) and place it on ice. After two hour's compound treatment, aspirate the medium from 12-well plates, add 70 ul lysis buffer to each well and keep the plates on ice for 5 min. Then scrape the cell lysate off the plates and transfer it to 1.5 ml eppendorf tubes. Keep the tube on ice for more 10 min, centrifugate the lysate at 13000 rpm, 4 degrees for 15 min and transfer the supernatant to clean tubes.

Western Blot

Determine protein concentration for each sample using Quickstart Bradford protein quantitation kit. Mix 20 ug protein sample with 4 times loading buffer, heat them at 100° C. for 5 min, store the sample in −80° C. or perform Western blot assay directly. For Western blot assay, load 20 ug samples and 10 ul Pre-stained Protein Maker into 4-12% SDS-PAGE gradient gel. Run the samples at 100 V in the stacking gel and at 120 V in resolving gel until the Bromophenol dye reaches the bottom. Transfer the electrophoresed proteins to a PVDF membrane using Bio-Rad's Transblot for 120 min at 300 mA. Following the completion of transfer, the membrane is blocked with 5% non-fat milk for 2 hours at room temperature before incubated with primary antibody (p-AMPK and p-ACC) at 4° C. overnight. On the next day wash the membrane twice with TBST, add secondary antibody and incubate for 1 hour at room temperature. Wash the membrane twice with TBST. Develop p-AMPK and p-ACC protein expression level on the film in dark room with Amersham ECL plus kit. The bands of each sample are quantitated by Bio-Rad system, The $AC_{1.3}$ value is analyzed using Prism 5.0.

Compounds as described above have activities in one of the foregoing tests between 0.0001 µM and 50 µM. Preferred compounds have activities in one of the foregoing tests between 0.0001 µM and 10 µM. Particularly preferred compounds have activities in one of the foregoing tests between 0.0001 µM and 1 µM.

The results obtained for representative compounds of formula (I) are indicated in Tables 1 and 2 below.

TABLE 1

| Example | Activity AC1.3 (ACCp) (µM) |
|---|---|
| 1 | 1.4 |
| 4 | 6.23 |
| 6 | 3.5 |
| 7 | <16 |
| 8 | <32 |
| 9 | 4.5 |
| 10 | <0.2 |
| 11 | 0.3 |
| 12 | 1.86 |
| 13 | 0.4 |
| 14 | 4.7 |
| 15 | 0.1 |
| 16 | 3.21 |
| 17 | 0.05 |
| 18 | 20 |
| 22 | 0.16 |
| 30 | 0.002 |
| 31 | 2 |
| 39 | 1.4 |
| 40 | 6.17 |
| 41 | 1.16 |
| 45 | <8 |
| 46 | <8 |
| 47 | 62.4 |
| 49 | 6.93 |
| 53 | 11.7 |
| 55 | 0.7 |
| 57 | 0.61 |
| 58 | 0.36 |
| 59 | 0.74 |
| 60 | 7.33 |
| 62 | 68 |
| 63 | 5.2 |
| 65 | 12.8 |
| 69 | 0.1 |
| 70 | 0.57 |
| 72 | 3.49 |
| 73 | 0.1 |
| 74 | 1.67 |
| 75 | 0.3 |
| 76 | 0.57 |

TABLE 2

| Example | Activity AC1.3 (AMPKp) (µM) |
|---|---|
| 4 | 6.76 |
| 5 | 9 |
| 12 | 5.70 |
| 15 | 0.1 |
| 16 | 19.4 |
| 17 | 0.41 |
| 18 | 7.98 |
| 22 | 0.02 |
| 25 | 0.21 |
| 27 | 0.01 |
| 28 | 0.02 |
| 32 | 0.002 |
| 33 | 0.08 |
| 34 | 0.08 |
| 35 | 0.24 |
| 40 | 6.6 |
| 49 | 0.15 |
| 50 | 0.16 |
| 51 | 0.18 |
| 52 | 0.55 |
| 53 | 4.79 |
| 54 | 0.03 |
| 56 | 0.03 |
| 57 | 0.85 |
| 58 | 0.46 |
| 59 | 7.73 |
| 61 | 0.1 |

TABLE 2-continued

| Example | Activity AC1.3 (AMPKp) (µM) |
|---|---|
| 64 | 0.1 |
| 66 | 12.8 |
| 67 | 0.02 |
| 68 | 0.003 |
| 71 | 0.08 |
| 72 | 0.14 |
| 74 | 0.06 |
| 76 | 3.12 |
| 78 | 28.9 |
| 79 | 4.46 |
| 81 | 0.43 |
| 82 | 0.02 |
| 83 | 0.01 |
| 84 | 0.2 |
| 85 | 0.03 |
| 86 | 0.003 |
| 87 | 0.002 |

Example A

A compound of formula (I) can be used in a manner known per se as the active ingredient for the production of tablets of the following composition:

| Per tablet | |
|---|---|
| Active ingredient | 200 mg |
| Microcrystalline cellulose | 155 mg |
| Corn starch | 25 mg |
| Talc | 25 mg |
| Hydroxypropylmethylcellulose | 20 mg |
| Total | 425 mg |

Example B

A compound of formula (I) can be used in a manner known per se as the active ingredient for the production of capsules of the following composition:

| Per capsule | |
|---|---|
| Active ingredient | 100.0 mg |
| Corn starch | 20.0 mg |
| Lactose | 95.0 mg |
| Talc | 4.5 mg |
| Magnesium stearate | 0.5 mg |
| Total | 220.0 mg |

The invention claimed is:
1. A compound of formula (I)

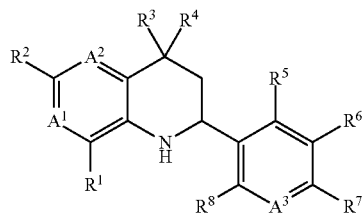

(I)

wherein
    $A^1$ is nitrogen or —$CR^{10}$—,
    $A^2$ is nitrogen or —CH—;
    $A^3$ is nitrogen or —$CR^9$—;
    one of $R^1$, $R^2$ and $R^{10}$ is -$A^4$-$SO_2$-$R^{11}$ and the other ones are independently selected from the group consisting of hydrogen, alkyl and halogen,
    $A^4$ is absent or —$NR^{12}$—C(O)—;
$R^3$ and $R^4$ are independently selected from the group consisting of alkyl and phenyl,
    or $R^3$ and $R^4$ together with the carbon atom to which they are attached form cycloalkyl,
    $R^5$, $R^6$, $R^7$, $R^8$ and $R^9$ are independently selected from the group consisting of hydrogen, alkyl, haloalkyl, alkoxy, halogen, alkylamino, dialkylamino, hydroxyphenyl, morpholinyl, piperazinyl, alkylpiperazinyl, phenylpiperazinyl, phenylaminocarbonyl, oxo-oxazolidinyl, aminocarbonyl, cyano, alkylsulfonyl, alkylphenyl, alkoxyphenyl, alkylphenylpiperazinyl, dialkylphenylpiperazinyl, halophenylpiperazinyl, alkyl-1H-tetrazolyl, cycloalkyl-1H-tetrazolyl, pyrrolidinyl, carboxyalkylamino and carboxycycloalkylamino,
    $R^{11}$ is selected from the group consisting of alkyl, cycloalkyl, alkylamino, cycloalkylamino and morpholinyl, and
    $R^{12}$ is hydrogen or alkyl;
or a pharmaceutically acceptable salt or ester thereof.

2. A compound according to claim 1, wherein one of $R^1$, $R^2$ and $R^{10}$ is -$A^4$-$SO_2$—$R^{11}$ and the others are independently selected from the group consisting of hydrogen, fluoro and chloro.

3. A compound according to claim 1, wherein $R^3$ and $R^4$ are both alkyl at the same time, or $R^3$ and $R^4$ together with the carbon atom to which they are attached form cycloalkyl.

4. A compound according to claim 1, wherein $R^3$ and $R^4$ are both methyl at the same time.

5. A compound according to claim 1, wherein $R^5$ and $R^8$ are independently selected from the group consisting of hydrogen, alkyl and halogen.

6. A compound according to claim 1, wherein $R^5$ and $R^8$ are independently selected from hydrogen and methyl.

7. A compound according to claim 1, wherein $R^6$ and $R^9$ are independently selected from the group consisting of hydrogen, halogen, cyano, alkoxy, haloalkyl, dialkylamino, carboxyalkylamino, carboxycycloalkylamino, alkylsulfonyl, aminocarbonyl, morpholinyl, pyrrolidinyl, alkylphenyl, hydroxyphenyl, piperazinyl, alkylpiperazinyl, phenylpiperazinyl, alkylphenylpiperazinyl, dialkylphenylpiperazinyl, halophenylpiperazinyl, phenylaminocarbonyl, alkoxyphenyl, oxo-oxazolidinyl, alkyl-1-H-tetrazolyl and cycloalkyl-1-H-tetrazolyl.

8. A compound according to claim 1, wherein $R^6$ and $R^9$ are independently selected from the group consisting of hydrogen, trifluoromethyl, morpholinyl, pyrrolidinyl, t-butylphenyl, hydroxyphenyl, piperazinyl, phenylpiperazinyl, methylphenylpiperazinyl, fluorophenylpiperazinyl and cyclopropyl-1-H-tetrazolyl.

9. A compound according to claim 1, wherein one of $R^6$ and $R^9$ is hydrogen.

10. A compound according to claim 1, wherein $R^7$ is hydrogen or halogen.

11. A compound according to claim 1, wherein $R^{11}$ is selected from the group consisting of methyl, propyl, isopropyl, cyclopropyl, isopropylamino, cyclobutylamino and morpholinyl.

12. A compound according to claim 1 selected from the group consisting of:
  Cyclopropanesulfonic acid [4,4-dimethyl-2-(3-morpholin-4-yl-phenyl)-1,2,3,4-tetrahydroquinoline-6-carbonyl]-amide;
  2'-(5-Fluoro-2-methylphenyl)-N-(methylsulfonyl)-2',3'-dihydro-1'H-spiro[cyclopropane-1,4'-quinoline]-6'-carboxamide;
  2'-(2,4-Difluorophenyl)-N-(methylsulfonyl)-2',3'-dihydro-1'H-spiro[cyclopropane-1,4'-quinoline]-6'-carboxamide;
  N-[2-(3-Fluoro-5-morpholin-4-yl-phenyl)-4,4-dimethyl-1,2,3,4-tetrahydro-quinoline-6-carbonyl]-methanesulfonamide;
  N-(methylsulfonyl)-2'-(3-morpholinophenyl)-2',3'-dihydro-1'H-spiro[cyclopentane-1,4'-quinoline]-6'-carboxamide;
  Cyclopropanesulfonic acid [2-(3-fluoro-5-morpholin-4-yl-phenyl)-4,4-dimethyl-1,2,3,4-tetrahydro-quinoline-6-carbonyl]-amide;
  N-[2-(3-chloro-4-fluoro-phenyl)-4-methyl-4-phenyl-1,2,3,4-tetrahydro-quinoline-6-carbonyl]-methanesulfonamide;
  Propane-1-sulfonic acid [2-(3-chloro-4-fluoro-phenyl)-4,4-dimethyl-1,2,3,4-tetrahydro-quinoline-6-carbonyl]-amide;
  Propane-2-sulfonic acid [4,4-dimethyl-2-(3-morpholin-4-yl-phenyl)-1,2,3,4-tetrahydroquinoline-6-carbonyl]-amide; and
  N-[4,4-dimethyl-2-(3-morpholin-4-yl-phenyl)-1,2,3,4-tetrahydro-quinoline-8-carbonyl]-methanesulfonamide.

13. A compound according to claim 1 selected from the group consisting of:
  Cyclopropanesulfonic acid [4,4-dimethyl-2-(3-morpholin-4-yl-phenyl)-1,2,3,4-tetrahydro-quinoline-8-carbonyl]-amide;
  4,4-Dimethyl-6-(morpholine-4-sulfonyl)-2-(3-morpholin-4-yl-phenyl)-1,2,3,4-tetrahydro-quinoline;
  4,4-Dimethyl-2-(3-morpholin-4-yl-phenyl)-1,2,3,4-tetrahydro-quinoline-6-sulfonic acid isopropylamide;
  4,4-Dimethyl-6-(morpholine-4-sulfonyl)-2-(3-piperazin-1-yl-phenyl)-1,2,3,4-tetrahydro-quinoline;
  4,4-Dimethyl-2-(3-morpholin-4-yl-phenyl)-1,2,3,4-tetrahydro-quinoline-6-sulfonic acid cyclobutylamide;
  2-(3-Fluoro-5-morpholin-4-yl-phenyl)-4,4-dimethyl-1,2,3,4-tetrahydro-quinoline-6-sulfonic acid cyclobutylamide;
  2-(2'-Hydroxy-biphenyl-3-yl)-4,4-dimethyl-1,2,3,4-tetrahydro-quinoline-6-sulfonic acid cyclobutylamide;
  N-(4,4-Dimethyl-2-pyridin-3-yl-1,2,3,4-tetrahydro-quinoline-6-carbonyl)-methanesulfonamide;
  Cyclopropanesulfonic acid (4,4-dimethyl-2-pyridin-3-yl-1,2,3,4-tetrahydro-quinoline-6-carbonyl)-amide; and
  3-(6-Methanesulfonylaminocarbonyl-4,4-dimethyl-1,2,3,4-tetrahydro-quinolin-2-yl)-N-phenyl-benzamide.

14. A compound according to claim 1 selected from the group consisting of:
  3-(6-Cyclopropanesulfonylaminocarbonyl-4,4-dimethyl-1,2,3,4-tetrahydro-quinolin-2-yl)-N-phenyl-benzamide;
  N-[4,4-dimethyl-2-(2-methyl-5-morpholin-4-yl-phenyl)-1,2,3,4-tetrahydro-quinoline-6-carbonyl]-methanesulfonamide;
  N-[2-(2-chloro-5-morpholin-4-yl-phenyl)-4,4-dimethyl-1,2,3,4-tetrahydro-quinoline-6-carbonyl]-methanesulfonamide;
  Cyclopropanesulfonic acid [4,4-dimethyl-2-(2-methyl-5-morpholin-4-yl-phenyl)-1,2,3,4-tetrahydro-quinoline-6-carbonyl]-amide;
  Cyclopropanesulfonic acid [2-(2-chloro-5-morpholin-4-yl-phenyl)-4,4-dimethyl-1,2,3,4-tetrahydro-quinoline-6-carbonyl]-amide;
  N-{2-[2-chloro-5-(2-oxo-oxazolidin-3-yl)-phenyl]-4,4-dimethyl-1,2,3,4-tetrahydro-quinoline-6-carbonyl}-methanesulfonamide;
  N-{4,4-dimethyl-2-[2-methyl-5-(2-oxo-oxazolidin-3-yl)-phenyl]-1,2,3,4-tetrahydro-quinoline-6-carbonyl}-methanesulfonamide;
  Cyclopropanesulfonic acid {4,4-dimethyl-2-[2-methyl-5-(2-oxo-oxazolidin-3-yl)-phenyl]-1,2,3,4-tetrahydro-quinoline-6-carbonyl}-amide;
  Cyclopropanesulfonic acid {2-[2-chloro-5-(2-oxo-oxazolidin-3-3-yl)-phenyl]-4,4-dimethyl-1,2,3,4-tetrahydro-quinoline-6-carbonyl}-amide; and
  N-[4,4-Dimethyl-2-(3-trifluoromethyl-phenyl)-1,2,3,4-tetrahydro-quinoline-6-carbonyl]-methanesulfonamide.

15. A compound according to claim 1 selected from the group consisting of:
  Cyclopropanesulfonic acid [4,4-dimethyl-2-(3-trifluoromethyl-phenyl)-1,2,3,4-tetrahydro-quinoline-6-carbonyl]-amide;
  3-(6-Methanesulfonylaminocarbonyl-4,4-dimethyl-1,2,3,4-tetrahydro-quinolin-2-yl)-benzamide;
  N-[2-(3-cyano-phenyl)-4,4-dimethyl-1,2,3,4-tetrahydro-quinoline-6-carbonyl]-methanesulfonamide;
  3-(6-Cyclopropanesulfonylaminocarbonyl-4,4-dimethyl-1,2,3,4-tetrahydro-quinolin-2-yl)-benzamide;
  Cyclopropanesulfonic acid [2-(3-cyano-phenyl)-4,4-dimethyl-1,2,3,4-tetrahydro-quinoline-6-carbonyl]-amide;
  N-[2-(3-methoxy-phenyl)-4,4-dimethyl-1,2,3,4-tetrahydro-quinoline-6-carbonyl]-methanesulfonamide;
  N-[2-(3-methanesulfonyl-phenyl)-4,4-dimethyl-1,2,3,4-tetrahydro-quinoline-6-carbonyl]-methanesulfonamide;
  Cyclopropanesulfonic acid [2-(3-methanesulfonyl-phenyl)-4,4-dimethyl-1,2,3,4-tetrahydro-quinoline-6-carbonyl]-amide;
  N-[2-(4'-tert-butyl-biphenyl-3-yl)-4,4-dimethyl-1,2,3,4-tetrahydro-quinoline-6-carbonyl]-methanesulfonamide; and
  Cyclopropanesulfonic acid [2-(4'-tert-butyl-biphenyl-3-yl)-4,4-dimethyl-1,2,3,4-tetrahydroquinoline-6-carbonyl]-amide.

16. A compound according to claim 1 selected from the group consisting of:
  Cyclopropanesulfonic acid {2-[3-(1-cyclopropyl-1H-tetrazol-5-yl)-phenyl]-4,4-dimethyl-1,2,3,4-tetrahydro-quinoline-6-carbonyl}-amide;
  Cyclopropanesulfonic acid {4,4-dimethyl-2-[3-(1-methyl-1H-tetrazol-5-yl)-phenyl]-1,2,3,4-tetrahydro-quinoline-6-carbonyl}-amide;
  N-{2-[3-(1-cyclopropyl-1H-tetrazol-5-yl)-phenyl]-4,4-dimethyl-1,2,3,4-tetrahydro-quinoline-6-carbonyl}-methanesulfonamide;
  N-{4,4-dimethyl-2-[3-(1-methyl-1H-tetrazol-5-yl)-phenyl]-1,2,3,4-tetrahydro-quinoline-6-carbonyl}-methanesulfonamide;
  N-[2-(4'-isopropoxy-biphenyl-3-yl)-4,4-dimethyl-1,2,3,4-tetrahydro-quinoline-6-carbonyl]-methanesulfonamide;

Cyclopropanesulfonic acid [2-(4'-isopropoxy-biphenyl-3-yl)-4,4-dimethyl-1,2,3,4-tetrahydro-quinoline-6-carbonyl]-amide;
Cyclopropanesulfonic acid [2-(2-ethyl-5-morpholin-4-yl-phenyl)-4,4-dimethyl-1,2,3,4-tetrahydro-quinoline-6-carbonyl]-amide;
Cyclopropanesulfonic acid [2-(2-ethyl-phenyl)-4,4-dimethyl-1,2,3,4-tetrahydro-quinoline-6-carbonyl]-amide;
N-(2-{5-[4-(2,4-dimethyl-phenyl)-piperazin-1-yl]-pyridin-3-yl}-4,4-dimethyl-1,2,3,4-tetrahydro-quinoline-6-carbonyl)-methanesulfonamide; and
Cyclopropanesulfonic acid (2-{5-[4-(2,4-dimethyl-phenyl)-piperazin-1-yl]-pyridin-3-yl}-4,4-dimethyl-1,2,3,4-tetrahydro-quinoline-6-carbonyl)-amide.

17. A compound according to claim 1 selected from the group consisting of:
Cyclopropanesulfonic acid {4,4-dimethyl-2-[3-(4-methyl-piperazin-1-yl)-phenyl]-1,2,3,4-tetrahydro-quinoline-6-carbonyl}-amide;
Cyclopropanesulfonic acid [4,4-dimethyl-2-(3-pyrrolidin-1-yl-phenyl)-1,2,3,4-tetrahydroquinoline-6-carbonyl]-amide;
N-(2-{3-[4-(2,4-dimethyl-phenyl)-piperazin-1-yl]-phenyl}-4,4-dimethyl-1,2,3,4-tetrahydroquinoline-6-carbonyl)-methanesulfonamide;
N-[4,4-dimethyl-2-(5-morpholin-4-yl-pyridin-3-yl)-1,2,3,4-tetrahydro-quinoline-6-carbonyl]-methanesulfonamide;
N-[4,4-dimethyl-2-(3-morpholin-4-yl-phenyl)-1,2,3,4-tetrahydro-quinoline-7-carbonyl]-methanesulfonamide;
N-[6-fluoro-4,4-dimethyl-2-(3-morpholin-4-yl-phenyl)-1,2,3,4-tetrahydro-quinoline-8-carbonyl]-methanesulfonamide;
N-{6-fluoro-4,4-dimethyl-2-[3-(4-o-tolyl-piperazin-1-yl)-phenyl]-1,2,3,4-tetrahydro-quinoline-8-carbonyl}-methanesulfonamide;
Cyclopropanesulfonic acid {6-fluoro-4,4-dimethyl-2-[3-(4-o-tolyl-piperazin-1-yl)-phenyl]-1,2,3,4-tetrahydro-quinoline-8-carbonyl}-amide;
N-(6-fluoro-2-{3-[4-(2-fluoro-phenyl)-piperazin-1-yl]-phenyl}-4,4-dimethyl-1,2,3,4-tetrahydro-quinoline-8-carbonyl)-methanesulfonamide; and
Cyclopropanesulfonic acid (6-fluoro-2-{3-[4-(2-fluoro-phenyl)-piperazin-1-yl]-phenyl}-4,4-dimethyl-1,2,3,4-tetrahydro-quinoline-8-carbonyl)-amide.

18. A compound according to claim 1 selected from the group consisting of:
Cyclopropanesulfonic acid [2-(3-dimethylamino-phenyl)-6-fluoro-4,4-dimethyl-1,2,3,4-tetrahydro-quinoline-8-carbonyl]-amide;
N-[6-chloro-4,4-dimethyl-2-(3-morpholin-4-yl-phenyl)-1,2,3,4-tetrahydro-quinoline-8-carbonyl]-methanesulfonamide;
Cyclopropanesulfonic acid [6-chloro-4,4-dimethyl-2-(3-morpholin-4-yl-phenyl)-1,2,3,4-tetrahydro-quinoline-8-carbonyl]-amide;
N-{6-chloro-4,4-dimethyl-2-[3-(2-oxo-oxazolidin-3-yl)-phenyl]-1,2,3,4-tetrahydro-quinoline-8-carbonyl}-methanesulfonamide;
Cyclopropanesulfonic acid {6-chloro-4,4-dimethyl-2-[3-(2-oxo-oxazolidin-3-yl)-phenyl]-1,2,3,4-tetrahydro-quinoline-8-carbonyl}-amide;
Cyclopropanesulfonic acid [4,4,8-trimethyl-2-(3-morpholin-4-yl-phenyl)-1,2,3,4-tetrahydro-quinoline-6-carbonyl]-amide;
N-{4,4-dimethyl-2-[3-(4-methyl-piperazin-1-yl)-phenyl]-1,2,3,4-tetrahydro-quinoline-8-carbonyl}-methanesulfonamide;
N-{6-fluoro-4,4-dimethyl-2-[3-(4-p-tolyl-piperazin-1-yl)-phenyl]-1,2,3,4-tetrahydro-quinoline-8-carbonyl}-methanesulfonamide;
N-[6-fluoro-4,4-dimethyl-2-(4-methyl-3-pyrrolidin-1-yl-phenyl)-1,2,3,4-tetrahydro-quinoline-8-carbonyl]-methanesulfonamide; and
Cyclopropanesulfonic acid [6-fluoro-4,4-dimethyl-2-(4-methyl-3-pyrrolidin-1-yl-phenyl)-1,2,3,4-tetrahydro-quinoline-8-carbonyl]-amide.

19. A compound according to claim 1 selected from the group consisting of:
N-[6-chloro-4,4-dimethyl-2-(4-methyl-3-pyrrolidin-1-yl-phenyl)-1,2,3,4-tetrahydro-quinoline-8-carbonyl]-methanesulfonamide;
Cyclopropanesulfonic acid [6-chloro-4,4-dimethyl-2-(4-methyl-3-pyrrolidin-1-yl-phenyl)-1,2,3,4-tetrahydro-quinoline-8-carbonyl]-amide;
N-{2-[5-(4-tert-Butyl-phenyl)-pyridin-3-3-yl]-4,4-dimethyl-1,2,3,4-tetrahydro-quinoline-6-carbonyl}-methanesulfonamide;
Cyclopropanesulfonic acid {2-[5-(4-tert-butyl-phenyl)-pyridin-3-yl]-4,4-dimethyl-1,2,3,4-tetrahydro-quinoline-6-carbonyl}-amide;
Cyclopropanesulfonic acid [4,4-dimethyl-2-(3-morpholin-4-yl-phenyl)-1,2,3,4-tetrahydro-quinoline-6-carbonyl]-methyl-amide;
Cyclopropanesulfonic acid [4,4-dimethyl-2-[3-(4-phenyl-piperazin-1-yl)-phenyl]-1,2,3,4-tetrahydro-quinoline-8-carbonyl]-amide;
Cyclopropanesulfonic acid [2-(3-chloro-4-fluoro-phenyl)-4,4-dimethyl-1,2,3,4-tetrahydro-[1,7]naphthyridine-6-carbonyl]-amide;
Cyclopropanesulfonic acid [6-(3-chloro-4-fluoro-phenyl)-8,8-dimethyl-5,6,7,8-tetrahydro-[1,5]naphthyridine-2-carbonyl]-amide;
Cyclopropanesulfonic acid [8,8-dimethyl-6-(3-morpholin-4-yl-phenyl)-5,6,7,8-tetrahydro-[1,5]naphthyridine-2-carbonyl]-amide; and
N-[8,8-dimethyl-6-(3-morpholin-4-yl-phenyl)-5,6,7,8-tetrahydro-[1,5]naphthyridine-2-carbonyl]-methanesulfonamide.

20. A compound according to claim 1 selected from the group consisting of:
N-[6-(3-chloro-4-fluoro-phenyl)-8,8-dimethyl-5,6,7,8-tetrahydro-[1,5]naphthyridine-2-carbonyl]-methanesulfonamide;
2-{3-[4,4-Dimethyl-6-(morpholine-4-sulfonyl)-1,2,3,4-tetrahydro-quinolin-2-yl]-phenylamino}-2-methyl-propionic acid;
1-{3-[4,4-Dimethyl-6-(morpholine-4-sulfonyl)-1,2,3,4-tetrahydro-quinolin-2-yl]-phenylamino}-cyclopropanecarboxylic acid;
1-[3-(6-Cyclobutylsulfamoyl-4,4-dimethyl-1,2,3,4-tetrahydro-quinolin-2-yl)-phenylamino]-cyclopropanecarboxylic acid;
2-[3-(6-Cyclobutylsulfamoyl-4,4-dimethyl-1,2,3,4-tetrahydro-quinolin-2-yl)-phenylamino]-2-methyl-propionic acid;
2-[3-(6-Cyclobutylsulfamoyl-4,4-dimethyl-1,2,3,4-tetrahydro-quinolin-2-yl)-5-fluoro-phenylamino]-2-methyl-propionic acid; and
1-[3-(6-Cyclobutylsulfamoyl-4,4-dimethyl-1,2,3,4-tetrahydro-quinolin-2-yl)-5-fluoro-phenylamino]-cyclopropanecarboxylic acid.

21. A compound according to claim 1 selected from the group consisting of:
- Cyclopropanesulfonic acid [4,4-dimethyl-2-(3-morpholin-4-yl-phenyl)-1,2,3,4-tetrahydroquinoline-6-carbonyl]-amide;
- Cyclopropanesulfonic acid [2-(3-fluoro-5-morpholin-4-yl-phenyl)-4,4-dimethyl-1,2,3,4-tetrahydro-quinoline-6-carbonyl]-amide;
- Propane-2-sulfonic acid [4,4-dimethyl-2-(3-morpholin-4-yl-phenyl)-1,2,3,4-tetrahydroquinoline-6-carbonyl]-amide;
- N-[4,4-dimethyl-2-(3-morpholin-4-yl-phenyl)-1,2,3,4-tetrahydro-quinoline-8-carbonyl]-methanesulfonamide;
- Cyclopropanesulfonic acid [4,4-dimethyl-2-(3-morpholin-4-yl-phenyl)-1,2,3,4-tetrahydro-quinoline-8-carbonyl]-amide;
- 4,4-Dimethyl-2-(3-morpholin-4-yl-phenyl)-1,2,3,4-tetrahydro-quinoline-6-sulfonic acid isopropylamide;
- 4,4-Dimethyl-6-(morpholine-4-sulfonyl)-2-(3-piperazin-1-yl-phenyl)-1,2,3,4-tetrahydro-quinoline;
- 4,4-Dimethyl-2-(3-morpholin-4-yl-phenyl)-1,2,3,4-tetrahydro-quinoline-6-sulfonic acid cyclobutylamide;
- N-[4,4-dimethyl-2-(2-methyl-5-morpholin-4-yl-phenyl)-1,2,3,4-tetrahydro-quinoline-6-carbonyl]-methanesulfonamide.

22. A compound according to claim 1 selected from the group consisting of:
- N-[4,4-dimethyl-2-(3-trifluoromethyl-phenyl)-1,2,3,4-tetrahydro-quinoline-6-carbonyl]-methanesulfonamide;
- Cyclopropanesulfonic acid [4,4-dimethyl-2-(3-trifluoromethyl-phenyl)-1,2,3,4-tetrahydro-quinoline-6-carbonyl]-amide;
- N-[2-(4'-tert-butyl-biphenyl-3-yl)-4,4-dimethyl-1,2,3,4-tetrahydro-quinoline-6-carbonyl]-methanesulfonamide;
- Cyclopropanesulfonic acid {2-[3-(1-cyclopropyl-1H-tetrazol-5-yl)-phenyl]-4,4-dimethyl-1,2,3,4-tetrahydroquinoline-6-carbonyl}-amide;
- N-[4,4-dimethyl-2-(3-morpholin-4-yl-phenyl)-1,2,3,4-tetrahydro-quinoline-7-carbonyl]-methanesulfonamide;
- N-[6-fluoro-4,4-dimethyl-2-[3-(4-o-tolyl-piperazin-1-yl)-phenyl]-1,2,3,4-tetrahydro-quinoline-8-carbonyl]-methanesulfonamide;
- Cyclopropanesulfonic acid {6-fluoro-4,4-dimethyl-2-[3-(4-o-tolyl-piperazin-1-yl)-phenyl]-1,2,3,4-tetrahydroquinoline-8-carbonyl}-amide;
- N-(6-fluoro-2-{3-[4-(2-fluoro-phenyl)-piperazin-1-yl]-phenyl}-4,4-dimethyl-1,2,3,4-tetrahydro-quinoline-8-carbonyl)-methanesulfonamide;
- N-[6-fluoro-4,4-dimethyl-2-(4-methyl-3-pyrrolidin-1-yl-phenyl)-1,2,3,4-tetrahydro-quinoline-8-carbonyl]-methanesulfonamide; and
- Cyclopropanesulfonic acid [6-fluoro-4,4-dimethyl-2-(4-methyl-3-pyrrolidin-1-yl-phenyl)-1,2,3,4-tetrahydroquinoline-8-carbonyl]-amide.

23. A compound according to claim 1 selected from the group consisting of:
- N-{2-[5-(4-tert-butyl-phenyl)-pyridin-3-yl]-4,4-dimethyl-1,2,3,4-tetrahydro-quinoline-6-carbonyl}-methanesulfonamide;
- Cyclopropanesulfonic acid {2-[5-(4-tert-butyl-phenyl)-pyridin-3-yl]-4,4-dimethyl-1,2,3,4-tetrahydro-quinoline-6-carbonyl}-amide;
- Cyclopropanesulfonic acid [4,4-dimethyl-2-(3-morpholin-4-yl-phenyl)-1,2,3,4-tetrahydro-quinoline-6-carbonyl]-methyl-amide; and
- Cyclopropanesulfonic acid {4,4-dimethyl-2-[3-(4-phenyl-piperazin-1-yl)-phenyl]-1,2,3,4-tetrahydro-quinoline-8-carbonyl}-amide.

24. A pharmaceutical composition comprising a compound according to claim 1 and a therapeutically inert carrier.

* * * * *